(12) United States Patent
Liang et al.

(10) Patent No.: US 10,906,915 B2
(45) Date of Patent: Feb. 2, 2021

(54) SUBSTITUTED PYRAZOLOAZEPIN-4-ONES AND THEIR USE AS PHOSPHODIESTERASE INHIBITORS

(71) Applicant: LEO Pharma A/S, Ballerup (DK)

(72) Inventors: Xifu Liang, Ballerup (DK); Jens Larsen, Ballerup (DK); Simon Feldbaek Nielsen, Ballerup (DK); Peter Andersen, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 16/468,420

(22) PCT Filed: Dec. 12, 2016

(86) PCT No.: PCT/EP2016/080548
§ 371 (c)(1),
(2) Date: Jun. 11, 2019

(87) PCT Pub. No.: WO2018/108230
PCT Pub. Date: Jun. 21, 2018

(65) Prior Publication Data
US 2020/0010477 A1    Jan. 9, 2020

(51) Int. Cl.
*C07D 491/20*    (2006.01)
(52) U.S. Cl.
CPC .................. *C07D 491/20* (2013.01)
(58) Field of Classification Search
None
See application file for complete search history.

(56) References Cited

FOREIGN PATENT DOCUMENTS

| WO | WO 01/49689 A2 | 7/2001 |
| WO | WO 2004/098520 A2 | 11/2004 |
| WO | WO 2007/040435 A1 | 4/2007 |
| WO | WO 2008/060597 A2 | 5/2008 |
| WO | WO 2008/104175 A2 | 9/2008 |

OTHER PUBLICATIONS

Holden, Colin A, B.Sc., et al., "Monocyte Localization of Elevated cAMP Phosphodiesterase Activity in Atopic Dermatitis," The Society for Investigative Dermatology, vol. 87, No. 3, pp. 372-376 (1986).
Houslay, Miles D. et al., "Phosphodiesterase-4 as a therapeutic target," Drug Discovery Today, vol. 1, No. 22, pp. 1503-1519 (2005).
Kroegel, Claus et al., "Phosphodiesterase-4 inhibitors as a novel approach for the treatment of respiratory disease: cilomilast," Exp. Opinion Investig. Drugs, vol. 16, No. 1, pp. 109-124 (2007).
Lipworth, Brian J, "Phosphodiesterase-4 inhibitors for asthma and chronic obstructive pulmonary disease," Lancet, vol. 265, pp. 167-175 (2005).
Smith, Victoria Boswell et al., "Selective phosphodiesterase 4 inhibitors in the treatment of allergy and inflammation," Curr. Opinion Investig. Drugs, vol. 6, No. 11, pp. 1136-1142 (2006).
International Search Report for International Application No. PCT/EP2016/080548, dated Jun. 2, 2017. (2 pages).
Written Opinion of the International Searching Authority for International Application No. PCT/EP2016/080548. (5 pages).

*Primary Examiner* — Kamal A Saeed
(74) *Attorney, Agent, or Firm* — Finnegan, Henderson, Farabow, Garrett & Dunner, LLP

(57) ABSTRACT

The present invention relates to novel substituted pyrazoloazepin-4-ones with phosphodiesterase inhibitory activity, as well as to their use as therapeutic agents in the treatment of inflammatory diseases and conditions.

12 Claims, No Drawings

SUBSTITUTED PYRAZOLOAZEPIN-4-ONES AND THEIR USE AS PHOSPHODIESTERASE INHIBITORS

This application is a national stage filing under 35 U.S.C. § 371 of International Application No. PCT/EP2016/080548, filed on Dec. 12, 2016. The contents of this application is incorporated herein by reference.

FIELD OF THE INVENTION

The present invention relates to novel substituted pyrazoloazepin-4-ones with phosphodiesterase inhibitory activity, and to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes. As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, psoriasis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, Exp. Opinion *Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175).

Numerous PDE4 inhibitors have been studied for their therapeutic effect on inflammatory diseases, primarily asthma and COPD.

WO 2007/040435 (Astrazeneca AB) discloses 5,6-dihydropyrazolo[3,4-e][1,4]-diazepin-4(1H)-one derivatives for the treatment of asthma and chronic obstructive pulmonary disease. The compounds are stated to be selective inhibitors of PDE4 over other PDEs.

WO 2001/049689 (Warner-Lambert Company) discloses pyrazolo[3,4-e]diazepines. The compounds are stated to inhibit the PDE4 enzyme.

WO2008/060597 (Vertex Pharmaceuticals Inc) relates to compounds as protein kinase inhibitors.

WO2004/098520 (IRM LLC) relates to compounds as protein kinase inhibitors.

There is a continuous need for developing novel PDE4 inhibitors which have a more favourable therapeutic window, i.e. fewer adverse effects, while retaining their therapeutic effect.

SUMMARY OF THE INVENTION

It is an object of the present invention to provide novel compounds. In one aspect the present invention relates to PDE4 inhibitors that could have a stability profile in biological tissue that implies that a low systemic exposure of the compounds to be observed upon e.g. topical administration, indicating that the compounds of the present invention could have high clearance in human liver microsomes, that they could hydrolyse in human whole blood and could display stability towards enzymatic hydrolyses in human keratinocytes.

In one aspect the invention provides a compound of general formula (I)

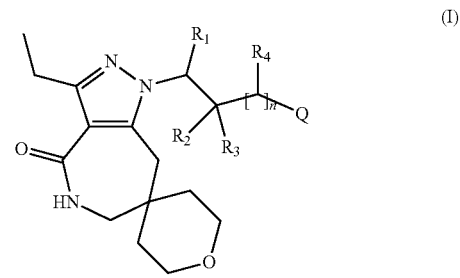

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$, or wherein said aryl is optionally benzodioxole; and wherein said $(C_1-C_6)$alkyl, $(C_3-C_6)$cycloalkyl are optionally substituted with one or more substituents independently selected from $R_7$;

$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$, —C(O)R$_x$, —C(O)NR$_a$R$_b$ and —OR$_x$;

$R_7$ consists of halogen, hydroxyl, cyano, $(C_1-C_4)$alkoxy, —C(O)NR$_a$R$_b$, —C(O)OR$_a$, —S(O)$_2$R$_x$, —S(O)$_2$NR$_a$R$_b$, —OR$_x$, and —SR$_x$;

$R_x$ consists of $(C_1-C_4)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)$R_x$; or pharmaceutically acceptable salts, hydrates or solvates thereof.

In another aspect, the invention provides pharmaceutical compositions comprising a compound of general formula (I) as defined above together with a pharmaceutically acceptable vehicle or excipient or pharmaceutically acceptable carrier(s), optionally together with one or more other therapeutically active compound(s).

In another aspect, the invention provides the use of a compound of the invention, for the manufacture of pharmaceutical compositions for the prophylaxis, treatment, prevention or amelioration of a disease, disorder or condition responsive to PDE4 inhibitory activity.

In yet another aspect the invention provides a method for treatment, prevention or alleviation of diseases, disorders or conditions responsive to PDE4 inhibitory activity, and which method comprises the step of administering to a living animal body a therapeutically effective amount of the compound of formula (I) of the invention.

Other objects of the invention will be apparent to the person skilled in the art from the following detailed description and examples.

DETAILED DESCRIPTION OF THE INVENTION

In one aspect the invention provides a compound of Formula (I)

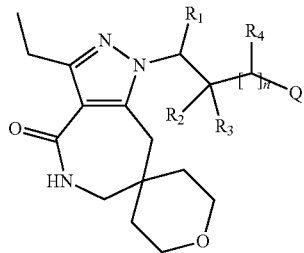

(I)

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$, or wherein said aryl is benzodioxole; and wherein said $(C_1-C_6)$alkyl, $(C_3-C_6)$cycloalkyl are optionally substituted with one or more substituents independently selected from $R_7$; $R_6$ consists of halogen, cyano, hydroxyl, $(C_1-C_4)$alkyl, halo$(C_1-C_4)$alkyl, $(C_1-C_4)$alkyloxy, —S(O)$_2$$R_x$, —S(O)$_2$NR$_a$R$_b$—C(O)R$_x$, C(O)NR$_a$R$_b$ and —OR$_x$;

$R_7$ consists of halogen, hydroxyl, cyano, $(C_1-C_4)$alkoxy, —C(O)NR$_a$R$_b$, —C(O)OR$_a$, —S(O)$_2$R$_x$, —S(O)$_2$NR$_a$R$_b$, —OR$_x$, and —SR$_x$;

$R_x$ consists of $(C_1-C_4)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)$R_x$; and pharmaceutically acceptable salts, hydrates or solvates thereof.

In another aspect the invention provides a compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$; and wherein said $(C_1-C_6)$alkyl, $(C_3-C_6)$cycloalkyl are optionally substituted with one or more substituents independently selected from $R_7$;

$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$—C(O)R$_x$, C(O)NR$_a$R$_b$ and —OR$_x$;

$R_7$ consists of halogen, hydroxyl, cyano, $(C_1-C_4)$alkoxy, —C(O)NR$_a$R$_b$, —C(O)OR$_a$, —S(O)$_2$R$_x$, —S(O)$_2$NR$_a$R$_b$, —OR$_x$, and —SR$_x$;

$R_x$ consists of $(C_1-C_4)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)$R_x$; or a pharmaceutically acceptable salt, hydrate or solvate thereof.

In another aspect the invention provides a compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl or oxetanyl ring;

n=0, 1 or 2;

Q is selected from the group consisting of —O—C(O)—$R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$, or wherein said aryl is optionally benzodioxole; and wherein said $(C_1-C_6)$alkyl, $(C_3-C_6)$cycloalkyl are optionally substituted with one or more substituents independently selected from $R_7$;

$R_6$ consists of halogen, cyano, hydroxyl, $(C_1-C_4)$alkyl, halo$(C_1-C_4)$alkyl, $(C_1-C_4)$alkyloxy, $—S(O)_2R_x$, $—S(O)_2NR_aR_b$ $—C(O)R_x$, $C(O)NR_aR_b$ and $—OR_x$;

$R_7$ consists of halogen, hydroxyl, cyano, $(C_1-C_4)$alkoxy, $—C(O)NR_aR_b$, $—C(O)OR_a$, $—S(O)_2R_x$, $—S(O)_2NR_aR_b$, $—OR_x$, and $—SR_x$;

$R_x$ consists of $(C_1-C_4)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or $—C(O)R_x$; or a pharmaceutically acceptable salts, hydrates or solvates thereof.

In another aspect the invention provides a compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl or oxetanyl ring;

n=0, 1 or 2;

Q is selected from the group consisting of $—O—C(O)—R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, phenyl; wherein said phenyl is optionally substituted with one or more substituents independently selected from $R_6$; and wherein said $(C_1-C_6)$alkyl, $(C_3-C_6)$cycloalkyl are optionally substituted with one or more substituents independently selected from $R_7$;

$R_6$ consists of halogen, cyano, hydroxyl, $(C_1-C_4)$alkyl, halo$(C_1-C_4)$alkyl, $(C_1-C_4)$alkyloxy, $—S(O)_2R_x$, $—S(O)_2NR_aR_b$ $—C(O)R_x$, $C(O)NR_aR_b$ and $—OR_x$;

$R_7$ consists of halogen, hydroxyl, cyano, $(C_1-C_4)$alkoxy, $—C(O)NR_aR_b$, $—C(O)OR_a$, $—S(O)_2R_x$, $—S(O)_2NR_aR_b$, $—OR_x$, and $—SR_x$;

$R_x$ consists of $(C_1-C_4)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or $—C(O)R_x$; or a pharmaceutically acceptable salt, hydrate or solvate thereof.

In another aspect the invention provides a compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of $—O—C(O)—R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, $—S(O)_2R_x$, $—S(O)_2NR_aR_b$ and $—OR_x$;

$R_x$ is $(C_1-C_4)$alkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl; and pharmaceutically acceptable salts, hydrates or solvates thereof.

In one embodiment of the present invention, $R_1$ and $R_4$ are both hydrogen.

In another embodiment of the present invention, one of $R_2$ and $R_3$ is hydrogen and the other one of $R_2$ and $R_3$ is $(C_1-C_4)$alkyl.

In another embodiment of the present invention, $R_2$ and $R_3$ are both hydrogen.

In another embodiment of the present invention, $R_2$ and $R_3$ are both $(C_1-C_4)$alkyl, e.g. both methyl.

In another embodiment of the present invention, $R_2$ and $R_3$ together with the carbon atom to which they are attached form a cyclopropyl, cyclobutyl, cyclopentyl, oxetanyl, tetrahydrofuranyl, or tetrahydropyranyl ring.

In another embodiment of the present invention, $R_2$ and $R_3$ together with the carbon atom to which they are attached form a cyclopropyl or oxetanyl ring.

In another embodiment of the present invention, n is 1.

In another embodiment of the present invention, $R_5$ is $(C_1-C_6)$alkyl.

In another embodiment of the present invention, $R_5$ is $(C_3-C_6)$cycloalkyl, e.g. cyclopentyl.

In another embodiment of the present invention, $R_5$ is aryl, optionally substituted with one or more substituents independently selected from $R_6$.

In another embodiment of the present invention, $R_5$ is phenyl, optionally substituted with one or more substituents independently selected from $R_6$.

In another embodiment of the present invention, $R_5$ is phenyl, substituted with one substituent selected from $R_6$.

In another embodiment of the present invention, $R_5$ is phenyl, substituted with two substituents independently selected from $R_6$.

In another embodiment of the present invention, $R_6$ consists of halogen, cyano, hydroxyl, $(C_1-C_4)$alkyl, halo$(C_1-C_4)$alkyl and $(C_1-C_4)$alkyloxy.

In another embodiment of the present invention, $R_6$ is $(C_1-C_4)$alkyl, e.g. methyl, ethyl.

In another embodiment of the present invention, $R_6$ is $—S(O)_2R_x$.

In another embodiment of the present invention, $R_x$ is methyl.

In another embodiment of the present invention, $R_6$ is $—C(O)R_a$.

In another embodiment of the present invention, $R_6$ is $C(O)NR_aR_b$.

In another embodiment of the present invention, $R_6$ is $—S(O)_2NR_aR_b$.

In another embodiment of the present invention $R_7$ consists of halogen, hydroxyl, $(C_1-C_4)$alkoxy, $—C(O)NR_aR_b$, $—C(O)OR_a$, $—S(O)_2R_x$, $—OR_x$, and $—SR_x$.

In another embodiment of the present invention, $R_a$ and $R_b$ are independently selected from the group consisting of hydrogen and $(C_1-C_4)$alkyl.

In another embodiment of the present invention, $R_a$ and $R_b$ are both $(C_1\text{-}C_4)$alkyl, e.g. both methyl.

In another embodiment of the present invention, when $R_5$ is substituted with one of $R_6$ consisting of $-S(9)_2R_x$ and $-S(O)_2NR_aR_b$, the substitutent is in the para position.

In another embodiment of the present invention, $R_1$ and $R_4$ are both hydrogen, one of $R_2$ and $R_3$ is hydrogen and the other one of $R_2$ and $R_3$ is $(C_1\text{-}C_4)$alkyl, n is 1, $R_5$ is phenyl, $R_6$ is $-S(O)_2R_x$ or $-S(O)_2NR_aR_b$, $R_x$ is $(C_1\text{-}C_4)$alkyl and $R_a$ and $R_b$ are independently selected from the group consisting of hydrogen and $(C_1\text{-}C_4)$alkyl.

In another embodiment of the present invention, all of $R_1$, $R_2$, $R_3$, $R_4$ are hydrogen, n is 1, $R_5$ is phenyl, and $R_6$ is $(C_1\text{-}C_4)$alkyl.

In another embodiment of the present invention, all of $R_1$, $R_2$, $R_3$, $R_4$ are hydrogen, n is 1, $R_5$ is selected from the group consisting of $(C_1\text{-}C_6)$alkyl, $(C_3\text{-}C_6)$cycloalkyl, $(C_1\text{-}C_6)$alkoxy, and aryl; wherein said aryl is optionally substituted with one or more substituents independently selected from halogen, cyano, hydroxyl, $(C_1\text{-}C_4)$alkyl, halo$(C_1\text{-}C_4)$alkyl, $(C_1\text{-}C_4)$alkyloxy, $-S(O)_2R_x$, $-S(O)_2NR_aR_b$, $-C(O)R_x$, $C(O)NR_aR_b$, or wherein said aryl is optionally benzodioxole; and wherein said $(C_1\text{-}C_6)$alkyl, $(C_3\text{-}C_6)$cycloalkyl are optionally substituted with with one or more substituents independently selected from halogen, hydroxyl, $(C_1\text{-}C_4)$alkoxy, $-C(O)NR_aR_b$, $-C(O)OR_a$, $-S(O)_2R_x$, $-OR_x$, and $-SR_x$; $R_x$ consists of $(C_1\text{-}C_4)$alkyl and $(C_3\text{-}C_6)$cycloalkyl; $R_a$ and $R_b$ are independently selected from the group consisting of hydrogen, $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$.

In another embodiment of the present invention, all of $R_1$, $R_2$, $R_3$, $R_4$ are hydrogen, n is 1, $R_5$ is phenyl which is optionally substituted with one or more substituents independently selected from halogen, cyano, $(C_1\text{-}C_4)$alkyl, halo$(C_1\text{-}C_4)$alkyl, and $(C_1\text{-}C_4)$alkyloxy.

In another embodiment of the present invention, all of $R_1$, $R_2$, $R_3$, $R_4$ are hydrogen, n is 1, $R_5$ is phenyl which is optionally substituted with one or more substituents independently selected from the group consisting of $-S(O)_2R_x$, $-S(O)_2NR_aR_b$, $-C(O)R_x$, $C(O)NR_aR_b$; $R_x$ consists of $(C_1\text{-}C_4)$alkyl and $(C_3\text{-}C_6)$cycloalkyl; $R_a$ and $R_b$ are independently selected from the group consisting of hydrogen and $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$.

In another embodiment of the present invention, all of $R_1$, $R_2$, $R_3$, $R_4$ are hydrogen, n is 1, $R_5$ is phenyl substituted with $C(O)NR_aR_b$, wherein $R_a$ and $R_b$ are independently selected from the group consisting of hydrogen and $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$; and $R_x$ is $(C_1\text{-}C_4)$alkyl.

In another embodiment of the present invention, $R_1$ and $R_4$ are both hydrogen, one of $R_2$ and $R_3$ is hydrogen and the other one of $R_2$ and $R_3$ is $(C_1\text{-}C_4)$alkyl, n is 1, $R_5$ is selected from the group consisting of $(C_1\text{-}C_6)$alkyl, $(C_3\text{-}C_6)$cycloalkyl and aryl; wherein said aryl is optionally substituted with one or more substituents independently selected from halogen, cyano, $(C_1\text{-}C_4)$alkyl, halo$(C_1\text{-}C_4)$alkyl, $(C_1\text{-}C_4)$alkyloxy, $-S(O)_2R_x$, $-S(O)_2NR_aR_b$ and $-C(O)R_x$; $R_x$ consists of $(C_1\text{-}C_4)$alkyl and $(C_3\text{-}C_6)$cycloalkyl; $R_a$ and $R_b$ are independently selected from the group consisting of hydrogen, $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$.

In another embodiment of the present invention, $R_1$ and $R_4$ are both hydrogen, one of $R_2$ and $R_3$ is hydrogen and the other one of $R_2$ and $R_3$ is $(C_1\text{-}C_4)$alkyl, n is 1, $R_5$ is phenyl which is optionally substituted with one or more substituents independently selected from halogen, cyano, $(C_1\text{-}C_4)$alkyl, halo$(C_1\text{-}C_4)$alkyl, $(C_1\text{-}C_4)$alkyloxy, $-S(O)_2R_x$, $-S(O)_2NR_aR_b$, and $-C(O)R_x$; $R_x$ consists of $(C_1\text{-}C_4)$alkyl and $(C_3\text{-}C_6)$cycloalkyl; $R_a$ and $R_b$ are independently selected from the group consisting of hydrogen, $(C_1\text{-}C_4)$-alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$.

In another embodiment of the present invention, $R_1$ and $R_4$ are both hydrogen, one of $R_2$ and $R_3$ is hydrogen and the other one of $R_2$ and $R_3$ is $(C_1\text{-}C_4)$alkyl, n is 1, $R_5$ is phenyl substituted with $C(O)NR_aR_b$, wherein $R_a$ and $R_b$ are independently selected from the group consisting of hydrogen and $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$; and $R_x$ is $(C_1\text{-}C_4)$alkyl.

In another embodiment of the present invention, $R_1$ and $R_4$ are both hydrogen, one of $R_2$ and $R_3$ is hydrogen and the other one of $R_2$ and $R_3$ is $(C_1\text{-}C_4)$alkyl, n is 1, $R_5$ is phenyl optionally substituted with halogen, $(C_1\text{-}C_4)$alkyl and $(C_1\text{-}C_4)$alkyloxy.

In another embodiment of the present invention, $R_1$ and $R_4$ are both hydrogen, $R_2$ and $R_3$ are both $(C_1\text{-}C_4)$alkyl, n is 1, $R_5$ is selected from the group consisting of $(C_1\text{-}C_6)$alkyl, $(C_3\text{-}C_6)$cycloalkyl and aryl; wherein said aryl is optionally substituted with one or more substituents independently selected from halogen, cyano, $(C_1\text{-}C_4)$alkyl, halo$(C_1\text{-}C_4)$alkyl, $(C_1\text{-}C_4)$alkyloxy, $-S(O)_2R_x$, $-S(O)_2NR_aR_b$, $-C(O)R_x$, $C(O)NR_aR_b$ and $-OR_x$; $R_x$ consists of $(C_1\text{-}C_4)$alkyl and $(C_3\text{-}C_6)$cycloalkyl; $R_a$ and $R_b$ are independently selected from the group consisting of hydrogen, $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more of $-C(O)R_x$.

In another embodiment of the present invention, $R_1$ and $R_4$ are both hydrogen, $R_2$ and $R_3$ are both $(C_1\text{-}C_4)$alkyl, n is 1, $R_5$ is phenyl which is optionally substituted with one or more substituents independently selected from halogen, cyano, $(C_1\text{-}C_4)$alkyl, halo$(C_1\text{-}C_4)$alkyl, $(C_1\text{-}C_4)$alkyloxy, $-S(O)_2R_x$, $-S(O)_2NR_aR_b$, $-C(O)R_x$, $C(O)NR_aR_b$ and $-OR_x$; $R_x$ consists of $(C_1\text{-}C_4)$alkyl and $(C_3\text{-}C_6)$cycloalkyl; $R_a$ and $R_b$ are independently selected from the group consisting of hydrogen, $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more of $-C(O)R_x$.

In another embodiment of the present invention, $R_1$ and $R_4$ are both hydrogen, $R_2$ and $R_3$ are both $(C_1\text{-}C_4)$alkyl, n is 1, $R_5$ is phenyl substituted with $C(O)NR_aR_b$, wherein $R_a$ and $R_b$ are independently selected from the group consisting of hydrogen and $(C_1\text{-}C_4)$alkyl, or $R_a$ and $R_b$ together with the nitrogen to which they are attached form a 4-6 membered heterocycloalkyl, wherein said heterocycloalkyl is optionally substituted with one or more $(C_1\text{-}C_4)$alkyl or $-C(O)R_x$; and $R_x$ is $(C_1\text{-}C_4)$alkyl.

In another embodiment of the present invention, $R_1$ and $R_4$ are both hydrogen, $R_2$ and $R_3$ together with the carbon atom to which they are attached form a cyclopropyl ring, n is 1, $R_5$ is phenyl substituted with one or more substituents independently selected from halogen, $(C_1-C_4)$alkyl, and $(C_1-C_4)$alkyloxy.

In another embodiment of the present invention, $R_1$ and $R_4$ are both hydrogen, $R_2$ and $R_3$ together with the carbon atom to which they are attached form a oxetanyl ring, n is 1, $R_5$ is phenyl substituted with one or more substituents independently selected from halogen, $(C_1-C_4)$alkyl, and $(C_1-C_4)$alkyloxy.

In another embodiment of the present invention, $R_1$ is $(C_1-C_4)$alkyl, all of $R_2$, $R_3$, $R_4$ are hydrogen, n is 1, $R_5$ is phenyl optionally substituted with one or more substituents independently selected from halogen, $(C_1-C_4)$alkyl, and $(C_1-C_4)$alkyloxy.

In another embodiment of the present invention, all of $R_1$, $R_2$, $R_3$, $R_4$ are hydrogen, n is 2, $R_5$ is $R_5$ is phenyl which is optionally substituted with one or more substituents independently selected from halogen, $(C_1-C_4)$alkyl, $-S(O)_2R_x$, $-S(O)_2NR_aR_b$, and $-C(O)R_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$alkyl, or $R_a$ and $R_b$ together with the nitrogen to which they are attached form a 4-6 membered heterocycloalkyl.

In another embodiment of the present invention, all of $R_1$, $R_2$, $R_3$, $R_4$ are hydrogen, n is 2, $R_5$ is phenyl substituted with $C(O)NR_aR_b$, wherein $R_a$ and $R_b$ are independently selected from the group consisting of hydrogen and $(C_1-C_4)$alkyl, or $R_a$ and $R_b$ together with the nitrogen to which they are attached form a 4-6 membered heterocycloalkyl.

In another embodiment of the present invention, all of $R_1$, $R_2$, $R_3$ are hydrogen, n is 0, $R_5$ is phenyl which is optionally substituted with one or more substituents independently selected from halogen, $(C_1-C_4)$alkyl, and $(C_1-C_4)$alkyloxy.

Specific examples of compounds of formula (I) may be selected from the group consisting of:

3-(3-Ethyl-4-oxo-spiro[6,8-dihydro-5H-pyrazolo[4,3-c]azepine-7,4'-tetrahydropyran]-1-yl)propyl 4-methylbenzoate (compound 101);

3-(3-Ethyl-4-oxo-spiro[6,8-dihydro-5H-pyrazolo[4,3-c]azepine-7,4'-tetrahydropyran]-1-yl)propyl 4-ethylbenzoate (compound 102);

[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(methylsulfamoyl)benzoate (compound 103);

[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(dimethylsulfamoyl)benzoate (compound 104);

[(2R)-3-(3-ethyl-4-oxo-spiro[6,8-dihydro-5H-pyrazolo[4,3-c]azepine-7,4'-tetrahydro-pyran]-1-yl)-2-methyl-propyl] 4-methylsulfonylbenzoate (compound 105); and pharmaceutically acceptable salts, hydrates or solvates thereof.

Definitions

As used throughout the present specification and appended claims, the following terms have the indicated meaning:

The term "alkyl" is intended to indicate a radical obtained when one hydrogen atom is removed from a branched or linear hydrocarbon. Said alkyl comprises 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term alkoxyalkyl is intended to indicate an alkyl group as defined above substituted with one or more alkoxy groups as defined above, e.g. methoxymethyl, ethoxymethyl, 2-methoxyethyl, 2-ethoxyethyl, 3-methoxyprop-1-yl, and the like The term "haloalkyl" is intended to indicate an alkyl group as defined herein substituted with one or more halogen atoms as defined herein, e.g. fluoro or chloro, such as fluoromethyl, difluoromethyl or trifluoromethyl.

The terms "haloalkyloxy" and "haloalkoxy" are intended to indicate a haloalkyl group as defined herein which is appended to the parent molecular moiety through an oxygen atom, such as difluoromethoxy or trifluoromethoxy.

The term "halogen" is intended to indicate a substituent from the 7th main group of the periodic table, such as fluoro, chloro and bromo.

The term "alkylthio" is intended to indicate a radical of the formula —S—R', wherein R' is alkyl as indicated herein, wherein the alkyl group is appended to the parent molecular moiety through a sulphur atom, e.g. —S—CH$_3$ (methylthio) or —S—CH$_2$CH$_3$ (ethylthio).

The term "cyano" is intended to indicate a —CN group attached to the parent molecular moiety through the carbon atom.

The term "cycloalkyl" is intended to indicate a saturated cycloalkane hydrocarbon radical, comprising 3-7 carbon atoms, 3-6 carbon atoms, 3-5 carbon atoms, 3-4 carbon atoms, e.g. cyclopropyl, cyclobutyl, cyclopentyl and cyclohexyl.

The term "aryl" is intended to indicate a radical of aromatic carbocyclic rings comprising 6-13 carbon atoms, 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydronaphtyl and fluorenyl.

The term "heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "heterocycloalkyl" is intended to indicate a cycloalkane radical as described herein, wherein one or more carbon atoms are replaced by heteroatoms, comprising 1-6 carbon atoms, e.g. 2-5 or 2-4 carbon atoms, further comprising 1-3 heteroatoms, preferably 1 to 2 heteroatoms, selected from O, N, or S, S(═O) or S(═O)$_2$. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl, tetrahydrofuranyl, tetrahydropyranyl, tetrahydrothiophenyl, tetrahydrothiopyranyl.

The term "(4-6) membered heterocycloalkyl" is intended to indicate a heterocyloalkyl as defined herein, comprising 4-6 ring-atoms, and comprising 1-5 carbon atoms, e.g. 2-5 or 2-4 carbon atoms, further comprising 1-3 heteroatoms, preferably 1 to 2 heteroatoms, selected from O, N, S, S(=O) or S(=O)$_2$. Representative examples of (4-6) membered heterocycloalkyl groups include azetidinyl, dioxanyl, dioxolanyl, imidazolidinyl, morpholinyl, thiomorpholinyl, thiomorpholinyl-1-oxide, thiomorpholinyl-1,1-dioxide, oxetanyl, piperazinyl, piperidinyl, pyrrolidinyl, tetrahydrofuranyl, tetrahydropyranyl, tetrahydrothiopyranyl, tetrahydrothiophenyl, thietanyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

In some instances, the number of carbon atoms in a hydrocarbon radical (e.g. alkyl, cycloalkyl and aryl) is indicated by the prefix "$(C_a-C_b)$", wherein a is the minimum number and b is the maximum number of carbons in the hydrocarbon radical. Thus, for example $(C_1-C_4)$alkyl is intended to indicate an alkyl radical comprising from 1 to 4 carbon atoms, and $(C_3-C_6)$cycloalkyl is intended to indicate a cycloalkyl radical comprising from 3 to 5 carbon ring atoms.

The term "hydroxyalkyl" is intended to indicate an alkyl group as defined above substituted with one or more hydroxy, e.g. hydroxymethyl, hydroxyethyl, hydroxypropyl.

The term "hydroxyl" is intended to indicate an —OH group.

The term "oxo" is intended to indicate an oxygen atom which is connected to the parent molecular moiety via a double bond (=O).

The term "thioxo" is intended to indicate a sulfur atom which is connected to the parent molecular moiety via a double bond (=S).

The group C(O) is intended to represent a carbonyl group (C=O).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc. The compounds of the invention may be obtained in crystalline form either directly by concentration from an organic solvent or by crystallisation or re-crystallisation from an organic solvent or mixture of said solvent and a co-solvent that may be organic or inorganic, such as water. The crystals may be isolated in essentially solvent-free form or as a solvate, such as a hydrate. The invention covers all crystalline modifications and forms and also mixtures thereof.

Compounds of formula (I) may or may not comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as-selective crystallization and chromatographic techniques, e.g. high pressure liquid chromatography using chiral stationary phases. Enantiomers may be separated from each other by selective crystallization of their diastereomeric salts which may be formed with optically active amines, such as l-ephedrine, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. If a specific stereoisomer is desired, said compound will be synthesized by stereoselective or stereospecific methods of preparation. These methods will advantageously employ chiral pure starting materials. Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

Deuterated analogues. Any formula given herein is also intended to represent unlabled forms as well as isotopically labled forms of the compounds. For example, any hydrogen represented by "H" in any of the formulae herein is intended to represent all isotypic forms of hydrogen, e.g. $^1$H, $^2$H or D, $^3$H. Enrichment with heavier isotopes, particularly deuterium (i.e. $^2$H or D) may afford certain therapeutic advantages due to for example an increased metabolic skin stability or an increased, systemic, in vivo clearance. Changes that would result in reduced dosage requirements or an improvement in therapeutic index. It is understood that deuterium in this context is regarded as a substituent of a compound of the formula (I).

Isotopically-enriched compounds of formula (I) can generally be prepared by conventional techniques known to those skilled in the art or by processes analogous to those described in the accompanying Preparations and Examples using any appropriate isotopically enriched reagent in place of the non-enriched reagent previously employed.

Medical Use

As the compounds of the invention could exhibit PDE4 inhibitory activity, the compounds could be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

In one embodiment, the compounds of the present invention are considered useful for the treatment, prevention or alleviation of dermal diseases or conditions.

In another embodiment, the compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

In another embodiment, the compounds of the present invention are considered useful for the treatment or alleviation of atopic dermatitis.

In another embodiment, the compounds of the present invention are considered useful for the treatment or alleviation of psoriasis.

In another embodiment, the compounds of the present invention are considered useful for the treatment or alleviation of alopecia areata.

In another embodiment, the compounds of the present invention are considered useful for the treatment or alleviation of acne.

In another embodiment, the compounds of the present invention are considered useful for the treatment or alleviation of pruritis.

In another embodiment, the compounds of the present invention are considered useful for the treatment or alleviation of eczema.

Compounds of the invention, optionally in combination with other active compounds, may be useful for the treatment of dermal diseases or conditions, in particular for the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema. Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula (I), optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

In the form of a dosage unit, the compound may be administered one or more times a day at appropriate intervals, always depending, however, on the condition of the patient, and in accordance with the prescription made by the medical practitioner. Conveniently, a dosage unit of a topical formulation contain between 0.001 mg and 1000 mg, preferably between 0.01 mg and 100 mg, such as 0.1-50 mg of a compound of formula (I). Also, conveniently, a dosage unit of a topical formulation contain between 0.01 mg and 10 g mg, preferably between 0.1 mg and 1000 mg, such as 1-500 mg of a compound of formula (I).

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.0001 to 10 mg/kg body weight, e.g. in the range from 0.001 to 5 mg/kg body weight. Also, in general a single dose will be in the range from 0.001 to 100 mg/kg body weight, e.g. in the range from 0.01 to 10 mg/kg body weight. The compound may be administered as a bolus (i.e. the entire daily dosis is administered at once) or in divided doses two or more times a day.

In the context of topical treatment it may be more appropriate to refer to a "usage unit", which denotes unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimetre of the skin of from 0.1 mg to 50 mg and preferably from 0.2 mg to 5 mg of the final formulation in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics,* 9th Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramus-cular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifying agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula (I) may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semi-solid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops. Compositions for ophthalmic treatment may additionally contain cyclodextrin.

For topical administration, the compound of formula (I) may typically be present in an amount of from 0.001 to 20% by weight of the composition, such as 0.01% to about 10%, but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, 3th ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula (I) may include one or more additional ingredients such as diluents, buffers, flavouring agents, colourant, surface active agents, thickeners, penetration enhancing agents, solubility enhancing agents preservatives, e.g. methyl hydroxybenzoate (including antioxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, JAK inhibitors, other PDEs, salicylates, indomethacin, flufenamate, naproxen, timegadine, gold salts, penicillamine, serum cholesterol lowering agents, retinoids, zinc salts, salicylazosulfa-pyridine and calcineurin inhibitors.

Methods of Preparation

The compounds of the present invention can be prepared in a number of ways well known to those skilled in the art of synthesis. The compounds of formula (I) may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate may be purified if required using standard methods well known to a synthetic organist chemist, e.g. methods described in "Purification of Laboratory Chemicals", 6$^{th}$ ed. 2009, W. Amarego and C. Chai, Butterworth-Heinemann.

Starting materials are either known or commercially available compounds or can be prepared by routine synthetic methods well known to a person skilled in the art.

$^1$H nuclear magnetic resonance (NMR) spectra were recorded at 300 or 600 MHz unless otherwise specified. Chemical shift values (δ, in ppm) are quoted relative to internal tetramethylsilane (δ=0.00) standards. The value of a multiplet, either defined doublet (d), triplet (t), quartet (q) or (m) at the approximate midpoint is given unless a range is quoted. (br) indicates a broad peak, whilst (s) indicates a singlet. The organic solvents used were usually anhydrous. Chromatography was performed on Merck silica gel 60 (0.040-0-063 mm). The solvent ratios indicated refer to v:v unless otherwise noted. All NMR spectra are recorded in DMSO-d$_6$ unless another solvent is stated.

Analytical UPLC/MS

Analytical UPLC/MS is performed on a Waters Acquity UPLC-system and SQD-MS. Column: Waters Acquity HSS T3 1.8 μm, 2.1×50 mm; solventsystem: A=10 mM Ammonium acetate in water+0.1% HCOOH and B=acetonitrile+0.1% HCOOH; flow rate=1.2 mL/min; method (1.4 min): Linear gradient method from 5% B to 95% B over 0.9 minutes then 95% B for 0.3 minutes. Column temperature is 60° C.

Preparative Purification HPLC/MS:

Preparative HPLC/MS was performed on a Waters AutoPurification system with a Waters SQD2 mass spectrometer. This includes three steps, pre-analysis, preparative purification and re-analysis on the purified compound.

Solvent: A=0.1% formic acid and solvent B=acetonitrile with 0.1% formic acid.

Analytical Pre-Analysis Using the Following Method:
Column: Waters SUNFIRE C-18, 100 mm×4.6 mm, 5 μm
Flow rate=1.2 mL/min. (method 10 min)

Method: Linear gradient method going from 10% B to 95% B in 6.5 minutes and staying at 95% B for another 1.5 minutes to obtain the retention time of the compounds provides the following four different preparative gradient methods:

Preparative Methods:
Column: Waters SUNFIRE C-18, 100 mm×19 mm, 5 μm
Flow rate=20 ml/min. (method 8 min)

0-3 min: 5% B for 2 minutes followed by a linear gradient method going from 5% B to 35% B in 3 minutes and going to 100% B and staying at 100% B for another 1.4 minutes.

3.01-5 min: 15% B for 1 minutes followed by a linear gradient method going from 15% B to 55% B in 4 minutes and going to 100% B and staying at 100% B for another 1.4 minutes.

5.01-7.5 min: 30% B for 1 minutes followed by a linear gradient method going from 30% B to 70% B in 4 minutes and going to 100% B and staying at 100% B for another 1.4 minutes.

7.51-10 min: 50% B for 1 minutes followed by a linear gradient method going from 50% B to 100% B in 4 minutes and staying at 100% B for another 1.5 minutes.

The fractions were collected based on ion traces of relevant ions and PDA signal (240-400 nm).

Re-Analysis Method for Fractions:
Column: Waters Xselect C18; 50×3.0 mm 5 μm
Flow rate=1.2 mL/min. (method 5 min)
Method: Linear gradient method going from 10% B to 95% B in 3 minutes and staying at 95% B for another 0.5 min.

Instruments:
Waters 2767 Sample Manager
Waters 2545 Binary Gradient Module
Waters SFO System Fluidics Organizer
Waters 515 HPLC Pump
Waters 2998 Photodiode Array Detector
Waters SQDetector 2
LCMS Method "XE Metode 7 CM"

A quality check was performed on a Waters LCT Premier MS instrument and a Waters Aquity UPLC.

Column: Waters Aquity UPLC HSS T3 1.8 μm, 2.1×50 mm, at 40° C.

Solvents: A=10 mM ammonium acetate+0.1% HCOOH, B=MeCN+0.1% HCOOH.

Flow: 0.7 ml/min. Injection volume 2 μl. UV detection range 240-400 nm.

| Gradient: | Time | % A | % B |
| --- | --- | --- | --- |
| | 0.00 min | 99 | 1 |
| | 0.50 min | 94 | 6 |
| | 1.00 min | 94 | 6 |
| | 2.60 min | 5 | 95 |
| | 3.80 min | 5 | 95 |
| | 3.81 min | 99 | 1 |
| | 4.80 min | 99 | 1 |

The MW confirmation and purity was extracted and checked with OpenLynx.

The following abbreviations have been used throughout:
ACN acetonitrile
DCE 1,2-dichloroethane
DCM dichloromethane
DMAP N,N-dimethylpyridin-4-amine
DMF N,N-dimethylformamide
DMSO dimethylsulfoxide
EDAC (3-dimethylamino-propyl)-ethyl-carbodiimide EtOH ethanol
MeOH methanol
EtOAc ethyl acetate
L litre
LAH lithium aluminium hydride
Me methyl
NMR nuclear magnetic resonance
PG protecting group
PPTS p-toluenesulfonate
RT room temperature
THF tetrahydrofuran
TEA triethylamine General Methods Compounds of general formula (I) of the invention may for example be prepared according to the following non-limiting general methods and examples. $R_1$, $R_2$, $R_3$, $R_4$, Q and n are as previously defined for the compounds of general formula (I):

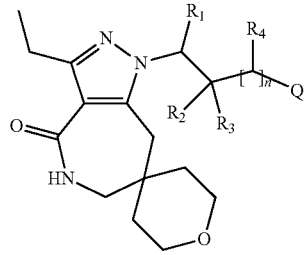
(I)

a) Synthesis of Compound 004 is Outlined in Scheme 1

Compound 004 is prepared as described in WO 2008/110308 in three steps.

Scheme 1

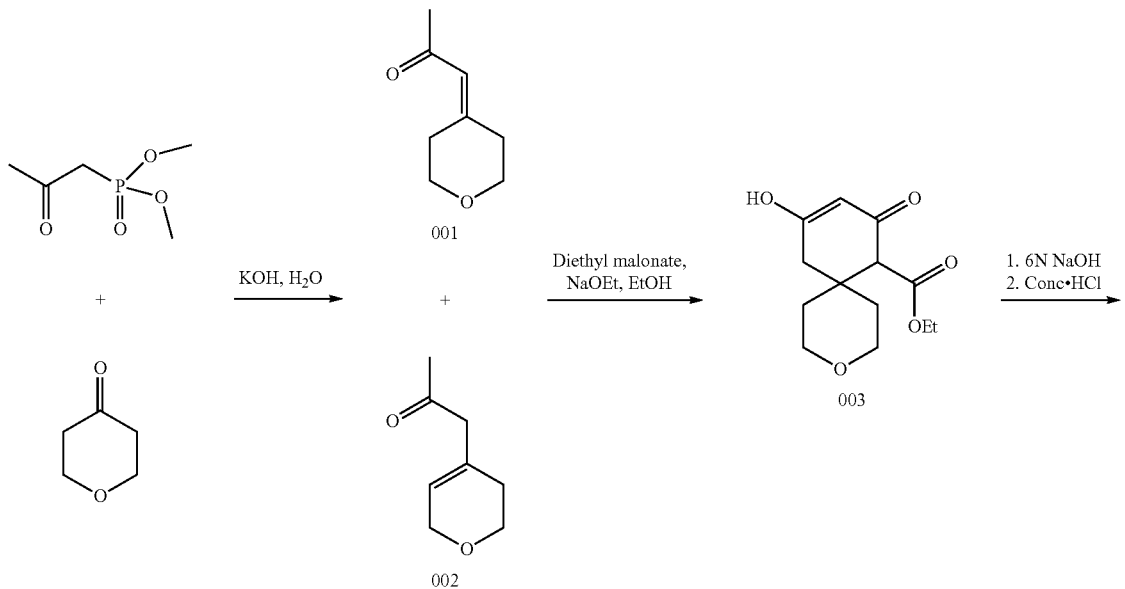

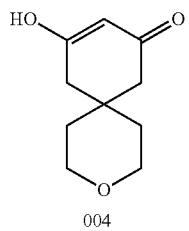
004 b) Synthesis of Compound 006 is Outlined in Scheme 2

Compound 006 is prepared according to standard procedures known to a chemist skilled in the art of organic synthesis. Reaction of compound 004 with propionyl chloride or propionic anhydride in the presence of a base such as pyridine, triethylamine, or diisopropylethylamine in a solvent such as DCM, THF gives compound 005. Treatment of acetone cyanohydrin, Et$_3$N delivers Compound 006.

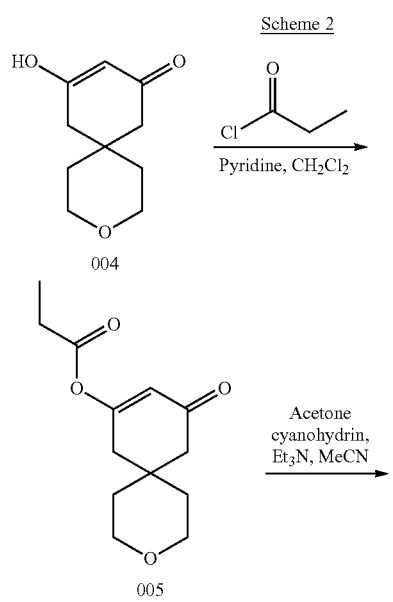

c) Synthesis of a Compound of General Formula (V) is Outlined in Scheme 3

A compound of general formula (II) may be prepared by treatment of compound 006 with a compound of general formula (III) in the presence of a suitable acid such as acetic acid and 4-toluenesulphonic acid or in the absence of an acid in a suitable solvent such as methanol, ethanol, propanol, isopropanol, butanol, and THF at suitable temperature between rt and 150° C. (preferably 50° C. to 120° C.).

A compound of general formula (II) may also be prepared by treatment of compound 006 with a compound of formula (III) in the presence of a suitable base such as triethylamine, K$_2$CO$_3$, Bu$_4$NOH, KOH in a suitable solvent such as methanol, ethanol, propanol, isopropanol, butanol, and THF at suitable temperature between rt and 150° C. (preferably 50° C. to 120° C.), especially when a compound of general formula (II) is in a salt form such as hydrochloride and oxalate.

A compound of general formula (III) may be commercially available or prepared according to standard procedures known to a chemist skilled in the art of organic synthesis (for examples, see: Geyer, Gabriel, J. Am. Chem. Soc. (1954), 76, 1283-1285; Ghali, N. I. 3. Org. Chem. (1981), 46 (26), 5413-14; Kim, Yongju, ACS Medicinal Chemistry Letters (2012), 3 (2), 151-154). The protecting group may be acyl such as acetyl and benzoyl or tetrahydrapyranyl, but not limited to these.

A compound of general formula (IV) may be prepared by procedures similar to those described, for example, by Bardakos, Vasilios et al. Chem Ber. (1976), 109, 1898-1910; Wang, Xiao-Feng et al. J. Med. Chem. (2014), 57 (4), 1390-1402. Typically, a compound of general formula (IV) may be prepared by treatment of formula (II) with hydrazoic acid, sodium azide or trimethylsilyl azide in the presence of a suitable Brønsted-Lowry acid such as hydrochloride, sulfuric acid, methanesulfonic acid, trifluoroacetic acid, phosphoric acid, trifluoromethanesulfonic acid, and trifluoroborane etherate or a mixture of two or more of these or in the presence of a suitable Lewis acid such as trifluoroborane etherate in a suitable solvent such as water, dichloromethane, chloroform, acetic acid, methanesulfonic acid, toluene, and benzene or a mixture of two or more of these at a suitable temperature between 0° C. to 100° C.

A compound of formula (V) represents a protected alcohol. A compound of general formula (IV) may be prepared by removal of a protecting group according to standard procedures known to a chemist skilled in the art of organic synthesis (for a review on protecting group, see: Kocienski, Philip J. Protecting groups, Georg Thieme Verlag, Stuttgart, New York, 2004).

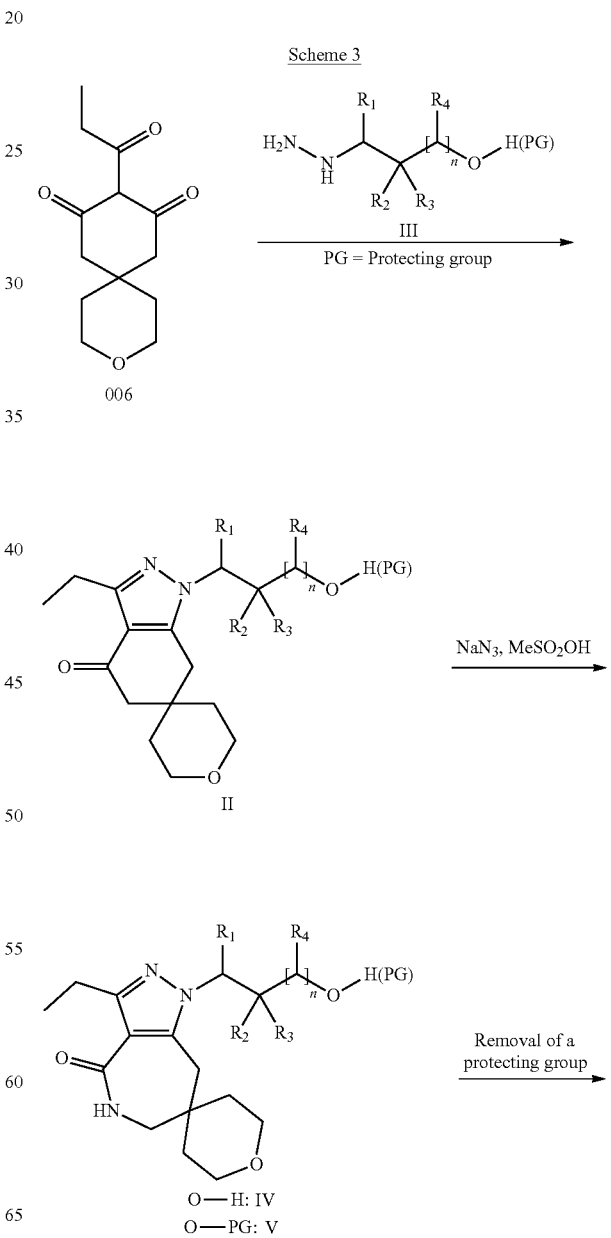

-continued

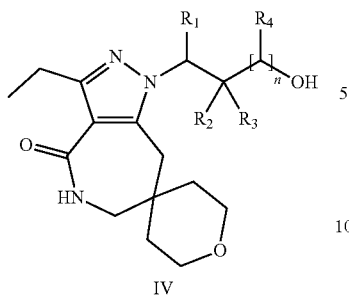

d) Synthesis of a Compound of General Formula I where Q Represents —O—C(O)—R$_5$ (R$_5$ is as Previous Defined) is Outlined in Scheme 4

A compound of general formula (I) where Q represents —O—C(O)—R$_5$ may be prepared from a compound of formula (IV) according to standard procedures known to a chemist skilled in the art of organic synthesis (for ester formation, see: Junzo Otera, Esterification: Methods, Reactions, and Applications, Wiley-VCH, Weinheim (2004)).

For example, a compound of general formula (I) may be prepared by reaction of a compound of general formula (IV) with HO—(CO)—R$_5$ in the presence of a suitable couplings reagent such as DCC, EDAC and a suitable catalyst such as DMAP in a suitable solvent such dichloromethane, dichloroethane, acetonitrile and ethyl acetate.

Scheme 4

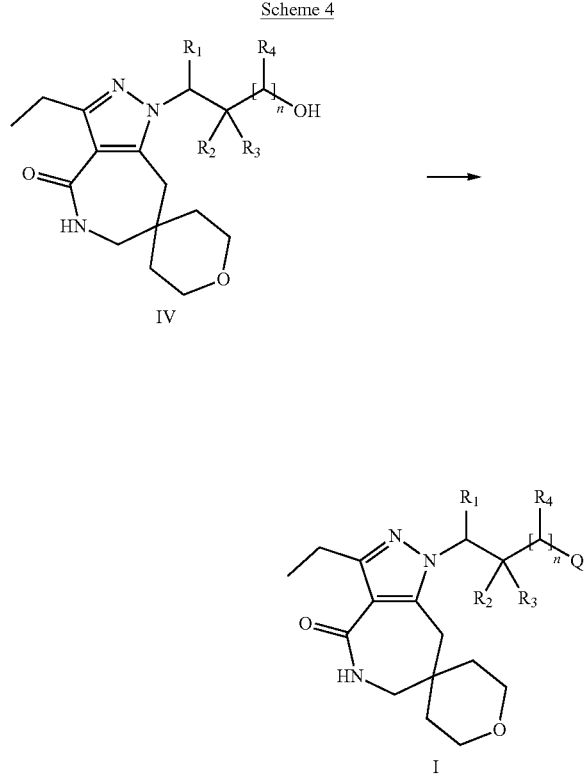

PREPARATIONS AND EXAMPLES

Preparation 1 (Compounds 001 and 002)

1-Tetrahydropyran-4-ylidenepropan-2-one and 1-(3, 6-dihydro-2H-pyran-4-yl)propan-2-one

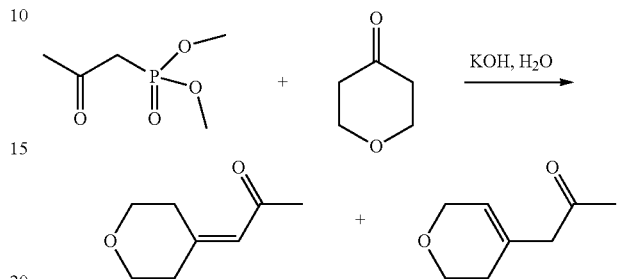

To a solution of KOH (40 g, 722.9 mmol) in H$_2$O (200 mL) and EtOH (800 mL) at 0° C., 1-dimethoxyphosphoryl-propan-2-one (100 g, 602.04 mmol) in EtOH (100 mL) and tetrahydropyran-4-one (60 g, 602.04 mmol) in EtOH (100 mL) were added and stirred at 26° C. for 4 h. On completion of the reaction, excess solvent was evaporated under vacuum and the resulting residue was treated with water (200 mL) and extracted with diethyl ether (2×200 mL). The combined organic layers were washed with brine (200 mL), dried over Na$_2$SO$_4$, and concentrated in vacuum to afford the title compounds as pale yellow liquid (crude). The crude was used for the next step without any further purification.

Preparation 2 (Compound 003)

Ethyl 8-hydroxy-10-oxo-3-oxaspiro[5.5]undec-8-ene-11-carboxylate

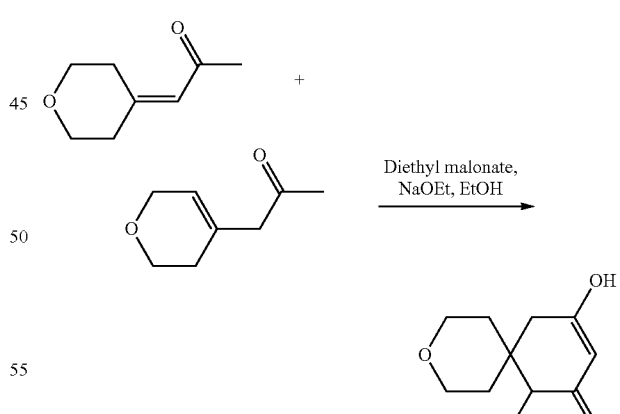

To a solution of EtONa (97.14 g, 1428 mmol) in ethanol (800 mL), diethyl malonate (114 g, 714.28 mmol) and 1-tetrahydropyran-4-ylidenepropan-2-one and 1-(3,6-dihydro-2H-pyran-4-yl)propan-2-one (100 g, 713.3 mmol) in EtOH (200 mL) were added slowly and stirred at reflux temperature for 16 h. On completion excess solvent was evaporated under vacuum to afford the title compound as Preparation 3 (Compound 004)

8-Hydroxy-3-oxaspiro[5.5]undec-8-en-10-one

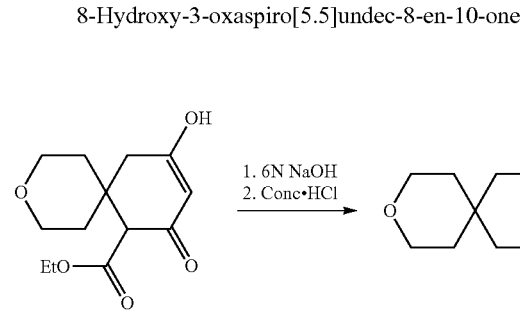

To ethyl 8-hydroxy-10-oxo-3-oxaspiro[5.5]undec-8-ene-11-carboxylate (100 g, 393.3 mmol), 6N NaOH (1 L) was added and stirred for 16 h at 26° C. Then conc.HCl (500 mL) was added slowly at 0° C. to adjust the pH to −2 and refluxed for 4 h. On completion of the reaction, reaction mixture was treated with water and extracted with EtOAc (2×500 mL). The combined organic layers were washed with brine (500 mL), dried over $Na_2SO_4$, concentrated in vacuo, and purified by washed with diethyl ether to afford the title compound as a brown solid.

$^1$H NMR (300 MHz, DMSO-$d_6$) δ 11.02 (s, 1H), 5.19 (s, 1H), 3.71-3.45 (m, 4H), 2.29 (s, 4H), 1.45 (t, J=5.4 Hz, 4H).

Preparation 4 (Compound 005)

(10-Oxo-3-oxaspiro[5.5]undec-8-en-8-yl) propanoate

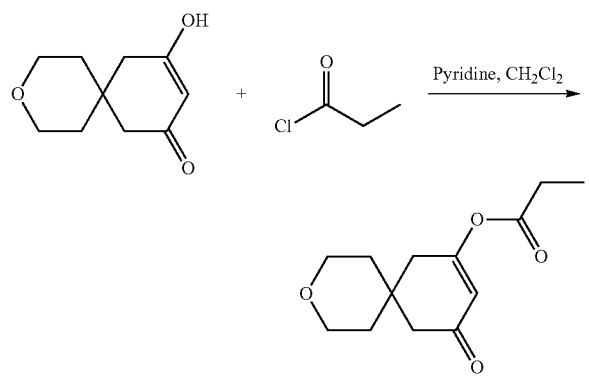

To a solution of 8-hydroxy-3-oxaspiro[5.5]undec-8-en-10-one (90 g, 494.5 mmol) in DCM (1.5 L), Pyridine (58.6 g, 741.7 mmol) and propionyl chloride (45.5 g, 494.5 mmol) were added slowly at 0° C. and it was stirred for 4 h at 26° C. On completion the reaction mixture was treated with 1N.HCl and the organic layer was washed with brine (700 mL), dried over $Na_2SO_4$, and concentrated to afford the title compound as a brown liquid.

$^1$H NMR (300 MHz, CDCl$_3$) δ 5.91 (d, J=1.2 Hz, 1H), 3.68 (t, J=5.4 Hz, 4H), 2.56 (d, J=1.3 Hz, 2H), 2.51 (q, J=7.5, 2H), 2.44 (s, 2H), 1.73-1.49 (m, 4H), 1.22 (t, J=7.5, 3H).

Preparation 5 (Compound 006)

9-Propanoyl-3-oxaspiro[5.5]undecane-8,10-dione

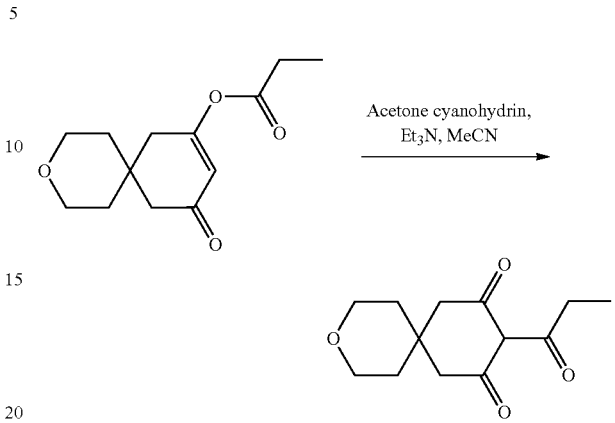

To a solution of (10-oxo-3-oxaspiro[5.5]undec-8-en-8-yl) propanoate (90 g, 378.15 mmol) in ACN (1500 mL), TEA (38.2 g, 378.15 mmol) and acetone cyanohydrin (48 g, 567.22 mmol) were added at 0° C. and stirred for 3 h at 26° C. On completion excess solvent was evaporated under vacuum and the resulting residue was purified by silica gel column chromatography (1% MeOH in DCM as eluent) to afford the title compound as a pale yellow liquid.

$^1$H NMR (300 MHz, CDCl$_3$) δ 3.77-3.58 (m, 4H), 3.06 (q, J=7.2 Hz, 2H), 2.67 (s, 2H), 2.51 (s, 2H), 1.62-1.47 (m, 4H), 1.13 (t, J=7.3 Hz, 3H).

Preparation 6 (Compound 007)

3-Hydrazinopropan-1-ol

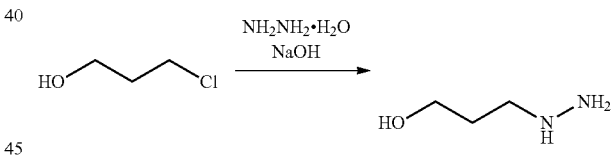

A solution of NaOH (42.5 g, 1063 mmol) and $N_2H_4 \cdot H_2O$ (269.5 g, 5319 mmol) was heated up to 100° C., 3-chloropropan-1-ol (100 g, 1063 mmol) was added at same temperature and stirred for 5 h. On completion excess solvent was evaporated under vacuum, the resulting residue was treated with EtOH and the resulting solid was filtered. Filtrate was concentrated and the excess $N_2H_4 \cdot H_2O$ was removed under downward distillation, to afford the title compound as a colorless liquid (crude), which was used for the next step without any further purification.

Preparation 7 (Compound 008)

3-Ethyl-1-(3-hydroxypropyl)spiro[5,7-dihydroindazole-6,4'-tetrahydropyran]-4-one

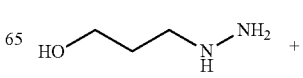

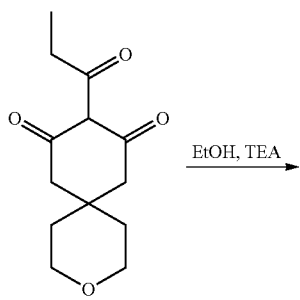

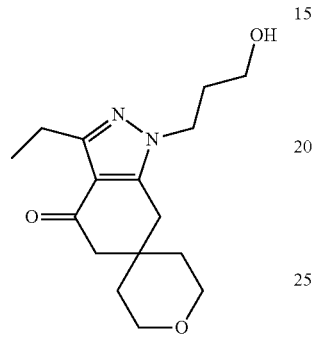

To a solution of 9-propanoyl-3-oxaspiro[5.5]undecane-8,10-dione (160 g, 671.7 mmol) in ethanol (1.6 Lit), TEA (135.7 g, 1344.5 mmol) and 3-hydrazinopropan-1-ol (72.6 g, 806 mmol) were added slowly and stirred at 80° C. for 16 h. On completion excess solvent was evaporated under vacuum and the resulting residue was purified by silica gel (100-200 mesh) column chromatography (5% MeOH in DCM as eluent) to afford the title compound as a yellow liquid.

$^{1}$H NMR (300 MHz, CDCl$_3$) δ 4.24-4.13 (m, 2H), 3.71 (t, J=5.4 Hz, 4H), 3.61 (td, J=5.8, 2.2 Hz, 2H), 2.95-2.76 (m, 4H), 2.52 (s, 2H), 2.13-1.95 (m, 2H), 1.73-1.50 (m, 4H), 1.23 (t, J=7.5 Hz, 3H).

HPLC-Retention time (XE Metode 7 CM): 1.59 minutes. Detected "M+1"-mass: 308.19.

Preparation 8 (Compound 009)

3-(3-Ethyl-4-oxo-spiro[5,7-dihydroindazole-6,4'-tetrahydropyran]-1-yl)propyl Benzoate

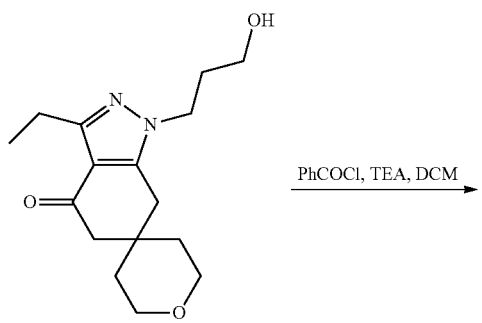

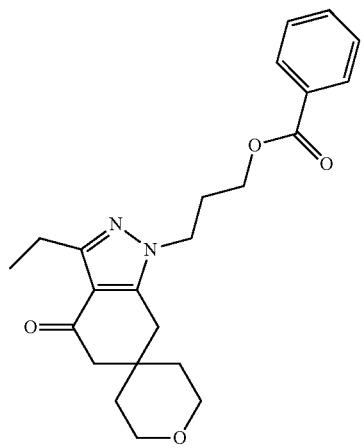

To a solution of 3-ethyl-1-(3-hydroxypropyl)spiro[5,7-dihydroindazole-6,4'-tetrahydropyran]-4-one (160 g, 547.9 mmol) in DCM (1.6 L), TEA (138.3 g, 1369.8 mmol) and Benzoyl chloride (153.4 g, 1095.9 mmol) were added slowly at 0° C. and stirred for 16 h a 26° C. On completion of the reaction, volatiles were evaporated under vacuum and the resulting residue was treated with water. The organic layer was washed with brine (500 mL), dried over Na$_2$SO$_4$, concentrated and purified by silica gel (100-200 mesh) column chromatography (70% EtOAc in PE as eluent) to afford the title compound as a pale yellow liquid, which was used directly in the next step.

Preparation 9 (Compound 010)

3-(3-Ethyl-4-oxo-spiro[6,8-dihydro-5H-pyrazolo[4,3-c]azepine-7,4'-tetrahydropyran]-1-yl)propyl Benzoate

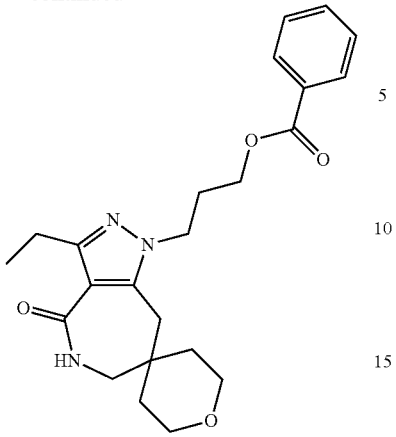

To a solution of 3-(3-ethyl-4-oxo-spiro[5,7-dihydroindazole-6,4'-tetrahydropyran]-1-yl)propyl benzoate (160 g, 404.0 mmol) in CH$_3$SO$_3$H (775.8 g, 8080.8 mmol), NaN$_3$ (131.3 g, 2020.2 mmol) was added portion wise at 0° C. and stirred for 16 h at 26° C. On completion, the reaction mixture was diluted with water at 0° C. and extracted with 10% MeOH: DCM (2×250 mL). The combined organic layers were dried over Na$_2$SO$_4$, concentrated, and purified by silica gel (100-200 mesh) column chromatography (5% MeOH in DCM as eluent) to afford the title compound as pale yellow liquid.

$^1$H NMR (600 MHz, DMSO-d$_6$) δ 7.99-7.86 (m, 2H), 7.75-7.59 (m, 1H), 7.52 (t, J=7.8 Hz, 2H), 7.40 (t, J=5.8 Hz, 1H), 4.27 (t, J=5.9 Hz, 2H), 4.16 (t, J=6.7 Hz, 2H), 3.57 (dt, J=12.0, 4.9 Hz, 2H), 3.49 (ddd, J=11.7, 6.8, 4.7 Hz, 2H), 2.98 (d, J=5.8 Hz, 2H), 2.75 (s, 2H), 2.72 (q, J=7.5 Hz, 2H), 2.20 (p, J=6.5 Hz, 2H), 1.44-1.30 (m, 4H), 1.09 (t, J=7.5 Hz, 3H).

HPLC-Retention time (XE Metode 7 CM): 2.04 minutes. Detected "M+1"-mass: 412.23.

Preparation 10 (Compound 011)

3-Ethyl-1-(3-hydroxypropyl)spiro[6,8-dihydro-5H-pyrazolo[4,3-c]azepine-7,4'-tetrahydropyran]-4-one

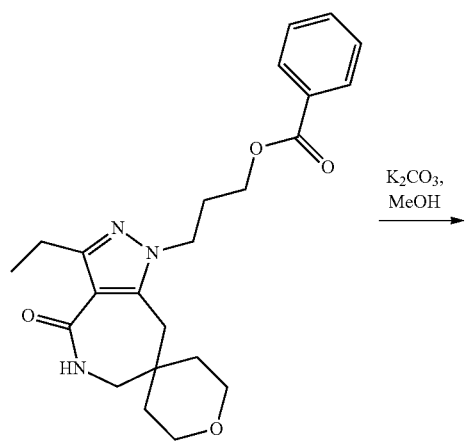

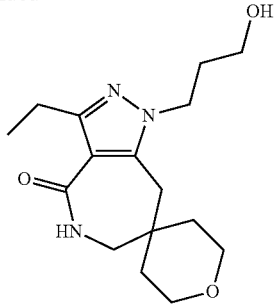

To a solution of 3-(3-ethyl-4-oxo-spiro[6,8-dihydro-5H-pyrazolo[4,3-c]azepine-7,4'-tetrahydropyran]-1-yl)propyl benzoate (85 g, 206.81 mmol) in MeOH (850 mL), K$_2$CO$_3$ (57 g, 413.62 mmol) was added at 0° C. and stirred for 3 h at 26° C. On completion, the reaction was filtered and it was washed with MeOH. The filtrate was concentrated and purified by Neutral Alumina column chromatography (5% MeOH in DCM as eluent) to afford the title compound as off-white solid.

$^1$H NMR (400 MHz, DMSO-d$_6$) δ 7.39 (t, J=5.7 Hz, 1H), 4.58 (s, 1H), 4.01 (t, J=7.1 Hz, 2H), 3.77-3.46 (m, 4H), 3.38 (t, J=6.0 Hz, 2H), 3.01 (d, J=5.7 Hz, 2H), 2.85-2.66 (m, 4H), 1.84 (p, J=6.5 Hz, 2H), 1.44 (t, J=5.6 Hz, 4H), 1.11 (t, J=7.5 Hz, 3H).

HPLC-Retention time (XE Metode 7 CM): 1.59 minutes. Detected "M+1"-mass: 308.19.

Preparation 11 (Compound 012)

Methyl (2S)-2-methyl-3-tetrahydropyran-2-yloxy-propanoate

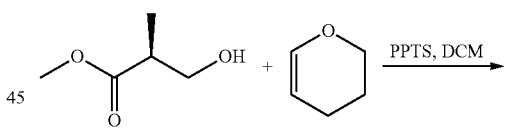

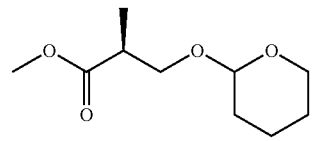

Methyl (2S)-3-hydroxy-2-methyl-propanoate (30 g, 356 mmol) was added to a solution of 3,4-dihydro-2H-pyran (16 g, 135 mmol) and PPTS (2 g, 8 mmol) in DCM (50 mL) at rt. After 2 h, the reaction was washed with H$_2$O (100 mL), saturated aqueous NaHCO$_3$ (100 mL) and with brine (100 mL), dried (MgSO$_4$), and concentrated in vacuo to afford the title compound as a colorless liquid, which was used in the next step without characterization.

Preparation 12 (Compound 013)

(2R)-2-Methyl-3-tetrahydropyran-2-yloxy-propan-1-ol

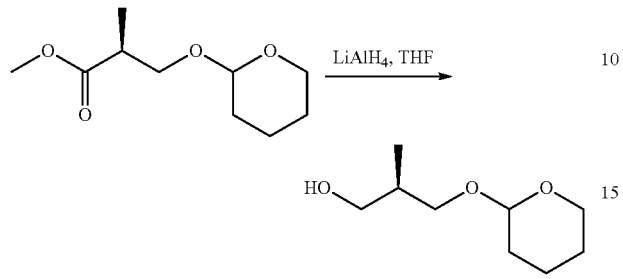

Methyl (2S)-2-methyl-3-tetrahydropyran-2-yloxy-propanoate (31 g, 153 mmol) was cooled to 0° C. and treated dropwise with 200 mL (200 mmol) of LAH (1 M in THF). The solution was stirred at rt for 1 h. Under ice-bath cooling, to the solution was dropwise added 2N NaOH (40 m) (very slow addition). The mixture was filtered. The filtrate was concentrated. The residue was purified by chromatography (heptane/ethyl acetate 4:1 ($R_f$=0.1) to heptane/ethyl acetate 0:1), giving the title compound as a colorless oil.

$^1$H NMR (300 Hz, CDCl$_3$) δ 4.58 (1H, br), 3.93-3.29 (m, 6H), 2.67-2.49 (m, 1H), 2.13-1.94 (m, 1H), 1.90-1.42 (m, 6H), 0.98-0.83 (m, 3H).

Preparation 13 (Compound 014)

[(2S)-2-Methyl-3-tetrahydropyran-2-yloxy-propyl] methanesulfonate

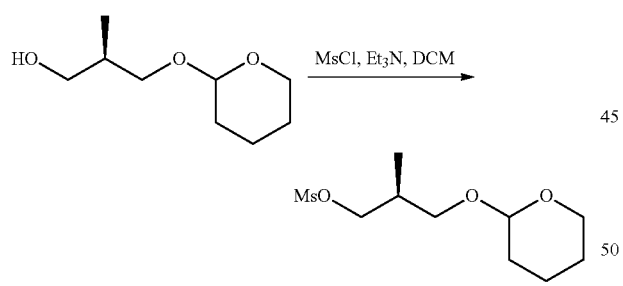

To a solution of (2R)-2-methyl-3-tetrahydropyran-2-yloxy-propan-1-ol (18 g, 103.3 mmol) and Et$_3$N (20 g) in DCM (100 mL) was dropwise added methanesulfonyl chloride (14.2 g, 124 mmol) at 0° C. The obtained mixture was stirred at rt for 0.5 h and washed with H$_2$O, 1 N HCl and NaHCO$_3$ solution. The organic phase was dried over Na$_2$SO$_4$ and concentrated in vacuo, giving the title compound as a brown syrup.

$^1$H NMR (300 MHz, CDCl$_3$) δ 4.62-4.50 (m, 1H), 4.35-4.09 (m, 2H), 3.83 (ddt, J=11.1, 7.4, 3.7 Hz, 1H), 3.73 (dd, J=9.8, 5.2 Hz, 0.5H), 3.67 (dd, J=9.9, 7.0 Hz, 0.5H), 3.56-3.46 (m, 1H), 3.37 (dd, J=9.8, 5.0 Hz, 0.5H), 3.30 (dd, J=9.8, 7.1 Hz, 0.5H), 3.01/3.01 (s, 3H), 2.31-2.10 (m, 1H), 1.93-1.45 (m, 6H), 1.04 (dd, J=6.9, 2.8 Hz, 3H).

Preparation 14 (Compound 015)

[(2R)-2-Methyl-3-tetrahydropyran-2-yloxy-propyl] hydrazine

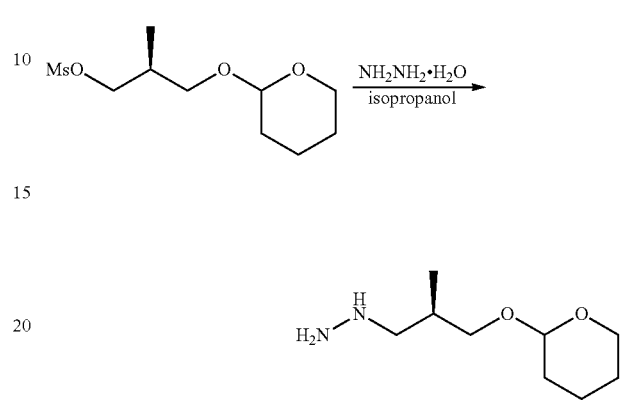

A solution of [(2S)-2-methyl-3-tetrahydropyran-2-yloxy-propyl] methanesulfonate From Preparation 13 (103 mmol) and hydrazine monohydrate (30 mL) in isopropanol (100 mL) was heated to reflux for 2 h. The mixture was then concentrated in vacuo. The residue was taken up in DCM and washed with brine. The aqueous phase was extracted twice with DCM. The combined organic phases were dried over Na$_2$SO$_4$ and concentrated in vacuo, giving the title compound (crude). The crude was used directly in the next step without further purification.

Preparation 15 (Compound 016)

3-Ethyl-1-[(2R)-2-methyl-3-tetrahydropyran-2-yloxy-propyl]spiro[5,7-dihydroindazole-6,4'-tetrahydropyran]-4-one

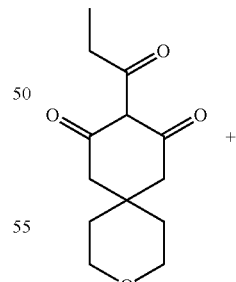

+

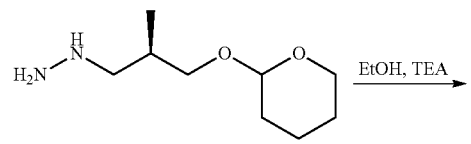

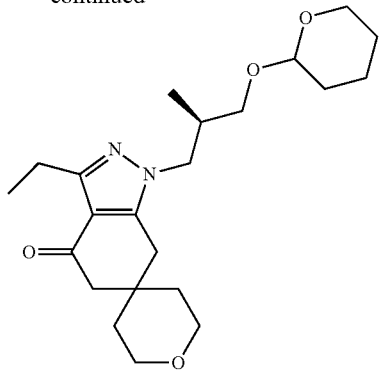

A solution of 9-propanoyl-3-oxaspiro[5.5]undecane-8,10-dione (15 g, 63 mmol) and [(2R)-2-Methyl-3-tetrahydropyran-2-yloxy-propyl]hydrazine (15 g, 80 mmol) in isopropanol (100 mL) was heated reflux for 5 h. The solution was concentrated in vacuo. The residue was purified by chromatography (ethyl acetate, $R_f$=0.41), giving the as an oil. The compound was used in the next step without characterization.

Preparation 16 (Compound 017)

3-Ethyl-1-[(2R)-3-hydroxy-2-methyl-propyl]spiro[5,7-dihydroindazole-6,4'-tetrahydropyran]-4-one

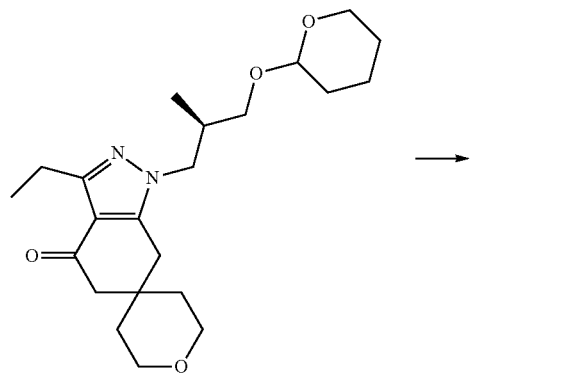

To a solution of 3-ethyl-1-[(2R)-2-methyl-3-tetrahydropyran-2-yloxy-propyl]spiro[5,7-dihydroindazole-1-tetrahydropyran]-4-one (27 g, 69 mmol) in MeOH/H$_2$O (3:1, 200 mL) was added methanesulfonic acid (2 mL) at rt. The solution was stirred at 50° C. for 1 h and concentrated in vacuo in order to remove MeOH. The aqueous mixture was diluted with water and extracted three times with DCM. The combined organic phases were dried and concentrated in vacuo. The residue was purified by chromatography (ethyl acetate/MeOH 20:1), giving the title compound as an oil.

$^1$H NMR (300 MHz, DMSO-d$_6$) δ 4.63 (t, J=5.2 Hz, 1H), 4.05 (dd, J=13.7, 6.5 Hz, 1H), 3.81 (dd, J=13.7, 7.7 Hz, 1H), 3.68-3.50 (m, 4H), 3.37-3.15 (m, 2H), 2.95-2.82 (m, 2H), 2.80-2.65 (m, 2H), 2.41 (s, 2H), 2.15-2.00 (m, 1H), 1.53-1.39 (m, 4H), 1.13 (t, J=7.5 Hz, 3H), 0.80 (d, J=6.8 Hz, 3H).

Preparation 17 (Compound 018)

3-Ethyl-1-[(2R)-3-hydroxy-2-methyl-propyl]spiro[6,8-dihydro-5H-pyrazolo[4,3-c]azepine-7,4'-tetrahydropyran]-4-one

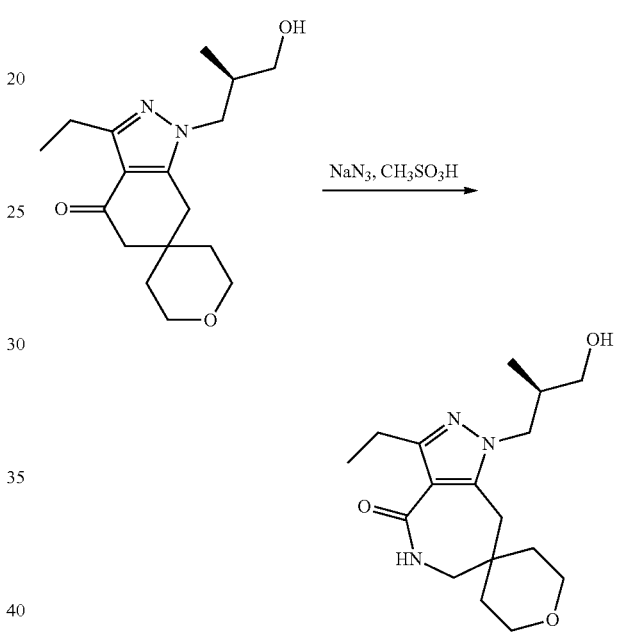

To a solution of 3-ethyl-1-[(2R)-3-hydroxy-2-methyl-propyl]spiro[5,7-dihydroindazole-'6,4'-tetrahydropyran]-4-one (17 g, 55.5 mmol) in methanesulfonic acid (100 mL) was added sodium azide (7.2 g, 111 mmol) in portion at rt (exothermic). The obtained reaction mixture was stirred at rt for 2 h. To the mixture was added 400 mL of water. The mixture was neutralized with NaOH and concentrated. The residue was taken up in EtOH (400 mL). The precipitate was filtered off and washed with EtOH. The filtrate was concentrated in vacuo. The residue was taken up in DCM. The precipitate was filtered off and washed with DCM. The filtrate was concentrated in vacuo. The residue was purified twice by chromatography (DCM/MeOH 10:1), giving the title compound as a white solid.

$^1$H NMR (600 MHz, DMSO-d$_6$) δ 7.41 (t, J=5.7 Hz, 1H), 4.64 (t, J=5.1 Hz, 1H), 4.00 (dd, J=13.9, 6.5 Hz, 1H), 3.73 (dd, J=13.9, 7.8 Hz, 1H), 3.69-3.60 (m, 2H), 3.58-3.50 (m, 2H), 3.30-3.20 (m, 2H), 3.01 (d, J=5.8 Hz, 2H), 2.81-2.79 (m, 4H), 2.16-2.01 (m, 1H), 1.50-1.40 (m, 4H), 1.11 (t, J=7.5 Hz, 3H), 0.81 (d, J=6.8 Hz, 3H).

HPLC-Retention time (XE Metode 7 CM): 1.67 minutes. Detected "M+1"-mass: 321.21.

General Procedure 1: Esterification

To a solution of an acid (2 equiv) in DMF (0.1 mL) were added a solution of an alcohol (0.013 mmol) in DMF (0.1 mL) and a solution of DMAP (2 equiv) in DMF (0.1 mL). To this resulting solution was added a suspension of EDAC (2.7 equiv) in DMF (0.1 mL). The mixture was shaken at 50° C. overnight. The crude was subjected to preparative LCMS purification, giving an ester.

General Procedure 2: Esterification

An alcohol (0.013 mmol) was dissolved in DCE (0.15 mL). A solution of an acid (2 equiv) in DCE (0.2 mL) and a solution of DMAP (1 equiv) in DCE (0.1 mL) were added. To the resulting mixture was added EDAC (2 equiv). The mixture was then shaken at 50° C. overnight and concentrated in vacuo. The residue was redissolved in DMF (0.3 mL) and subjected to preparative LCMS purification, giving an ester.

Example 1 (Compound 101)

3-(3-Ethyl-4-oxo-spiro[6,8-dihydro-5H-pyrazolo[4,3-c]azepine-7,4'-tetrahydropyran]-1-yl)propyl 4-methylbenzoate

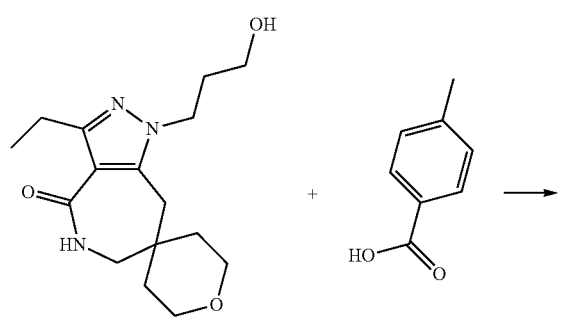

4-Methylbenzoic acid and 3-ethyl-1-(3-hydroxypropyl) spiro[6,8-dihydro-5H-pyrazolo[4,3-c]azepine-7,4'-tetrahydropyran]-4-one were treated as described in the general procedure 1, giving the title compound.

$^1$H NMR (600 MHz, DMSO-d$_6$) δ 7.92-7.72 (m, 2H), 7.41 (t, J=5.7 Hz, 1H), 7.32 (d, 3=8.1 Hz, 2H), 4.24 (t, J=6.0 Hz, 2H), 4.15 (t, J=6.8 Hz, 2H), 3.63-3.53 (m, 2H), 3.54-3.45 (m, 2H), 2.98 (d, J=5.8 Hz, 2H), 2.79-2.67 (m, 4H), 2.38 (s, 3H), 2.18 (p, J=6.5 Hz, 2H), 1.45-1.32 (m, 4H), 1.10 (t, J=7.5 Hz, 3H).

HPLC-Retention time (XE Metode 7 CM): 2.12 minutes.
Detected "M+1"-mass: 426.24.

Example 2 (Compound 102)

3-(3-Ethyl-4-oxo-spiro[6,8-dihydro-5H-pyrazolo[4,3-c]azepine-7,4'-tetrahydropyran]-1-yl)propyl 4-ethylbenzoate

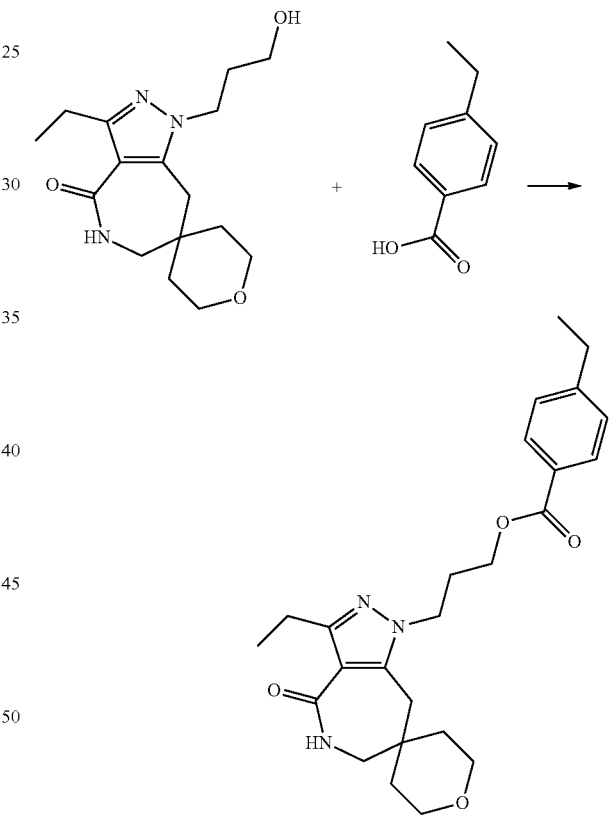

3-Ethyl-1-(3-hydroxypropyl)spiro[6,8-dihydro-5H-pyrazolo[4,3-c]azepine-7,4'-tetrahydropyran]-4-one and 4-ethylbenzoic acid were treated as described in General procedure 2, giving the title compound.

$^1$H NMR (300 MHz, DMSO-d$_6$) δ 7.85 (d, J=8.3 Hz, 2H), 7.48-7.29 (m, 3H), 4.24 (t, 3=6.0 Hz, 2H), 4.14 (t, J=6.7 Hz, 2H), 3.69-3.40 (m, 4H), 2.98 (d, J=5.7 Hz, 2H), 2.83-2.59 (m, 6H), 2.19 (p, J=6.4 Hz, 2H), 1.36 (t, J=5.4 Hz, 4H), 1.19 (t, J=7.6 Hz, 3H), 1.10 (t, J=7.5 Hz, 3H).

HPLC-Retention time (XE Metode 7 CM): 2.23 minutes.
Detected "M+1"-mass: 440.25.

Example 3 (Compound 103)

[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(methylsulfamoyl)benzoate

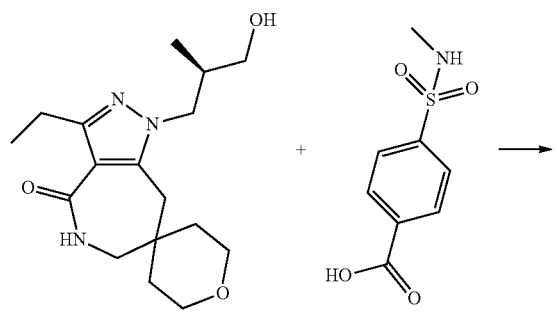

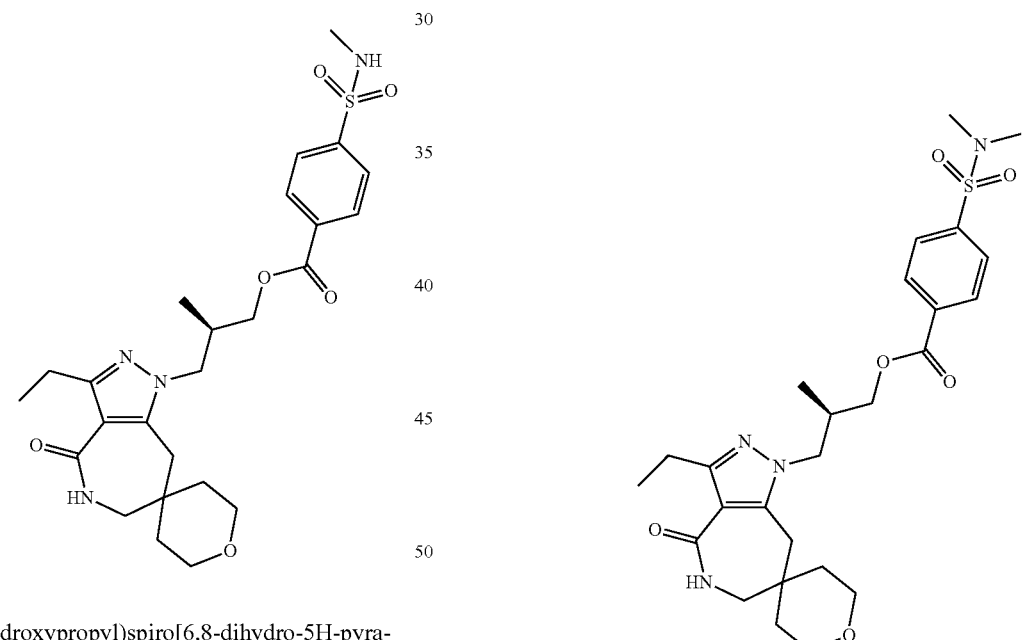

3-Ethyl-1-(3-hydroxypropyl)spiro[6,8-dihydro-5H-pyrazolo[4,3-c]azepine-7,4'-tetrahydropyran]-4-one and 4-(methylsulfamoyl)benzoic acid were treated as described in General procedure 2, giving the title compound.

$^1$H NMR (600 MHz, DMSO-$d_6$) δ 8.17-8.06 (m, 2H), 7.94-7.84 (m, 2H), 7.71 (s, 1H), 7.44 (t, J=5.8 Hz, 1H), 4.24 (dd, J=11.0, 6.2 Hz, 1H), 4.20-4.07 (m, 2H), 3.99 (dd, J=14.2, 6.7 Hz, 1H), 3.60 (dt, J=11.8, 4.9 Hz, 1H), 3.57-3.42 (m, 3H), 3.02-2.93 (m, 2H), 2.79 (d, J=16.6 Hz, 1H), 2.73-2.65 (m, 3H), 2.57-2.52 (m, 1H), 2.43 (s, 3H), 1.38 (t, J=5.5 Hz, 2H), 1.37-1.27 (m, 2H), 1.07 (t, J=7.5 Hz, 3H), 1.01 (d, J=6.9 Hz, 3H).

HPLC-Retention time (XE Metode 7 CM): 2.02 minutes.

Detected "M+1"-mass: 519.23.

Example 4 (Compound 104)

[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(dimethylsulfamoyl)benzoate

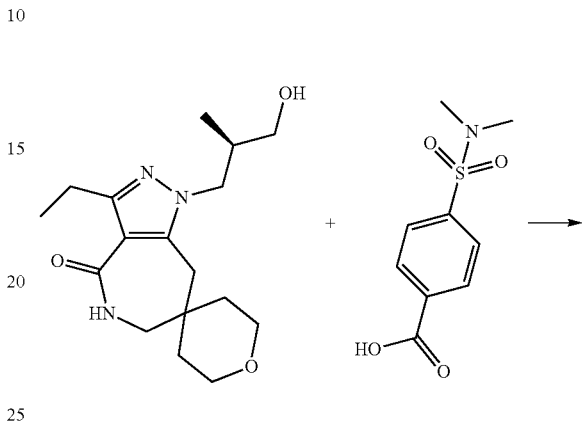

3-Ethyl-1-(3-hydroxypropyl)spiro[6,8-dihydro-5H-pyrazolo[4,3-c]azepine-7,4'-tetrahydropyran]-4-one and 4-(dimethylsulfamoyl)benzoic acid were treated as described in General procedure 2, giving the title compound.

$^1$H NMR (300 MHz, DMSO-$d_6$) δ 8.19-8.07 (m, 2H), 7.90-7.82 (m, 2H), 7.36 (t, J=5.7 Hz, 1H), 4.34-3.91 (m, 4H), 3.65-3.39 (m, 4H), 2.98 (d, J=5.7 Hz, 2H), 2.89-2.61 (m, 10H), 2.75-2.60 (m, 1H), 1.48-1.24 (m, 4H), 1.06 (t, J=7.5 Hz, 3H), 1.02 (d, J=7.0 Hz, 3H).

HPLC-Retention time (XE Metode 7 CM): 2.12 minutes.

Detected "M+1"-mass: 533.24.

Example 5 (Compound 105)

[(2R)-3-(3-ethyl-4-oxo-spiro[6,8-dihydro-5H-pyrazolo[4,3-c]azepine-7,4'-tetrahydro-pyran]-1-yl)-2-methyl-propyl] 4-methylsulfonylbenzoate

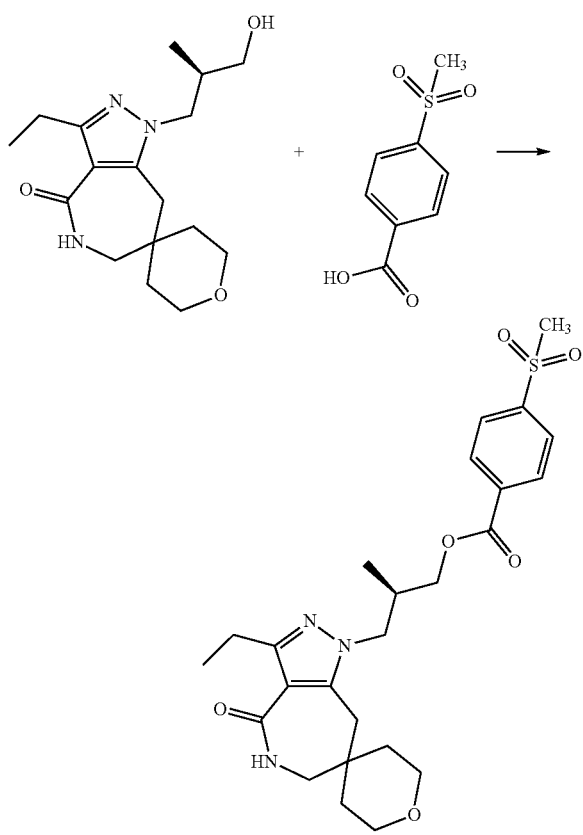

3-Ethyl-1-(3-hydroxypropyl)spiro[6,8-dihydro-5H-pyrazolo[4,3-c]azepine-7,4'-tetrahydropyran]-4-one and 4-methylsulfonylbenzoic acid were treated as described in General procedure 2, giving the title compound.

$^1$H NMR (600 MHz, DMSO-d$_6$) δ8.17-8.10 (m, 2H), 8.08-8.03 (m, 2H), 7.40 (t, J=5.8 Hz, 1H), 4.25 (dd, J=11.0, 6.3 Hz, 1H), 4.18 (dd, J=11.0, 5.1 Hz, 1H), 4.11 (dd, J=14.1, 7.8 Hz, 1H), 3.99 (dd, J=14.1, 6.6 Hz, 1H), 3.60 (dt, J=11.8, 4.9 Hz, 1H), 3.58-3.43 (m, 3H), 3.28 (s, 3H), 3.04-2.91 (m, 2H), 2.78 (d, J=16.5 Hz, 1H), 2.74-2.64 (m, 3H), 2.60-2.51 (m, 1H), 1.39 (t, J=5.4 Hz, 2H), 1.37-1.27 (m, 2H), 1.08 (t, J=7.5 Hz, 3H), 1.01 (d, J=6.8 Hz, 3H).

HPLC-Retention time (XE Metode 7 CM): 1.99 minutes.
Detected "M+1"-mass: 504.21.

PDE4 Assay

The human PDE4D catalytic domain (UniProt no. Q08499 [5380-L740]) was incubated with a mixture of non-labelled cAMP (cyclic adenosine monophosphate) and fluorescein amidite (FAM) conjugated cAMP and titrated test or reference compound. Following brief incubation the enzymatic reaction was stopped by addition of binding buffer containing nanoparticles with immobilized trivalent metal ions capable of binding 1) AMP phospho groups and 2) terbium (Tb) donor fluorophores. Subsequent excitation of the Tb donor triggers time-resolved FRET to adjacent FAM acceptor molecules resulting in light emission. In the presence of a PDE4 inhibitor, AMP generation was reduced resulting in a lower fluorescence signal. The cAMP phosphodiester is not bound by the detection system.

The results were calculated as the molar concentrations resulting in 50% inhibition of the substrate cleavage compared to controls samples, and are expressed as a range of IC$_{50}$ (nM).

The results are shown in Table 1 below.

PDE4 IC$_{50}$ Ranges
* indicates that IC$_{50}$ values are >500 nM
** indicates that IC$_{50}$ values are >100 and <500 nM
*** indicates that IC$_{50}$ values are <100 nM

TABLE 1

| Example | Compound | PDE4 IC$_{50}$ range |
| --- | --- | --- |
| 1 | 101 | *** |
| 2 | 102 | *** |
| 3 | 103 | *** |
| 4 | 104 | *** |
| 5 | 105 | *** |

The Examples 6-139 shown in Table 2 were prepared by reacting Compound 011 as described in General Procedure (G.P.) 1 or 2 with the appropriate acid:

TABLE 2

| Ex. | Cmpd | Structure | IUPAC Name | G.P. | HPLC Rt (min) | PDE4 IC$_{50}$ range |
| --- | --- | --- | --- | --- | --- | --- |
| 6 | 106 | 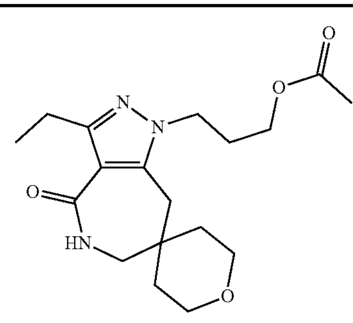 | 3-(3-ethyl-4-oxo-spiro[6,8-dihydro-5H-pyrazolo[4,3-c]azepine-7,4'-tetrahydropyran]-1-yl)propyl acetate | 2 | 1.87 | ** |

TABLE 2-continued

| Ex. | Cmpd | Structure | IUPAC Name | G.P. | HPLC Rt (min) | PDE4 IC$_{50}$ range |
|---|---|---|---|---|---|---|
| 7 | 107 | 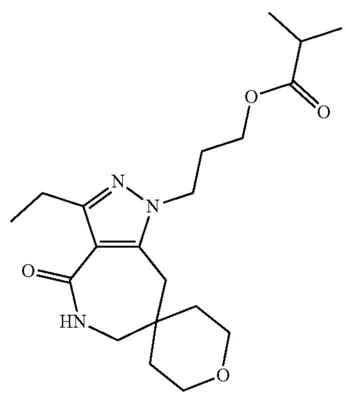 [SMILES: CCc1nn(CCCOC(=O)C(C)C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylpropanoate | 2 | 1.96 | ** |
| 8 | 108 | 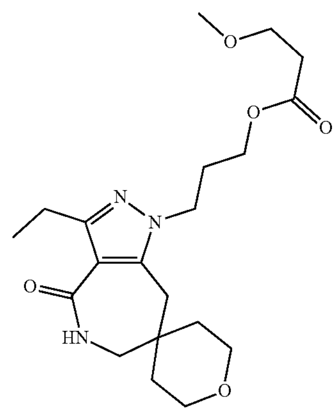 [SMILES: CCc1nn(CCCOC(=O)CCOC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methoxypropanoate | 1 | 1.80 | * |
| 9 | 109 | 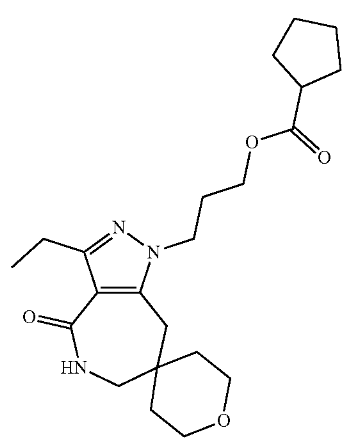 [SMILES: CCc1nn(CCCOC(=O)C2CCCC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl cyclopentanecarboxylate | 2 | 2.08 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 10 | 110 | 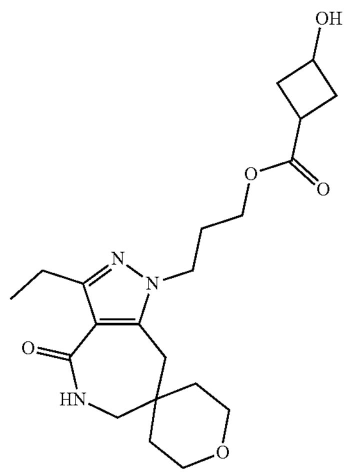 [SMILES: CCc1nn(CCCOC(=O)C2CC(O)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-hydroxycyclobutane-carboxylate | 1 | 1.71 | ** |
| 11 | 111 | 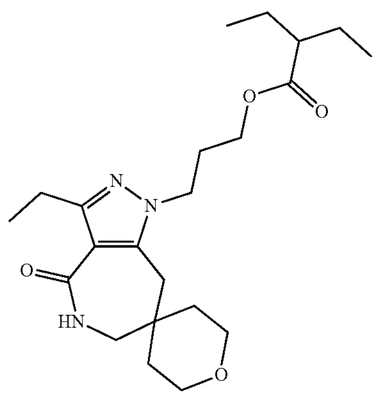 [SMILES: CCc1nn(CCCOC(=O)C(CC)CC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-ethylbutanoate | 2 | 2.15 | *** |
| 12 | 112 | 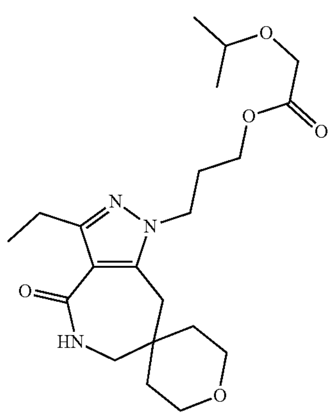 [SMILES: CCc1nn(CCCOC(=O)COC(C)C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-isopropoxyacetate | 1 | 1.89 | * |

TABLE 2-continued

| Ex. | Cmpd | Structure | IUPAC Name | G.P. | HPLC Rt (min) | PDE4 IC$_{50}$ range |
|---|---|---|---|---|---|---|
| 13 | 113 | 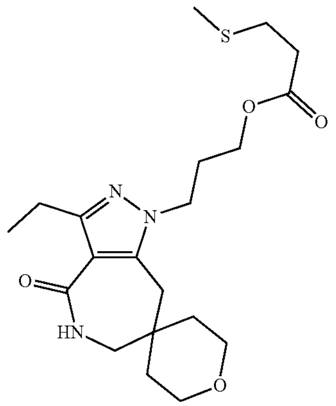 [SMILES: CCc1nn(CCCOC(=O)CCSC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylsulfanylpropanoate | 1 | 1.94 | ** |
| 14 | 114 | 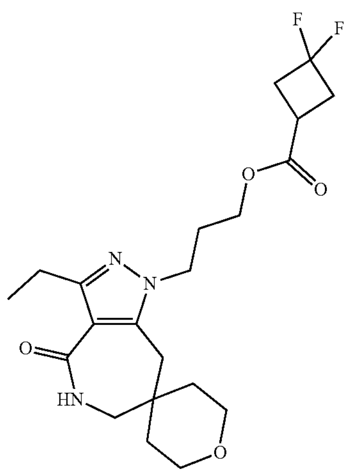 [SMILES: CCc1nn(CCCOC(=O)C2CC(F)(F)C2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,3-difluorocyclobutanecarboxylate | 1 | 2.00 | ** |
| 15 | 115 | 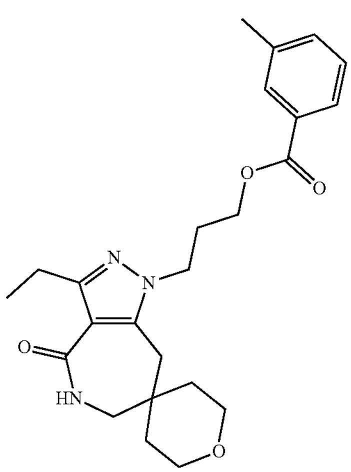 [SMILES: CCc1nn(CCCOC(=O)c2cccc(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylbenzoate | 1 | 2.13 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 16 | 116 | 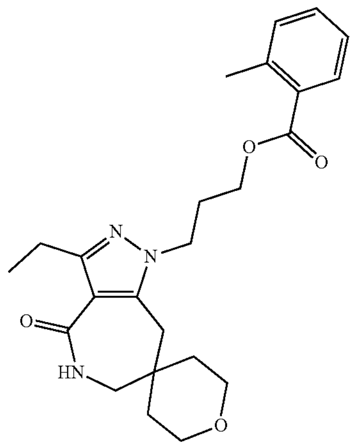 | 3-(3-ethyl-4-oxo-spiro[6,8-dihydro-5H-pyrazolo[4,3-c]azepine-7,4'-tetrahydropyran]-1-yl)propyl 2-methylbenzoate | 1 | 2.13 | *** |
| 17 | 117 | 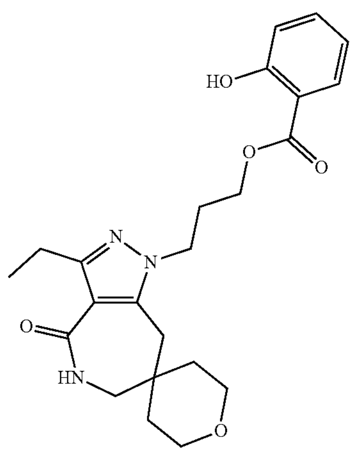 | 3-(3-ethyl-4-oxo-spiro[6,8-dihydro-5H-pyrazolo[4,3-c]azepine-7,4'-tetrahydropyran]-1-yl)propyl 2-hydroxybenzoate | 2 | 2.08 | *** |
| 18 | 118 | 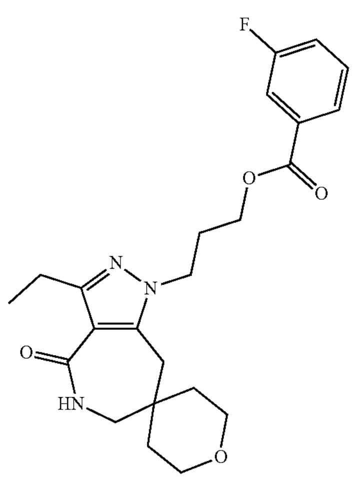 | 3-(3-ethyl-4-oxo-spiro[6,8-dihydro-5H-pyrazolo[4,3-c]azepine-7,4'-tetrahydropyran]-1-yl)propyl 3-fluorobenzoate | 2 | 2.08 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 19 | 119 | 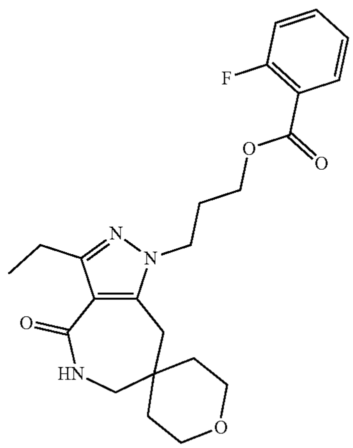 | 3-(3-ethyl-4-oxo-spiro[6,8-dihydro-5H-pyrazolo[4,3-c]azepine-7,4'-tetrahydropyran]-1-yl)propyl 2-fluorobenzoate | 2 | 2.04 | *** |
| 20 | 120 | 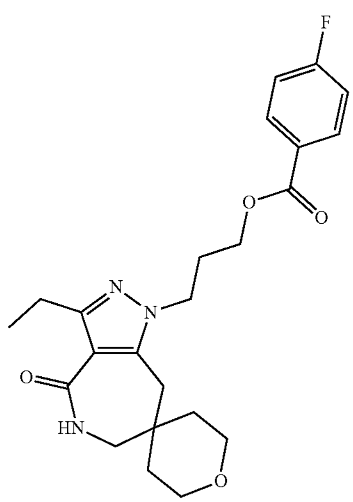 [SMILES: CCc1nn(CCCOC(=O)c2ccc(F)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluorobenzoate | 1 | 2.08 | *** |
| 21 | 121 | 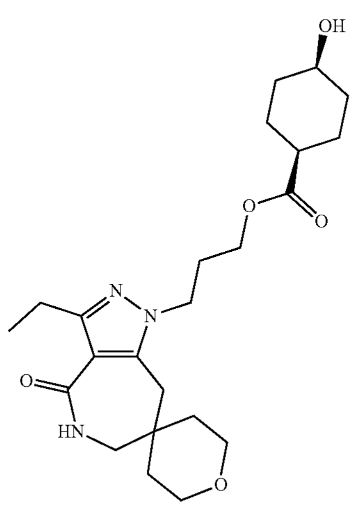 [SMILES: CCc1nn(CCCOC(=O)[C@H]2CC[C@@H](O)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl cis-4-hydroxycyclohexane-carboxylate | 1 | 1.79 | ** |

TABLE 2-continued

| Ex. | Cmpd | Structure | IUPAC Name | G.P. | HPLC Rt (min) | PDE4 IC$_{50}$ range |
|---|---|---|---|---|---|---|
| 22 | 122 | 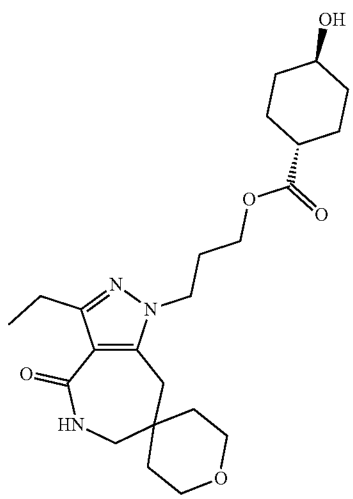 [SMILES: CCc1nn(CCCOC(=O)[C@H]2CC[C@H](O)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl trans-4-hydroxycyclohexane-carboxylate | 1 | 1.79 | ** |
| 23 | 123 | 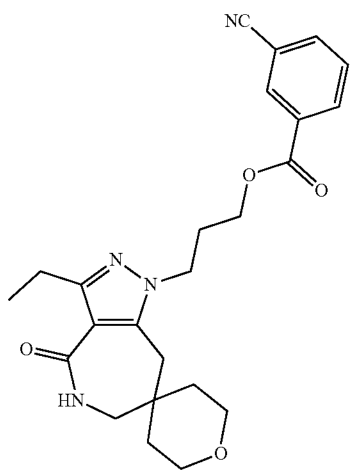 | 3-(3-ethyl-4-oxo-spiro[6,8-dihydro-5H-pyrazolo[4,3-c]azepine-7,4'-tetrahydropyran]-1-yl)propyl 3-cyanobenzoate | 2 | 2.00 | *** |
| 24 | 124 | 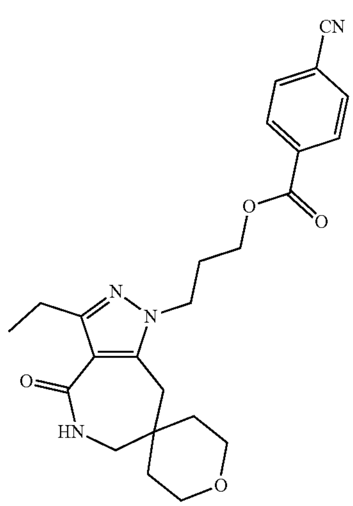 [SMILES: CCc1nn(CCCOC(=O)c2ccc(C#N)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-cyanobenzoate | 2 | 2.02 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 25 | 125 | 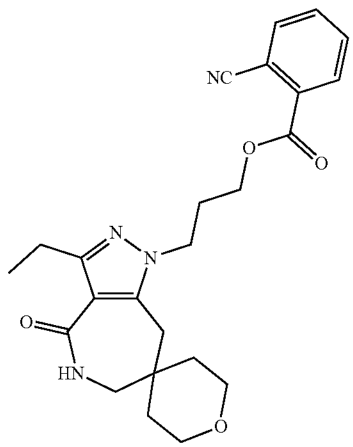 [SMILES: CCc1nn(CCCOC(=O)c2ccccc2C#N)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-cyanobenzoate | 1 | 1.98 | *** |
| 26 | 126 | 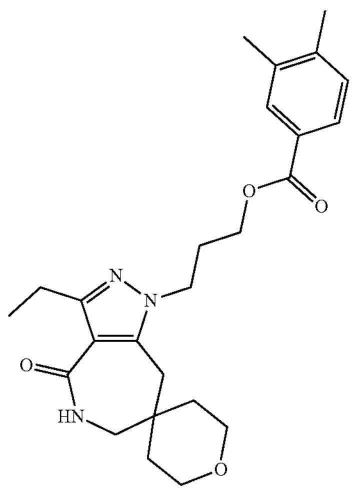 [SMILES: CCc1nn(CCCOC(=O)c2ccc(C)c(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,4-dimethylbenzoate | 2 | 2.20 | *** |
| 27 | 127 | 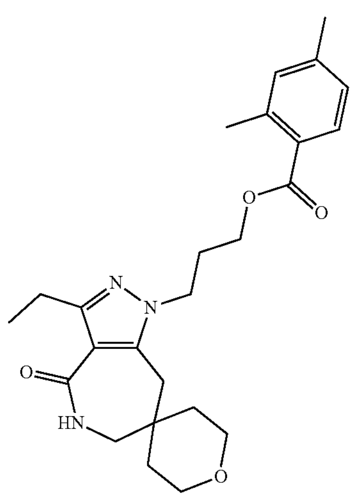 [SMILES: CCc1nn(CCCOC(=O)c2ccc(C)cc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,4-dimethylbenzoate | 2 | 2.23 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 28 | 128 | 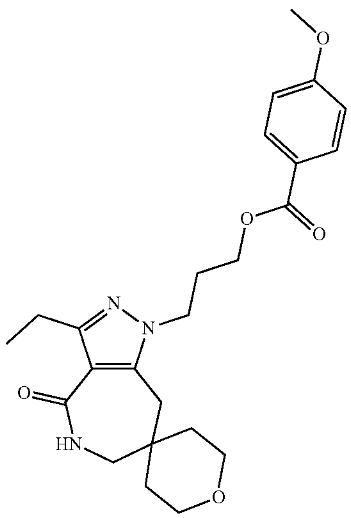 [SMILES: CCc1nn(CCCOC(=O)c2ccc(OC)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methoxybenzoate | 1 | 2.05 | *** |
| 29 | 129 | 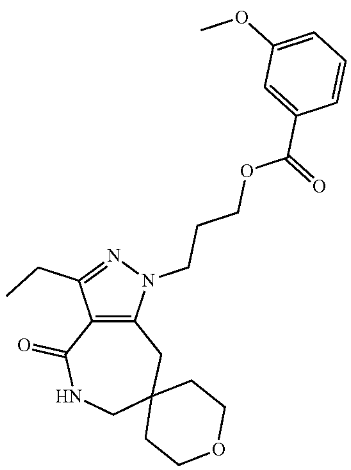 [SMILES: CCc1nn(CCCOC(=O)c2cccc(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methoxybenzoate | 1 | 2.07 | *** |
| 30 | 130 | 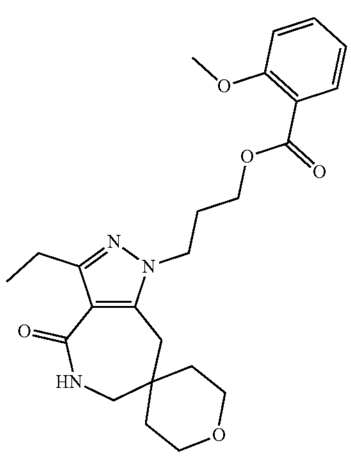 [SMILES: CCc1nn(CCCOC(=O)c2ccccc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methoxybenzoate | 1 | 1.98 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 31 | 131 | 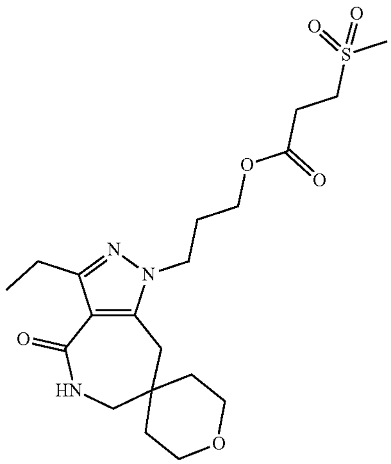 [SMILES: CCc1nn(CCCOC(=O)CCS(C)(=O)=O)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylsulfonylpropanoate | 1 | 1.72 | * |
| 32 | 132 | 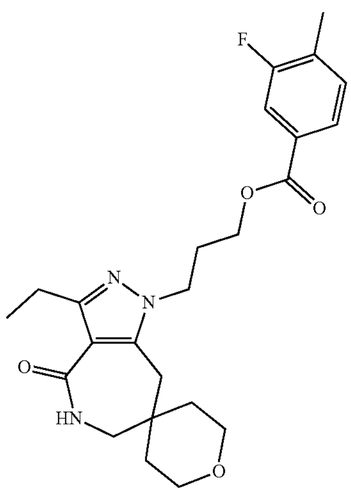 [SMILES: CCc1nn(CCCOC(=O)c2ccc(C)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-4-methyl-benzoate | 2 | 2.17 | *** |
| 33 | 133 | 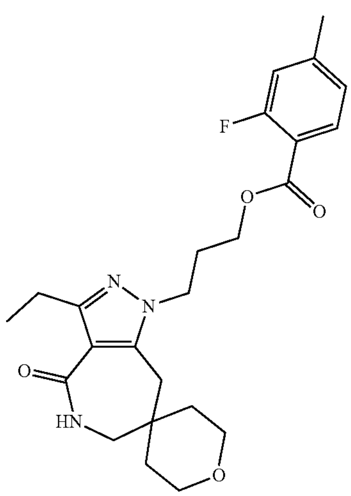 [SMILES: CCc1nn(CCCOC(=O)c2ccc(C)cc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-4-methyl-benzoate | 2 | 2.12 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 34 | 134 | 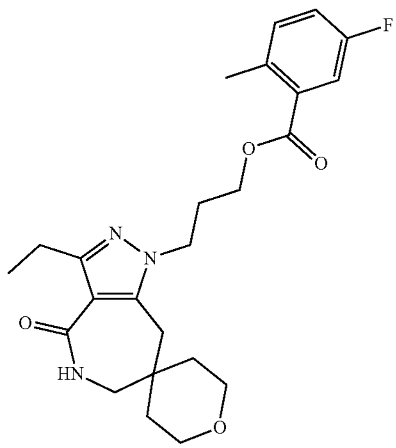 [SMILES: CCc1nn(CCCOC(=O)c2cc(F)ccc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-fluoro-2-methyl-benzoate | 2 | 2.17 | *** |
| 35 | 135 | 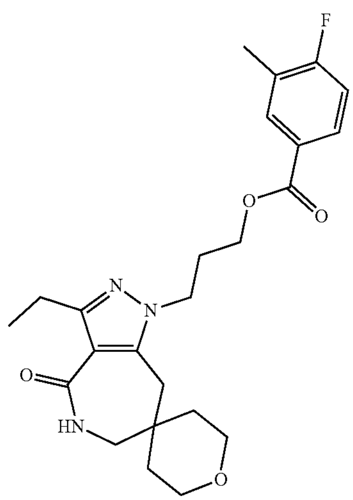 [SMILES: CCc1nn(CCCOC(=O)c2ccc(F)c(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluoro-3-methyl-benzoate | 1 | 2.17 | *** |
| 36 | 136 | 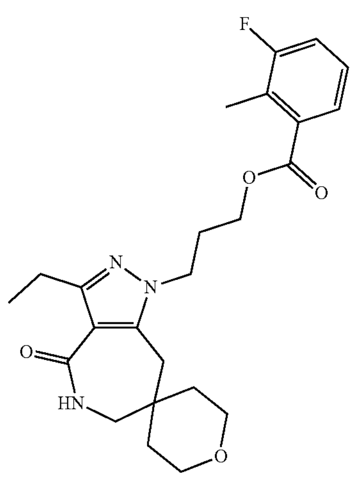 [SMILES: CCc1nn(CCCOC(=O)c2cccc(F)c2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-2-methyl-benzoate | 2 | 2.17 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 37 | 137 | 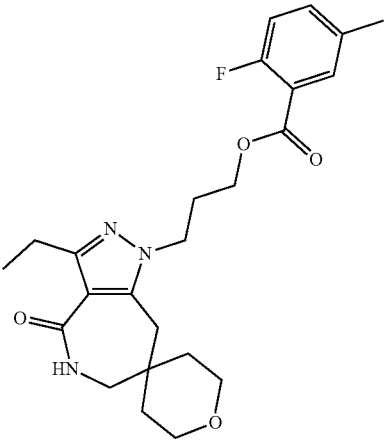 [SMILES: CCc1nn(CCCOC(=O)c2cc(C)ccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-5-methyl-benzoate | 1 | 2.13 | *** |
| 38 | 138 | 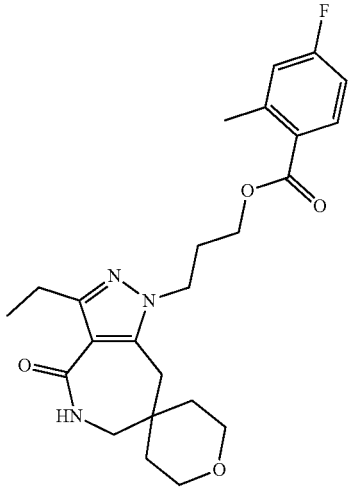 [SMILES: CCc1nn(CCCOC(=O)c2ccc(F)cc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluoro-2-methyl-benzoate | 2 | 2.17 | *** |
| 39 | 139 | 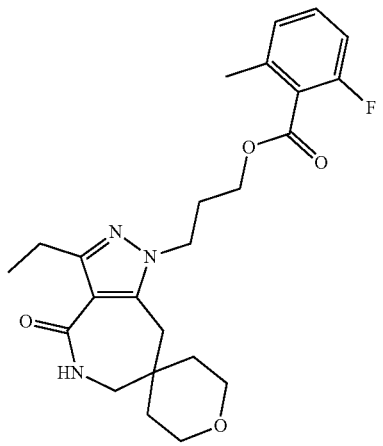 [SMILES: CCc1nn(CCCOC(=O)c2c(C)cccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-6-methyl-benzoate | 2 | 2.13 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 40 | 140 | 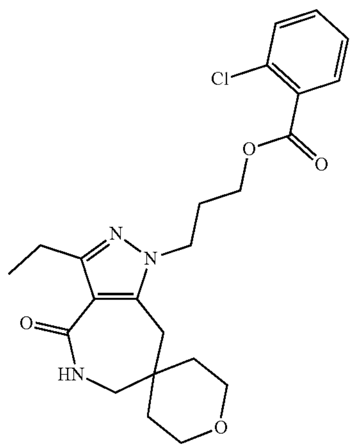 [SMILES: CCc1nn(CCCOC(=O)c2ccccc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chlorobenzoate | 1 | 2.10 | *** |
| 41 | 141 | 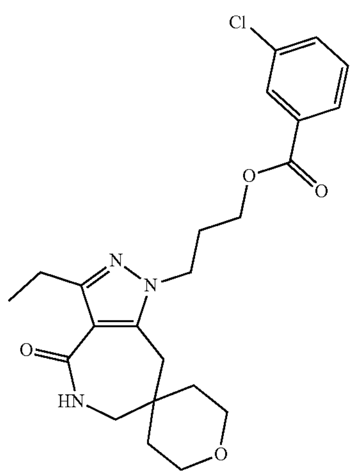 [SMILES: CCc1nn(CCCOC(=O)c2cccc(Cl)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chlorobenzoate | 1 | 2.16 | *** |
| 42 | 142 | 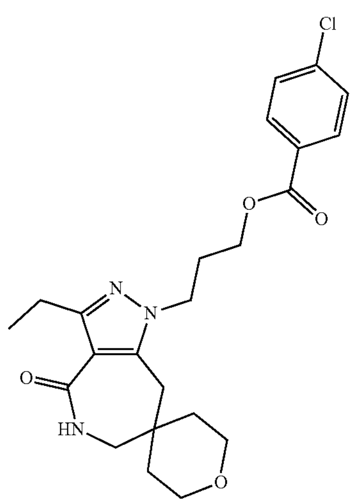 [SMILES: CCc1nn(CCCOC(=O)c2ccc(Cl)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-chlorobenzoate | 1 | 2.18 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 43 | 143 | 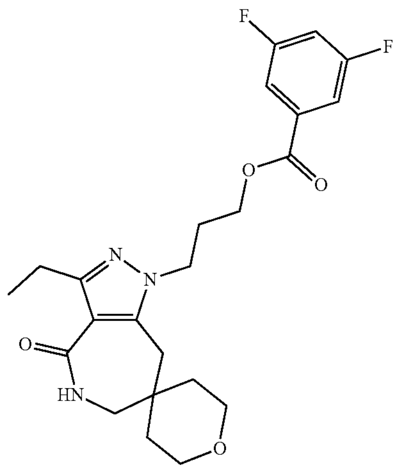 [SMILES: CCc1nn(CCCOC(=O)c2cc(F)cc(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,5-difluorobenzoate | 2 | 2.13 | *** |
| 44 | 144 | 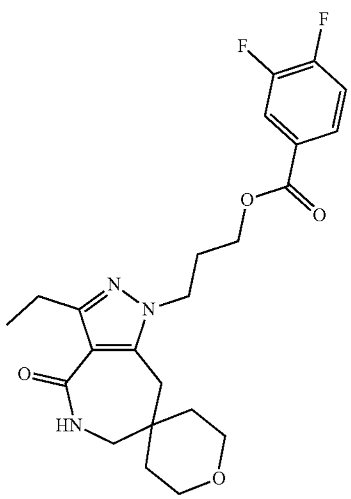 [SMILES: CCc1nn(CCCOC(=O)c2ccc(F)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,4-difluorobenzoate | 2 | 2.12 | *** |
| 45 | 145 | 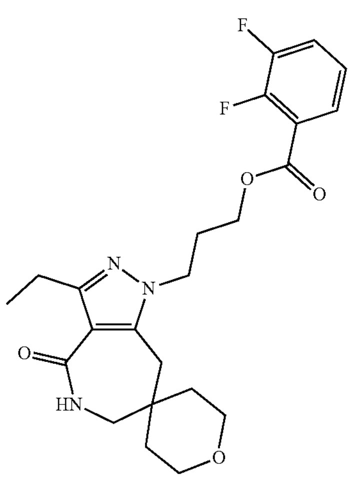 [SMILES: CCc1nn(CCCOC(=O)c2cccc(F)c2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,3-difluorobenzoate | 2 | 2.08 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 46 | 146 | 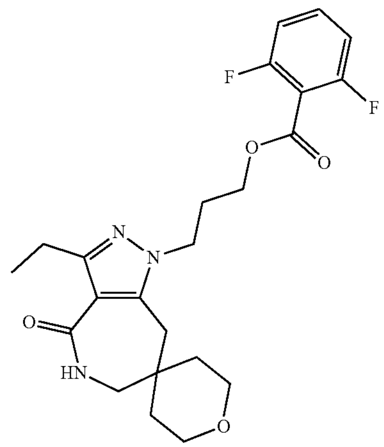 [SMILES: CCc1nn(CCCOC(=O)c2c(F)cccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,6-difluorobenzoate | 2 | 2.05 | *** |
| 47 | 147 | 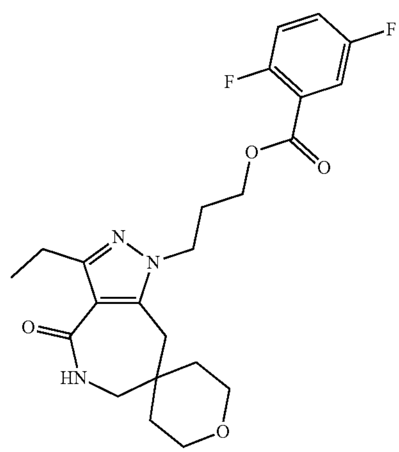 [SMILES: CCc1nn(CCCOC(=O)c2cc(F)ccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,5-difluorobenzoate | 2 | 2.07 | *** |
| 48 | 148 | 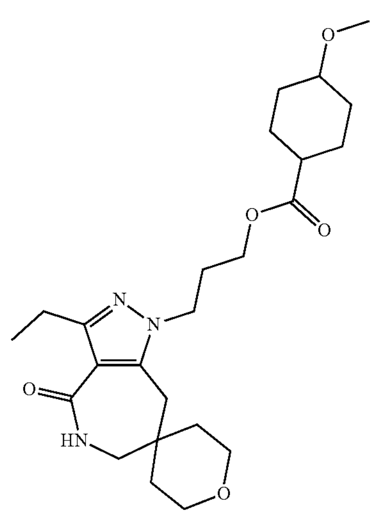 [SMILES: CCc1nn(CCCOC(=O)C2CCC(OC)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methoxycyclohexane-carboxylate | 1 | 1.95 | ** |

TABLE 2-continued

| Ex. | Cmpd | Structure | IUPAC Name | G.P. | HPLC Rt (min) | PDE4 IC$_{50}$ range |
|---|---|---|---|---|---|---|
| 49 | 149 | 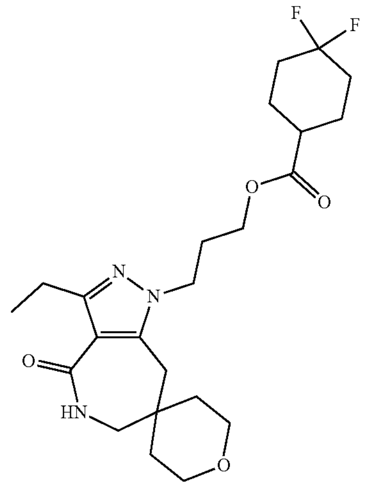 [SMILES: CCc1nn(CCCOC(=O)C2CCC(F)(F)CC2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4,4-difluorocyclohexane-carboxylate | 1 | 2.09 | ** |
| 50 | 150 | 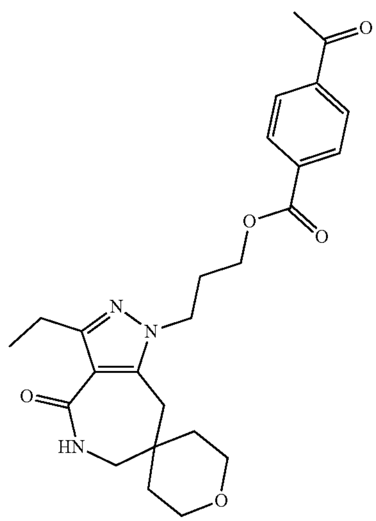 [SMILES: CCc1nn(CCCOC(=O)c2ccc(C(C)=O)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-acetylbenzoate | 2 | 2.00 | *** |
| 51 | 151 | 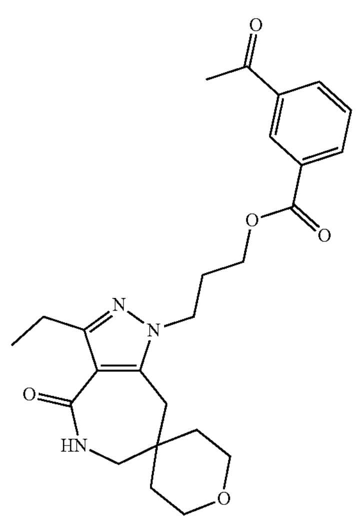 [SMILES: CCc1nn(CCCOC(=O)c2cccc(C(C)=O)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-acetylbenzoate | 2 | 1.99 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 52 | 152 | 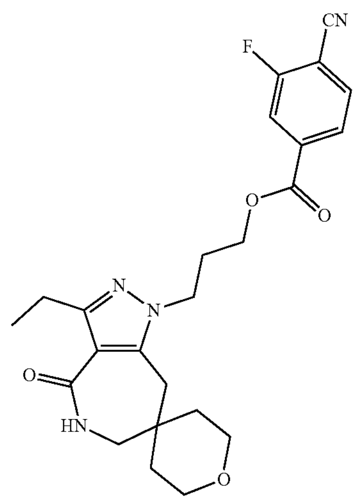 [SMILES: CCc1nn(CCCOC(=O)c2ccc(C#N)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-cyano-3-fluoro-benzoate | 2 | 2.07 | *** |
| 53 | 153 | 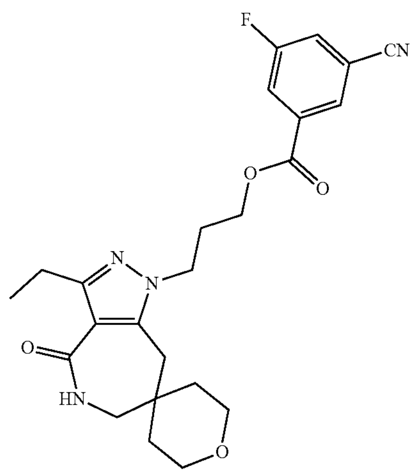 [SMILES: CCc1nn(CCCOC(=O)c2cc(F)cc(C#N)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-cyano-5-fluoro-benzoate | 2 | 2.06 | *** |
| 54 | 154 | 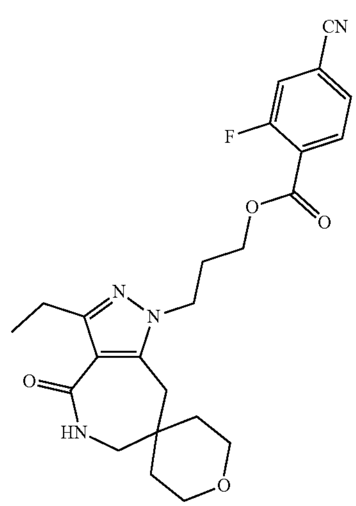 [SMILES: CCc1nn(CCCOC(=O)c2ccc(C#N)cc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-cyano-2-fluoro-benzoate | 1 | 2.04 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 55 | 155 | 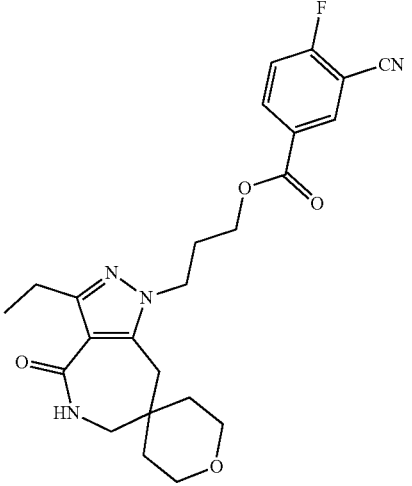 [SMILES: CCc1nn(CCCOC(=O)c2ccc(F)c(C#N)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-cyano-4-fluoro-benzoate | 2 | 2.06 | *** |
| 56 | 156 | 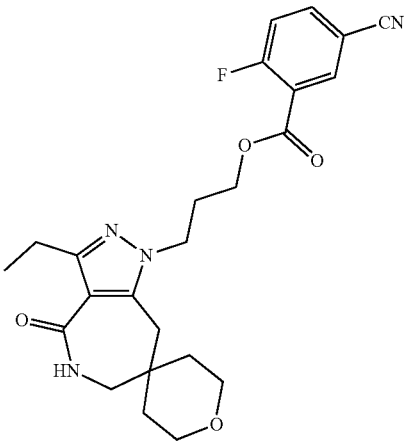 [SMILES: CCc1nn(CCCOC(=O)c2cc(C#N)ccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-cyano-2-fluoro-benzoate | 2 | 2.00 | *** |
| 57 | 157 | 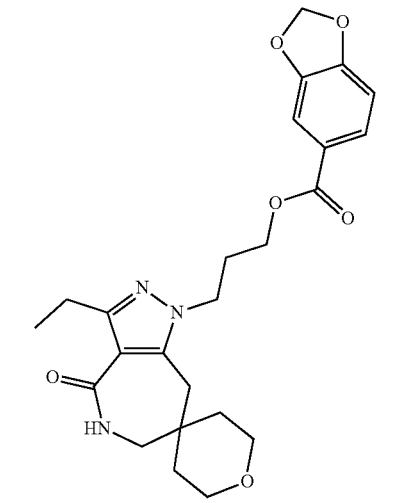 [SMILES: CCc1nn(CCCOC(=O)c2ccc3c(c2)OCO3)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 1,3-benzodioxole-5-carboxylate | 1 | 2.03 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 58 | 158 | 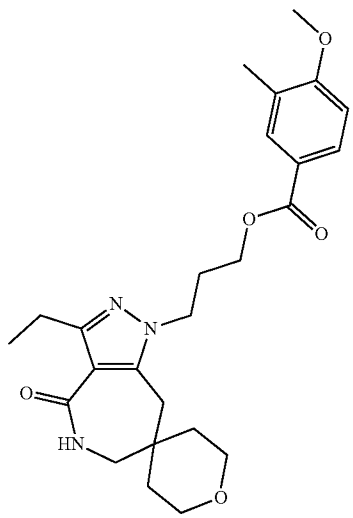 [SMILES: CCc1nn(CCCOC(=O)c2ccc(OC)c(C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methoxy-3-methyl-benzoate | 1 | 2.15 | *** |
| 59 | 159 | 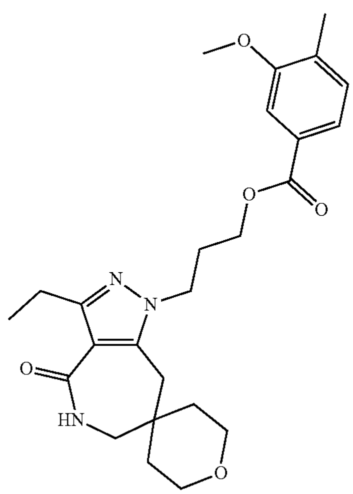 [SMILES: CCc1nn(CCCOC(=O)c2ccc(C)c(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methoxy-4-methyl-benzoate | 2 | 2.19 | *** |
| 60 | 160 | 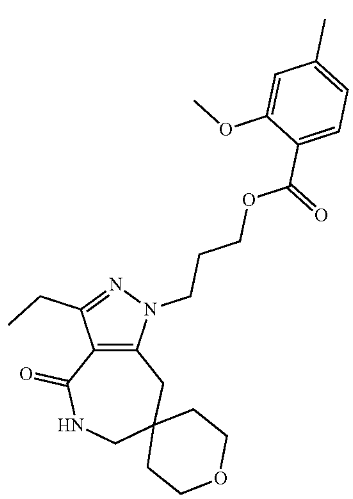 [SMILES: CCc1nn(CCCOC(=O)c2ccc(C)cc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methoxy-4-methyl-benzoate | 2 | 2.05 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 61 | 161 | 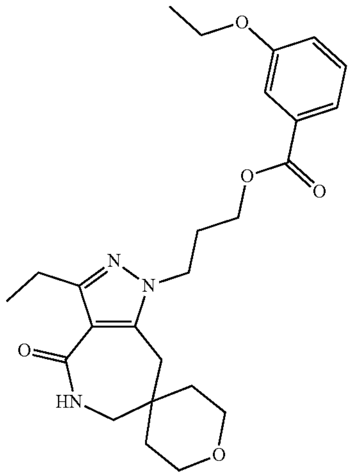 [SMILES: CCOc1cccc(C(=O)OCCCn2nc(CC)c3c2CC2(CCOCC2)CNC3=O)c1] | 3-(3-ethyl-4-oxo-spiro[6,8-dihydro-5H-pyrazolo[4,3-c]azepine-7,4'-tetrahydropyran]-1-yl)propyl 3-ethoxybenzoate | 2 | 2.16 | *** |
| 62 | 162 | 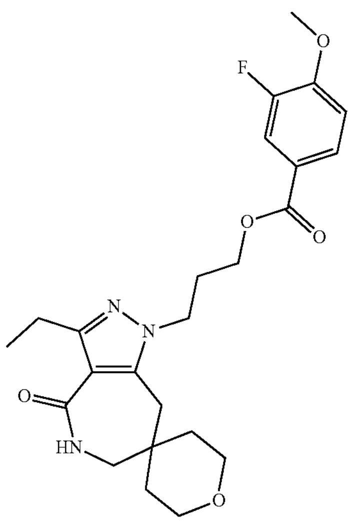 [SMILES: CCc1nn(CCCOC(=O)c2ccc(OC)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-4-methoxy-benzoate | 2 | 2.08 | *** |
| 63 | 163 | 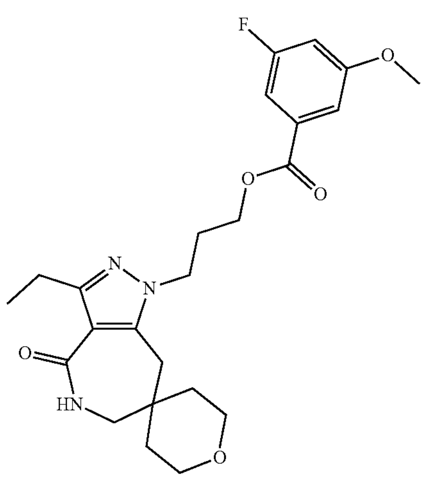 [SMILES: CCc1nn(CCCOC(=O)c2cc(F)cc(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-5-methoxy-benzoate | 2 | 2.13 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 64 | 164 | 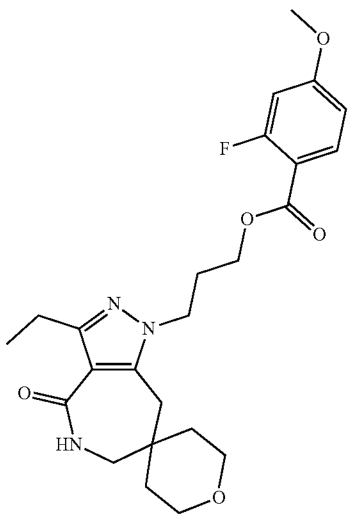 [SMILES: CCc1nn(CCCOC(=O)c2ccc(OC)cc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-4-methoxy-benzoate | 2 | 2.07 | *** |
| 65 | 165 | 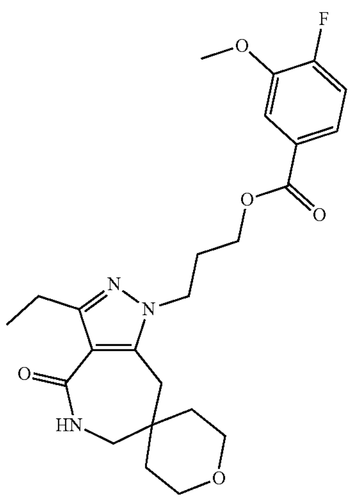 [SMILES: CCc1nn(CCCOC(=O)c2ccc(F)c(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluoro-3-methoxy-benzoate | 2 | 2.10 | *** |
| 66 | 166 | 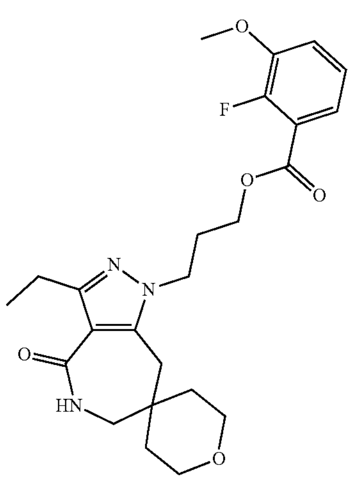 [SMILES: CCc1nn(CCCOC(=O)c2cccc(OC)c2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-3-methoxy-benzoate | 2 | 2.04 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 67 | 167 | 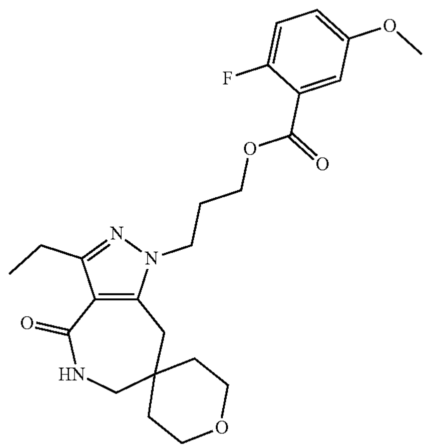 [SMILES: CCc1nn(CCCOC(=O)c2cc(OC)ccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-5-methoxy-benzoate | 2 | 2.07 | *** |
| 68 | 168 | 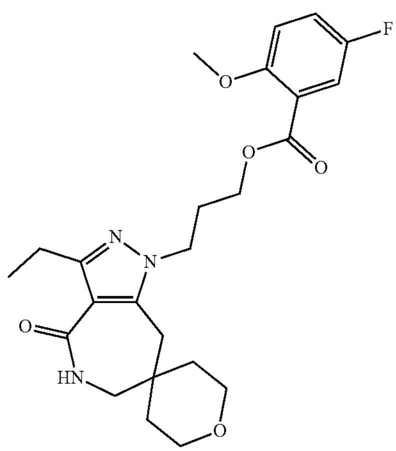 [SMILES: CCc1nn(CCCOC(=O)c2cc(F)ccc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-fluoro-2-methoxy-benzoate | 1 | 2.02 | *** |
| 69 | 169 | 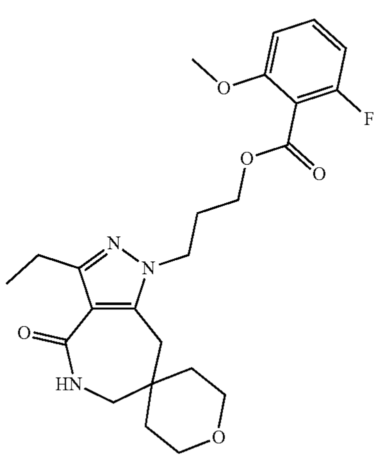 [SMILES: CCc1nn(CCCOC(=O)c2c(F)cccc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-6-methoxy-benzoate | 1 | 2.04 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 70 | 170 | 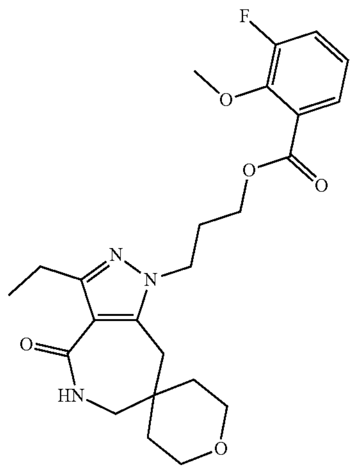 [SMILES: CCc1nn(CCCOC(=O)c2cccc(F)c2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-2-methoxy-benzoate | 2 | 2.08 | *** |
| 71 | 171 | 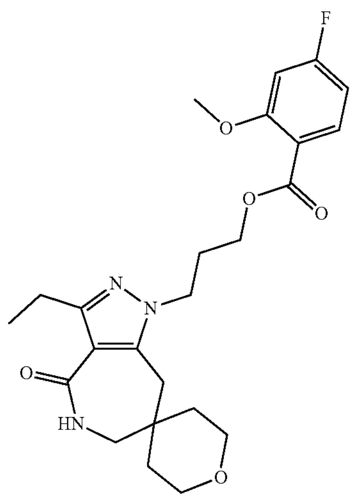 [SMILES: CCc1nn(CCCOC(=O)c2ccc(F)cc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluoro-2-methoxy-benzoate | 2 | 2.02 | *** |
| 72 | 172 | 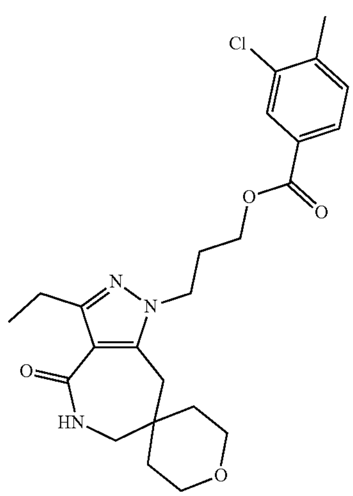 [SMILES: CCc1nn(CCCOC(=O)c2ccc(C)c(Cl)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-4-methyl-benzoate | 2 | 2.26 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 73 | 173 | 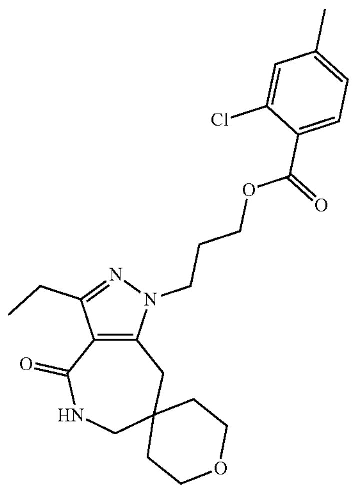 [SMILES: CCc1nn(CCCOC(=O)c2ccc(C)cc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-4-methyl-benzoate | 2 | 2.19 | *** |
| 74 | 174 | 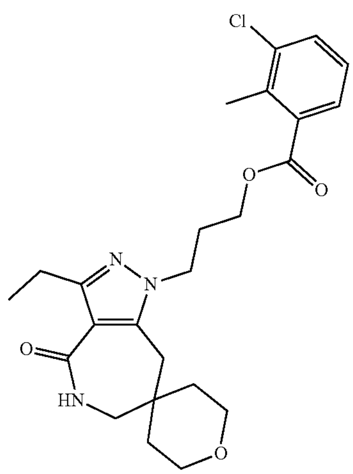 [SMILES: CCc1nn(CCCOC(=O)c2cccc(Cl)c2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-2-methyl-benzoate | 2 | 2.26 | *** |
| 75 | 175 | 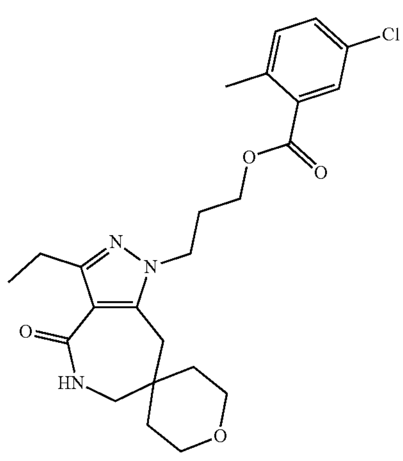 [SMILES: CCc1nn(CCCOC(=O)c2cc(Cl)ccc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-chloro-2-methyl-benzoate | 2 | 2.25 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 76 | 176 | 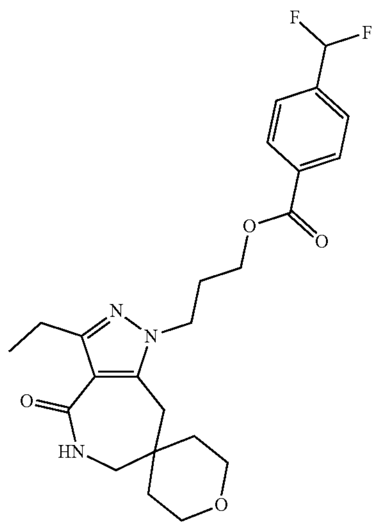 [SMILES: CCc1nn(CCCOC(=O)c2ccc(C(F)F)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(difluoromethyl)benzoate | 2 | 2.12 | *** |
| 77 | 177 | 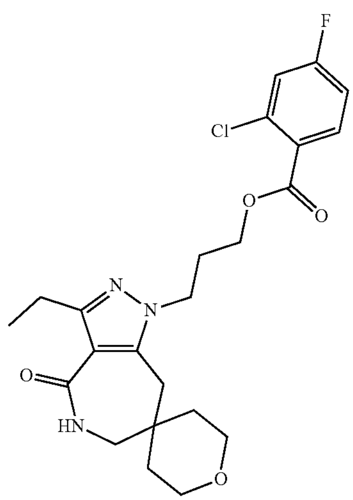 [SMILES: CCc1nn(CCCOC(=O)c2ccc(F)cc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-4-fluoro-benzoate | 2 | 2.15 | *** |
| 78 | 178 | 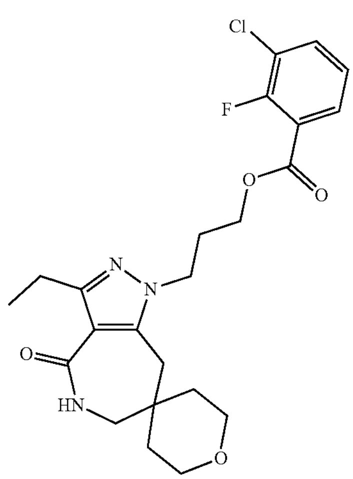 [SMILES: CCc1nn(CCCOC(=O)c2cccc(Cl)c2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-2-fluoro-benzoate | 2 | 2.15 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 79 | 179 | 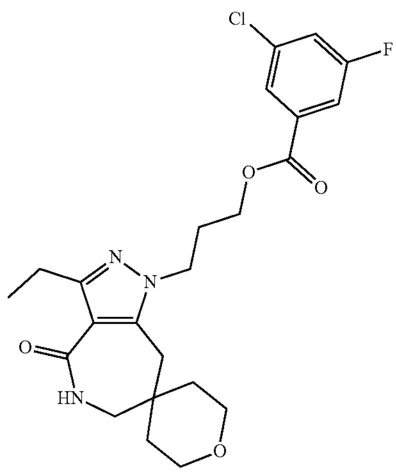 [SMILES: CCc1nn(CCCOC(=O)c2cc(F)cc(Cl)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-5-fluoro-benzoate | 2 | 2.21 | *** |
| 80 | 180 | 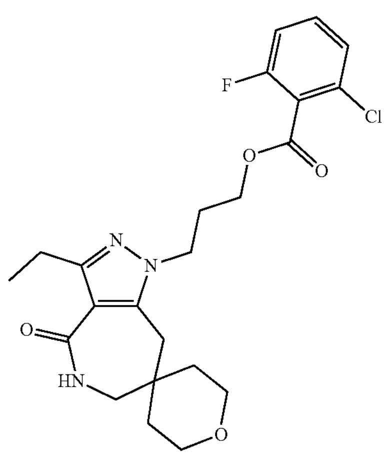 [SMILES: CCc1nn(CCCOC(=O)c2c(F)cccc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-6-fluoro-benzoate | 2 | 2.12 | *** |
| 81 | 181 | 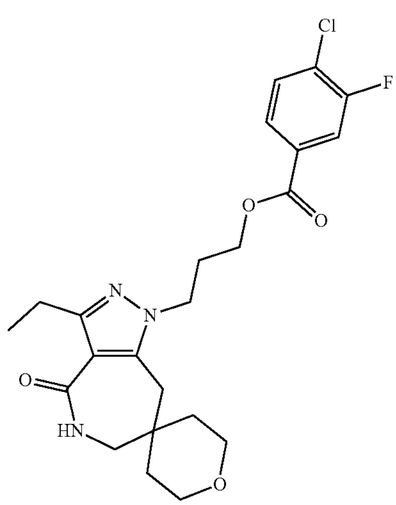 [SMILES: CCc1nn(CCCOC(=O)c2ccc(Cl)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-chloro-3-fluoro-benzoate | 2 | 2.21 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 82 | 182 | 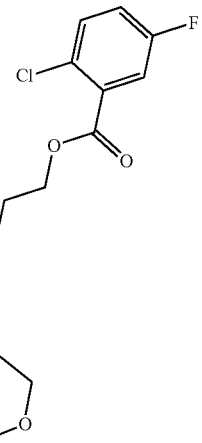 | 3-(3-ethyl-4-oxo-spiro[6,8-dihydro-5H-pyrazolo[4,3-c]azepine-7,4'-tetrahydropyran]-1-yl)propyl 2-chloro-5-fluoro-benzoate | 2 | 2.14 | *** |
| 83 | 183 | 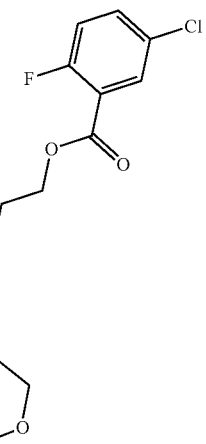 | 3-(3-ethyl-4-oxo-spiro[6,8-dihydro-5H-pyrazolo[4,3-c]azepine-7,4'-tetrahydropyran]-1-yl)propyl 5-chloro-2-fluoro-benzoate | 2 | 2.15 | *** |
| 84 | 184 | 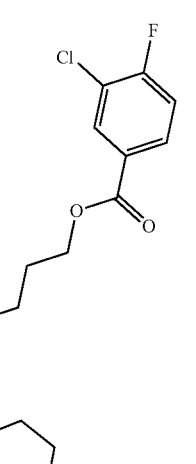 | 3-(3-ethyl-4-oxo-spiro[6,8-dihydro-5H-pyrazolo[4,3-c]azepine-7,4'-tetrahydropyran]-1-yl)propyl 3-chloro-4-fluoro-benzoate | 2 | 2.20 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 85 | 185 | 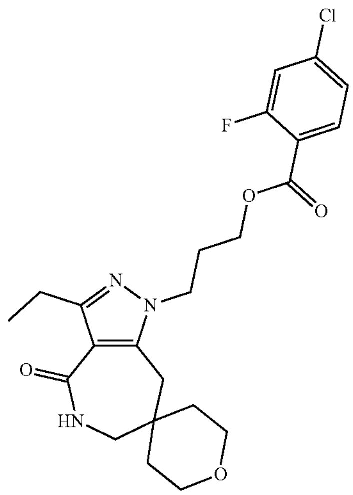 [SMILES: CCc1nn(CCCOC(=O)c2ccc(Cl)cc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-chloro-2-fluoro-benzoate | 2 | 2.18 | *** |
| 86 | 186 | 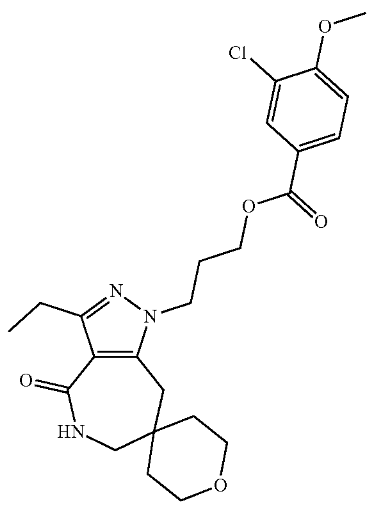 [SMILES: CCc1nn(CCCOC(=O)c2ccc(OC)c(Cl)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-4-methoxy-benzoate | 2 | 2.14 | *** |
| 87 | 187 | 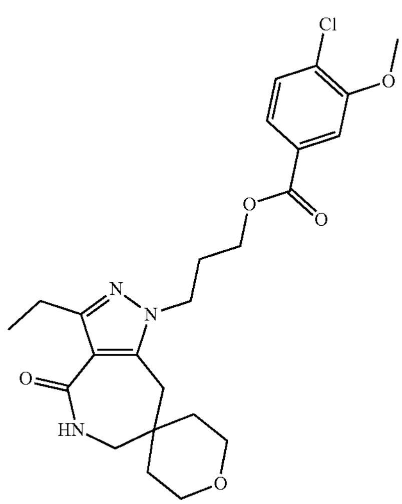 [SMILES: CCc1nn(CCCOC(=O)c2ccc(Cl)c(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-chloro-3-methoxy-benzoate | 2 | 2.19 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 88 | 188 | 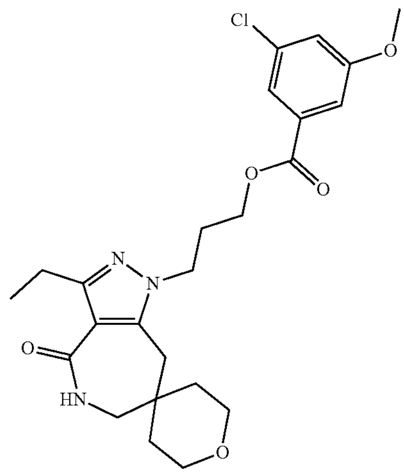 [SMILES: CCc1nn(CCCOC(=O)c2cc(Cl)cc(OC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-5-methoxy-benzoate | 2 | 2.22 | *** |
| 89 | 189 | 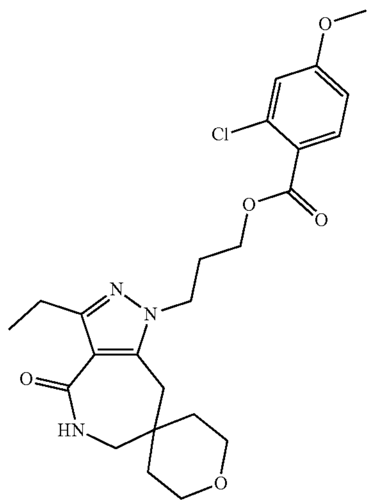 [SMILES: CCc1nn(CCCOC(=O)c2ccc(OC)cc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-4-methoxy-benzoate | 2 | 2.14 | *** |
| 90 | 190 | 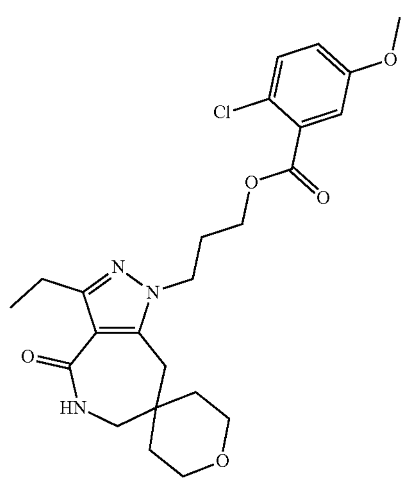 [SMILES: CCc1nn(CCCOC(=O)c2cc(OC)ccc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-5-methoxy-benzoate | 2 | 2.14 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 91 | 191 | 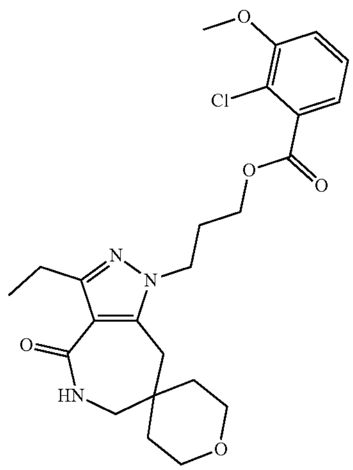 | 3-(3-ethyl-4-oxo-spiro[6,8-dihydro-5H-pyrazolo[4,3-c]azepine-7,4'-tetrahydropyran]-1-yl)propyl 2-chloro-3-methoxy-benzoate | 2 | 2.08 | *** |
| 92 | 192 | 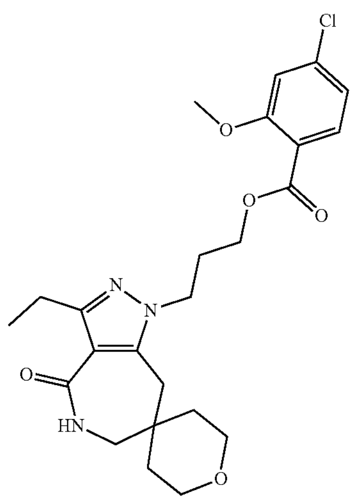 | 3-(3-ethyl-4-oxo-spiro[6,8-dihydro-5H-pyrazolo[4,3-c]azepine-7,4'-tetrahydropyran]-1-yl)propyl 4-chloro-2-methoxy-benzoate | 2 | 2.12 | *** |
| 93 | 193 | 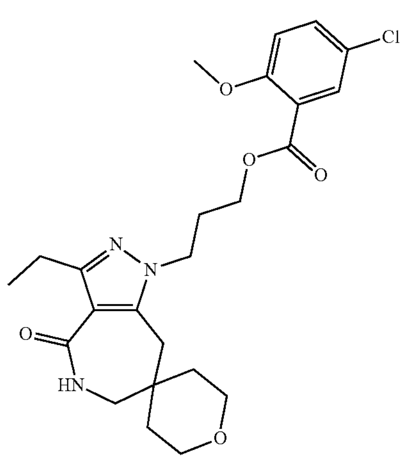 [SMILES: CCc1nn(CCCOC(=O)c2cc(Cl)ccc2OC)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-chloro-2-methoxy-benzoate | 2 | 2.10 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 94 | 194 | 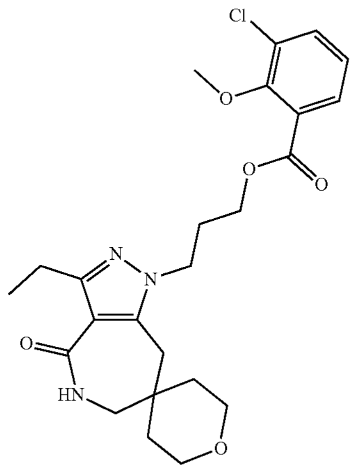 | 3-(3-ethyl-4-oxo-spiro[6,8-dihydro-5H-pyrazolo[4,3-c]azepine-7,4'-tetrahydropyran]-1-yl)propyl 3-chloro-2-methoxy-benzoate | 2 | 2.16 | *** |
| 95 | 195 | 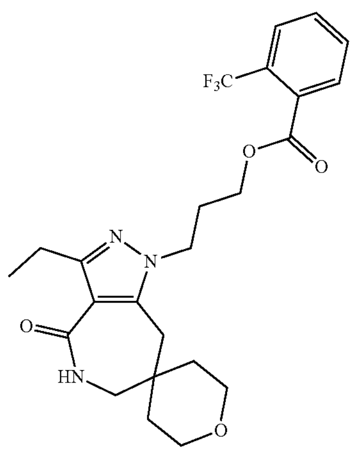 [SMILES: CCc1nn(CCCOC(=O)c2ccccc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-(trifluoromethyl)benzoate | 1 | 2.16 | *** |
| 96 | 196 | 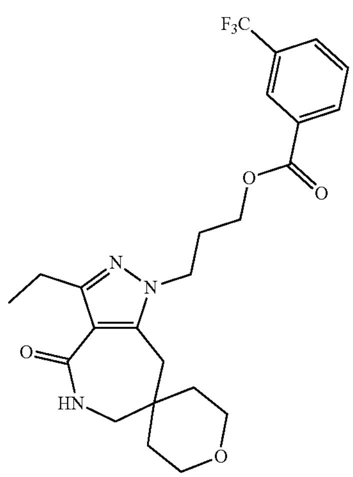 [SMILES: CCc1nn(CCCOC(=O)c2cccc(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(trifluoromethyl)benzoate | 2 | 2.22 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 97 | 197 | 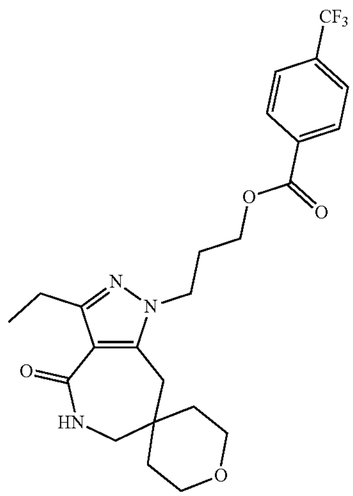 [SMILES: CCc1nn(CCCOC(=O)c2ccc(C(F)(F)F)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(trifluoromethyl)benzoate | 2 | 2.24 | *** |
| 98 | 198 | 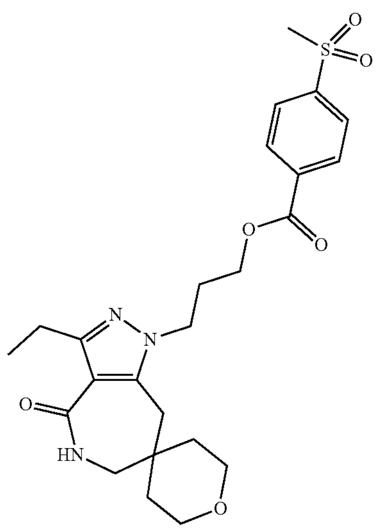 [SMILES: CCc1nn(CCCOC(=O)c2ccc(S(C)(=O)=O)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methylsulfonylbenzoate | 1 | 1.91 | *** |
| 99 | 199 | 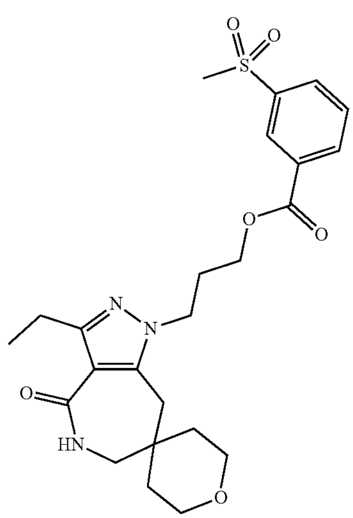 [SMILES: CCc1nn(CCCOC(=O)c2cccc(S(C)(=O)=O)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-methylsulfonylbenzoate | 2 | 1.90 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 100 | 200 | 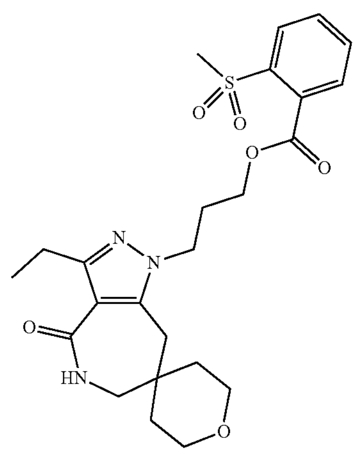 [SMILES: CCc1nn(CCCOC(=O)c2ccccc2S(C)(=O)=O)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methylsulfonylbenzoate | 2 | 1.91 | *** |
| 101 | 201 | 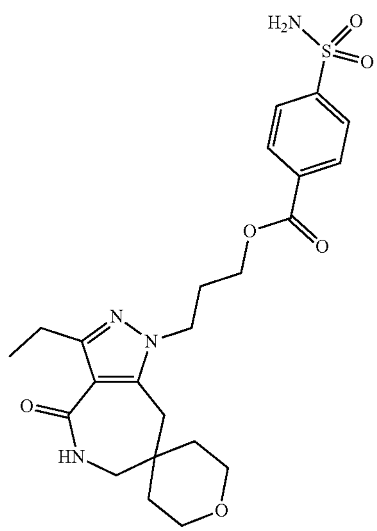 [SMILES: CCc1nn(CCCOC(=O)c2ccc(S(N)(=O)=O)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-sulfamoylbenzoate | 2 | 1.84 | *** |
| 102 | 202 | 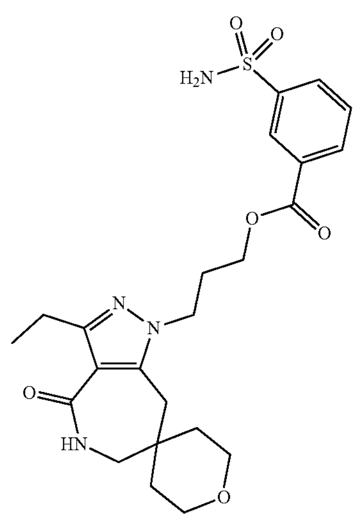 [SMILES: CCc1nn(CCCOC(=O)c2cccc(S(N)(=O)=O)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-sulfamoylbenzoate | 1 | 1.85 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 103 | 203 | 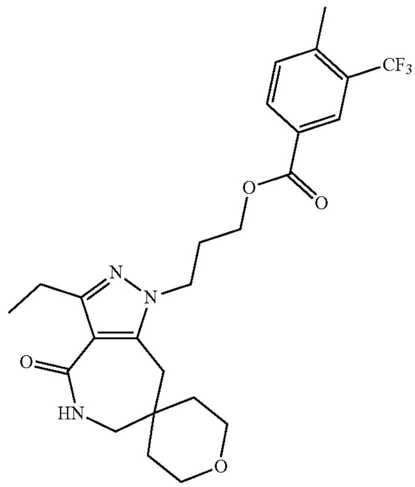 [SMILES: CCc1nn(CCCOC(=O)c2ccc(C)c(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methyl-3-(trifluoromethyl)benzoate | 2 | 2.30 | *** |
| 104 | 204 | 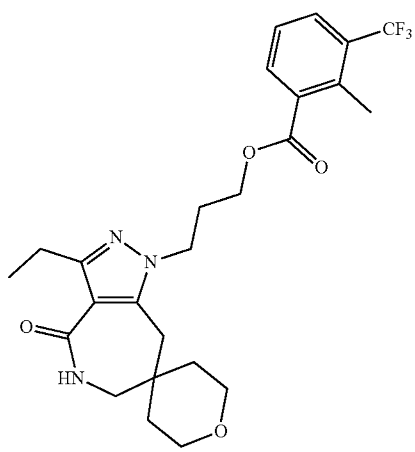 [SMILES: CCc1nn(CCCOC(=O)c2cccc(C(F)(F)F)c2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyl-3-(trifluoromethyl)benzoate | 2 | 2.29 | *** |
| 105 | 205 | 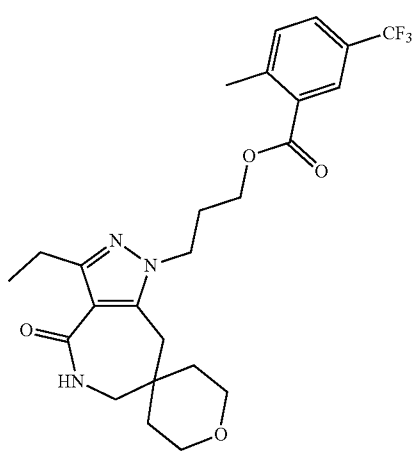 [SMILES: CCc1nn(CCCOC(=O)c2cc(C(F)(F)F)ccc2C)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-methyl-5-(trifluoromethyl)benzoate | 2 | 2.30 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 106 | 206 | 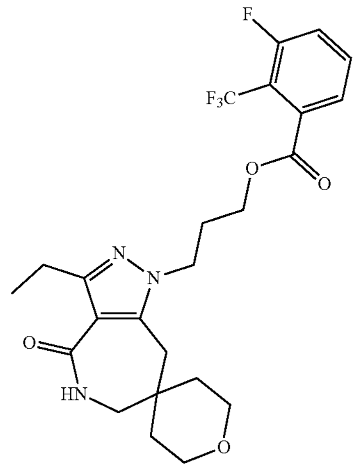 [SMILES: CCc1nn(CCCOC(=O)c2cccc(F)c2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-2-(trifluoromethyl)benzoate | 2 | 2.19 | *** |
| 107 | 207 | 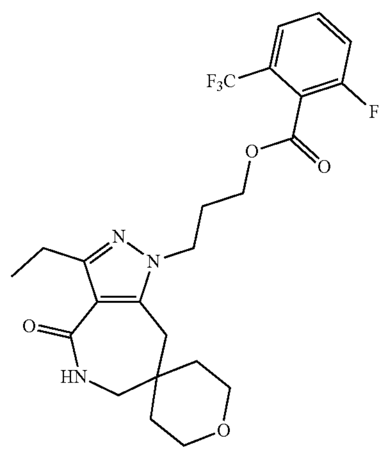 [SMILES: CCc1nn(CCCOC(=O)c2c(F)cccc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-6-(trifluoromethyl)benzoate | 2 | 2.18 | *** |
| 108 | 208 | 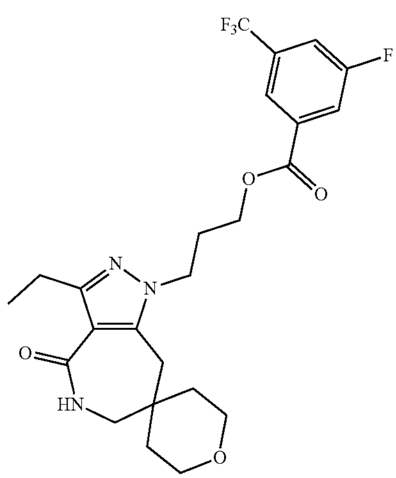 | 3-(3-ethyl-4-oxo-spiro[6,8-dihydro-5H-pyrazolo[4,3-c]azepine-7,4'-tetrahydropyran]-1-yl)propyl 3-fluoro-5-(trifluoromethyl)benzoate | 2 | 2.27 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 109 | 209 | 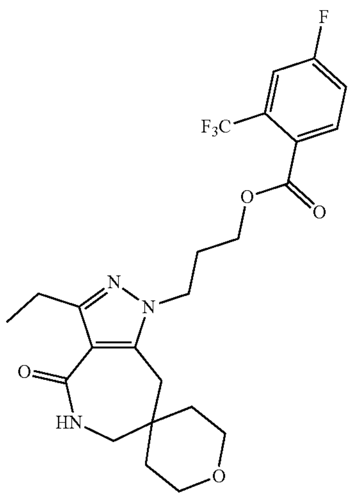 [SMILES: CCc1nn(CCCOC(=O)c2ccc(F)cc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-fluoro-2-(trifluoromethyl)benzoate | 2 | 2.21 | *** |
| 110 | 210 | 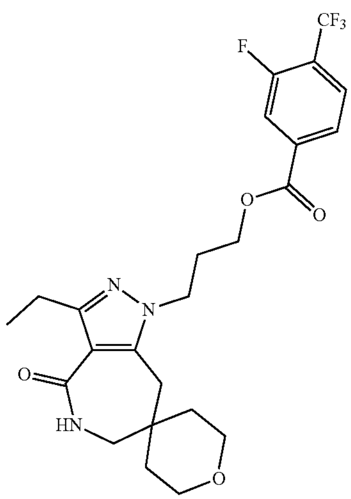 [SMILES: CCc1nn(CCCOC(=O)c2ccc(C(F)(F)F)c(F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-fluoro-4-(trifluoromethyl)benzoate | 2 | 2.27 | *** |
| 111 | 211 | 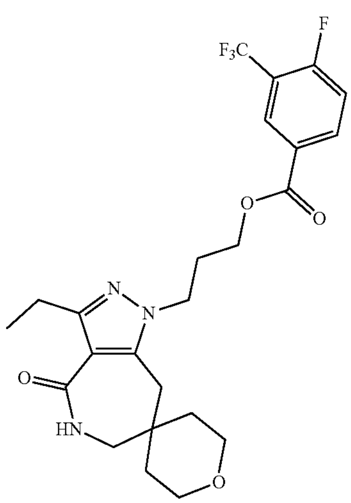 | 3-(3-ethyl-4-oxo-spiro[6,8-dihydro-5H-pyrazolo[4,3-c]azepine-7,4'-tetrahydropyran]-1-yl)propyl 4-fluoro-3-(trifluoromethyl)benzoate | 2 | 2.25 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 112 | 212 | 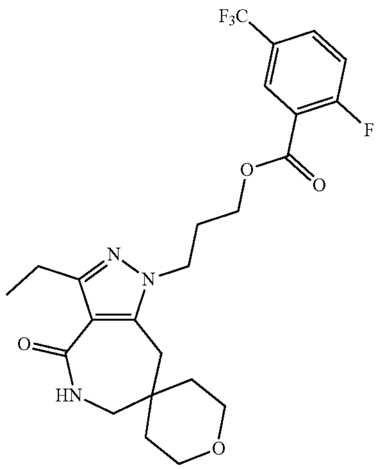 [SMILES: CCc1nn(CCCOC(=O)c2cc(C(F)(F)F)ccc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-5-(trifluoromethyl)benzoate | 2 | 2.21 | *** |
| 113 | 213 | 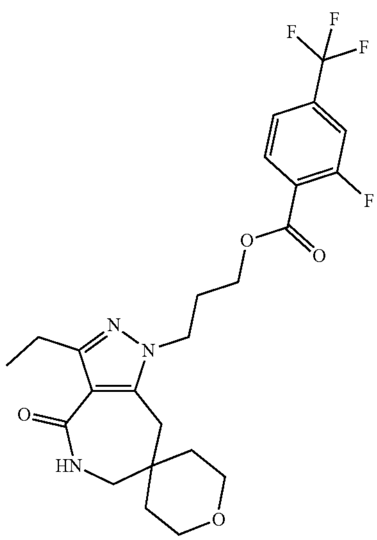 [SMILES: CCc1nn(CCCOC(=O)c2ccc(C(F)(F)F)cc2F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-fluoro-4-(trifluoromethyl)benzoate | 2 | 2.24 | *** |
| 114 | 214 | 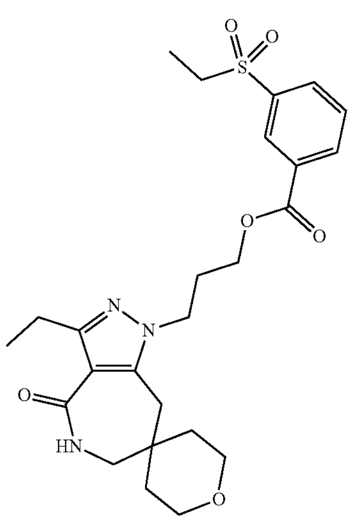 [SMILES: CCc1nn(CCCOC(=O)c2cccc(S(=O)(=O)CC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-ethylsulfonylbenzoate | 2 | 1.96 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 115 | 215 | 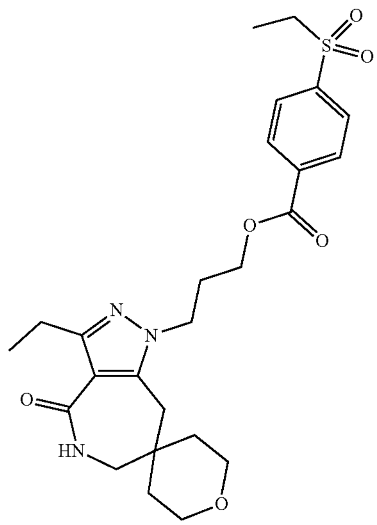 [SMILES: CCc1nn(CCCOC(=O)c2ccc(S(=O)(=O)CC)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-ethylsulfonylbenzoate | 2 | 1.97 | *** |
| 116 | 216 | 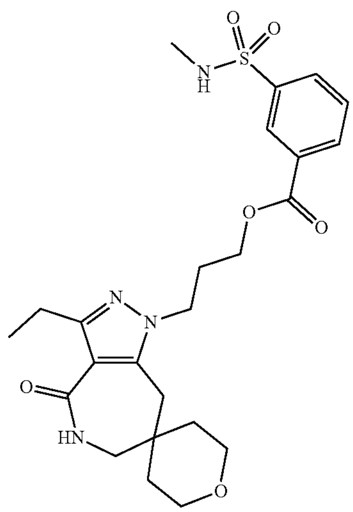 [SMILES: CCc1nn(CCCOC(=O)c2cccc(S(=O)(=O)NC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(methylsulfamoyl)benzoate | 2 | 1.93 | *** |
| 117 | 217 | 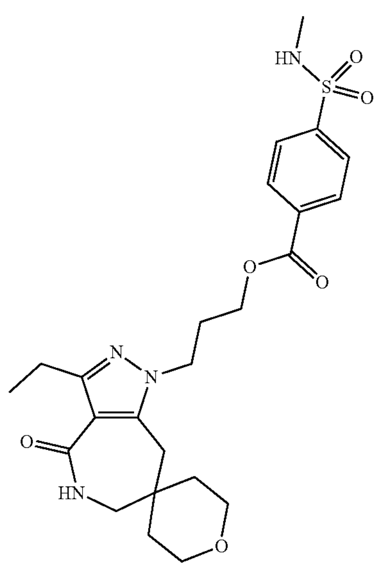 [SMILES: CCc1nn(CCCOC(=O)c2ccc(S(=O)(=O)NC)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(methylsulfamoyl)benzoate | 2 | 1.93 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 118 | 218 | 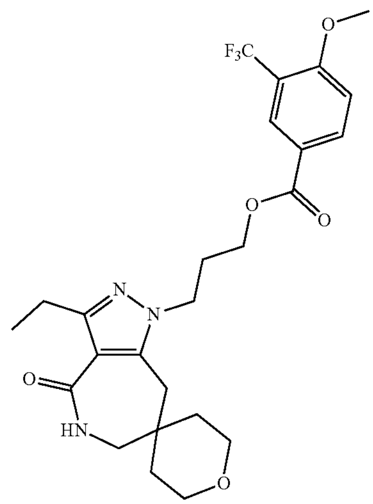 [SMILES: CCc1nn(CCCOC(=O)c2ccc(OC)c(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-methoxy-3-(trifluoromethyl)benzoate | 2 | 2.22 | *** |
| 119 | 219 | 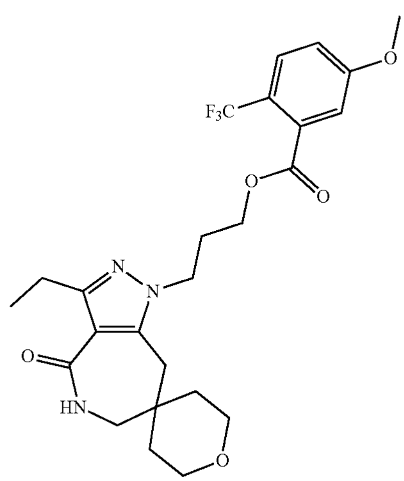 [SMILES: CCc1nn(CCCOC(=O)c2cc(OC)ccc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-methoxy-2-(trifluoromethyl)benzoate | 2 | 2.21 | *** |
| 120 | 220 | 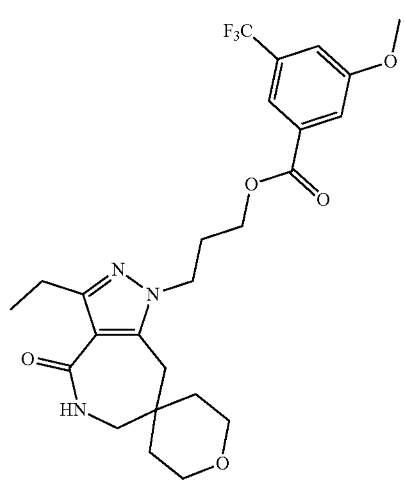 | 3-(3-ethyl-4-oxo-spiro[6,8-dihydro-5H-pyrazolo[4,3-c]azepine-7,4'-tetrahydropyran]-1-yl)propyl 3-methoxy-5-(trifluoromethyl)benzoate | 2 | 2.27 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 121 | 221 | 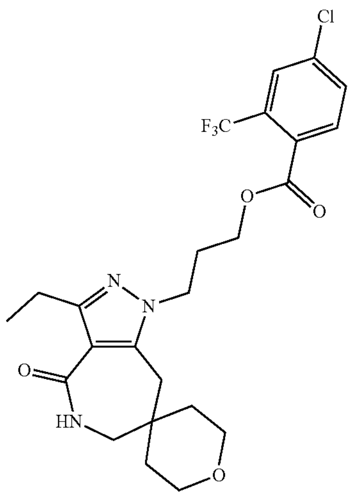 | 3-(3-ethyl-4-oxo-spiro[6,8-dihydro-5H-pyrazolo[4,3-c]azepine-7,4'-tetrahydropyran]-1-yl)propyl 4-chloro-2-(trifluoromethyl)benzoate | 2 | 2.30 | *** |
| 122 | 222 | 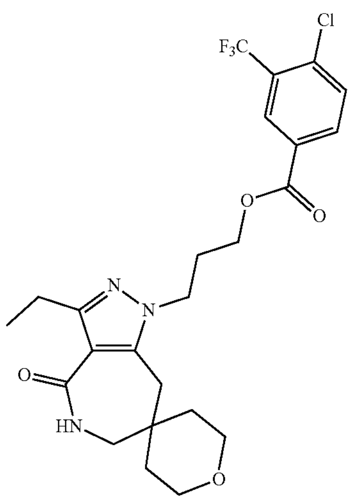 [SMILES: CCc1nn(CCCOC(=O)c2ccc(Cl)c(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-chloro-3-(trifluoromethyl)benzoate | 2 | 2.33 | *** |
| 123 | 223 | 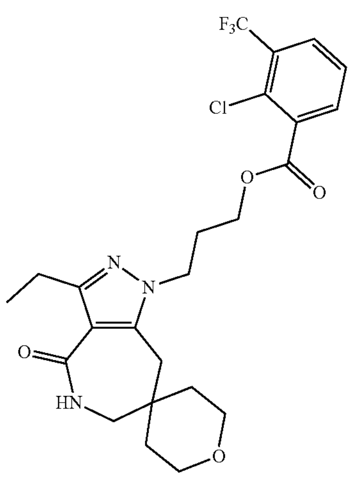 [SMILES: CCc1nn(CCCOC(=O)c2cccc(C(F)(F)F)c2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-3-(trifluoromethyl)benzoate | 2 | 2.25 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 124 | 224 | 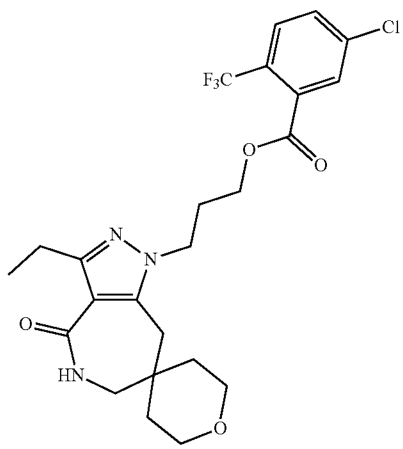 [SMILES: CCc1nn(CCCOC(=O)c2cc(Cl)ccc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 5-chloro-2-(trifluoromethyl)benzoate | 2 | 2.28 | *** |
| 125 | 225 | 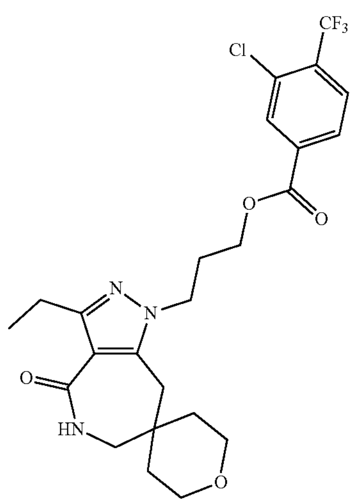 [SMILES: CCc1nn(CCCOC(=O)c2ccc(C(F)(F)F)c(Cl)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-4-(trifluoromethyl)benzoate | 2 | 2.33 | *** |
| 126 | 226 | 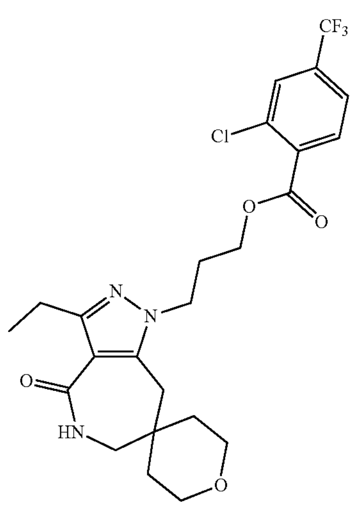 | 3-(3-ethyl-4-oxo-spiro[6,8-dihydro-5H-pyrazolo[4,3-c]azepine-7,4'-tetrahydropyran]-1-yl)propyl 2-chloro-4-(trifluoromethyl)benzoate | 2 | 2.30 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 127 | 227 | 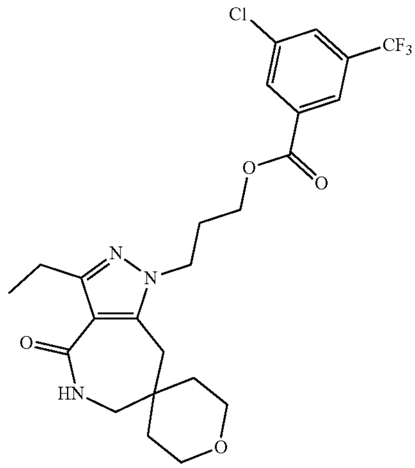 [SMILES: CCc1nn(CCCOC(=O)c2cc(Cl)cc(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-chloro-5-(trifluoromethyl)benzoate | 2 | 2.35 | *** |
| 128 | 228 | 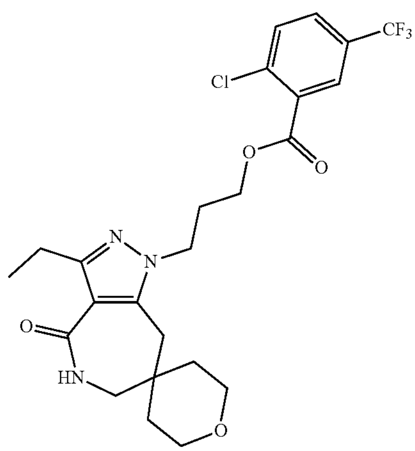 [SMILES: CCc1nn(CCCOC(=O)c2cc(C(F)(F)F)ccc2Cl)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2-chloro-5-(trifluoromethyl)benzoate | 2 | 2.28 | *** |
| 129 | 229 | 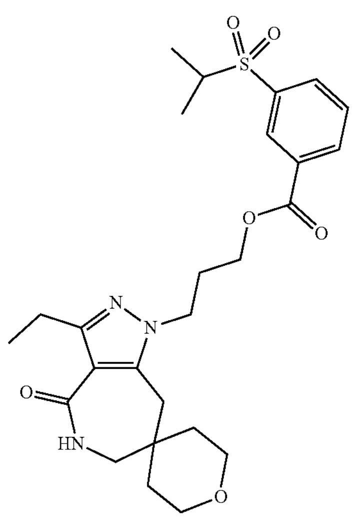 [SMILES: CCc1nn(CCCOC(=O)c2cccc(S(=O)(=O)C(C)C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-isopropylsulfonylbenzoate | 2 | 2.02 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 130 | 230 | 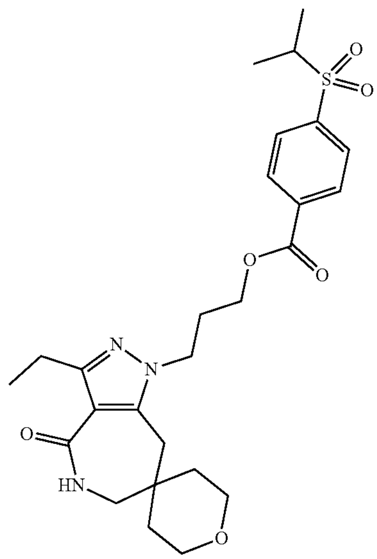 [SMILES: CCc1nn(CCCOC(=O)c2ccc(S(=O)(=O)C(C)C)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-isopropylsulfonylbenzoate | 2 | 2.02 | *** |
| 131 | 231 | 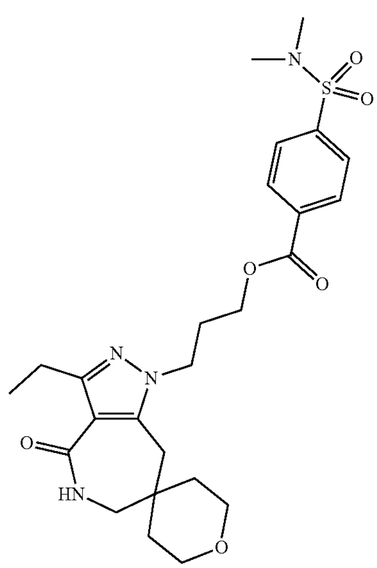 [SMILES: CCc1nn(CCCOC(=O)c2ccc(S(=O)(=O)N(C)C)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(dimethylsulfamoyl)benzoate | 2 | 2.03 | *** |

TABLE 2-continued
| Ex. | Cmpd | Structure | IUPAC Name | G.P. | HPLC Rt (min) | PDE4 IC$_{50}$ range |
|---|---|---|---|---|---|---|
| 132 | 232 | 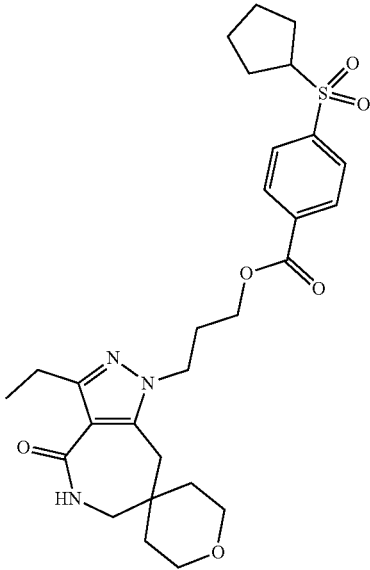 [SMILES: CCc1nn(CCCOC(=O)c2ccc(S(=O)(=O)C3CCCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-cyclopentylsulfonyl-benzoate | 2 | 2.13 | ** |
| 133 | 233 | 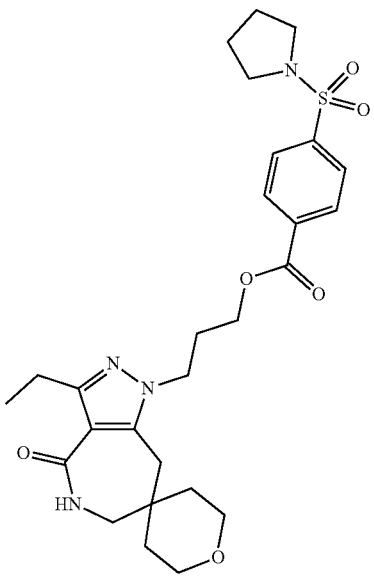 [SMILES: CCc1nn(CCCOC(=O)c2ccc(S(=O)(=O)N3CCCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-pyrrolidin-1-ylsulfonylbenzoate | 2 | 2.11 | |

TABLE 2-continued

| Ex. | Cmpd | Structure | IUPAC Name | G.P. | HPLC Rt (min) | PDE4 IC$_{50}$ range |
|---|---|---|---|---|---|---|
| 134 | 234 | 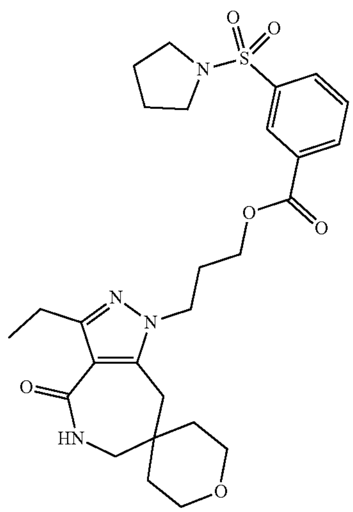 [SMILES: CCc1nn(CCCOC(=O)c2cccc(S(=O)(=O)N3CCCC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-pyrrolidin-1-ylsulfonylbenzoate | 2 | 2.10 | |
| 135 | 235 | 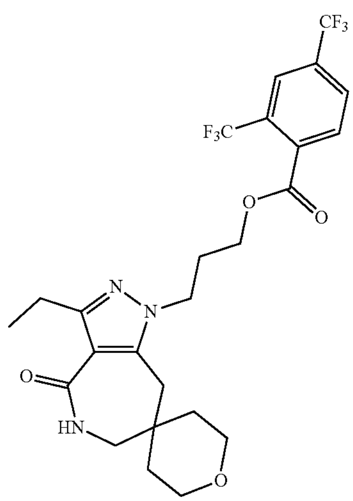 [SMILES: CCc1nn(CCCOC(=O)c2ccc(C(F)(F)F)cc2C(F)(F)F)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 2,4-bis(trifluoromethyl)benzoate | 2 | 2.34 | *** |
| 136 | 236 | 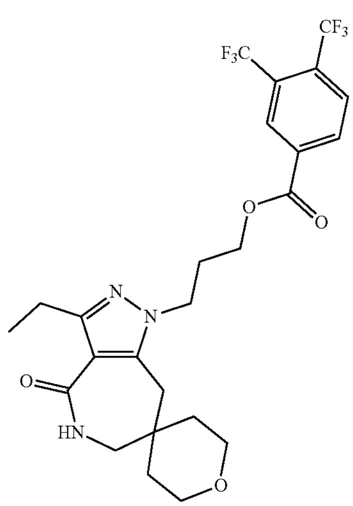 [SMILES: CCc1nn(CCCOC(=O)c2ccc(C(F)(F)F)c(C(F)(F)F)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3,4-bis(trifluoromethyl)benzoate | 2 | 2.37 | *** |

TABLE 2-continued

| Ex. | Cmpd | Structure | IUPAC Name | G.P. | HPLC Rt (min) | PDE4 IC$_{50}$ range |
|---|---|---|---|---|---|---|
| 137 | 237 | 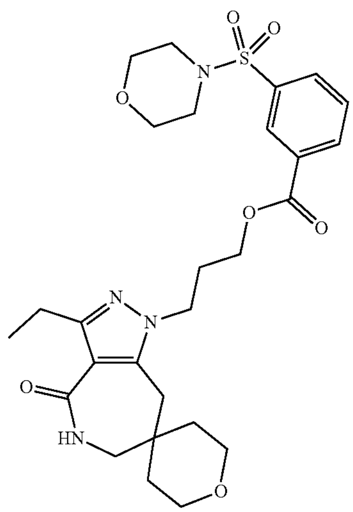 [SMILES: CCc1nn(CCCOC(=O)c2cccc(S(=O)(=O)N3CCOCC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-morpholinosulfonyl-benzoate | 2 | 2.02 | |
| 138 | 238 | 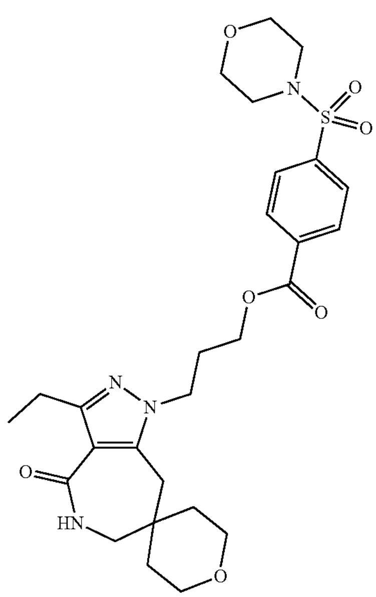 [SMILES: CCc1nn(CCCOC(=O)c2ccc(S(=O)(=O)N3CCOCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-morpholinosulfonyl-benzoate | 2 | 2.03 | |

TABLE 2-continued

| Ex. | Cmpd | Structure | IUPAC Name | G.P. | HPLC Rt (min) | PDE4 IC$_{50}$ range |
|---|---|---|---|---|---|---|
| 139 | 239 | 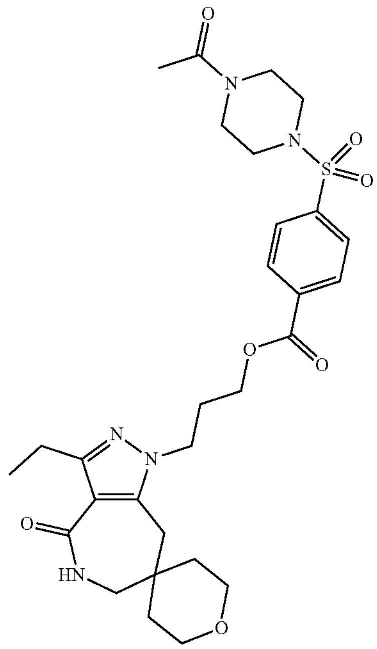 [SMILES: CCc1nn(CCCOC(=O)c2ccc(S(=O)(=O)N3CCN(C(C)=O)CC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(4-acetylpiperazin-1-yl)sulfonylbenzoate | 2 | 1.95 | |

Preparation 18 (Compound 240)

3-(3-Ethyl-4-oxo-spiro[6,8-dihydro-5H-pyrazolo[4,3-c]azepine-7,4'-tetrahydropyran]-1-yl)propyl 4-formylbenzoate

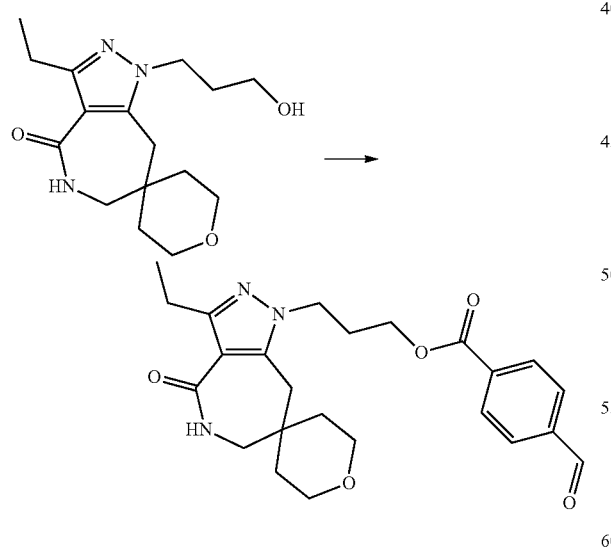

To a solution of 3-ethyl-1-(3-hydroxypropyl)spiro[6,8-dihydro-5H-pyrazolo[4,3-c]azepine-7,4-tetrahydropyran]-4-one (250 mg, 0.81 mmol) in MeCN (3 mL) was added 4-formylbenzoic acid (147 mg, 0.98 mmol), EDAC (187 mg, 0.98 mmol) and DMAP (10 mg, 0.082 mmol). The mixture was stirred overnight at 50° C. before it was evaporated to dryness under vacuum. Silica gel (100-200 mesh) column chromatography (0 to 15% MeOH in DCM as eluent) afforded the title compound.

Preparation 19 (Compound 241)

4-[3-(3-Ethyl-4-oxo-spiro[6,8-dihydro-5H-pyrazolo[4,3-c]azepine-7,4'-tetrahydropyran]-1-yl)propoxy-carbonyl]benzoic Acid

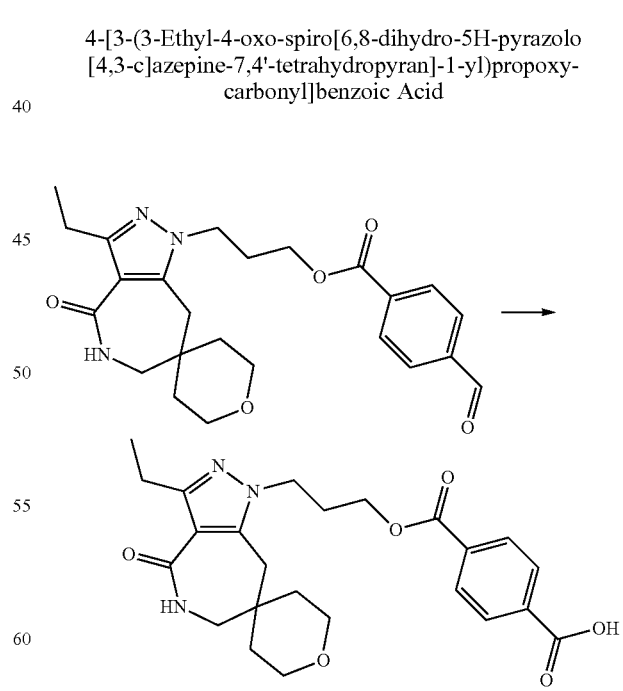

Jones Reagent (5 mL) was at 0° C. added to a solution of 3-(3-ethyl-4-oxo-spiro[6,8-dihydro-5H-pyrazolo[4,3-c]azepine-7,4'-tetrahydropyran]-1-yl)propyl 4-formylbenzoate (308 mg, 0.701 mmol) in acetone/water (45 mL, 2:1).

The solution was stirred at room temperature for 18 hours before isopropanol (5 mL) was added. The obtained mixture was stirred for another 30 min, diluted with water and extracted three times with DCM. The combined organic phases were concentrated in vacuo. Silica gel (100-200 mesh) column chromatography (0 to 15% MeOH in DCM as eluent) afforded the title compound.

$^1$H NMR (DMSO-d6) δ: 13.34 (s, 1H), 8.12-7.91 (m, 4H), 7.39 (t, J=5.7 Hz, 1H), 4.31 (t, J=5.9 Hz, 2H), 4.17 (t, J=6.6 Hz, 2H), 3.65-3.40 (m, 4H), 2.99 (d, J=5.7 Hz, 2H), 2.80-2.64 (m, 4H), 2.29-2.15 (m, 2H), 1.38 (t, J=5.4 Hz, 4H), 1.09 (t, J=7.5 Hz, 3H).

General Procedure 3: Amide Formation

DMF (0.2 mL) solutions of the acid (0.022 mmol), DIPEA (3 equiv.) and HATU (1.2 equiv.) were added to a vial containing an amine (2 equiv.) and the mixture was shaken at room temperature overnight. The crude was subjected to preparative LCMS purification, giving an amide.

The Examples 140-149 in Table 3 were prepared by reacting Compound 241 as described in General Procedure 3 with the appropriate amine:

TABLE 3

| Ex. | Cmpd | Structure | IUPAC Name | HPLC Rt (min) | PDE4 IC$_{50}$ range |
|---|---|---|---|---|---|
| 140 | 242 | 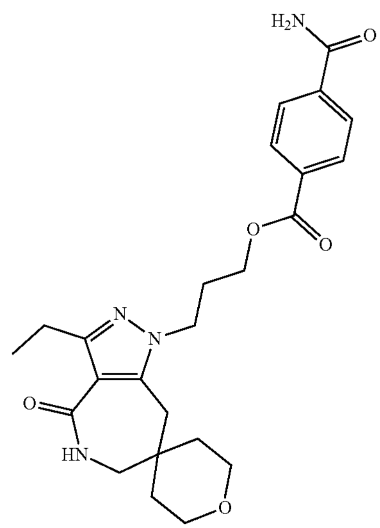 [SMILES: CCc1nn(CCCOC(=O)c2ccc(C(N)=O)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-carbamoylbenzoate | 1.78 | *** |
| 141 | 243 | 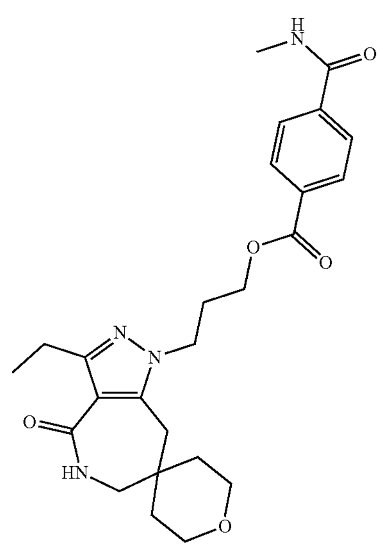 [SMILES: CCc1nn(CCCOC(=O)c2ccc(C(=O)NC)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(methylcarbamoyl)benzoate | 1.83 | *** |

TABLE 3-continued

| Ex. | Cmpd | Structure | IUPAC Name | HPLC Rt (min) | PDE4 IC$_{50}$ range |
|---|---|---|---|---|---|
| 142 | 244 | 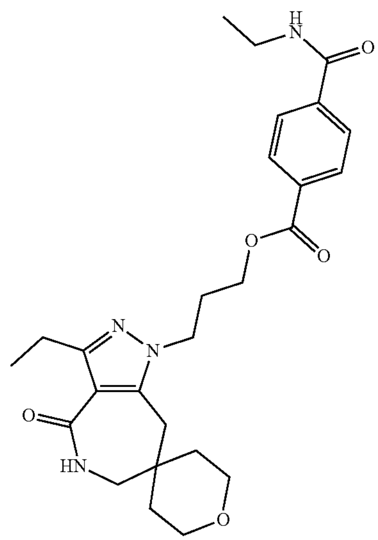 [SMILES: CCNC(=O)c1ccc(C(=O)OCCCn2nc(CC)c3c2CC2(CCOCC2)CNC3=O)cc1] | 3-(3-ethyl-4-oxo-spiro[6,8-dihydro-5H-pyrazolo[4,3-c]azepine-7,4'-tetrahydropyran]-1-yl)propyl 4-(ethylcarbamoyl)benzoate | 1.89 | *** |
| 143 | 245 | 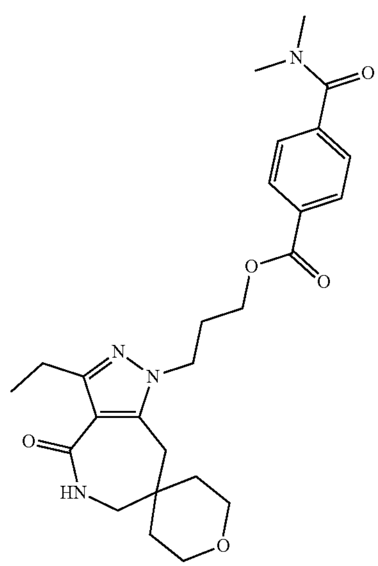 [SMILES: CCc1nn(CCCOC(=O)c2ccc(C(=O)N(C)C)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(dimethylcarbamoyl)-benzoate | 1.86 | ** |

TABLE 3-continued

| Ex. | Cmpd | Structure | IUPAC Name | HPLC Rt (min) | PDE4 IC$_{50}$ range |
|---|---|---|---|---|---|
| 144 | 246 | 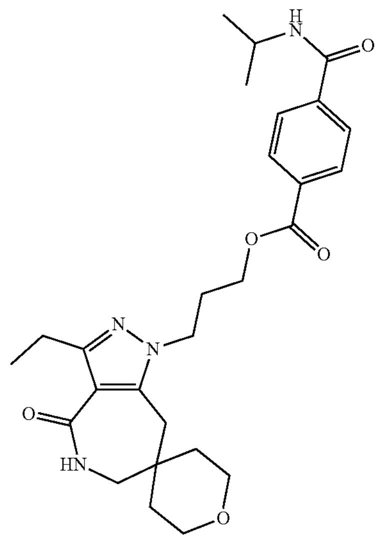 [SMILES: CCc1nn(CCCOC(=O)c2ccc(C(=O)NC(C)C)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(isopropylcarbamoyl)-benzoate | 1.97 | *** |
| 145 | 247 | 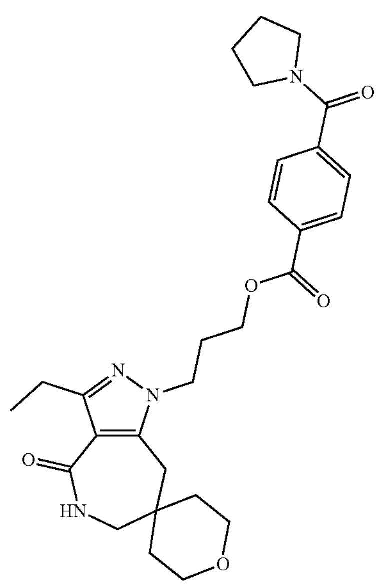 [SMILES: CCc1nn(CCCOC(=O)c2ccc(C(=O)N3CCCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(pyrrolidine-1-carbonyl)benzoate | 1.93 | ** |

TABLE 3-continued

| Ex. | Cmpd | Structure | IUPAC Name | HPLC Rt (min) | PDE4 IC$_{50}$ range |
|---|---|---|---|---|---|
| 146 | 248 | 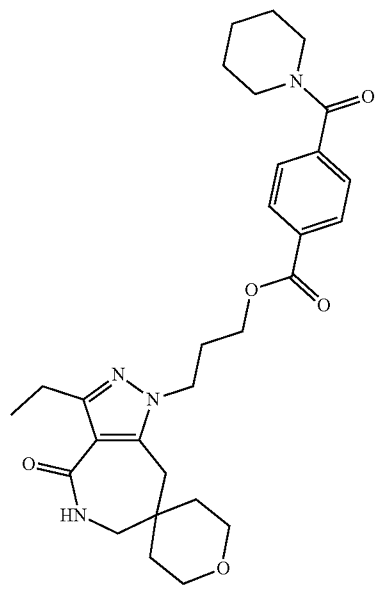 [SMILES: CCc1nn(CCCOC(=O)c2ccc(C(=O)N3CCCCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(piperidine-1-carbonyl)benzoate | 2.03 | *** |
| 147 | 249 | 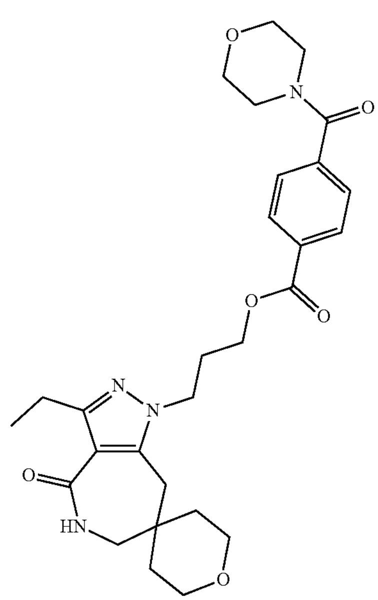 [SMILES: CCc1nn(CCCOC(=O)c2ccc(C(=O)N3CCOCC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(morpholine-4-carbonyl)benzoate | 1.86 | ** |

TABLE 3-continued

| Ex. | Cmpd | Structure | IUPAC Name | HPLC Rt (min) | PDE4 IC$_{50}$ range |
|---|---|---|---|---|---|
| 148 | 250 | 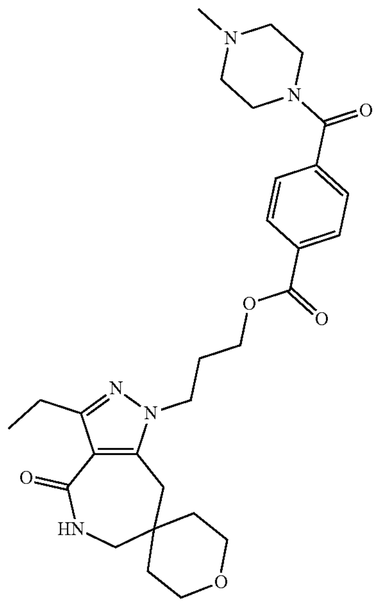 [SMILES: CCc1nn(CCCOC(=O)c2ccc(C(=O)N3CCN(C)CC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(4-methylpiperazine-1-carbonyl)benzoate | 1.67 | ** |
| 149 | 251 | 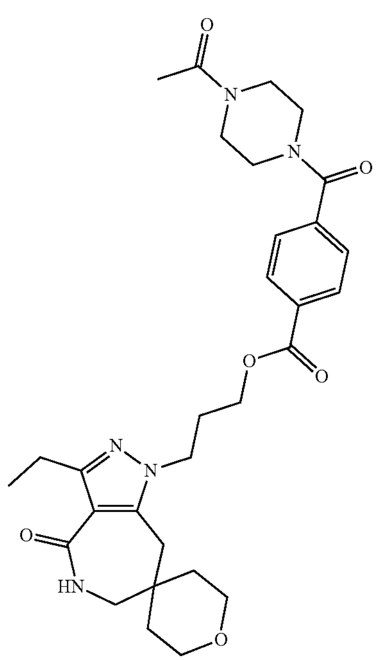 [SMILES: CCc1nn(CCCOC(=O)c2ccc(C(=O)N3CCN(C(C)=O)CC3)cc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 4-(4-acetylpiperazine-1-carbonyl)benzoate | 1.80 | ** |

Preparation 20 (Compound 252)

3-(3-Ethyl-4-oxo-spiro[6,8-dihydro-5H-pyrazolo[4,3-c]azepine-7,4'-tetrahydropyran]-1-yl)propyl 3-formylbenzoate

Preparation 21 (Compound 253)

3-[3-(3-Ethyl-4-oxo-spiro[6,8-dihydro-5H-pyrazolo[4,3-c]azepine-7,4'-tetrahydropyran]-1-yl)propoxy-carbonyl]benzoic Acid

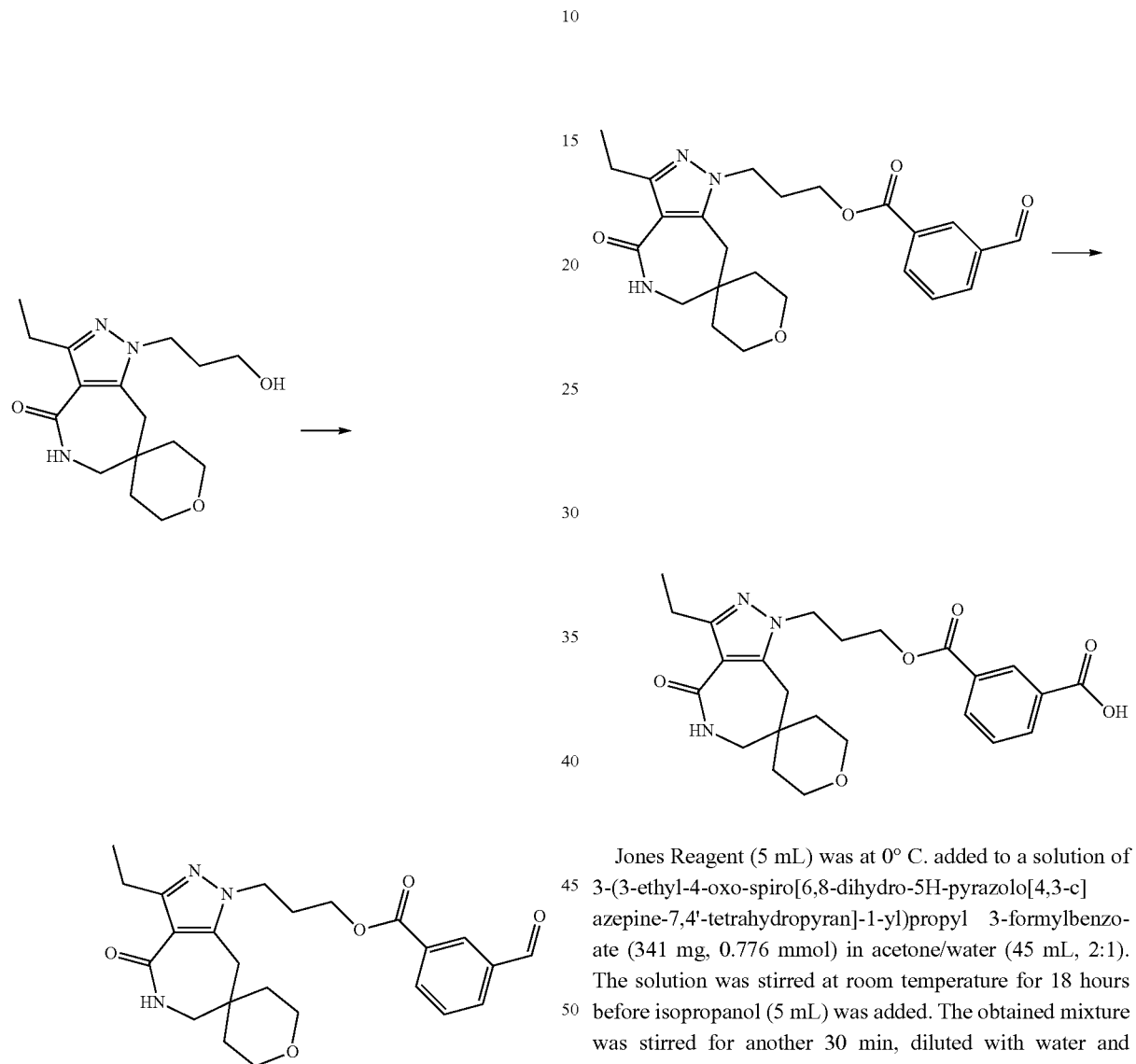

To a solution of 3-ethyl-1-(3-hydroxypropyl)spiro[6,8-dihydro-5H-pyrazolo[4,3-c]azepine-7,4'-tetrahydropyran]-4-one (250 mg, 0.81 mmol) in MeCN (3 mL) was added 3-formylbenzoic acid (147 mg, 0.98 mmol), EDAC (187 mg, 0.98 mmol) and DMAP (10 mg, 0.082 mmol). The mixture was stirred overnight at 50° C. before it was evaporated to dryness under vacuum. Silica gel (100-200 mesh) column chromatography (0 to 15% MeOH in DCM as eluent) afforded the title compound.

Jones Reagent (5 mL) was at 0° C. added to a solution of 3-(3-ethyl-4-oxo-spiro[6,8-dihydro-5H-pyrazolo[4,3-c]azepine-7,4'-tetrahydropyran]-1-yl)propyl 3-formylbenzoate (341 mg, 0.776 mmol) in acetone/water (45 mL, 2:1). The solution was stirred at room temperature for 18 hours before isopropanol (5 mL) was added. The obtained mixture was stirred for another 30 min, diluted with water and extracted three times with DCM. The combined organic phases were concentrated in vacuo. Silica gel (100-200 mesh) column chromatography (0 to 15% MeOH in DCM as eluent) afforded the title compound.

$^1$H NMR (DMSO-d6) δ: 13.31 (s, 1H), 8.51-8.42 (m, 1H), 8.23-8.10 (m, 2H), 7.71-7.61 (m, 1H), 7.44-7.32 (m, 1H), 4.31 (t, J=6.0 Hz, 2H), 4.16 (t, J=6.7 Hz, 2H), 3.66-3.38 (m, 4H), 2.99 (d, J=5.7 Hz, 2H), 2.79-2.63 (m, 4H), 2.31-2.14 (m, 2H), 1.38 (t, J=5.3 Hz, 4H), 1.09 (t, J=7.5 Hz, 3H).

The Examples 150-159 in Table 4 were prepared by reacting Compound 253 as described in General Procedure 3 with the appropriate amine:

TABLE 4

| Ex. | Cmpd | Structure | IUPAC Name | HPLC Rt (min) | PDE4 IC$_{50}$ range |
|---|---|---|---|---|---|
| 150 | 254 | 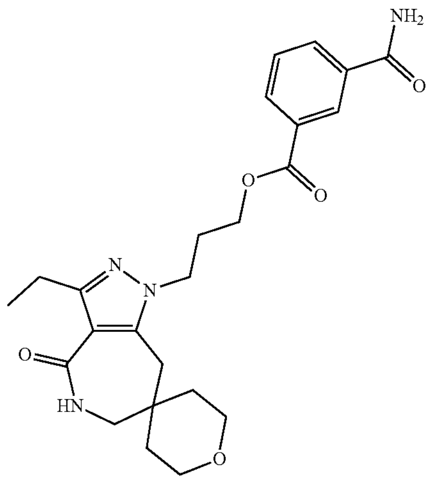 [SMILES: CCc1nn(CCCOC(=O)c2cccc(C(N)=O)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-carbamoylbenzoate | 1.79 | *** |
| 151 | 255 | 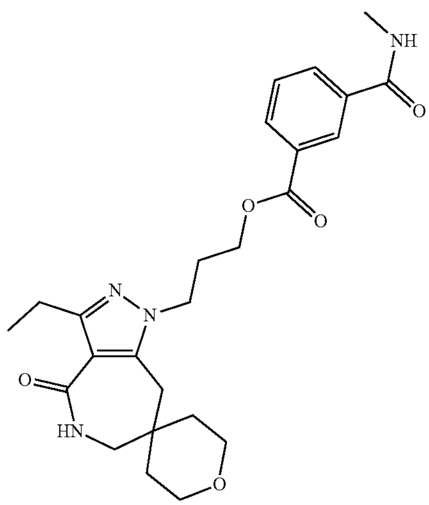 [SMILES: CCc1nn(CCCOC(=O)c2cccc(C(=O)NC)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(methylcarbamoyl)benzoate | 1.83 | *** |
| 152 | 256 | 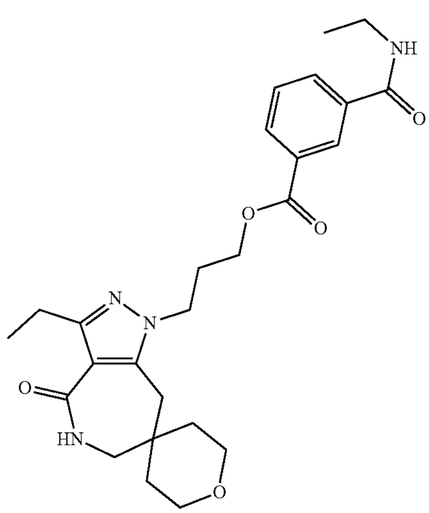 [SMILES: CCNC(=O)c1cccc(C(=O)OCCCn2nc(CC)c3c2CC2(CCOCC2)CNC3=O)c1] | 3-(3-ethyl-4-oxo-spiro[6,8-dihydro-5H-pyrazolo[4,3-c]azepine-7,4'-tetrahydropyran]-1-yl)propyl 3-(ethylcarbamoyl)benzoate | 1.89 | *** |

TABLE 4-continued

| Ex. | Cmpd | Structure | IUPAC Name | HPLC Rt (min) | PDE4 IC$_{50}$ range |
|---|---|---|---|---|---|
| 153 | 257 | 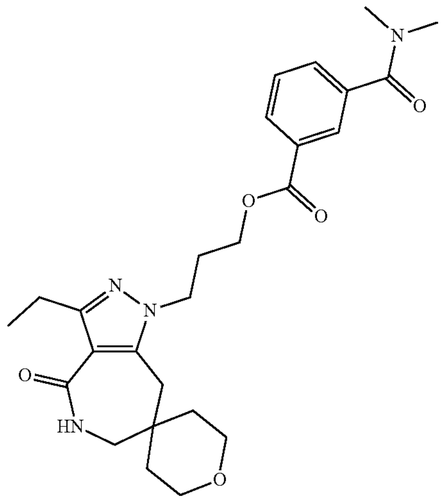 [SMILES: CCc1nn(CCCOC(=O)c2cccc(C(=O)N(C)C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(dimethylcarbamoyl)-benzoate | 1.86 | *** |
| 154 | 258 | 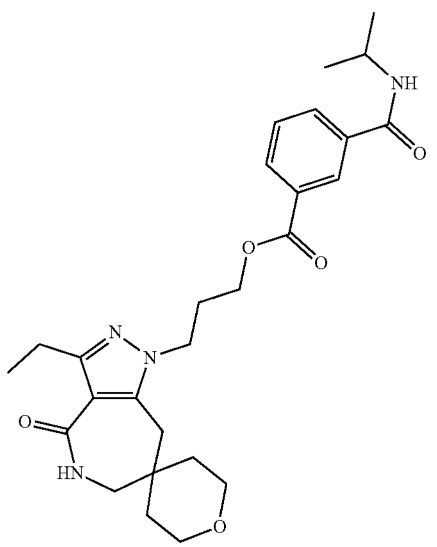 [SMILES: CCc1nn(CCCOC(=O)c2cccc(C(=O)NC(C)C)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(isopropylcarbamoyl)-benzoate | 1.96 | *** |
| 155 | 259 | 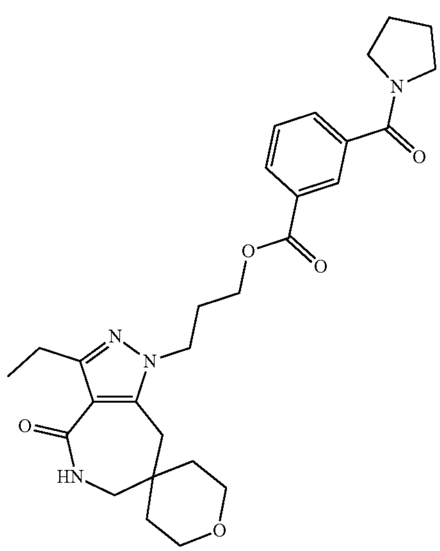 [SMILES: CCc1nn(CCCOC(=O)c2cccc(C(=O)N3CCCC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(pyrrolidine-1-carbonyl)benzoate | 1.93 | *** |

TABLE 4-continued
| Ex. | Cmpd | Structure | IUPAC Name | HPLC Rt (min) | PDE4 IC$_{50}$ range |
|---|---|---|---|---|---|
| 156 | 260 | 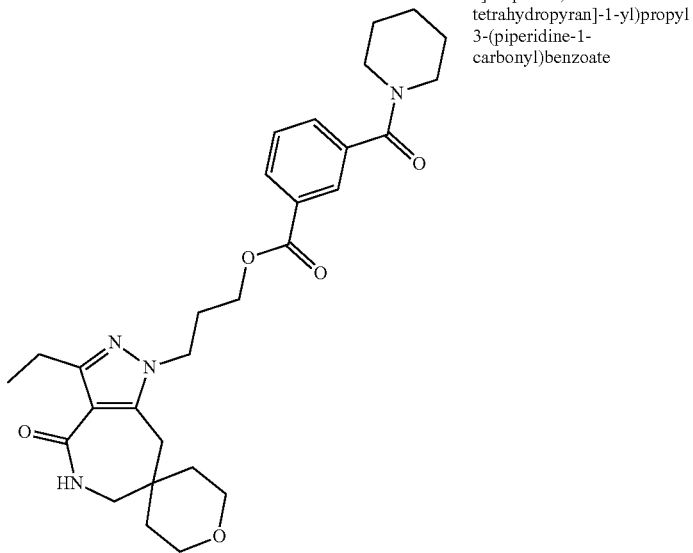 | 3-(3-ethyl-4-oxo-spiro[6,8-dihydro-5H-pyrazolo[4,3-c]azepine-7,4'-tetrahydropyran]-1-yl)propyl 3-(piperidine-1-carbonyl)benzoate | 2.03 | *** |
| 157 | 261 | 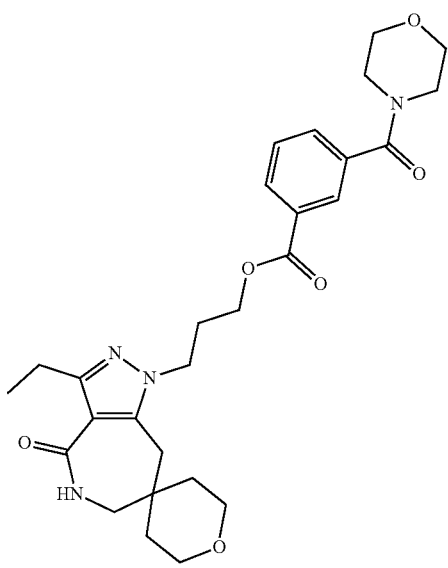 [SMILES: CCc1nn(CCCOC(=O)c2cccc(C(=O)N3CCOCC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(morpholine-4-carbonyl)benzoate | 1.86 | *** |

TABLE 4-continued

| Ex. | Cmpd | Structure | IUPAC Name | HPLC Rt (min) | PDE4 IC$_{50}$ range |
|---|---|---|---|---|---|
| 158 | 262 | 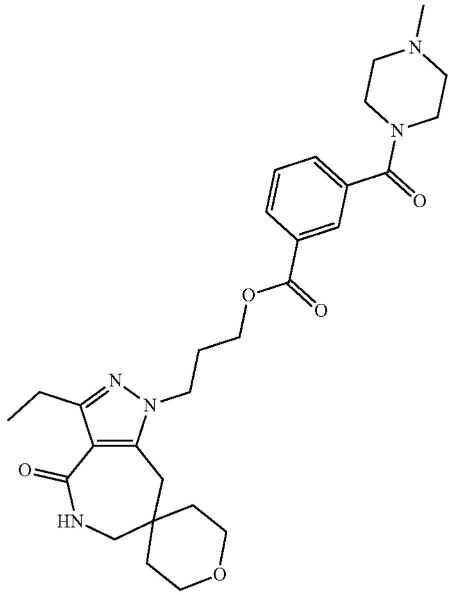 [SMILES: CCc1nn(CCCOC(=O)c2cccc(C(=O)N3CCN(C)CC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(4-methylpiperazine-1-carbonyl)benzoate | 1.67 | ** |
| 159 | 263 | 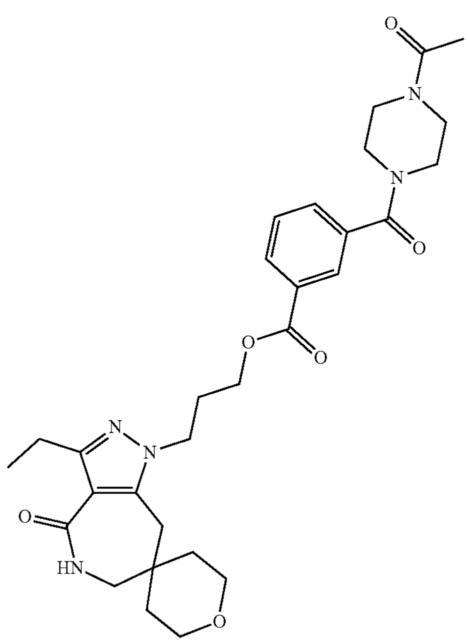 [SMILES: CCc1nn(CCCOC(=O)c2cccc(C(=O)N3CCN(C(C)=O)CC3)c2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)propyl 3-(4-acetylpiperazine-1-carbonyl)benzoate | 1.80 | *** |

The following Examples 160-251 in Table 5 were prepared by reacting Compound 018 as described in General Procedure 2 with the appropriate acid:

TABLE 5

| Ex. | Cmpd | Structure | IUPAC Name | HPLC Rt (min) | PDE4 IC$_{50}$ range |
|---|---|---|---|---|---|
| 160 | 264 | 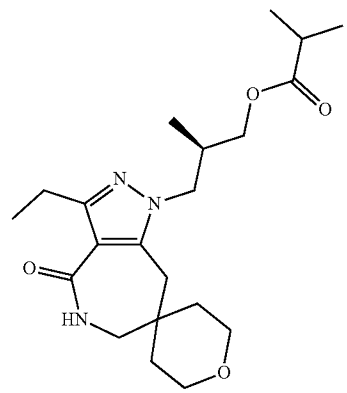 [SMILES: CCc1nn(C[C@@H](C)COC(=O)C(C)C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylpropanoate | 2.05 | *** |
| 161 | 265 | 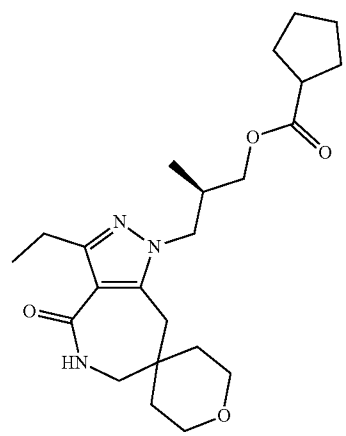 [SMILES: CCc1nn(C[C@@H](C)COC(=O)C2CCCC2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] cyclopentanecarboxylate | 2.18 | *** |
| 162 | 266 | 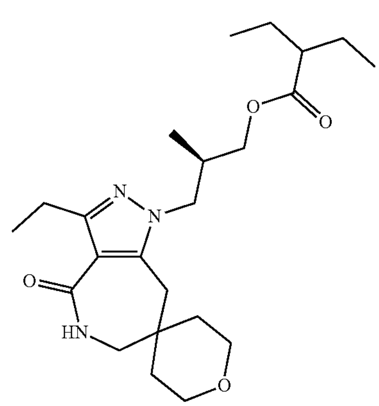 [SMILES: CCc1nn(C[C@@H](C)COC(=O)C(CC)CC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-ethylbutanoate | 2.24 | *** |

TABLE 5-continued

| Ex. | Cmpd | Structure | IUPAC Name | HPLC Rt (min) | PDE4 IC$_{50}$ range |
|---|---|---|---|---|---|
| 163 | 267 | 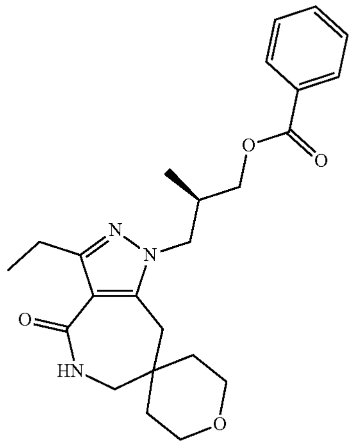 [SMILES: CCc1nn(C[C@@H](C)COC(=O)c2ccccc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] benzoate | 2.13 | *** |
| 164 | 268 | 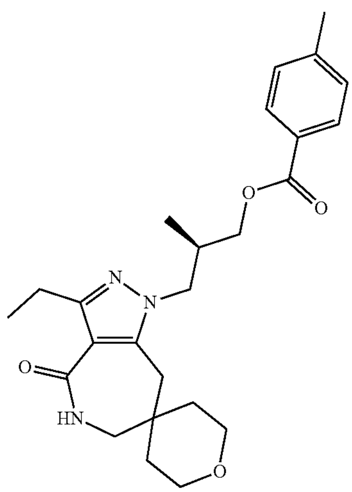 [SMILES: CCc1nn(C[C@@H](C)COC(=O)c2ccc(C)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methylbenzoate | 2.22 | *** |
| 165 | 269 | 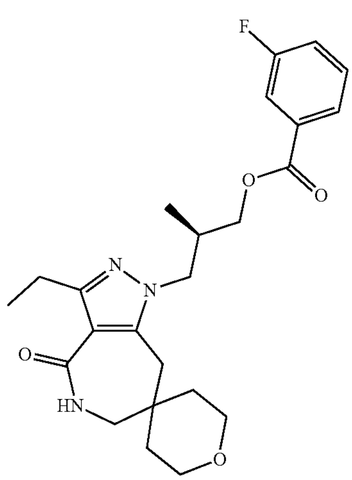 [SMILES: CCc1nn(C[C@@H](C)COC(=O)c2cccc(F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluorobenzoate | 2.17 | *** |

TABLE 5-continued

| Ex. | Cmpd | Structure | IUPAC Name | HPLC Rt (min) | PDE4 IC$_{50}$ range |
|---|---|---|---|---|---|
| 166 | 270 | 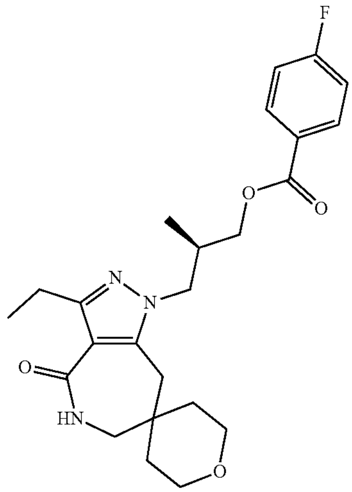 [SMILES: CCc1nn(C[C@@H](C)COC(=O)c2ccc(F)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluorobenzoate | 2.16 | *** |
| 167 | 271 | 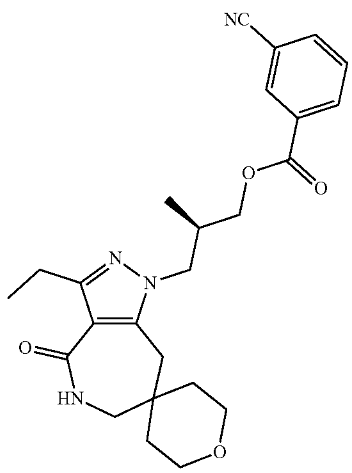 [SMILES: CCc1nn(C[C@@H](C)COC(=O)c2cccc(C#N)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyanobenzoate | 2.09 | *** |
| 168 | 272 | 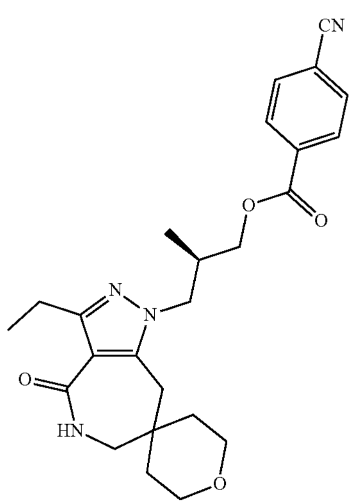 [SMILES: CCc1nn(C[C@@H](C)COC(=O)c2ccc(C#N)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyanobenzoate | 2.10 | *** |

TABLE 5-continued

| Ex. | Cmpd | Structure | IUPAC Name | HPLC Rt (min) | PDE4 IC$_{50}$ range |
|---|---|---|---|---|---|
| 169 | 273 | 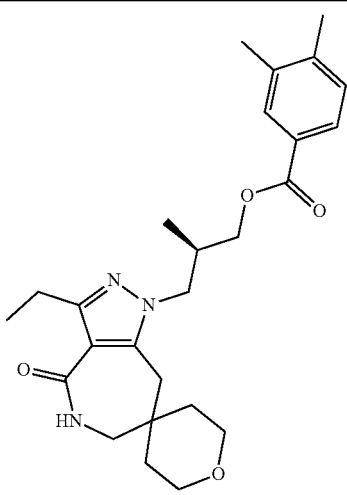 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-dimethylbenzoate | 2.29 | *** |
| 170 | 274 | 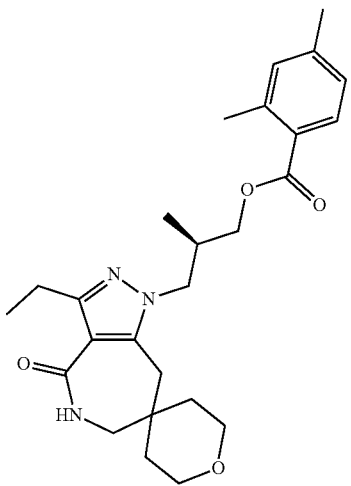 [SMILES: CCc1nn(C[C@@H](C)COC(=O)c2ccc(C)cc2C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2,4-dimethylbenzoate | 2.32 | *** |
| 171 | 275 | 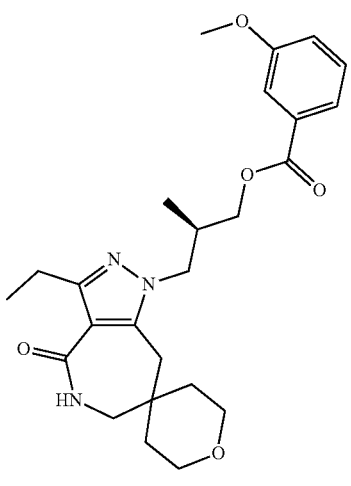 [SMILES: CCc1nn(C[C@@H](C)COC(=O)c2cccc(OC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxybenzoate | 2.15 | *** |

TABLE 5-continued

| Ex. | Cmpd | Structure | IUPAC Name | HPLC Rt (min) | PDE4 IC$_{50}$ range |
|---|---|---|---|---|---|
| 172 | 276 | 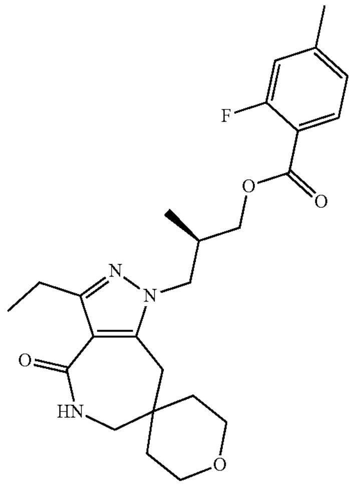 [SMILES: CCc1nn(C[C@@H](C)COC(=O)c2ccc(C)cc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methyl-benzoate | 2.22 | *** |
| 173 | 277 | 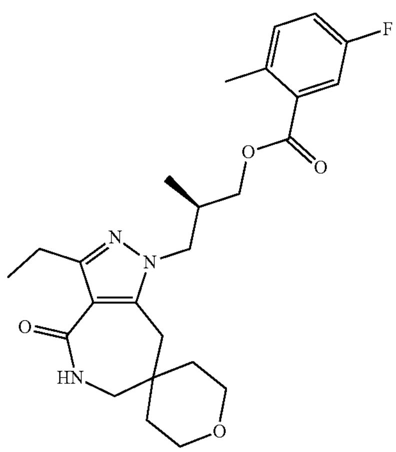 [SMILES: CCc1nn(C[C@@H](C)COC(=O)c2cc(F)ccc2C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-methyl-benzoate | 2.26 | *** |
| 174 | 278 | 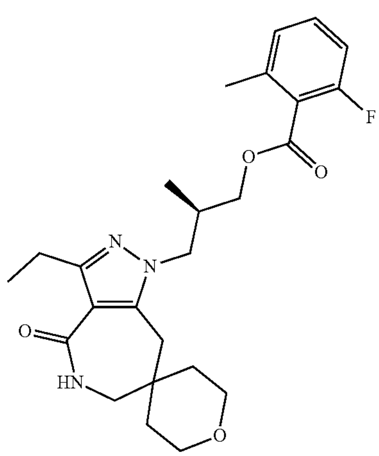 [SMILES: CCc1nn(C[C@@H](C)COC(=O)c2c(C)cccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methyl-benzoate | 2.21 | *** |

TABLE 5-continued

| Ex. | Cmpd | Structure | IUPAC Name | HPLC Rt (min) | PDE4 IC$_{50}$ range |
|---|---|---|---|---|---|
| 175 | 279 | 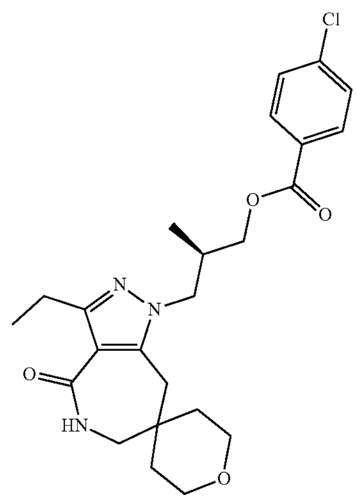 [SMILES: CCc1nn(C[C@@H](C)COC(=O)c2ccc(Cl)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chlorobenzoate | 2.27 | *** |
| 176 | 280 | 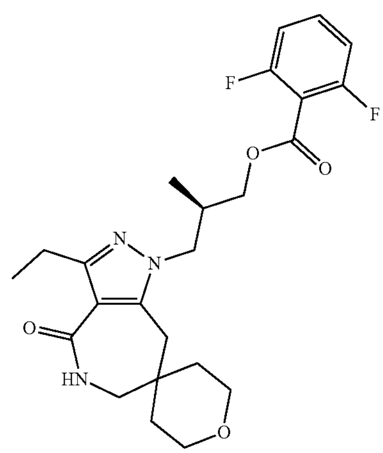 [SMILES: CCc1nn(C[C@@H](C)COC(=O)c2c(F)cccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2,6-difluorobenzoate | 2.13 | *** |
| 177 | 281 | 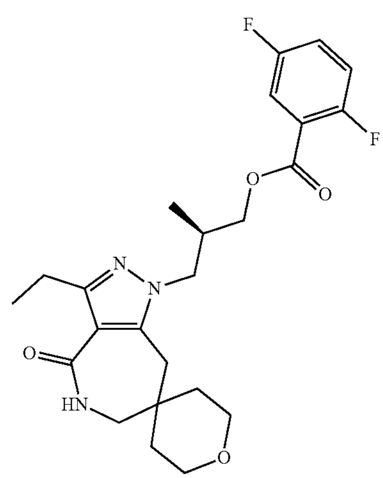 [SMILES: CCc1nn(C[C@@H](C)COC(=O)c2cc(F)ccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2,5-difluorobenzoate | 2.16 | *** |

TABLE 5-continued

| Ex. | Cmpd | Structure | IUPAC Name | HPLC Rt (min) | PDE4 IC$_{50}$ range |
|---|---|---|---|---|---|
| 178 | 282 | 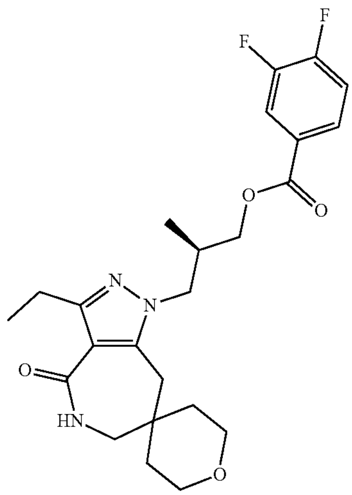 [SMILES: CCc1nn(C[C@@H](C)COC(=O)c2ccc(F)c(F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-difluorobenzoate | 2.21 | *** |
| 179 | 283 | 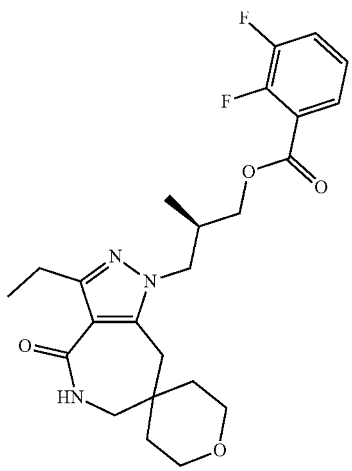 [SMILES: CCc1nn(C[C@@H](C)COC(=O)c2cccc(F)c2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2,3-difluorobenzoate | 2.17 | *** |
| 180 | 284 | 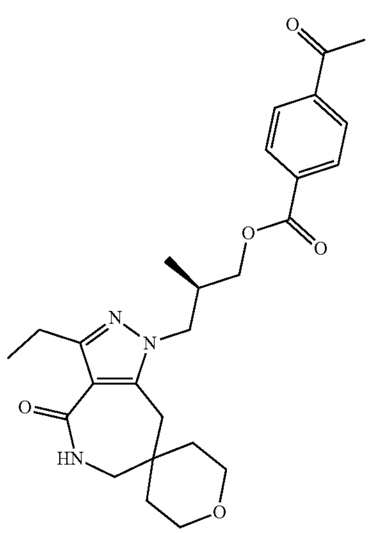 [SMILES: CCc1nn(C[C@@H](C)COC(=O)c2ccc(C(C)=O)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-acetylbenzoate | 2.09 | *** |

TABLE 5-continued

| Ex. | Cmpd | Structure | IUPAC Name | HPLC Rt (min) | PDE4 IC$_{50}$ range |
|---|---|---|---|---|---|
| 181 | 285 | 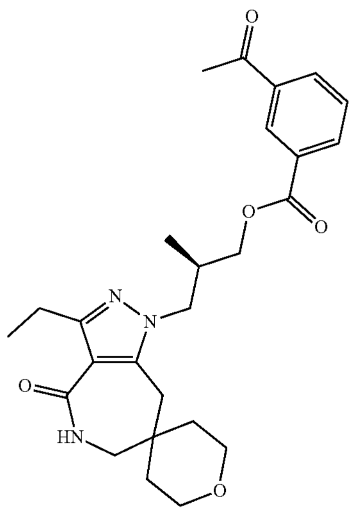 [SMILES: CCc1nn(C[C@@H](C)COC(=O)c2cccc(C(C)=O)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-acetylbenzoate | 2.07 | *** |
| 182 | 286 | 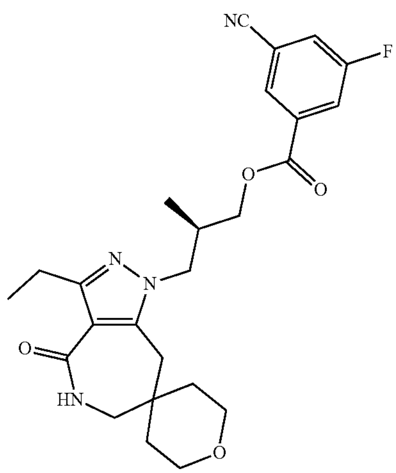 [SMILES: CCc1nn(C[C@@H](C)COC(=O)c2cc(F)cc(C#N)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-5-fluoro-benzoate | 2.14 | *** |
| 183 | 287 | 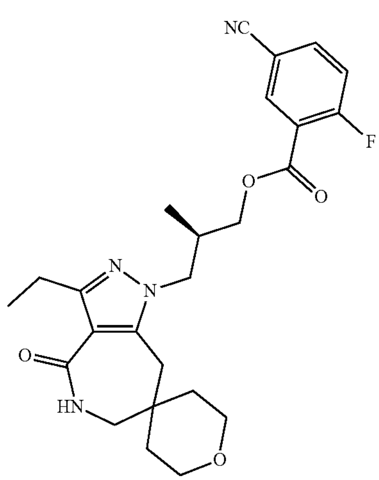 [SMILES: CCc1nn(C[C@@H](C)COC(=O)c2cc(C#N)ccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-cyano-2-fluoro-benzoate | 2.08 | *** |

TABLE 5-continued

| Ex. | Cmpd | Structure | IUPAC Name | HPLC Rt (min) | PDE4 IC$_{50}$ range |
|---|---|---|---|---|---|
| 184 | 288 | 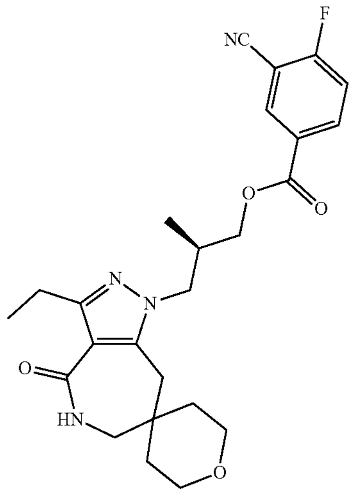 [SMILES: CCc1nn(C[C@@H](C)COC(=O)c2ccc(F)c(C#N)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-4-fluoro-benzoate | 2.14 | *** |
| 185 | 289 | 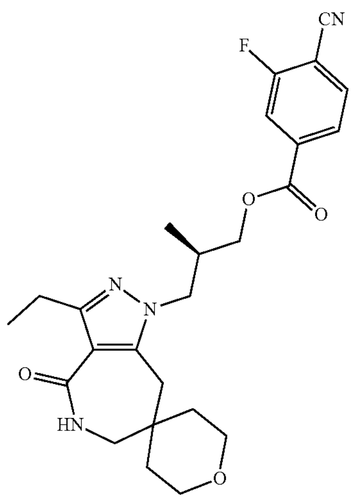 [SMILES: CCc1nn(C[C@@H](C)COC(=O)c2ccc(C#N)c(F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyano-3-fluoro-benzoate | 2.16 | *** |
| 186 | 290 | 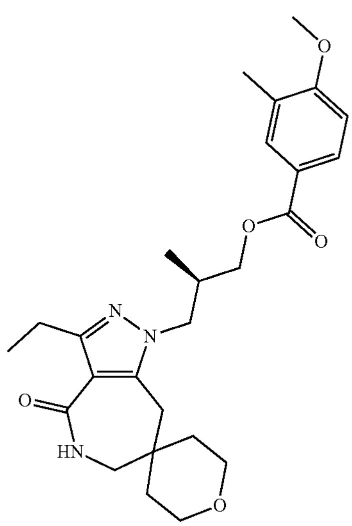 [SMILES: CCc1nn(C[C@@H](C)COC(=O)c2ccc(OC)c(C)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-methyl-benzoate | 2.24 | *** |

TABLE 5-continued

| Ex. | Cmpd | Structure | IUPAC Name | HPLC Rt (min) | PDE4 IC$_{50}$ range |
|---|---|---|---|---|---|
| 187 | 291 | 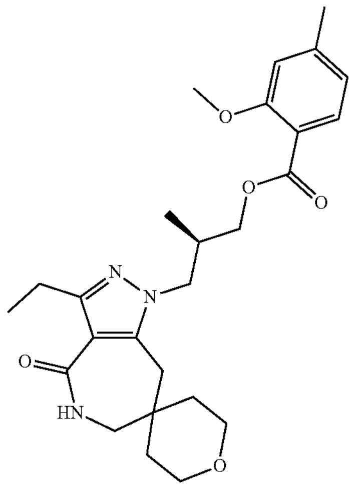 [SMILES: CCc1nn(C[C@@H](C)COC(=O)c2ccc(C)cc2OC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methoxy-4-methyl-benzoate | 2.14 | *** |
| 188 | 292 | 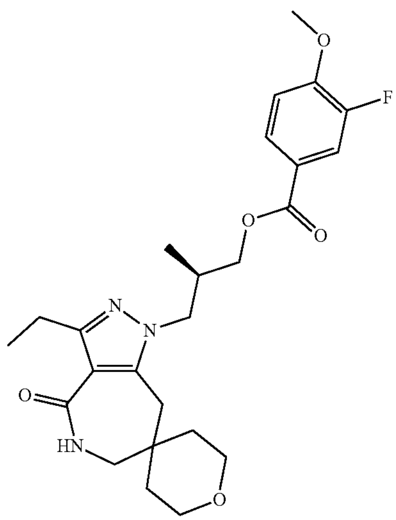 [SMILES: CCc1nn(C[C@@H](C)COC(=O)c2ccc(OC)c(F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-4-methoxy-benzoate | 2.16 | *** |
| 189 | 293 | 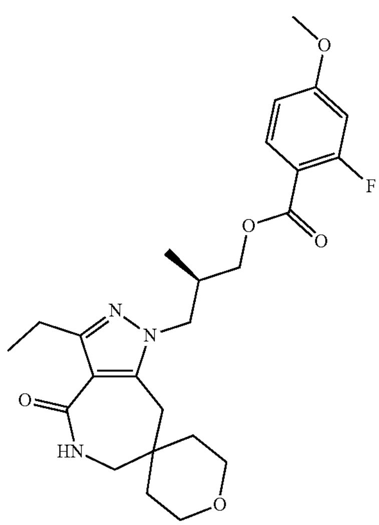 [SMILES: CCc1nn(C[C@@H](C)COC(=O)c2ccc(OC)cc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methoxy-benzoate | 2.16 | *** |

TABLE 5-continued

| Ex. | Cmpd | Structure | IUPAC Name | HPLC Rt (min) | PDE4 IC$_{50}$ range |
|---|---|---|---|---|---|
| 190 | 294 | 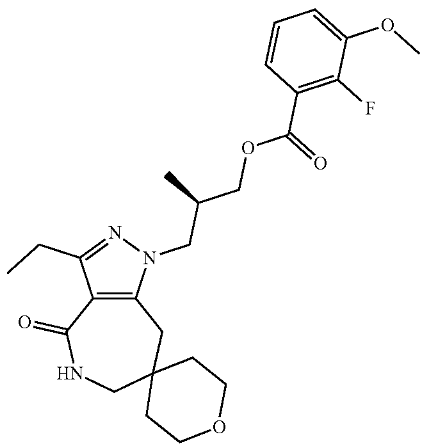 [SMILES: CCc1nn(C[C@@H](C)COC(=O)c2cccc(OC)c2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-3-methoxy-benzoate | 2.13 | *** |
| 191 | 295 | 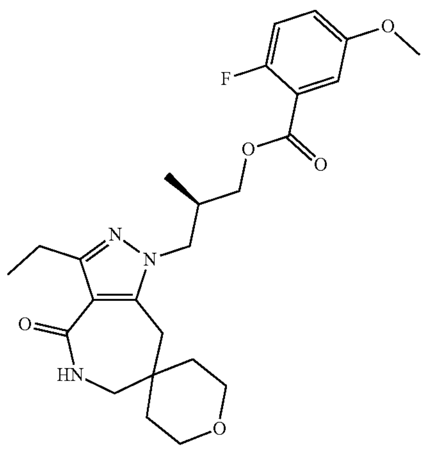 [SMILES: CCc1nn(C[C@@H](C)COC(=O)c2cc(OC)ccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-methoxy-benzoate | 2.16 | *** |
| 192 | 296 | 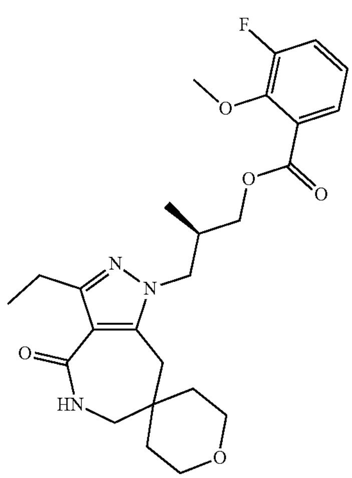 [SMILES: CCc1nn(C[C@@H](C)COC(=O)c2cccc(F)c2OC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-2-methoxy-benzoate | 2.16 | *** |

TABLE 5-continued

| Ex. | Cmpd | Structure | IUPAC Name | HPLC Rt (min) | PDE4 IC$_{50}$ range |
|---|---|---|---|---|---|
| 193 | 297 | 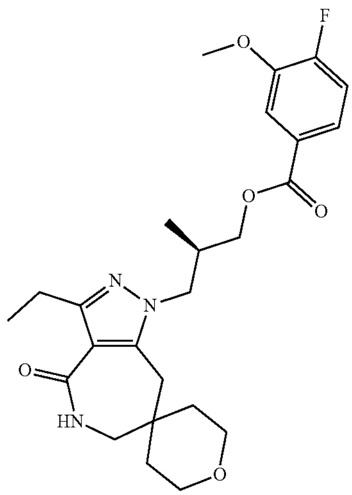 [SMILES: CCc1nn(C[C@@H](C)COC(=O)c2ccc(F)c(OC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-methoxy-benzoate | 2.18 | *** |
| 194 | 298 | 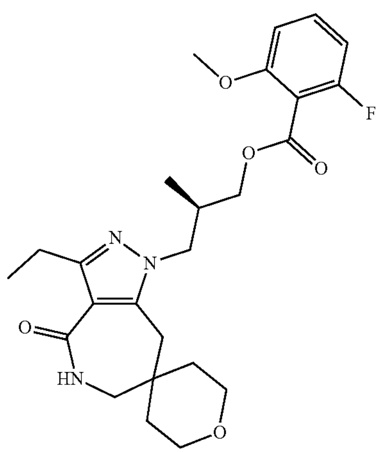 [SMILES: CCc1nn(C[C@@H](C)COC(=O)c2c(F)cccc2OC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methoxy-benzoate | 2.12 | *** |
| 195 | 299 | 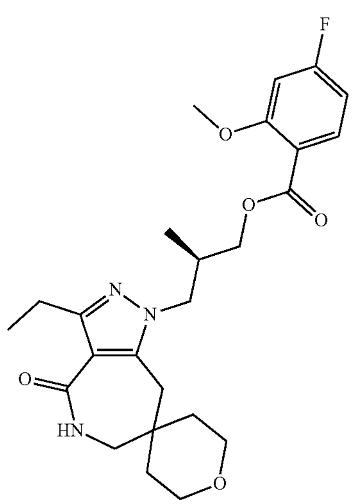 [SMILES: CCc1nn(C[C@@H](C)COC(=O)c2ccc(F)cc2OC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-methoxy-benzoate | 2.11 | *** |

TABLE 5-continued

| Ex. | Cmpd | Structure | IUPAC Name | HPLC Rt (min) | PDE4 IC$_{50}$ range |
|---|---|---|---|---|---|
| 196 | 300 | 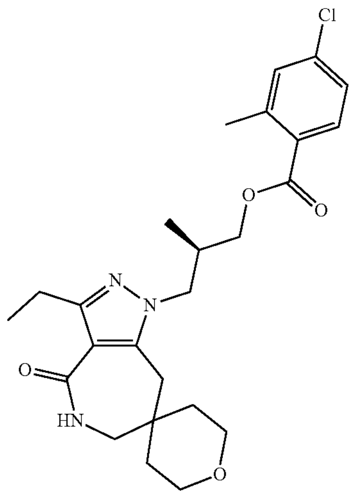 [SMILES: CCc1nn(C[C@@H](C)COC(=O)c2ccc(Cl)cc2C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methyl-benzoate | 2.37 | *** |
| 197 | 301 | 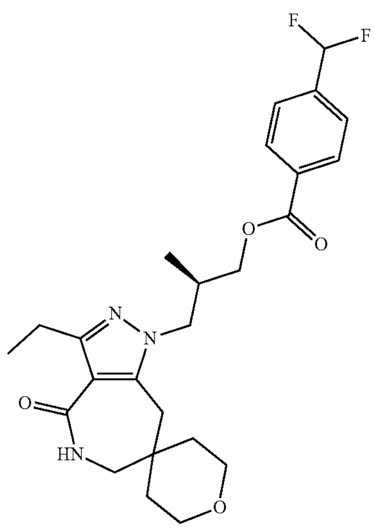 [SMILES: CCc1nn(C[C@@H](C)COC(=O)c2ccc(C(F)F)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(difluoromethyl)benzoate | 2.20 | *** |
| 198 | 302 | 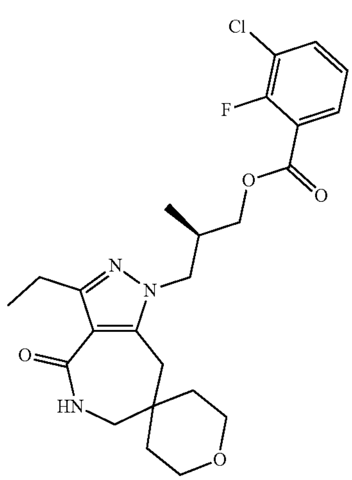 [SMILES: CCc1nn(C[C@@H](C)COC(=O)c2cccc(Cl)c2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-fluoro-benzoate | 2.24 | *** |

TABLE 5-continued

| Ex. | Cmpd | Structure | IUPAC Name | HPLC Rt (min) | PDE4 IC$_{50}$ range |
|---|---|---|---|---|---|
| 199 | 303 | 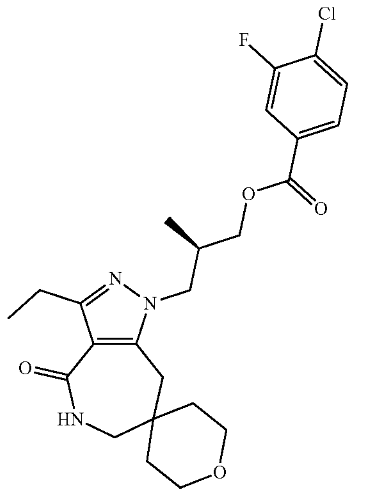 [SMILES: CCc1nn(C[C@@H](C)COC(=O)c2ccc(Cl)c(F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-fluoro-benzoate | 2.30 | *** |
| 200 | 304 | 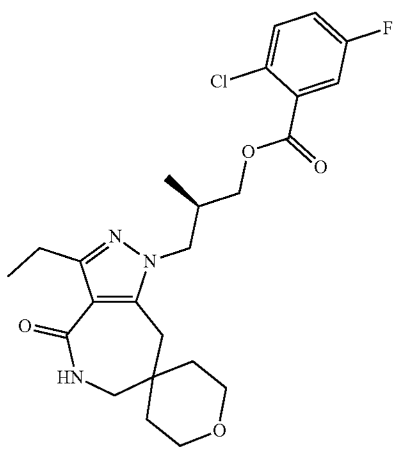 [SMILES: CCc1nn(C[C@@H](C)COC(=O)c2cc(F)ccc2Cl)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-fluoro-benzoate | 2.22 | *** |
| 201 | 305 | 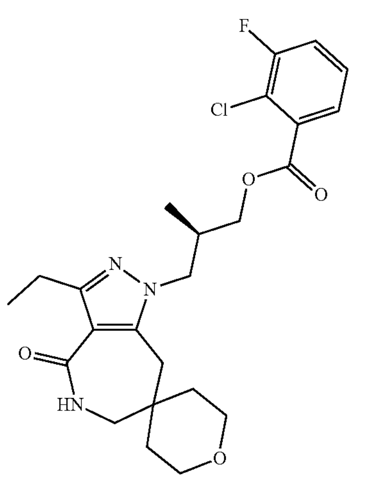 [SMILES: CCc1nn(C[C@@H](C)COC(=O)c2cccc(F)c2Cl)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-fluoro-benzoate | 2.22 | *** |

TABLE 5-continued

| Ex. | Cmpd | Structure | IUPAC Name | HPLC Rt (min) | PDE4 IC$_{50}$ range |
|---|---|---|---|---|---|
| 202 | 306 | 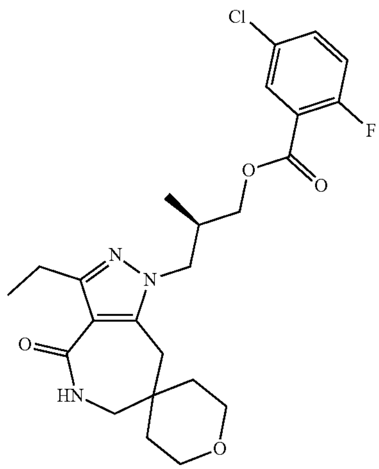 | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-fluoro-benzoate | 2.25 | *** |
| 203 | 307 | 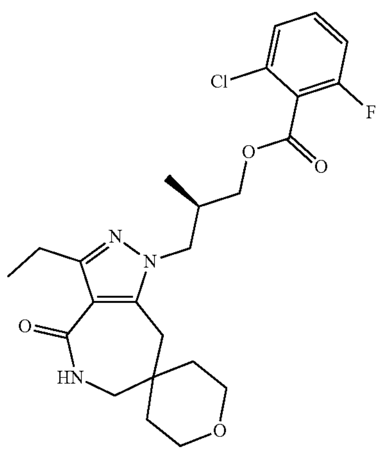 | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-6-fluoro-benzoate | 2.20 | *** |
| 204 | 308 | 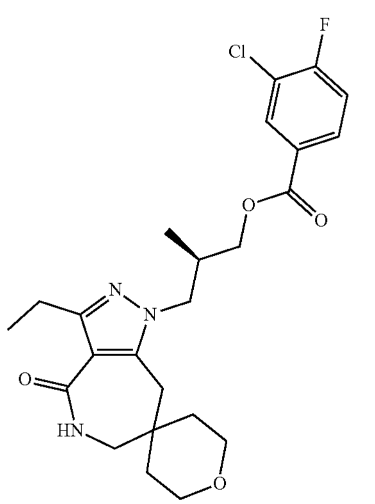 [SMILES: CCc1nn(C[C@@H](C)COC(=O)c2ccc(F)c(Cl)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-fluoro-benzoate | 2.29 | *** |

TABLE 5-continued

| Ex. | Cmpd | Structure | IUPAC Name | HPLC Rt (min) | PDE4 IC$_{50}$ range |
|---|---|---|---|---|---|
| 205 | 309 | 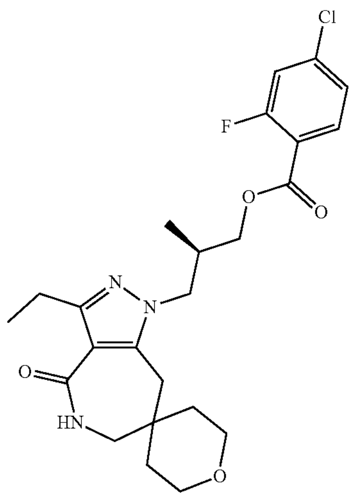 | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-fluoro-benzoate | 2.27 | *** |
| 206 | 310 | 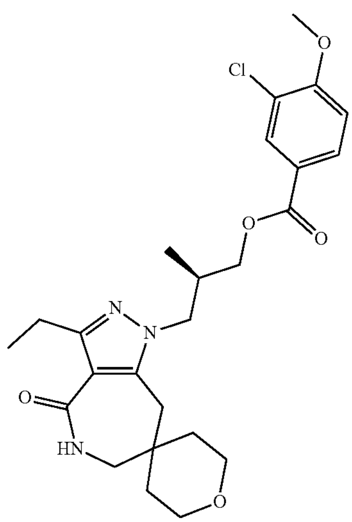 [SMILES: CCc1nn(C[C@@H](C)COC(=O)c2ccc(OC)c(Cl)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-methoxy-benzoate | 2.23 | *** |
| 207 | 311 | 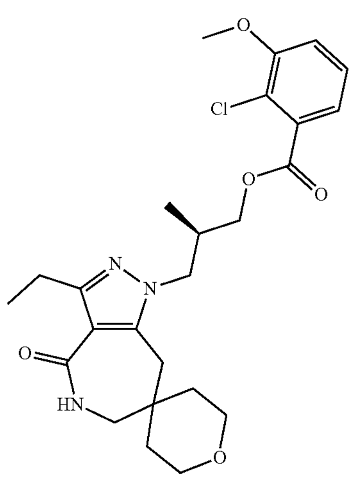 [SMILES: CCc1nn(C[C@@H](C)COC(=O)c2cccc(OC)c2Cl)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-methoxy-benzoate | 2.16 | *** |

TABLE 5-continued

| Ex. | Cmpd | Structure | IUPAC Name | HPLC Rt (min) | PDE4 IC$_{50}$ range |
|---|---|---|---|---|---|
| 208 | 312 | 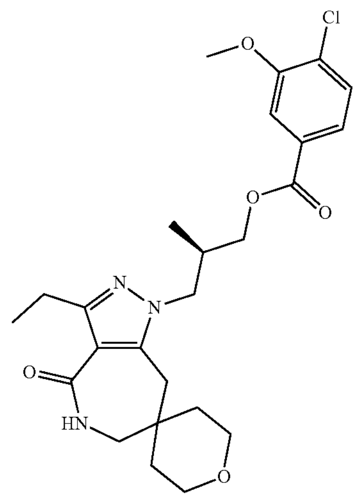 [SMILES: CCc1nn(C[C@@H](C)COC(=O)c2ccc(Cl)c(OC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-methoxy-benzoate | 2.27 | *** |
| 209 | 313 | 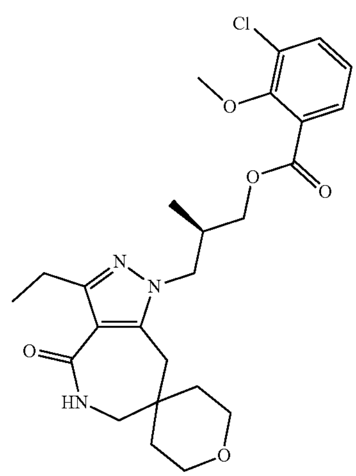 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-methoxy-benzoate | 2.25 | *** |
| 210 | 314 | 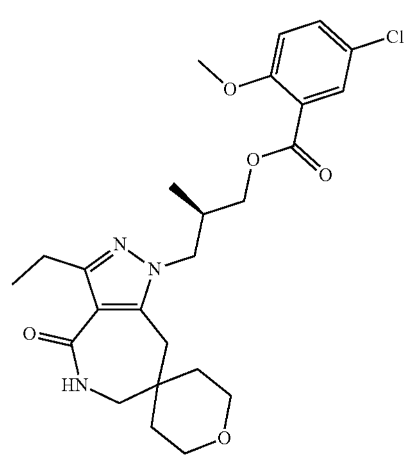 [SMILES: CCc1nn(C[C@@H](C)COC(=O)c2cc(Cl)ccc2OC)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-methoxy-benzoate | 2.19 | *** |

TABLE 5-continued

| Ex. | Cmpd | Structure | IUPAC Name | HPLC Rt (min) | PDE4 IC$_{50}$ range |
|---|---|---|---|---|---|
| 211 | 315 | 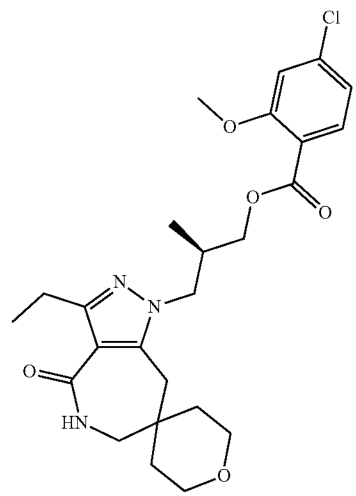 | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methoxy-benzoate | 2.21 | *** |
| 212 | 316 | 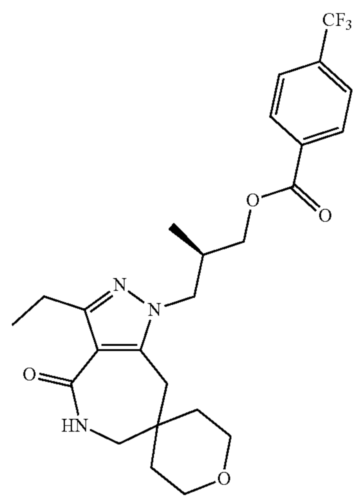 [SMILES: CCc1nn(C[C@@H](C)COC(=O)c2ccc(C(F)(F)F)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(trifluoromethyl)benzoate | 2.32 | *** |
| 213 | 317 | 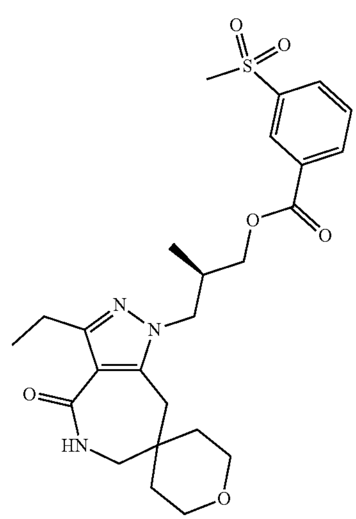 [SMILES: CCc1nn(C[C@@H](C)COC(=O)c2cccc(S(C)(=O)=O)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methylsulfonylbenzoate | 1.97 | *** |

TABLE 5-continued

| Ex. | Cmpd | Structure | IUPAC Name | HPLC Rt (min) | PDE4 IC$_{50}$ range |
|---|---|---|---|---|---|
| 214 | 318 | 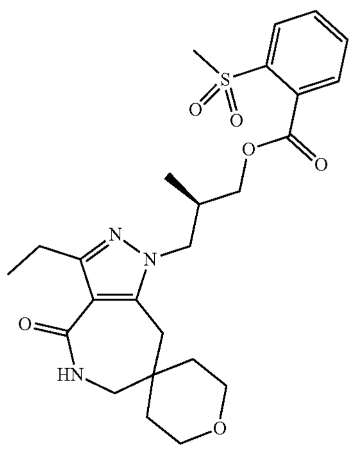 [SMILES: CCc1nn(C[C@@H](C)COC(=O)c2ccccc2S(C)(=O)=O)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylsulfonylbenzoate | 1.98 | *** |
| 215 | 319 | 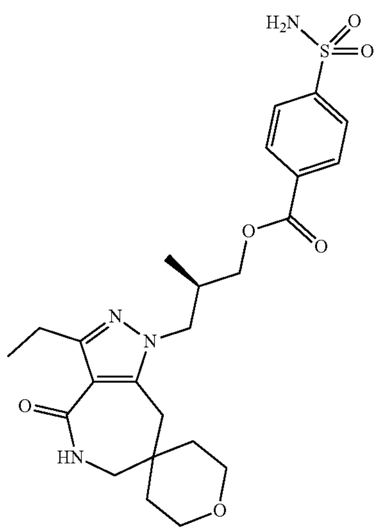 [SMILES: CCc1nn(C[C@@H](C)COC(=O)c2ccc(S(N)(=O)=O)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-sulfamoylbenzoate | 1.92 | *** |
| 216 | 320 | 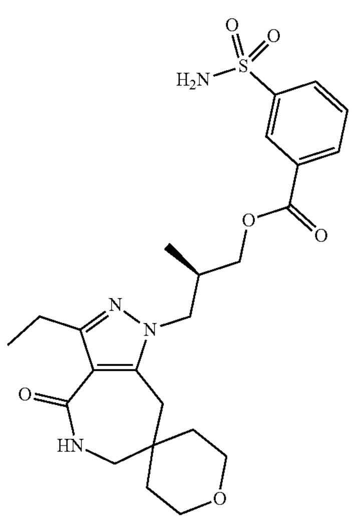 [SMILES: CCc1nn(C[C@@H](C)COC(=O)c2cccc(S(N)(=O)=O)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-sulfamoylbenzoate | 1.92 | **** |

TABLE 5-continued

| Ex. | Cmpd | Structure | IUPAC Name | HPLC Rt (min) | PDE4 IC$_{50}$ range |
|---|---|---|---|---|---|
| 217 | 321 | 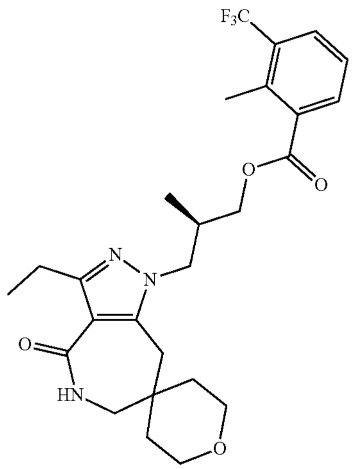 [SMILES: CCc1nn(C[C@@H](C)COC(=O)c2cccc(C(F)(F)F)c2C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-3-(trifluoromethyl)benzoate | 2.38 | *** |
| 218 | 322 | 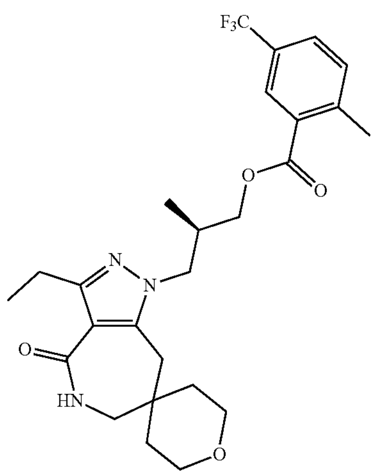 [SMILES: CCc1nn(C[C@@H](C)COC(=O)c2cc(C(F)(F)F)ccc2C)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-5-(trifluoromethyl)benzoate | 2.38 | *** |
| 219 | 323 | 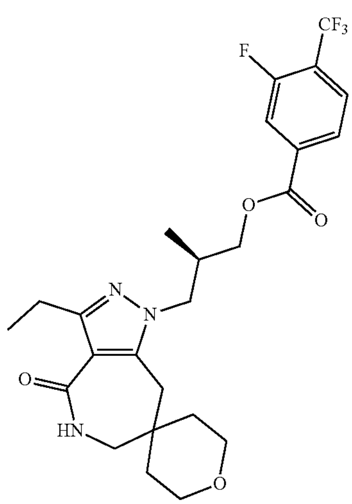 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-4-(trifluoromethyl)benzoate | 2.35 | *** |

TABLE 5-continued

| Ex. | Cmpd | Structure | IUPAC Name | HPLC Rt (min) | PDE4 IC$_{50}$ range |
|---|---|---|---|---|---|
| 220 | 324 | 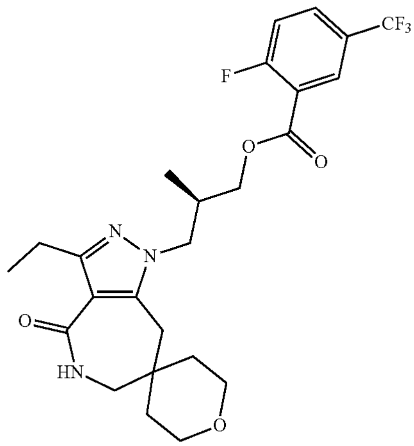 [SMILES: CCc1nn(C[C@@H](C)COC(=O)c2cc(C(F)(F)F)ccc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-(trifluoromethyl)benzoate | 2.30 | *** |
| 221 | 325 | 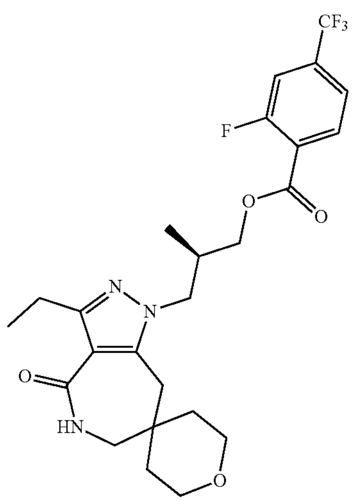 [SMILES: CCc1nn(C[C@@H](C)COC(=O)c2ccc(C(F)(F)F)cc2F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-(trifluoromethyl)benzoate | 2.32 | *** |
| 222 | 326 | 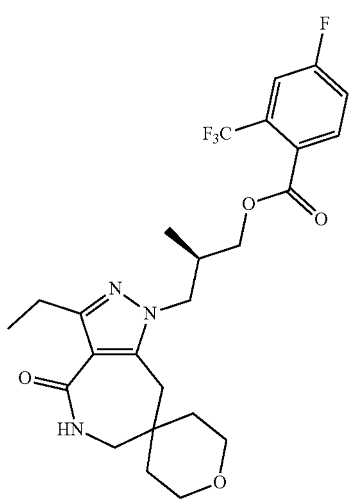 | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-(trifluoromethyl)benzoate | 2.29 | *** |

TABLE 5-continued

| Ex. | Cmpd | Structure | IUPAC Name | HPLC Rt (min) | PDE4 IC$_{50}$ range |
|---|---|---|---|---|---|
| 223 | 327 | 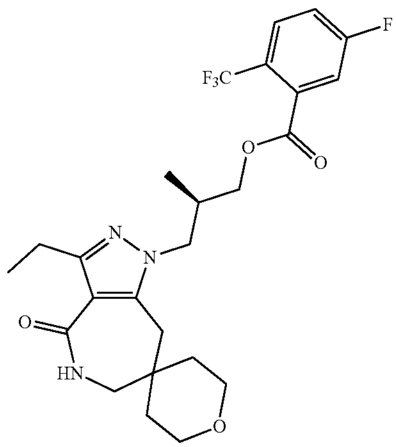 [SMILES: CCc1nn(C[C@@H](C)COC(=O)c2cc(F)ccc2C(F)(F)F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-(trifluoromethyl)benzoate | 2.28 | *** |
| 224 | 328 | 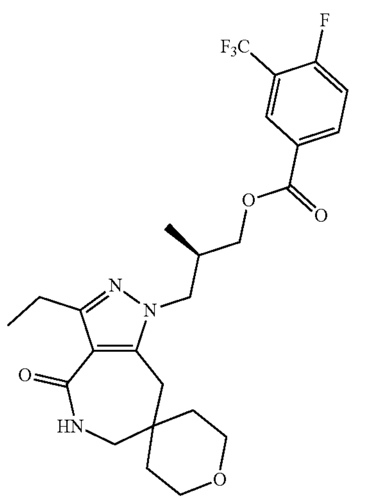 [SMILES: CCc1nn(C[C@@H](C)COC(=O)c2ccc(F)c(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-(trifluoromethyl)benzoate | 2.34 | *** |
| 225 | 329 | 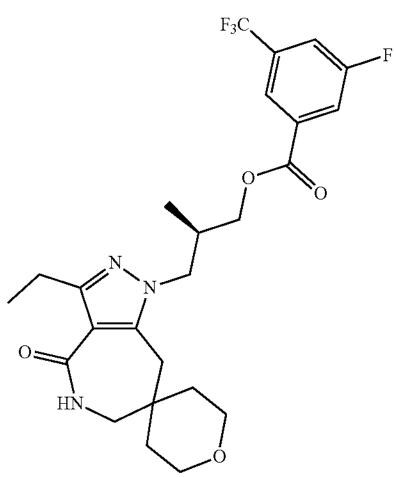 [SMILES: CCc1nn(C[C@@H](C)COC(=O)c2cc(F)cc(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-5-(trifluoromethyl)benzoate | 2.35 | *** |

TABLE 5-continued

| Ex. | Cmpd | Structure | IUPAC Name | HPLC Rt (min) | PDE4 IC$_{50}$ range |
|---|---|---|---|---|---|
| 226 | 330 | 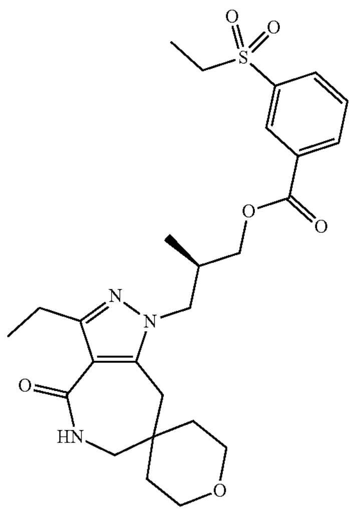 [SMILES: CCc1nn(C[C@@H](C)COC(=O)c2cccc(S(=O)(=O)CC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-ethylsulfonylbenzoate | 2.04 | *** |
| 227 | 331 | 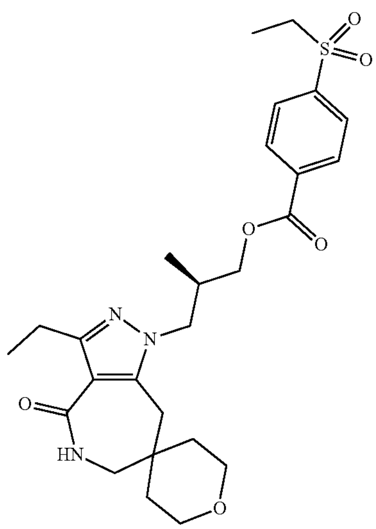 [SMILES: CCc1nn(C[C@@H](C)COC(=O)c2ccc(S(=O)(=O)CC)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-ethylsulfonylbenzoate | 2.05 | *** |
| 228 | 332 | 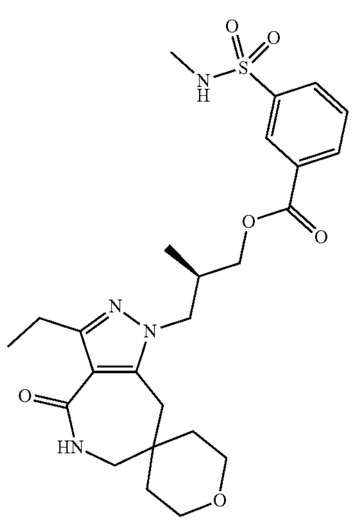 [SMILES: CCc1nn(C[C@@H](C)COC(=O)c2cccc(S(=O)(=O)NC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(methylsulfamoyl)benzoate | 2.00 | *** |

TABLE 5-continued

| Ex. | Cmpd | Structure | IUPAC Name | HPLC Rt (min) | PDE4 IC$_{50}$ range |
|---|---|---|---|---|---|
| 229 | 333 | 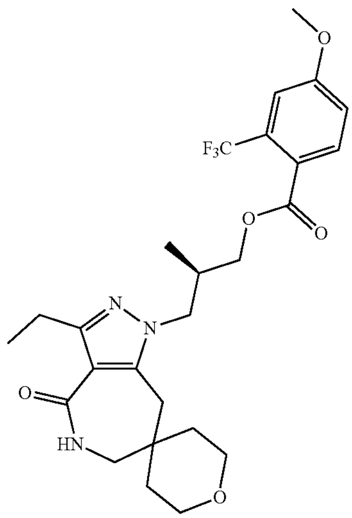 [SMILES: CCc1nn(C[C@@H](C)COC(=O)c2ccc(OC)cc2C(F)(F)F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-2-(trifluoromethyl)benzoate | 2.28 | *** |
| 230 | 334 | 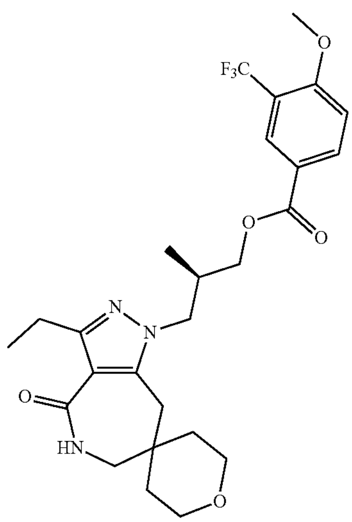 [SMILES: CCc1nn(C[C@@H](C)COC(=O)c2ccc(OC)c(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-(trifluoromethyl)benzoate | 2.30 | *** |
| 231 | 335 | 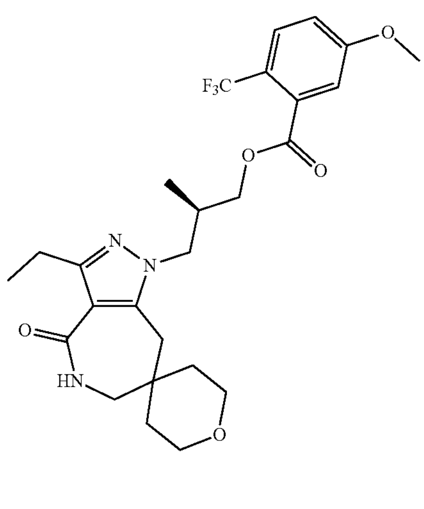 [SMILES: CCc1nn(C[C@@H](C)COC(=O)c2cc(OC)ccc2C(F)(F)F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-methoxy-2-(trifluoromethyl)benzoate | 2.28 | *** |

TABLE 5-continued

| Ex. | Cmpd | Structure | IUPAC Name | HPLC Rt (min) | PDE4 IC$_{50}$ range |
|---|---|---|---|---|---|
| 232 | 336 | 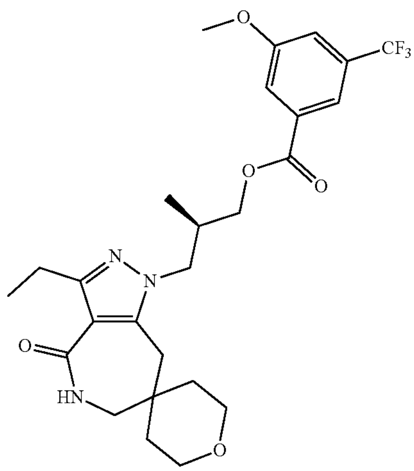 [SMILES: CCc1nn(C[C@@H](C)COC(=O)c2cc(OC)cc(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-5-(trifluoromethyl)benzoate | 2.36 | *** |
| 233 | 337 | 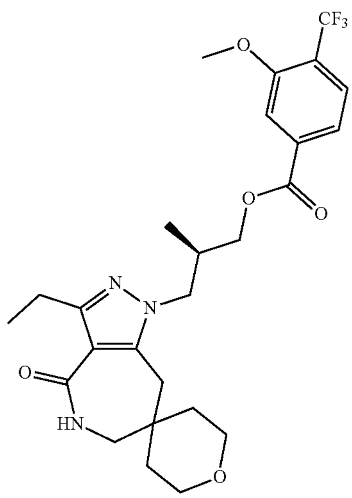 [SMILES: CCc1nn(C[C@@H](C)COC(=O)c2ccc(C(F)(F)F)c(OC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-4-(trifluoromethyl)benzoate | 2.35 | *** |
| 234 | 338 | 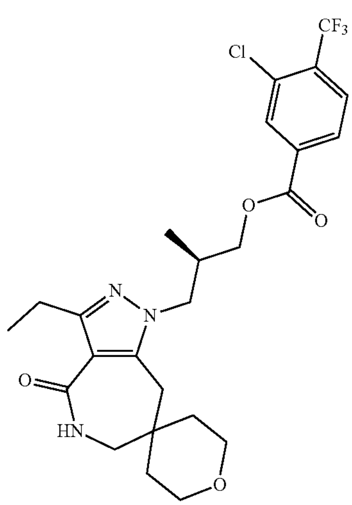 [SMILES: CCc1nn(C[C@@H](C)COC(=O)c2ccc(C(F)(F)F)c(Cl)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-(trifluoromethyl)benzoate | 2.42 | *** |

TABLE 5-continued

| Ex. | Cmpd | Structure | IUPAC Name | HPLC Rt (min) | PDE4 IC$_{50}$ range |
|---|---|---|---|---|---|
| 235 | 339 | 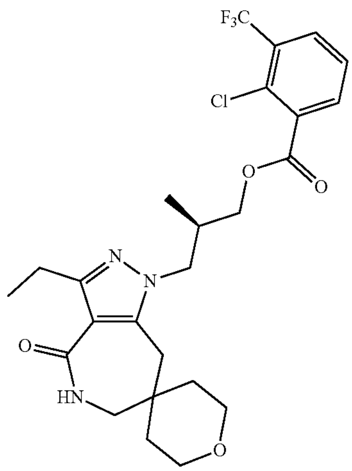 | [(2R)-3-(3-ethyl-4-oxo-spiro [6,8-dihydro-5H-pyrazolo[4,3-c]azepine-7,4'-tetrahydropyran]-1-yl)-2-methyl-propyl] 2-chloro-3-(trifluoromethyl)benzoate | 2.33 | *** |
| 236 | 340 | 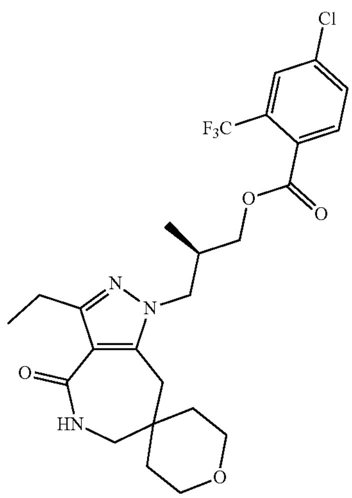 | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-(trifluoromethyl)benzoate | 2.38 | *** |
| 237 | 341 | 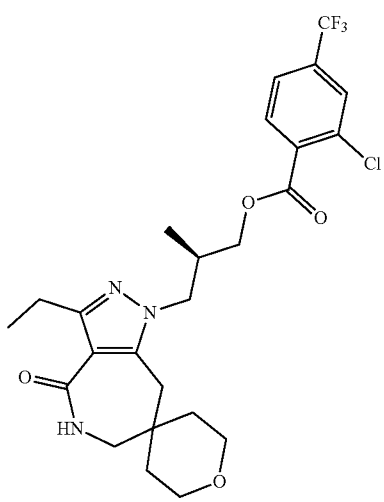 [SMILES: CCc1nn(C[C@@H](C)COC(=O)c2ccc(C(F)(F)F)cc2Cl)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-4-(trifluoromethyl)benzoate | 2.38 | *** |

TABLE 5-continued

| Ex. | Cmpd | Structure | IUPAC Name | HPLC Rt (min) | PDE4 IC$_{50}$ range |
|---|---|---|---|---|---|
| 238 | 342 | 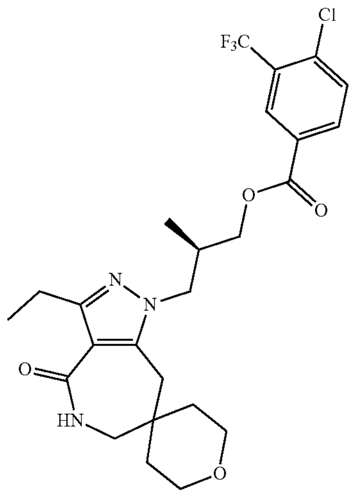 [SMILES: CCc1nn(C[C@@H](C)COC(=O)c2ccc(Cl)c(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-(trifluoromethyl)benzoate | 2.42 | *** |
| 239 | 343 | 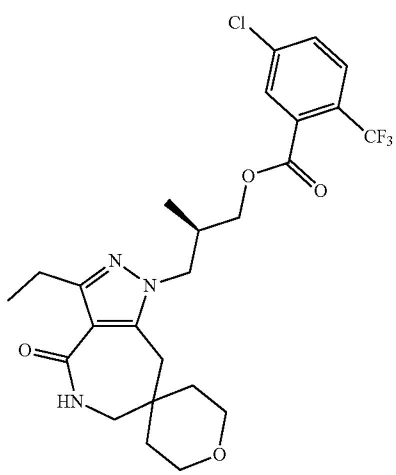 [SMILES: CCc1nn(C[C@@H](C)COC(=O)c2cc(Cl)ccc2C(F)(F)F)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-(trifluoromethyl)benzoate | 2.36 | *** |
| 240 | 344 | 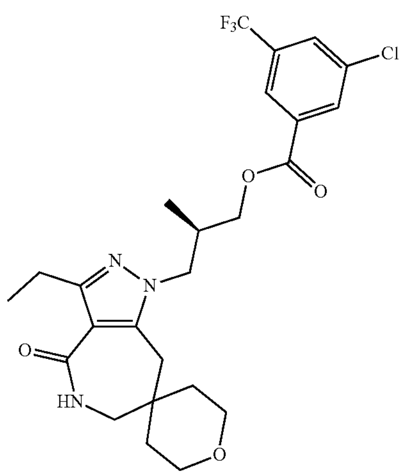 [SMILES: CCc1nn(C[C@@H](C)COC(=O)c2cc(Cl)cc(C(F)(F)F)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-5-(trifluoromethyl)benzoate | 2.44 | *** |

TABLE 5-continued

| Ex. | Cmpd | Structure | IUPAC Name | HPLC Rt (min) | PDE4 IC$_{50}$ range |
|---|---|---|---|---|---|
| 241 | 345 | 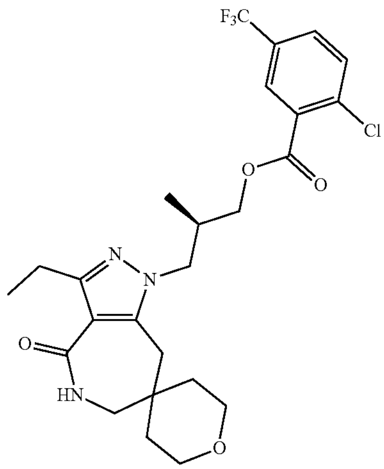 [SMILES: CCc1nn(C[C@@H](C)COC(=O)c2cc(C(F)(F)F)ccc2Cl)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-(trifluoromethyl)benzoate | 2.36 | *** |
| 242 | 346 | 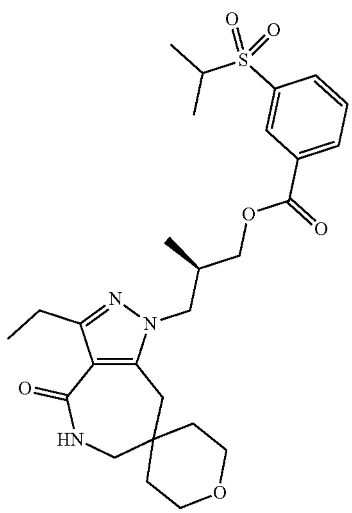 [SMILES: CCc1nn(C[C@@H](C)COC(=O)c2cccc(S(=O)(=O)C(C)C)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-isopropylsulfonylbenzoate | 2.10 | *** |
| 243 | 347 | 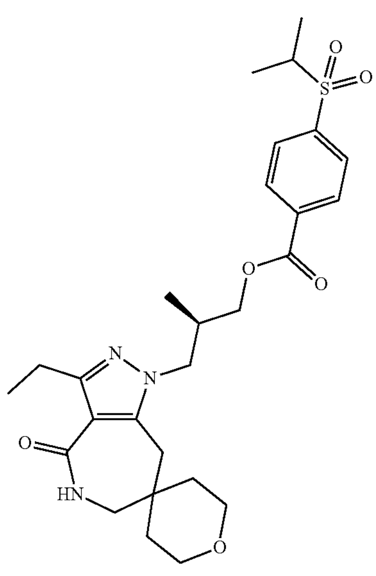 [SMILES: CCc1nn(C[C@@H](C)COC(=O)c2ccc(S(=O)(=O)C(C)C)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-isopropylsulfonylbenzoate | 2.11 | *** |

TABLE 5-continued

| Ex. | Cmpd | Structure | IUPAC Name | HPLC Rt (min) | PDE4 IC$_{50}$ range |
|---|---|---|---|---|---|
| 244 | 348 | 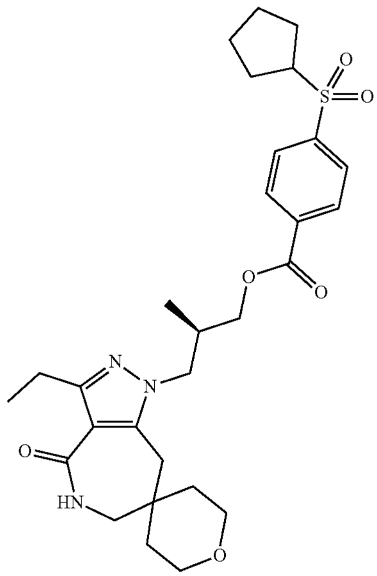 [SMILES: CCc1nn(C[C@@H](C)COC(=O)c2ccc(S(=O)(=O)C3CCCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyclopentylsulfonylbenzoate | 2.21 | **** |
| 245 | 349 | 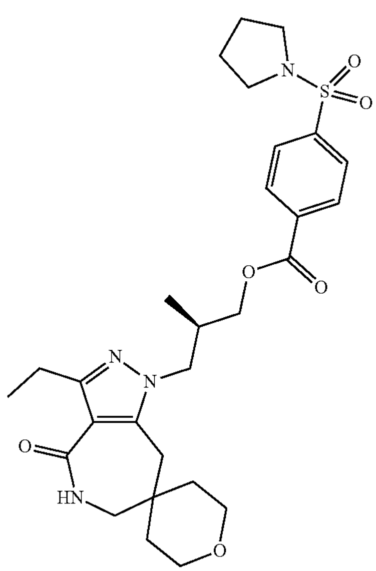 [SMILES: CCc1nn(C[C@@H](C)COC(=O)c2ccc(S(=O)(=O)N3CCCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-pyrrolidin-1-ylsulfonylbenzoate | 2.19 | *** |

TABLE 5-continued

| Ex. | Cmpd | Structure | IUPAC Name | HPLC Rt (min) | PDE4 IC$_{50}$ range |
|---|---|---|---|---|---|
| 246 | 350 | 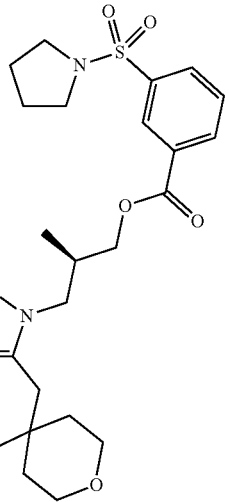 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-pyrrolidin-1-ylsulfonylbenzoate | 2.17 | *** |
| 247 | 351 | 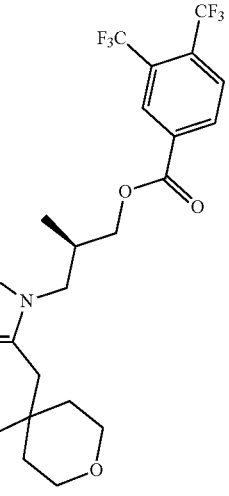 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-bis(trifluoromethyl)benzoate | 2.45 | *** |
| 248 | 352 | 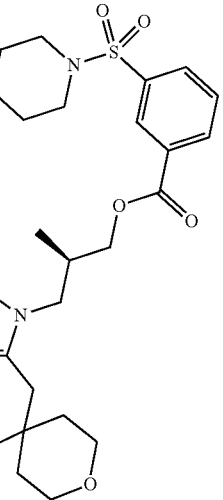 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-morpholinosulfonylbenzoate | 2.09 | *** |

TABLE 5-continued

| Ex. | Cmpd | Structure | IUPAC Name | HPLC Rt (min) | PDE4 IC$_{50}$ range |
|---|---|---|---|---|---|
| 249 | 353 | 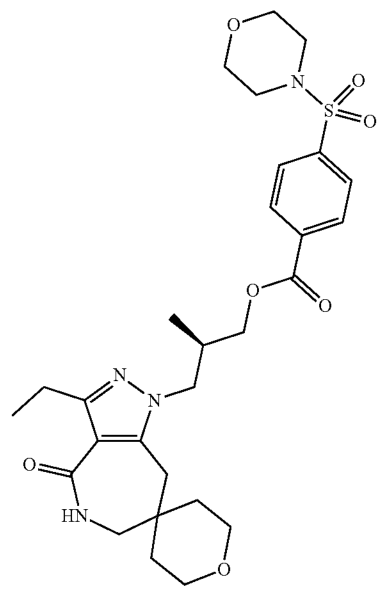 [SMILES: CCc1nn(C[C@@H](C)COC(=O)c2ccc(S(=O)(=O)N3CCOCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-morpholinosulfonylbenzoate | 2.11 | *** |
| 250 | 354 | 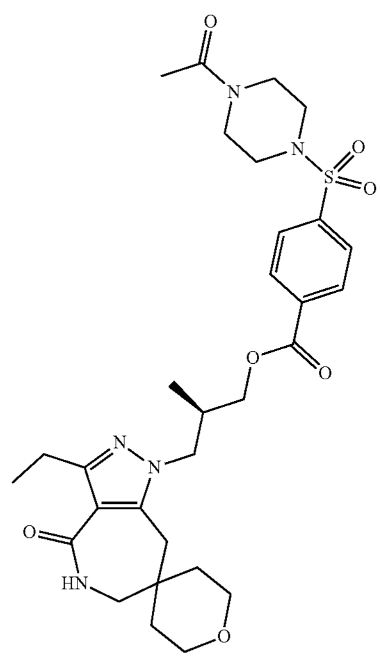 [SMILES: CCc1nn(C[C@@H](C)COC(=O)c2ccc(S(=O)(=O)N3CCN(C(C)=O)CC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazin-1-yl)sulfonylbenzoate | 2.02 | *** |

TABLE 5-continued

| Ex. | Cmpd | Structure | IUPAC Name | HPLC Rt (min) | PDE4 IC$_{50}$ range |
|---|---|---|---|---|---|
| 251 | 355 | 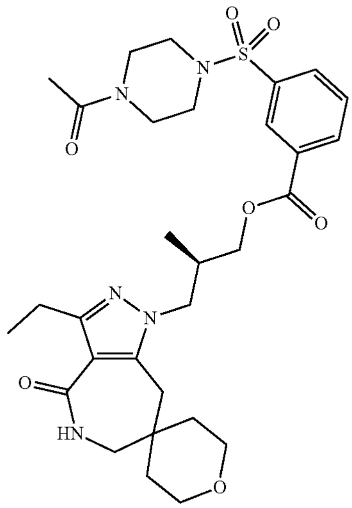 [SMILES: CCc1nn(C[C@@H](C)COC(=O)c2cccc(S(=O)(=O)N3CCN(C(C)=O)CC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazin-1-yl)sulfonylbenzoate | 2.00 | *** |

Preparation 22 (Compound 356)

[(2R)-3-(3-Ethyl-4-oxo-spiro[6,8-dihydro-5H-pyrazolo[4,3-c]azepine-7,4'-tetrahydropyran]-1-yl)-2-methyl-propyl] 4-formylbenzoate

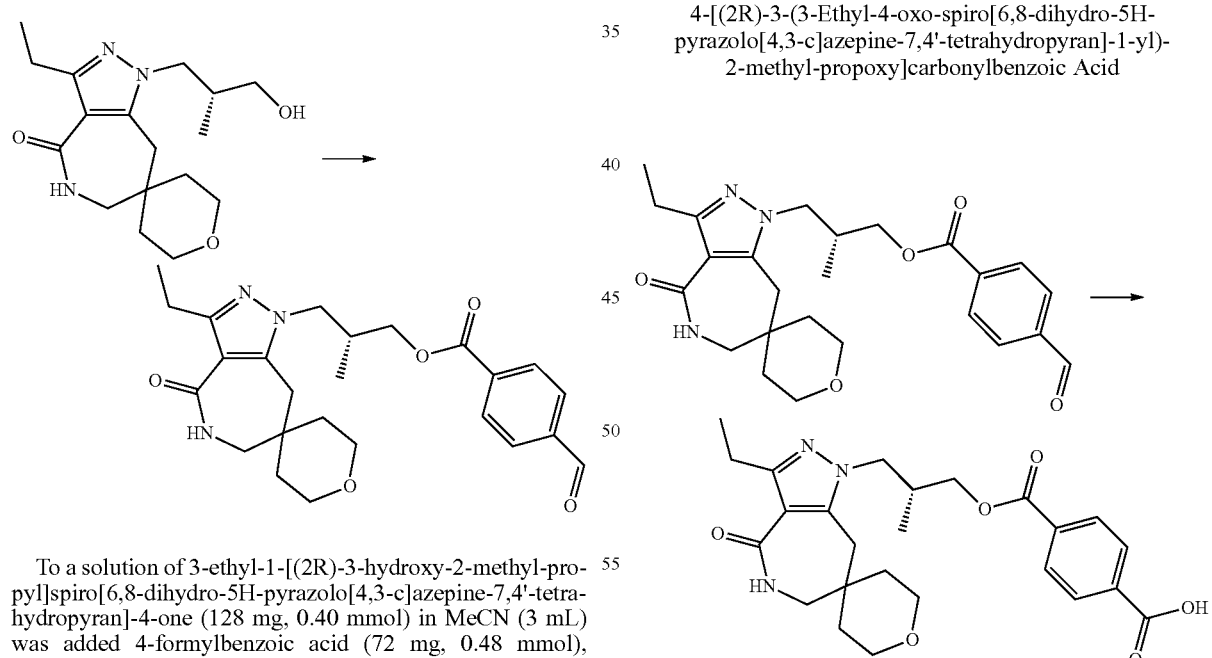

To a solution of 3-ethyl-1-[(2R)-3-hydroxy-2-methyl-propyl]spiro[6,8-dihydro-5H-pyrazolo[4,3-c]azepine-7,4'-tetrahydropyran]-4-one (128 mg, 0.40 mmol) in MeCN (3 mL) was added 4-formylbenzoic acid (72 mg, 0.48 mmol), EDAC (92 mg, 0.48 mmol) and DMAP (5 mg, 0.04 mmol). The mixture was shaken at 50° C. for ½ hour and then overnight at room temperature before it was evaporated to dryness under vacuum. Silica gel (100-200 mesh) column chromatography (0 to 15% MeOH in DCM as eluent, R$_f$ (DCM/MeOH: 20/1)=0.13) afforded the title compound as an oil.

$^1$H NMR (Chloroform-d) δ: 10.11 (s, 1H), 8.22-8.08 (m, 2H), 8.02-7.88 (m, 2H), 6.31-5.90 (m, 1H), 4.34-4.21 (m, 2H), 4.11 (dd, J=14.0, 7.5 Hz, 1H), 3.96 (dd, J=14.0, 6.9 Hz, 1H), 3.74-3.54 (m, 4H), 3.13 (d, J=5.8 Hz, 2H), 2.88 (q, J=7.5 Hz, 2H), 2.79-2.60 (m, 3H), 1.64-1.40 (m, 4H), 1.24 (t, J=7.5 Hz, 3H), 1.10 (d, J=7.0 Hz, 3H).

Preparation 23 (Compound 357)

4-[(2R)-3-(3-Ethyl-4-oxo-spiro[6,8-dihydro-5H-pyrazolo[4,3-c]azepine-7,4'-tetrahydropyran]-1-yl)-2-methyl-propoxy]carbonylbenzoic Acid Jones Reagent (1 mL) was added at room temperature to a solution of [(2R)-3-(3-ethyl-4-oxo-spiro[6,8-dihydro-5H-pyrazolo[4,3-c]azepine-7,4'-tetrahydropyran]-1-yl)-2-methyl-propyl] 4-formylbenzoate (60 mg, 0.13 mmol) in acetone/water (9 mL, 2:1). The solution was stirred at room temperature for 18 hours before isopropanol (1 mL) was added. The obtained mixture was stirred for another 30 min, diluted with water and extracted three times with DCM. The combined organic phases were concentrated in vacuo. Silica gel (100-200 mesh) column chromatography (R$_f$(MeOH/AcOH/DCM: 1/0.02/10)=0.31) afforded the title compound.

$^1$H NMR (DMSO-d6) δ: 13.45 (s, 1H), 8.08-7.99 (m, 4H), 7.45 (t, J=5.8 Hz, 1H), 4.23 (dd, J=11.0, 6.3 Hz, 1H), 4.16 (dd, J=11.0, 5.0 Hz, 1H), 4.12 (dd, J=14.1, 7.8 Hz, 1H), 3.99 (dd, J=14.1, 6.7 Hz, 1H), 3.60 (dt, J=11.8, 4.9 Hz, 1H), 3.57-3.44 (m, 3H), 3.04-2.92 (m, 2H), 2.80 (d, J=16.6 Hz, 1H), 2.75-2.66 (m, 3H), 2.57-2.48 (m, 1H), 1.39 (t, J=5.4 Hz, 2H), 1.37-1.30 (m, 2H), 1.08 (t, J=7.5 Hz, 3H), 1.01 (d, J=6.9 Hz, 3H).

HPLC-Retention time (XE Metode 7 CM): 1.94 minutes.

Detected "M+1"-mass: 470.21

The Examples 252-262 in Table 6 were prepared by reacting Compound 357 as described in General Procedure 3 with the appropriate amine:

TABLE 6

| Ex. | Cmpd | Structure | IUPAC Name | HPLC Rt (min) | PDE4 IC$_{50}$ range |
|---|---|---|---|---|---|
| 252 | 762 | 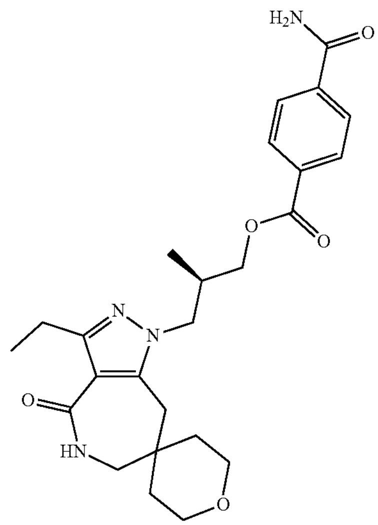 [SMILES: CCc1nn(C[C@@H](C)COC(=O)c2ccc(C(N)=O)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-carbamoylbenzoate | 1.86 | *** |
| 253 | 359 | 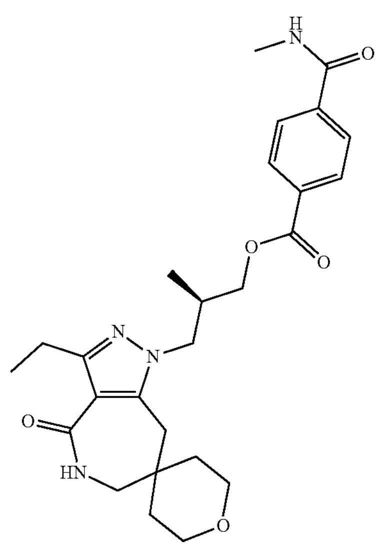 [SMILES: CCc1nn(C[C@@H](C)COC(=O)c2ccc(C(=O)NC)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(methylcarbamoyl)benzoate | 1.90 | *** |

TABLE 6-continued

| Ex. | Cmpd | Structure | IUPAC Name | HPLC Rt (min) | PDE4 IC$_{50}$ range |
|---|---|---|---|---|---|
| 254 | 360 | 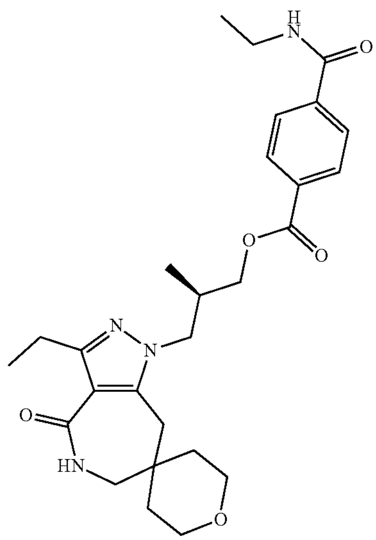 [SMILES: CCNC(=O)c1ccc(C(=O)OC[C@H](C)Cn2nc(CC)c3c2CC2(CCOCC2)CNC3=O)cc1] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(ethylcarbamoyl)benzoate | 1.97 | *** |
| 255 | 361 | 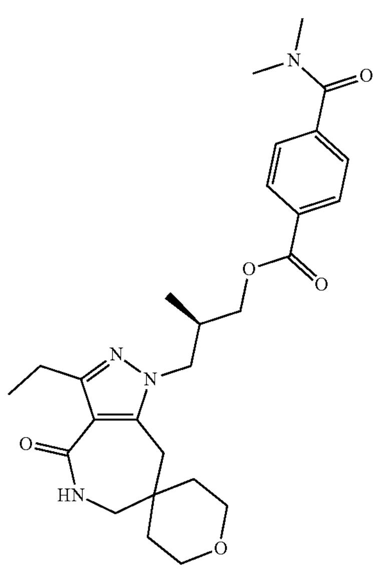 [SMILES: CCc1nn(C[C@@H](C)COC(=O)c2ccc(C(=O)N(C)C)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(dimethylcarbamoyl)benzoate | 1.93 | *** |

TABLE 6-continued

| Ex. | Cmpd | Structure | IUPAC Name | HPLC Rt (min) | PDE4 IC$_{50}$ range |
|---|---|---|---|---|---|
| 256 | 362 | 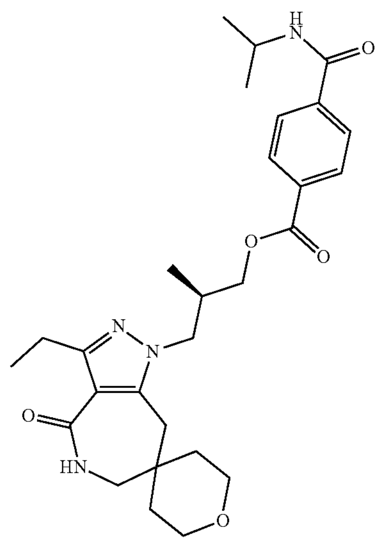 [SMILES: CCc1nn(C[C@@H](C)COC(=O)c2ccc(C(=O)NC(C)C)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(isopropylcarbamoyl)benzoate | 2.04 | *** |
| 257 | 363 | 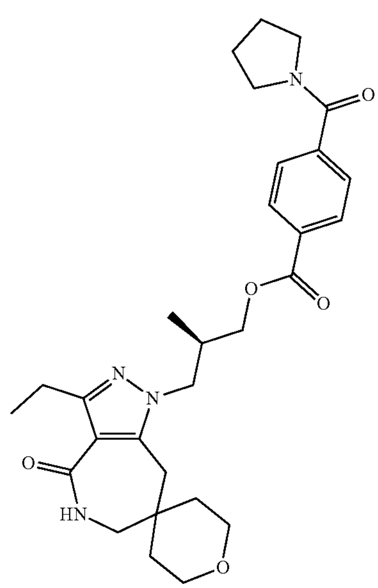 [SMILES: CCc1nn(C[C@@H](C)COC(=O)c2ccc(C(=O)N3CCCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(pyrrolidine-1-carbonyl)benzoate | 2.00 | *** |

TABLE 6-continued
| Ex. | Cmpd | Structure | IUPAC Name | HPLC Rt (min) | PDE4 IC$_{50}$ range |
|---|---|---|---|---|---|
| 258 | 364 | 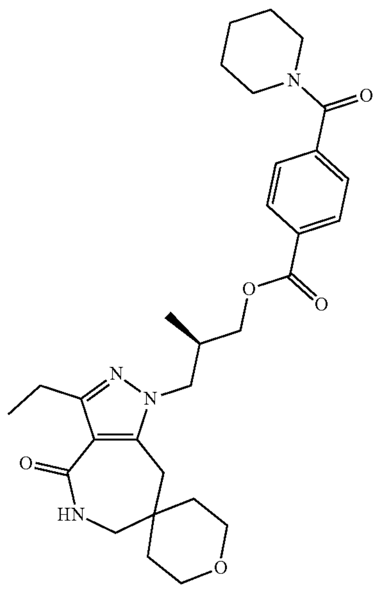 [SMILES: CCc1nn(C[C@@H](C)COC(=O)c2ccc(C(=O)N3CCCCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperidine-1-carbonyl)benzoate | 2.11 | *** |
| 259 | 365 | 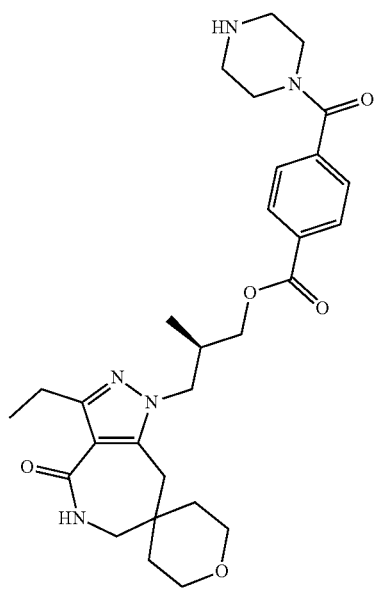 [SMILES: CCc1nn(C[C@@H](C)COC(=O)c2ccc(C(=O)N3CCNCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperazine-1-carbonyl)benzoate | 1.72 | *** |

TABLE 6-continued

| Ex. | Cmpd | Structure | IUPAC Name | HPLC Rt (min) | PDE4 IC$_{50}$ range |
|---|---|---|---|---|---|
| 260 | 366 | 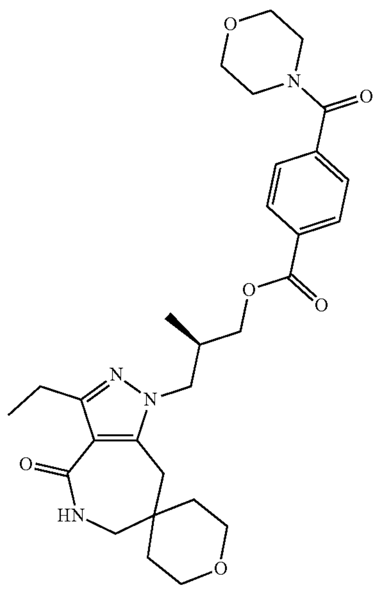 [SMILES: CCc1nn(C[C@@H](C)COC(=O)c2ccc(C(=O)N3CCOCC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(morpholine-4-carbonyl)benzoate | 1.93 | *** |
| 261 | 367 | 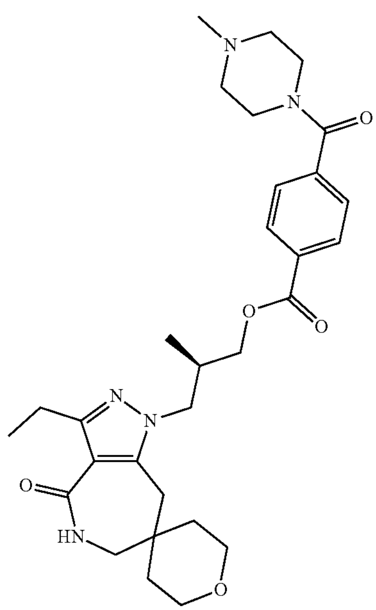 [SMILES: CCc1nn(C[C@@H](C)COC(=O)c2ccc(C(=O)N3CCN(C)CC3)cc2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-methylpiperazine-1-carbonyl)benzoate | 1.73 | *** |

TABLE 6-continued

| Ex. | Cmpd | Structure | IUPAC Name | HPLC Rt (min) | PDE4 IC$_{50}$ range |
|---|---|---|---|---|---|
| 262 | 368 | 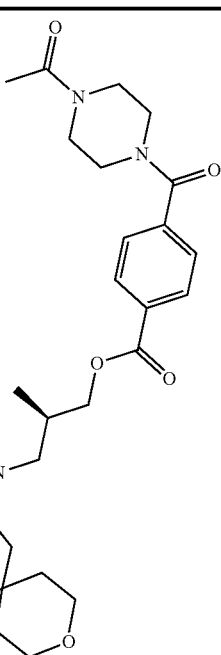 | [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazine-1-carbonyl)benzoate | 1.86 | *** |

Preparation 24 (Compound 369)

[(2R)-3-(3-Ethyl-4-oxo-spiro[6,8-dihydro-5H-pyrazolo[4,3-c]azepine-7,4'-tetrahydropyran]-1-yl)-2-methyl-propyl]3-formylbenzoate

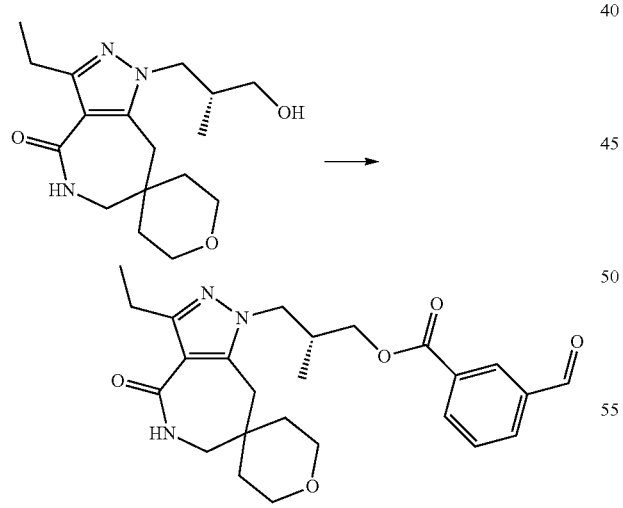

To a solution of 3-ethyl-1-[(2R)-3-hydroxy-2-methyl-propyl]spiro[6,8-dihydro-5H-pyrazolo[4,3-c]azepine-7,4'-tetrahydropyran]-4-one (64 mg, 0.20 mmol) in MeCN (2 mL) was added 3-formylbenzoic acid (36 mg, 0.24 mmol), EDAC (46 mg, 0.24 mmol) and DMAP (5 mg, 0.04 mmol). The mixture was shaken at 50° C. for 30 minutes and then overnight at room temperature before it was evaporated to dryness under vacuum. Silica gel (100-200 mesh) column chromatography (R$_f$(DCM/MeOH: 20/1)=0.13) afforded the title compound as an oil.

$^1$H NMR (Chloroform-d) δ: 10.09 (s, 1H), 8.53-8.45 (m, 1H), 8.26 (dt, 1H), 8.10 (dt, J=7.7, 1.5 Hz, 1H), 7.66 (t, J=7.7 Hz, 1H), 5.86 (s, 1H), 4.36-4.20 (m, 2H), 4.12 (dd, J=14.0, 7.6 Hz, 1H), 3.97 (dd, J=14.0, 7.0 Hz, 1H), 3.74-3.53 (m, 4H), 3.13 (d, J=5.8 Hz, 2H), 2.86 (q, J=7.5 Hz, 2H), 2.76-2.68 (m, 2H), 1.69 (s, 1H), 1.64-1.43 (m, 4H), 1.22 (t, J=7.5 Hz, 3H), 1.10 (d, J=6.9 Hz, 3H).

Preparation 25 (Compound 370)

3-[(2R)-3-(3-Ethyl-4-oxo-spiro[6,8-dihydro-5H-pyrazolo[4,3-c]azepine-7,4'-tetrahydropyran]-1-yl)-2-methyl-propoxy]carbonylbenzoic Acid

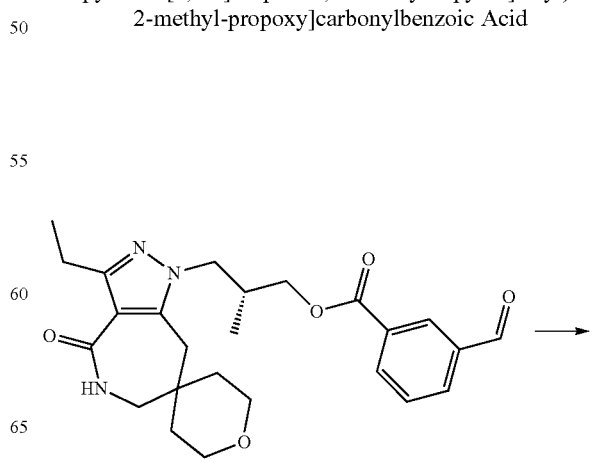

-continued

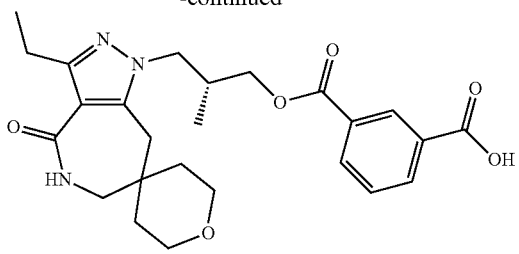

Jones Reagent (1 mL) was added at room temperature to a solution of [(2R)-3-(3-ethyl-4-oxo-spiro[6,8-dihydro-5H-pyrazolo[4,3-c]azepine-7,4'-tetrahydropyran]-1-yl)-2-methyl-propyl]-3-formylbenzoate (30 mg, 0.065 mmol) in acetone/water (9 mL, 2:1). The solution was stirred at room temperature for 18 hours before isopropanol (1 mL) was added. The obtained mixture was stirred for another 30 min, diluted with water and extracted three times with DCM. The combined organic phases were concentrated in vacuo. Silica gel (100-200 mesh) column chromatography (R$_f$(MeOH/AcOH/DCM: 1/0.02/10)=0.31) afforded the title compound.

$^1$H NMR (DMSO-d6) δ: 13.46 (s, 1H), 8.47 (t, J=1.8 Hz, 1H), 8.20 (dt, J=7.7, 1.5 Hz, 1H), 8.14 (dt, J=7.8, 1.5 Hz, 1H), 7.66 (t, J=7.8 Hz, 1H), 7.44 (t, J=5.8 Hz, 1H), 4.24 (dd, J=11.0, 6.2 Hz, 1H), 4.15 (dd, J=11.0, 5.3 Hz, 1H), 4.10 (dd, J=14.1, 7.5 Hz, 1H), 3.99 (dd, J=14.1, 6.9 Hz, 1H), 3.60 (dt, J=11.8, 4.9 Hz, 1H), 3.57-3.44 (m, 3H), 3.03-2.93 (m, 2H), 2.78 (d, J=16.5 Hz, 1H), 2.74-2.66 (m, 3H), 2.57-2.52 (m, 1H), 1.39 (t, J=5.4 Hz, 2H), 1.37-1.32 (m, 2H), 1.08 (t, J=7.5 Hz, 3H), 1.00 (d, J=6.9 Hz, 3H).

HPLC-Retention time (XE Metode 7 CM): 1.94 minutes.
Detected "M+1"-mass: 470.21

The Examples 263-273 in Table 7 were prepared by reacting Compound 370 as described in General Procedure 3 with the appropriate amine:

TABLE 7

| Ex. | Cmpd | Structure | IUPAC Name | HPLC Rt (min) | PDE4 IC$_{50}$ range |
|---|---|---|---|---|---|
| 263 | 371 | 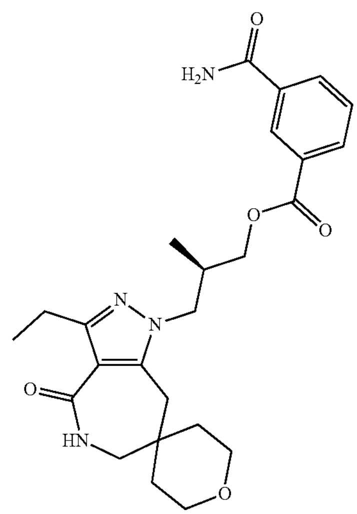 [SMILES: CCc1nn(C[C@@H](C)COC(=O)c2cccc(C(N)=O)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-carbamoylbenzoate | 1.85 | *** |
| 264 | 372 | 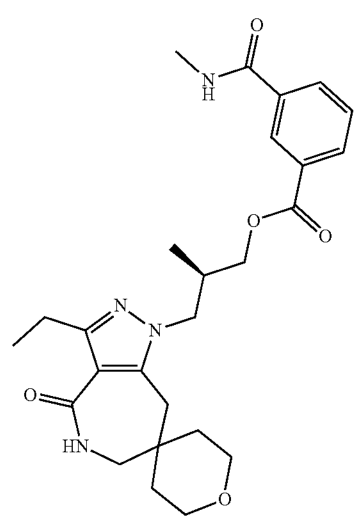 [SMILES: CCc1nn(C[C@@H](C)COC(=O)c2cccc(C(=O)NC)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(methylcarbamoyl)benzoate | 1.90 | *** |

TABLE 7-continued

| Ex. | Cmpd | Structure | IUPAC Name | HPLC Rt (min) | PDE4 IC$_{50}$ range |
|---|---|---|---|---|---|
| 265 | 373 | 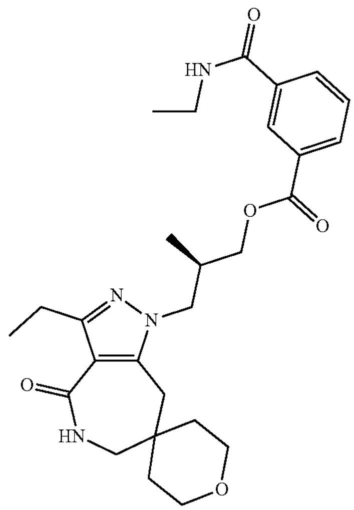 [SMILES: CCNC(=O)c1cccc(C(=O)OC[C@H](C)Cn2nc(CC)c3c2CC2(CCOCC2)CNC3=O)c1] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(ethylcarbamoyl)benzoate | 1.96 | *** |
| 266 | 374 | 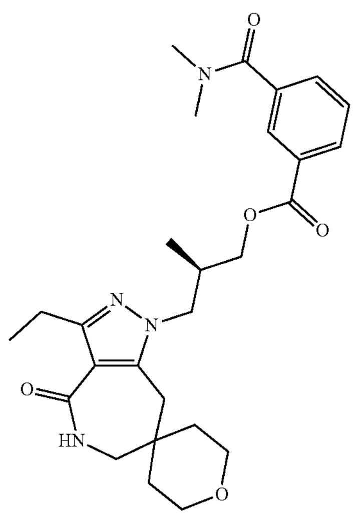 [SMILES: CCc1nn(C[C@@H](C)COC(=O)c2cccc(C(=O)N(C)C)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(dimethylcarbamoyl)benzoate | 1.93 | *** |
| 267 | 375 | 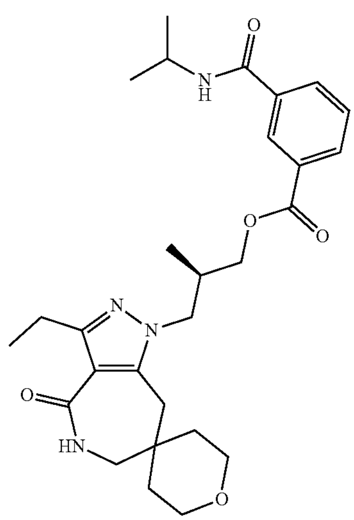 [SMILES: CCc1nn(C[C@@H](C)COC(=O)c2cccc(C(=O)NC(C)C)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(isopropylcarbamoyl)benzoate | 2.04 | *** |

TABLE 7-continued

| Ex. | Cmpd | Structure | IUPAC Name | HPLC Rt (min) | PDE4 IC$_{50}$ range |
|---|---|---|---|---|---|
| 268 | 376 | 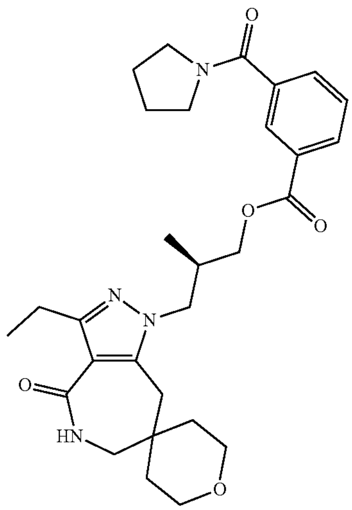 [SMILES: CCc1nn(C[C@@H](C)COC(=O)c2cccc(C(=O)N3CCCC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(pyrrolidine-1-carbonyl)benzoate | 2.00 | *** |
| 269 | 377 | 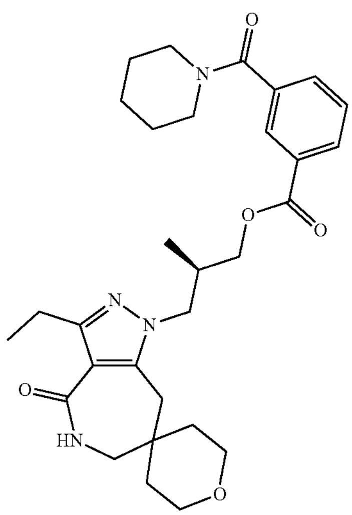 [SMILES: CCc1nn(C[C@@H](C)COC(=O)c2cccc(C(=O)N3CCCCC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperidine-1-carbonyl)benzoate | 2.10 | *** |
| 270 | 378 | 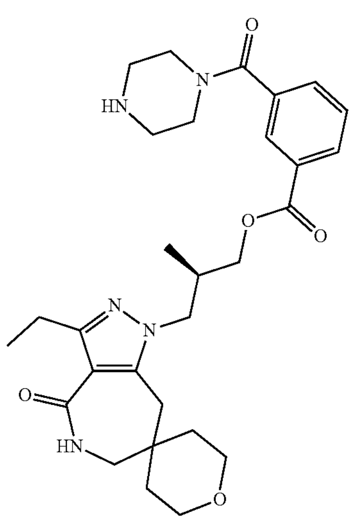 [SMILES: CCc1nn(C[C@@H](C)COC(=O)c2cccc(C(=O)N3CCNCC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperazine-1-carbonyl)benzoate | 1.72 | *** |

TABLE 7-continued

| Ex. | Cmpd | Structure | IUPAC Name | HPLC Rt (min) | PDE4 IC$_{50}$ range |
|---|---|---|---|---|---|
| 271 | 379 | 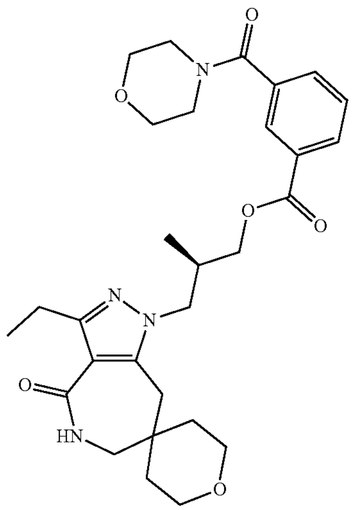 [SMILES: CCc1nn(C[C@@H](C)COC(=O)c2cccc(C(=O)N3CCOCC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(morpholine-4-carbonyl)benzoate | 1.93 | *** |
| 272 | 380 | 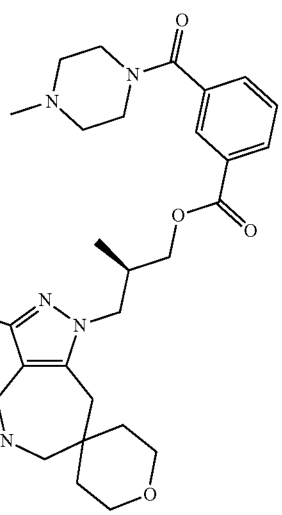 | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-methylpiperazine-1-carbonyl)benzoate | 1.73 | *** |
| 273 | 381 | 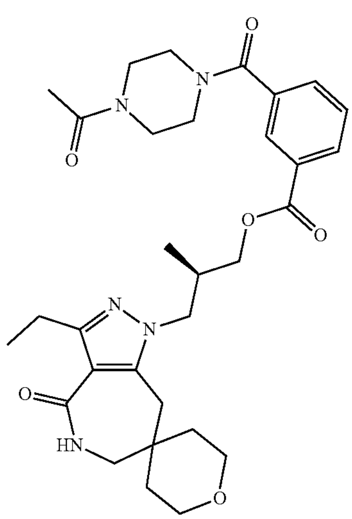 [SMILES: CCc1nn(C[C@@H](C)COC(=O)c2cccc(C(=O)N3CCN(C(C)=O)CC3)c2)c2c1C(=O)NCC1(CCOCC1)C2] | [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazine-1-carbonyl)benzoate | 1.86 | *** |

Preparation 26 (Compound 382)

3-Ethyl-1-[(2S)-3-hydroxy-2-methyl-propyl]spiro[6,8-dihydro-5H-pyrazolo[4,3-c]azepine-7,4'-tetrahydropyran]-4-one

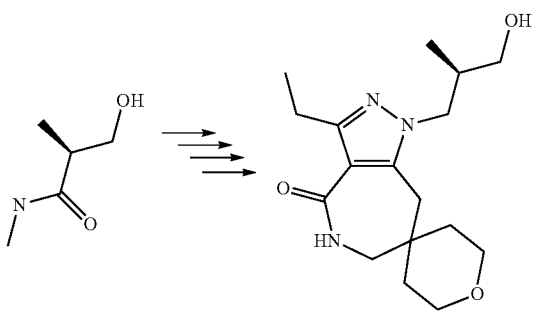

3-Ethyl-1-[(2S)-3-hydroxy-2-methyl-propyl]spiro[6,8-dihydro-5H-pyrazolo[4,3-c]azepine-7,4'-tetrahydropyran]-4-one was prepared in a manner similar to that of 3-ethyl-1-[(2R)-3-hydroxy-2-methyl-propyl]spiro[6,8-dihydro-5H-pyrazolo[4,3-c]-azepine-7,4'-tetrahydropyran]-4-one described in Preparation 11 to Preparation 17 using methyl (2R)-3-hydroxy-2-methyl-propanoate instead of methyl (2S)-3-hydroxy-2-methyl-propanoate as starting material.

$^1$H NMR (DMSO-d6) δ: 7.39 (t, J=5.6 Hz, 1H), 4.62 (t, J=5.1 Hz, 1H), 4.01 (dd, J=13.9, 6.5 Hz, 1H), 3.74 (dd, J=13.9, 7.7 Hz, 1H), 3.68-3.47 (m, 4H), 3.27 (t, J=5.4 Hz, 2H), 3.01 (d, J=5.7 Hz, 2H), 2.79-2.68 (m, 4H), 2.16-1.95 (m, 1H), 1.54-1.35 (m, 4H), 1.11 (t, J=7.5 Hz, 3H), 0.81 (d, J=6.8 Hz, 3H).

HPLC-Retention time (XE Metode 7 CM): 1.66 minutes.

Detected "M+1"-mass: 321.21.

The following Examples 274-279 in Table 8 were prepared by reacting Compound 382 as described in General Procedure 2 with the appropriate acid:

TABLE 8

| Ex. | Cmpd | Structure | IUPAC Name | HPLC Rt (min) | PDE4 IC$_{50}$ range |
|---|---|---|---|---|---|
| 274 | 383 | 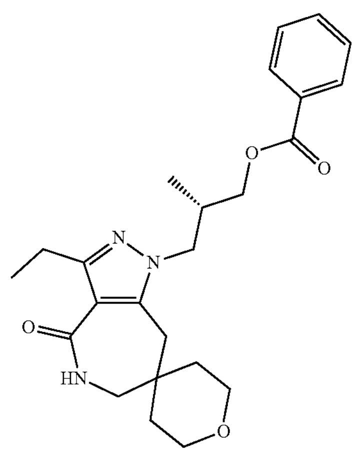 [SMILES: CCc1nn(C[C@H](C)COC(=O)c2ccccc2)c2c1C(=O)NCC1(CCOCC1)C2] | [(2S)-3-(3-ethyl-4-oxo-spiro[6,8-dihydro-5H-pyrazolo[4,3-c]azepine-7,4'-tetrahydropyran]-1-yl)-2-methyl-propyl] benzoate | 2.13 | *** |
| 275 | 384 | 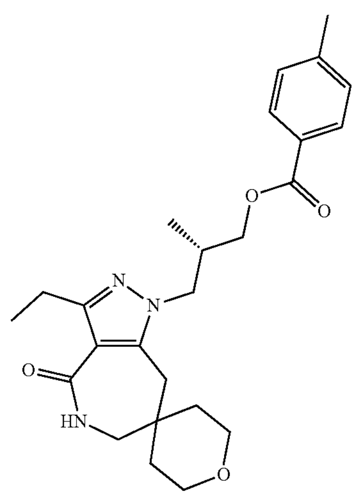 [SMILES: CCc1nn(C[C@H](C)COC(=O)c2ccc(C)cc2)c2c1C(=O)NCC1(CCOCC1)C2] | [(2S)-3-(3-ethyl-4-oxo-spiro[6,8-dihydro-5H-pyrazolo[4,3-c]azepine-7,4'-tetrahydropyran]-1-yl)-2-methyl-propyl] 4-methylbenzoate | 2.22 | *** |

TABLE 8-continued

| Ex. | Cmpd | Structure | IUPAC Name | HPLC Rt (min) | PDE4 IC$_{50}$ range |
|---|---|---|---|---|---|
| 276 | 385 | 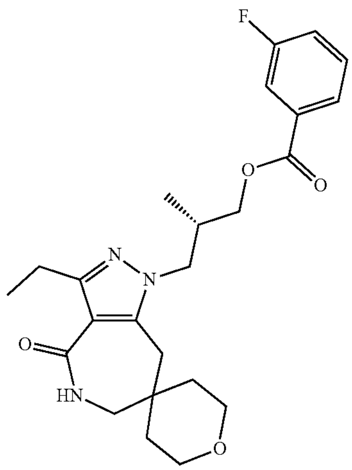 [SMILES: CCc1nn(C[C@H](C)COC(=O)c2cccc(F)c2)c2c1C(=O)NCC1(CCOCC1)C2] | [(2S)-3-(3-ethyl-4-oxo-spiro[6,8-dihydro-5H-pyrazolo[4,3-c]azepine-7,4'-tetrahydropyran]-1-yl)-2-methyl-propyl] 3-fluorobenzoate | 2.17 | *** |
| 277 | 386 | 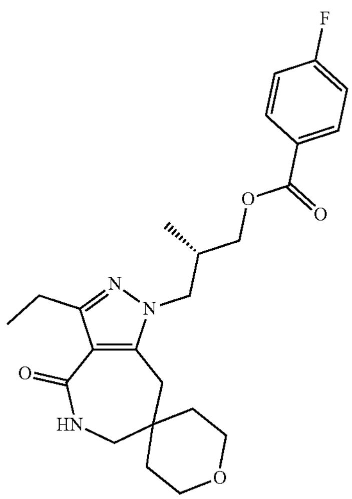 [SMILES: CCc1nn(C[C@H](C)COC(=O)c2ccc(F)cc2)c2c1C(=O)NCC1(CCOCC1)C2] | [(2S)-3-(3-ethyl-4-oxo-spiro[6,8-dihydro-5H-pyrazolo[4,3-c]azepine-7,4'-tetrahydropyran]-1-yl)-2-methyl-propyl] 4-fluorobenzoate | 2.16 | *** |
| 278 | 387 | 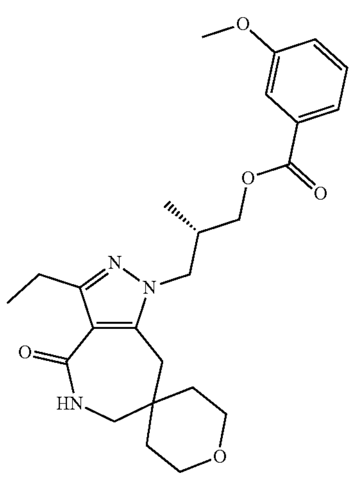 [SMILES: CCc1nn(C[C@H](C)COC(=O)c2cccc(OC)c2)c2c1C(=O)NCC1(CCOCC1)C2] | [(2S)-3-(3-ethyl-4-oxo-spiro[6,8-dihydro-5H-pyrazolo[4,3-c]azepine-7,4'-tetrahydropyran]-1-yl)-2-methyl-propyl] 3-methoxybenzoate | 2.15 | *** |

TABLE 8-continued

| Ex. | Cmpd | Structure | IUPAC Name | HPLC Rt (min) | PDE4 IC$_{50}$ range |
|---|---|---|---|---|---|
| 279 | 388 | 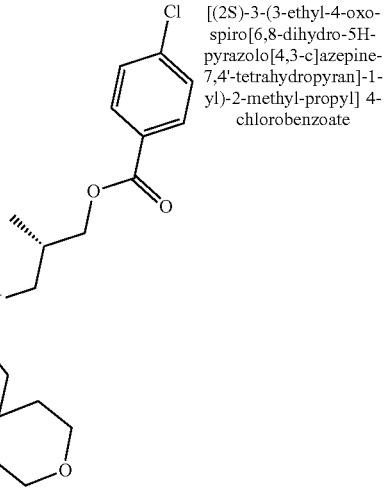 | [(2S)-3-(3-ethyl-4-oxo-spiro[6,8-dihydro-5H-pyrazolo[4,3-c]azepine-7,4'-tetrahydropyran]-1-yl)-2-methyl-propyl] 4-chlorobenzoate | 2.27 | *** |

Preparation 27 (Compound 389)

(3-Hydroxy-2,2-dimethyl-propyl) Benzoate

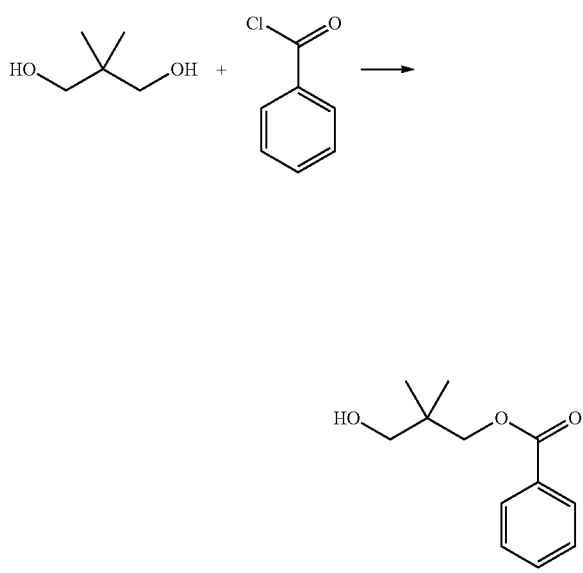

3-Hydroxy-2,2-dimethylpropanol (93.4 g, 900 mmol) was dissolved in DCM (600 mL), cooled in an ice bath under argon. DMAP (7.3 g, 60 mmol) and pyridine (48.3 mL, 600 mmol) was added, followed by dropwise addition of benzoyl chloride (42.2 g, 34.9 mL, 300 mmol) over 15 min. The mixture was stirred at rt for 3 days and quenched with 4N HCl (90 mL). After phase separation, the organic phase was washed with sat. NaHCO$_3$ (50 mL), water (50 mL) and brine (50 mL), dried over MgSO$_4$, filtered and concentrated in vacuo. Column chromatography (10% EtOAc in heptane) afforded the title compound.

Preparation 28 (Compound 390)

(2,2-Dimethyl-3-oxo-propyl) Benzoate

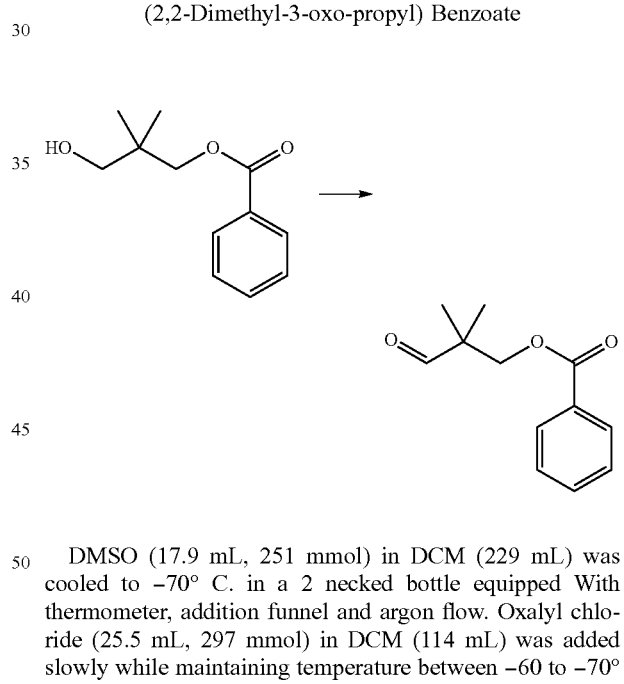

DMSO (17.9 mL, 251 mmol) in DCM (229 mL) was cooled to −70° C. in a 2 necked bottle equipped With thermometer, addition funnel and argon flow. Oxalyl chloride (25.5 mL, 297 mmol) in DCM (114 mL) was added slowly while maintaining temperature between −60 to −70° C. The mixture was stirred at −70° C. for 0.5 hour before (3-hydroxy-2,2-dimethyl-propyl) benzoate (47.6 g, 229 mmol) in DCM (229 mL) was added slowly while maintaining temperature between −60 and −70° C. The reaction mixture was stirred at −70° C. for 0.5 h. Triethylamine (127 mL, 914 mmol) was added slowly while maintaining temperature between −60 and −70° C. The mixture was stirred for 2 hours. Water (100 mL) was added and the mixture was phase separated. The aqueous phase was extracted with three times with DCM (3×50 mL) and the combined organic phases were washed with water (50 mL), brine (50 mL), dried over MgSO$_4$ and filtered. Concentrated in vacuo afforded approx. 60 g of reddish oil with precipitation. This mixture was suspended in DCM (20 mL) and filtered. Column chromatography (10 to 35% EtOAc in heptane) afforded the title compound.

$^1$H NMR (300 MHz, CDCl$_3$) δ 9.64 (s, 1H), 8.22-7.79 (m, 2H), 7.64-7.50 (m, 1H), 7.50-7.35 (m, 2H), 4.37 (s, 2H), 1.21 (s, 6H).

Preparation 29 (Compound 391)

[3-(2-Tert-butoxycarbonylhydrazino)-2,2-dimethyl-propyl] Benzoate

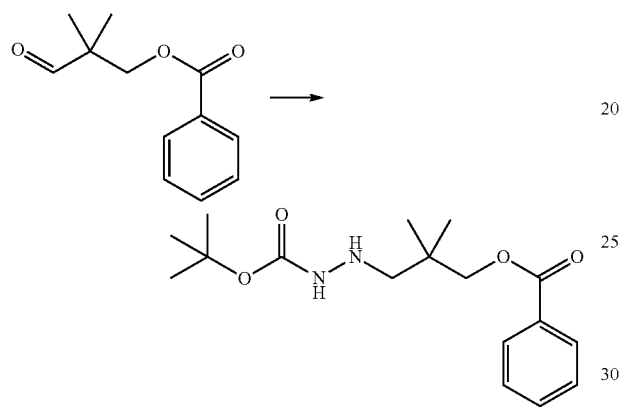

BOC—NHNH$_2$ (21.8 g, 165 mmol) and AcOH (28.3 mL, 495 mmol) was added to a solution of (2,2-dimethyl-3-oxo-propyl) benzoate (34.0 g, 165 mmol) in MeOH (200 mL). The reaction mixture was stirred at rt for 30 minutes before it was cooled to 0° C. Sodium cyanoborohydride (15.5 g, 247 mmol) was added portion wise over 5 minutes and the mixture was stirred for an additional 45 minutes at 0° C. The reaction was quenched with water (100 mL), and the mixture was extracted twice with DCM (2×200 mL). The combined organic phases were washed with water (100 mL), dried over MgSO$_4$, filtered and concentrated in vacuo. Column chromatography (heptane/ethyl acetate 9:1 to 1:1) afforded the title compound as an oil.

$^1$H NMR (300 MHz, CDCl$_3$) δ 8.20-7.99 (m, 2H), 7.63-7.50 (m, 1H), 7.50-7.37 (m, 2H), 6.13 (s, 1H), 4.23-4.15 (m, 1H), 4.14 (s, 2H), 2.86 (s, 2H), 1.42 (s, 9H), 1.04 (s, 6H).

Preparation 30 (Compound 392)

(3-Hydrazino-2,2-dimethyl-propyl) Benzoate Ditrifluoroacetic Acid Salt

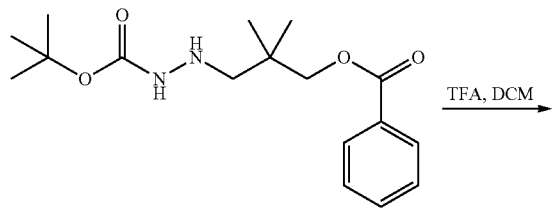

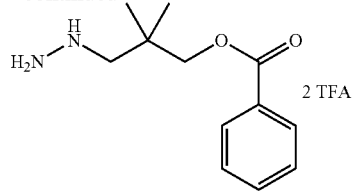

[3-(2-Tert-butoxycarbonylhydrazino)-2,2-dimethyl-propyl] benzoate (40 g, 124.1 mmol) was dissolved in DCM. TFA (50 mL) was added and the obtained solution was stirred at rt for 1 hour. Concentrated in vacuo gave the title compound. $^1$H NMR (300 MHz, CDCl$_3$) δ 8.03-7.96 (m, 2H), 7.64-7.53 (m, 1H), 7.50-7.40 (m, 2H), 4.20 (s, 2H), 3.09 (s, 2H), 1.16 (s, 6H).

Preparation 31 (Compound 393)

[3-(3-Ethyl-4-oxo-spiro[5,7-dihydroindazole-6,4'-tetrahydropyran]-1-yl)-2,2-dimethyl-propyl] Benzoate

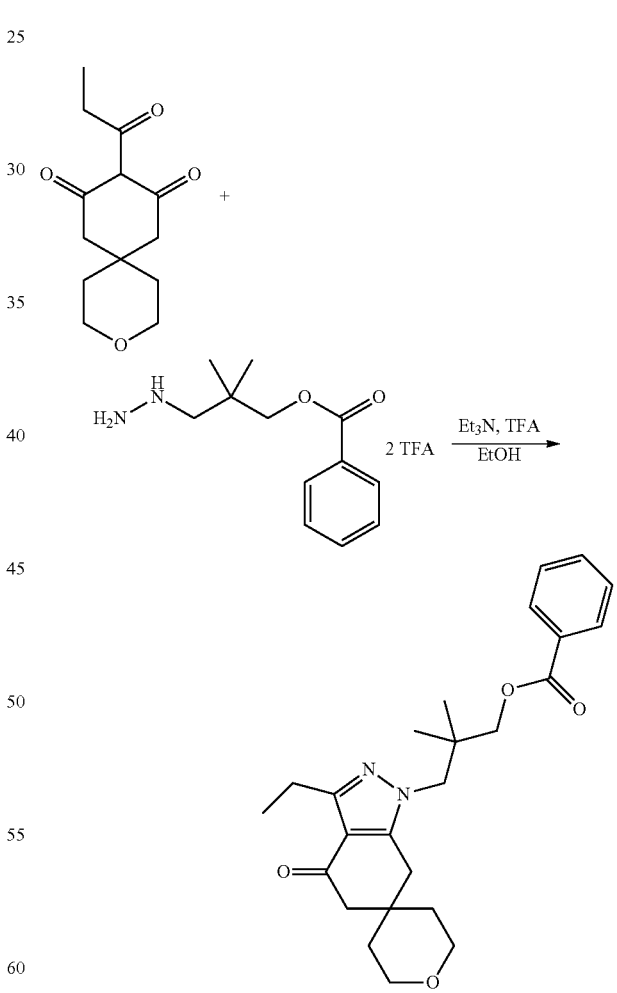

A mixture of 9-propanoyl-3-oxaspiro[5.5]undecane-8,10-dione (15 g, 63.0 mmol), (3-hydrazino-2,2-dimethyl-propyl) benzoate.2TFA (33.6 g, 74.6 mmol) and DIPEA (33.6 g, 251.8 mmol) in ethanol (200 mL) was stirred at rt for 10 minutes before it was heated to reflux for 2 hours. The mixture was then concentrated in vacuo. Water (100 mL) was added and the aqueous mixture was extracted three times with DCM (3×100 mL). The combined organic phases were dried over MgSO$_4$, filtered and concentrated in vacuo. Chromatography (heptane/ethyl acetate 9:1 to 1:9) gave the title product as an oil.

$^1$H NMR (300 MHz, CDCl$_3$) δ: 8.07-8.00 (m, 2H), 7.63-7.56 (m, 1H), 7.50-7.43 (m, 2H), 4.13 (s, 2H), 4.00 (s, 2H), 3.73-3.53 (m, 4H), 2.83 (q, J=7.5 Hz, 2H), 2.68 (s, 2H), 2.46 (s, 2H), 1.66-1.52 (m, 3H), 1.52-1.40 (m, 2H), 1.22 (t, J=7.5 Hz, 3H), 1.13 (s, 6H).

Example 280 (Compound 394)

[3-(3-Ethyl-4-oxo-spiro[6,8-dihydro-5H-pyrazolo[4,3-c]azepine-7,4'-tetrahydropyran]-1-yl)-2,2-dimethyl-propyl] Benzoate

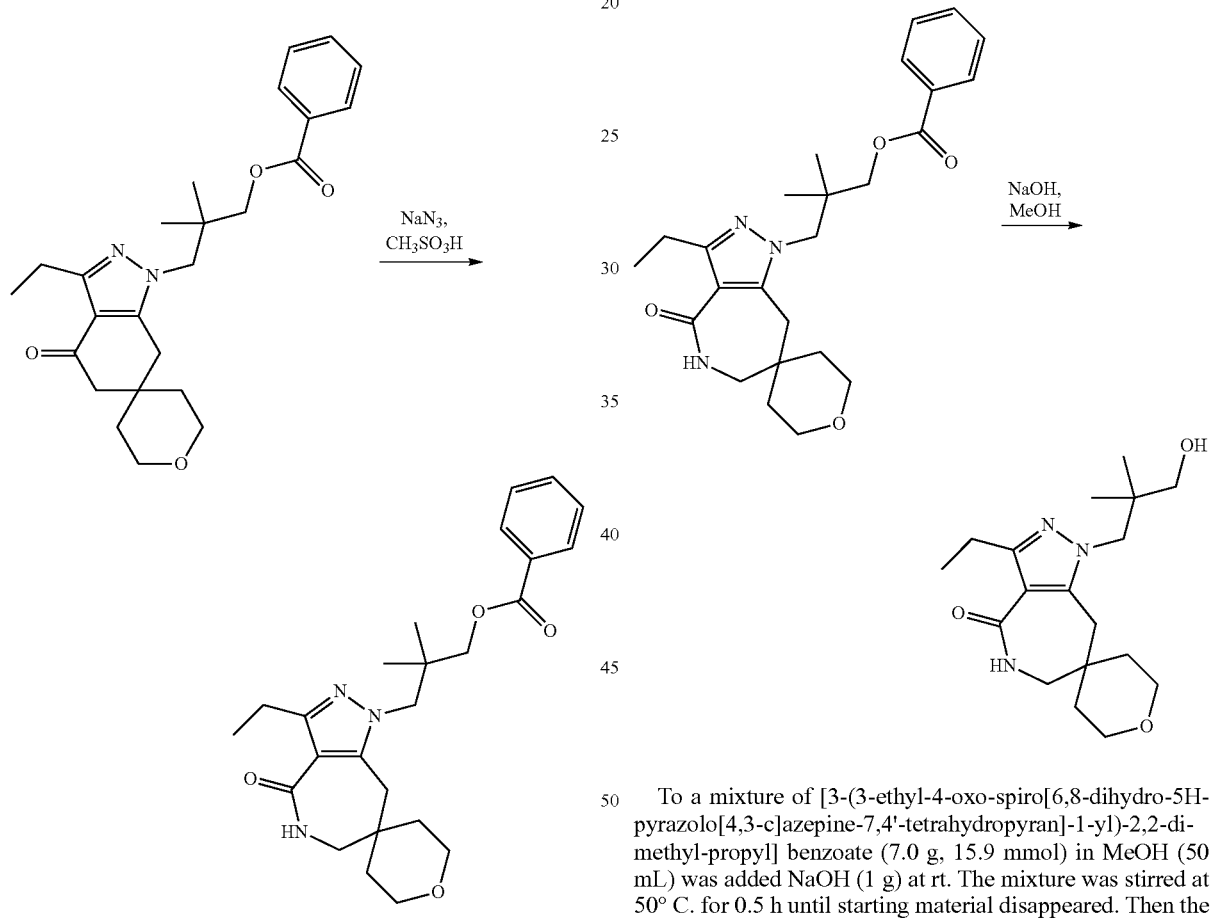

To a solution of [3-(3-ethyl-4-oxo-spiro[5,7-dihydroindazole-6,4'-tetrahydropyran]-1-yl)-2,2-dimethyl-propyl] benzoate (15 g, 35.3 mmol) in methanesulfonic acid (30 mL) and DCM (50 mL) was added sodium azide (11.5 g, 176.7 mmol) in portions at rt over 1 hour. Then the mixture was stirred at rt for 2 hours. The reaction was not complete. Ethanol (500 mL) was added to the mixture before it was neutralized with solid sodium hydroxide. The solid material was filtered off. The filtrate was concentrated in vacuo. The residue was taken up in chloroform (100 mL). The mixture was left standing for 30 minutes. The solid material was filtered off again. The filtrate was concentrated in vacuo. The residue was purified three times by chromatography (CHCl$_3$/MeOH 10:1, R$_f$=0.17), giving the title compound as a solid.

$^1$H NMR (600 MHz, DMSO-d6) δ 7.98 (t, J=7.7 Hz, 2H), 7.67 (t, J=7.7 Hz, 1H), 7.54 (t, J=7.7 Hz, 2H), 7.42 (t, J=5.7 Hz, 1H), 4.10 (s, 2H), 4.01 (s, 2H), 3.60-3.55 (m, 2H), 3.52-3.45 (m, 2H), 2.97 (d, J=5.7 Hz, 2H), 2.75 (s, 2H), 2.71 (q, J=7.5 Hz, 2H), 1.37 (t, J=5.4 Hz, 4H), 1.09 (t, J=7.5 Hz, 3H), 1.04 (s, 6H).

HPLC-Retention time (XE Metode 7 CM): 2.25 minutes. Detected "M+1"-mass: 440.25.

Preparation 32 (Compound 395)

3-Ethyl-1-(3-hydroxy-2,2-dimethyl-propyl)spiro[6,8-dihydro-5H-pyrazolo[4,3-c]azepine-7,4'-tetrahydropyran]-4-one

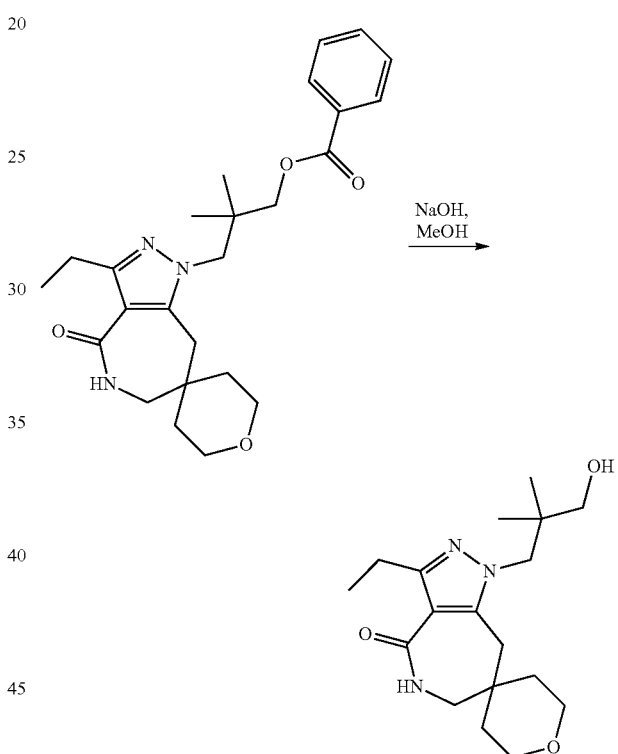

To a mixture of [3-(3-ethyl-4-oxo-spiro[6,8-dihydro-5H-pyrazolo[4,3-c]azepine-7,4'-tetrahydropyran]-1-yl)-2,2-dimethyl-propyl] benzoate (7.0 g, 15.9 mmol) in MeOH (50 mL) was added NaOH (1 g) at rt. The mixture was stirred at 50° C. for 0.5 h until starting material disappeared. Then the solution was neutralized by using 4N HCl and concentrated in vacuo. The residue was taken up in EtOH. The insoluble was filtered off. The filtrate was concentrated in vacuo. The residue was purified by chromatography (MeOH/DCM 1:10, R$_f$=0.36). Recrystallized in TBME/heptane gave the title compound as colorless crystals.

$^1$H NMR (300 MHz, DMSO-d6) δ 7.40 (t, J=5.7 Hz, 1H), 4.75 (t, J=5.3 Hz, 1H), 3.82 (s, 2H), 3.74-3.45 (m, 4H), 3.13 (d, J=5.2 Hz, 2H), 2.99 (d, J=5.6 Hz, 2H), 2.79 (s, 2H), 2.72 (d, J=7.5 Hz, 2H), 1.50-1.35 (m, 4H), 1.11 (t, J=7.5 Hz, 3H), 0.83 (s, 6H).

HPLC-Retention time (XE Metode 7 CM): 1.78 minutes. Detected "M+1"-mass: 336.22.

The following Examples 281-325 in Table 9 were prepared by reacting Compound 395 as described in General Procedure 2 with the appropriate acid:

TABLE 9

| Ex. | Cmpd | Structure | IUPAC Name | HPLC Rt (min) | PDE4 IC$_{50}$ range |
|---|---|---|---|---|---|
| 281 | 396 | 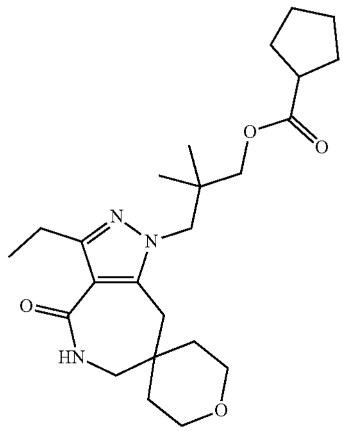 [SMILES: CCc1nn(CC(C)(C)COC(=O)C2CCCC2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] cyclopentanecarboxylate | 2.31 | *** |
| 282 | 397 | 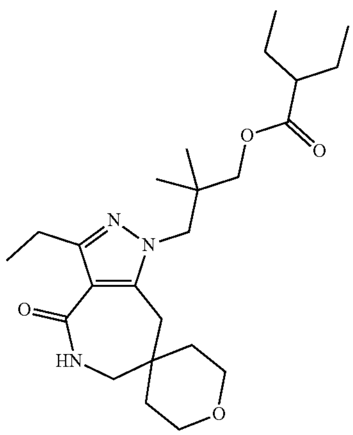 [SMILES: CCc1nn(CC(C)(C)COC(=O)C(CC)CC)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-ethylbutanoate | 2.37 | *** |
| 283 | 398 | 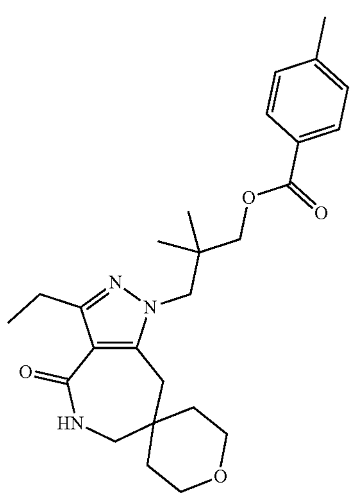 [SMILES: CCc1nn(CC(C)(C)COC(=O)c2ccc(C)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-methylbenzoate | 2.34 | *** |

TABLE 9-continued

| Ex. | Cmpd | Structure | IUPAC Name | HPLC Rt (min) | PDE4 IC$_{50}$ range |
|---|---|---|---|---|---|
| 284 | 399 | 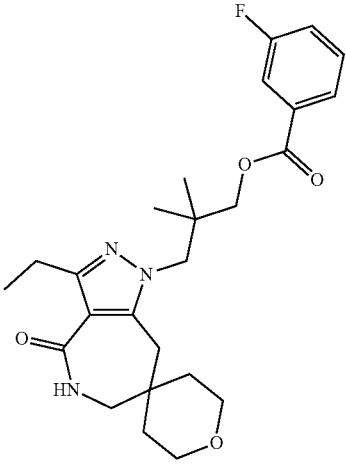 [SMILES: CCc1nn(CC(C)(C)COC(=O)c2cccc(F)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-fluorobenzoate | 2.29 | *** |
| 285 | 400 | 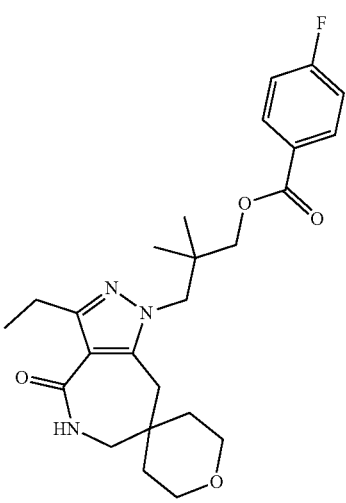 [SMILES: CCc1nn(CC(C)(C)COC(=O)c2ccc(F)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-fluorobenzoate | 2.28 | *** |
| 286 | 401 | 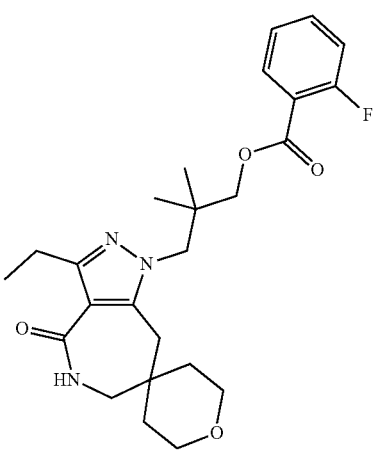 [SMILES: CCc1nn(CC(C)(C)COC(=O)c2ccccc2F)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-fluorobenzoate | 2.25 | *** |

TABLE 9-continued

| Ex. | Cmpd | Structure | IUPAC Name | HPLC Rt (min) | PDE4 IC$_{50}$ range |
|---|---|---|---|---|---|
| 287 | 402 | 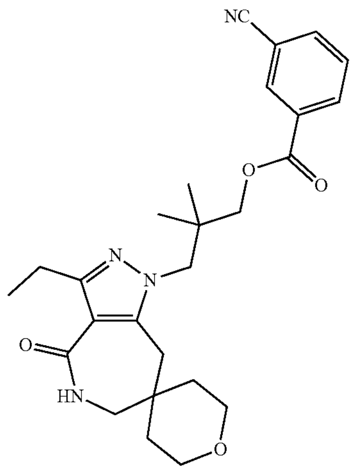 [SMILES: CCc1nn(CC(C)(C)COC(=O)c2cccc(C#N)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-cyanobenzoate | 2.20 | *** |
| 288 | 403 | 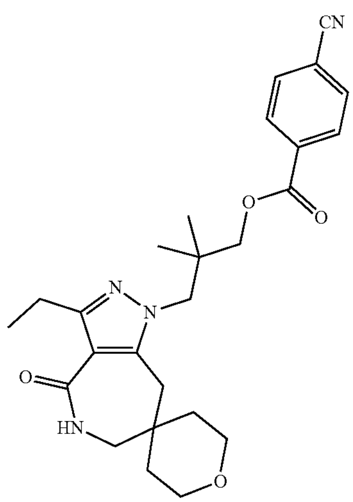 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyanobenzoate | 2.22 | *** |
| 289 | 404 | 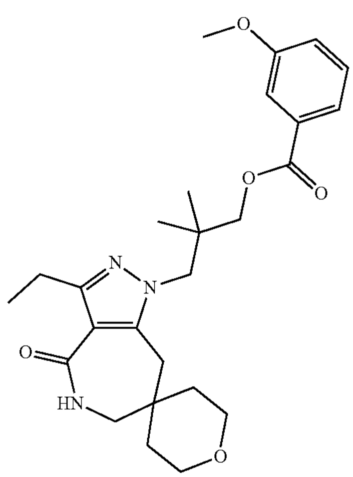 [SMILES: CCc1nn(CC(C)(C)COC(=O)c2cccc(OC)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-methoxybenzoate | 2.27 | *** |

TABLE 9-continued

| Ex. | Cmpd | Structure | IUPAC Name | HPLC Rt (min) | PDE4 IC$_{50}$ range |
|---|---|---|---|---|---|
| 290 | 405 | 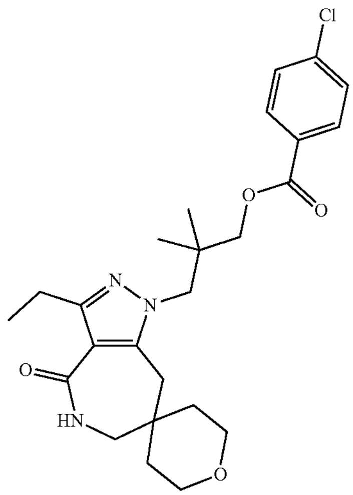 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-chlorobenzoate | 2.39 | *** |
| 291 | 406 | 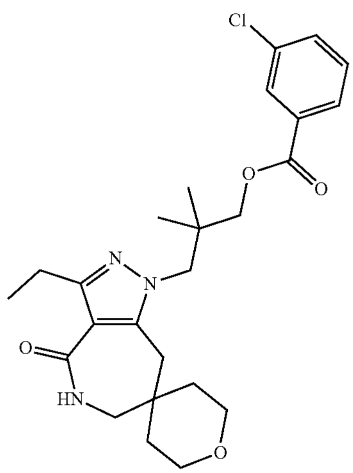 | [3-(3-ethyl-4-oxo-spiro[6,8-dihydro-5H-pyrazolo[4,3-c]azepine-7,4'-tetrahydropyran]-1-yl)-2,2-dimethyl-propyl] 3-chlorobenzoate | 2.38 | *** |
| 292 | 407 | 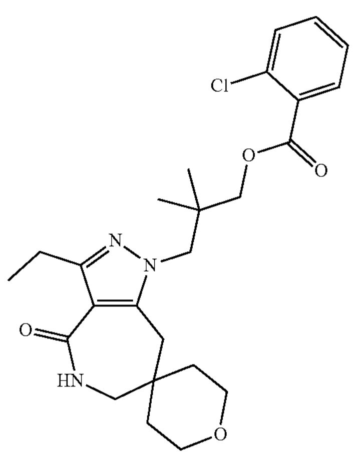 [SMILES: CCc1nn(CC(C)(C)COC(=O)c2ccccc2Cl)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-chlorobenzoate | 2.31 | *** |

TABLE 9-continued

| Ex. | Cmpd | Structure | IUPAC Name | HPLC Rt (min) | PDE4 IC$_{50}$ range |
|---|---|---|---|---|---|
| 293 | 408 | 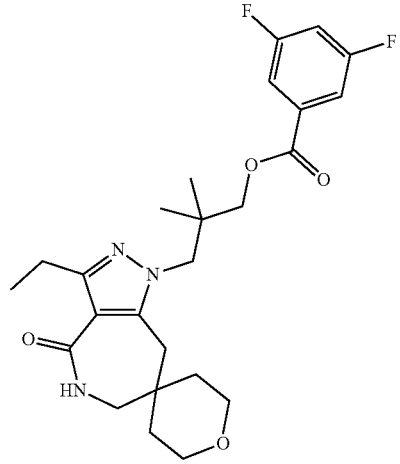 [SMILES: CCc1nn(CC(C)(C)COC(=O)c2cc(F)cc(F)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3,5-difluorobenzoate | 2.34 | *** |
| 294 | 409 | 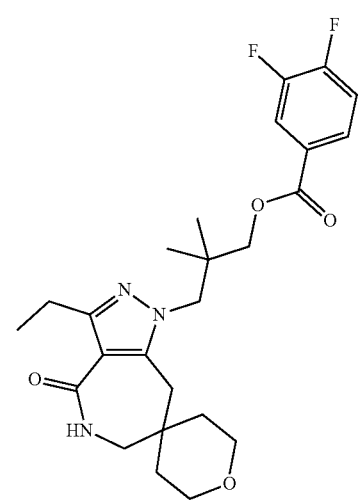 [SMILES: CCc1nn(CC(C)(C)COC(=O)c2ccc(F)c(F)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3,4-difluorobenzoate | 2.33 | *** |
| 295 | 410 | 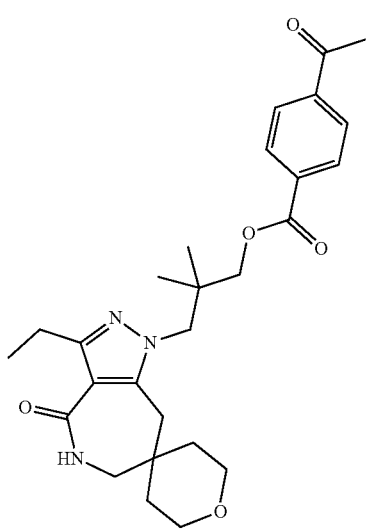 [SMILES: CCc1nn(CC(C)(C)COC(=O)c2ccc(C(C)=O)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-acetylbenzoate | 2.20 | *** |

TABLE 9-continued

| Ex. | Cmpd | Structure | IUPAC Name | HPLC Rt (min) | PDE4 IC$_{50}$ range |
|---|---|---|---|---|---|
| 296 | 411 | 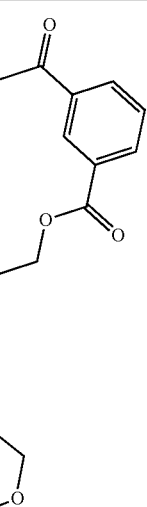 | [3-(3-ethyl-4-oxo-spiro[6,8-dihydro-5H-pyrazolo[4,3-c]azepine-7,4'-tetrahydropyran]-1-yl)-2,2-dimethyl-propyl] 3-acetylbenzoate | 2.18 | *** |
| 297 | 412 | 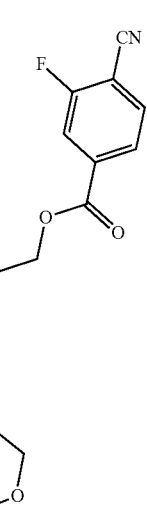 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyano-3-fluoro-benzoate | 2.27 | *** |
| 298 | 413 | 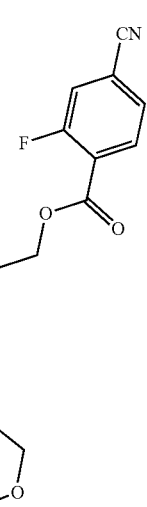 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyano-2-fluoro-benzoate | 2.23 | *** |

TABLE 9-continued

| Ex. | Cmpd | Structure | IUPAC Name | HPLC Rt (min) | PDE4 IC$_{50}$ range |
|---|---|---|---|---|---|
| 299 | 414 | 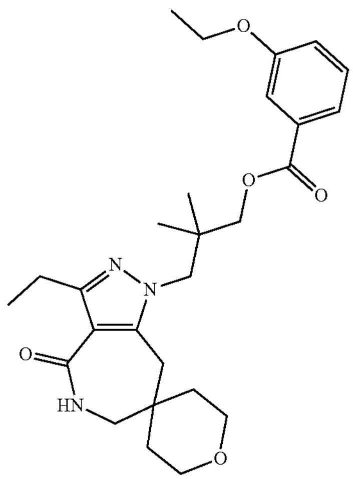 [SMILES: CCOc1cccc(C(=O)OCC(C)(C)Cn2nc(CC)c3c2CC2(CCOCC2)CNC3=O)c1] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-ethoxybenzoate | 2.37 | *** |
| 300 | 415 | 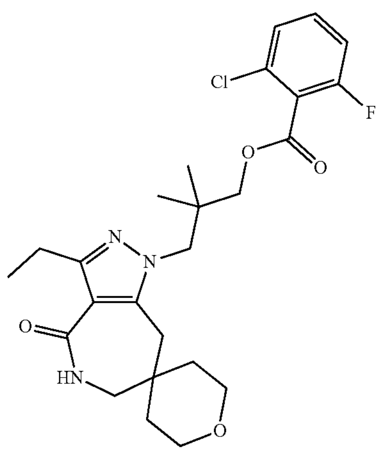 [SMILES: CCc1nn(CC(C)(C)COC(=O)c2c(F)cccc2Cl)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-6-fluoro-benzoate | 2.32 | *** |
| 301 | 416 | 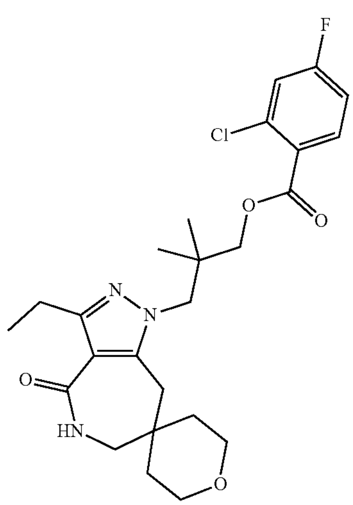 [SMILES: CCc1nn(CC(C)(C)COC(=O)c2ccc(F)cc2Cl)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-4-fluoro-benzoate | 2.36 | *** |

TABLE 9-continued

| Ex. | Cmpd | Structure | IUPAC Name | HPLC Rt (min) | PDE4 IC$_{50}$ range |
|---|---|---|---|---|---|
| 302 | 417 | 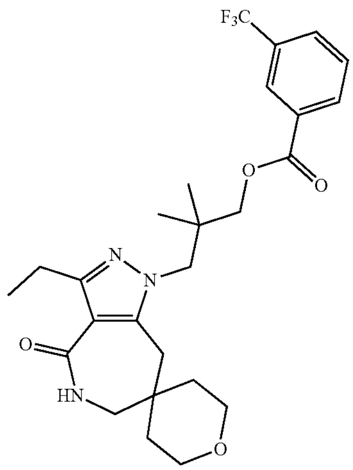 | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(trifluoromethyl)benzoate | 2.42 | *** |
| 303 | 418 | 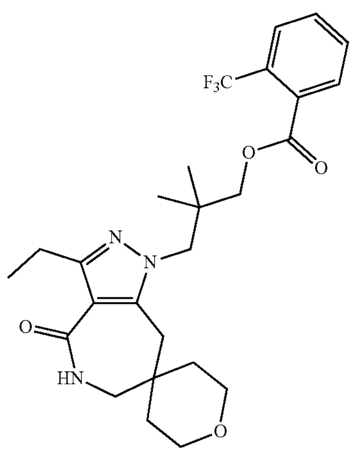 [SMILES: CCc1nn(CC(C)(C)COC(=O)c2ccccc2C(F)(F)F)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-(trifluoromethyl)benzoate | 2.35 | *** |
| 304 | 419 | 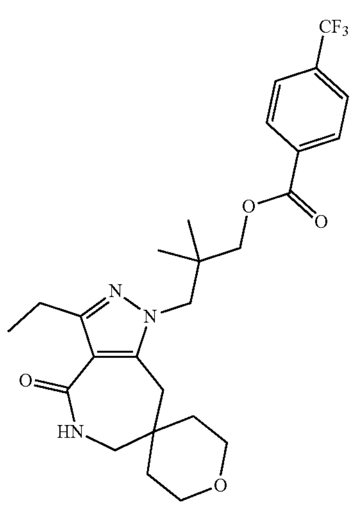 [SMILES: CCc1nn(CC(C)(C)COC(=O)c2ccc(C(F)(F)F)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(trifluoromethyl)benzoate | 2.44 | *** |

TABLE 9-continued

| Ex. | Cmpd | Structure | IUPAC Name | HPLC Rt (min) | PDE4 IC$_{50}$ range |
|---|---|---|---|---|---|
| 305 | 420 | 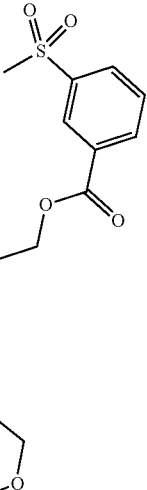 | [3-(3-ethyl-4-oxo-spiro[6,8-dihydro-5H-pyrazolo[4,3-c]azepine-7,4'-tetrahydropyran]-1-yl)-2,2-dimethyl-propyl] 3-methylsulfonylbenzoate | 2.07 | *** |
| 306 | 421 | 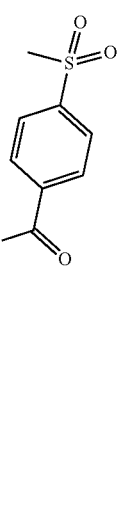 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-methylsulfonylbenzoate | 2.08 | *** |
| 307 | 422 | 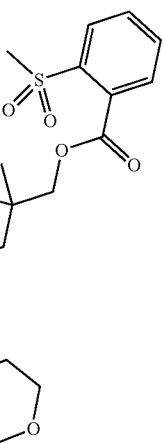 | [3-(3-ethyl-4-oxo-spiro[6,8-dihydro-5H-pyrazolo[4,3-c]azepine-7,4'-tetrahydropyran]-1-yl)-2,2-dimethyl-propyl] 2-methylsulfonylbenzoate | 2.07 | *** |

TABLE 9-continued

| Ex. | Cmpd | Structure | IUPAC Name | HPLC Rt (min) | PDE4 IC$_{50}$ range |
|---|---|---|---|---|---|
| 308 | 423 | 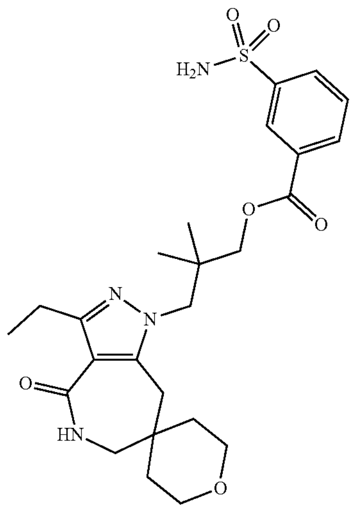 [SMILES: CCc1nn(CC(C)(C)COC(=O)c2cccc(S(N)(=O)=O)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-sulfamoylbenzoate | 2.01 | *** |
| 309 | 424 | 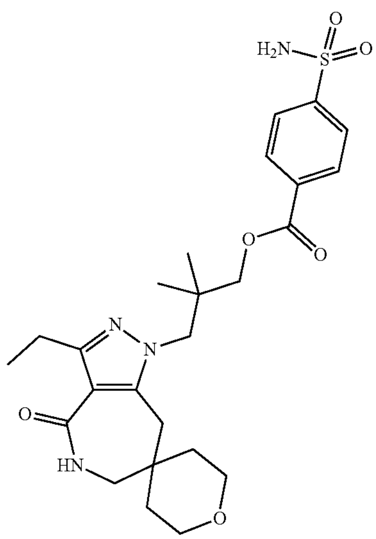 [SMILES: CCc1nn(CC(C)(C)COC(=O)c2ccc(S(N)(=O)=O)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-sulfamoylbenzoate | 2.01 | *** |
| 310 | 425 | 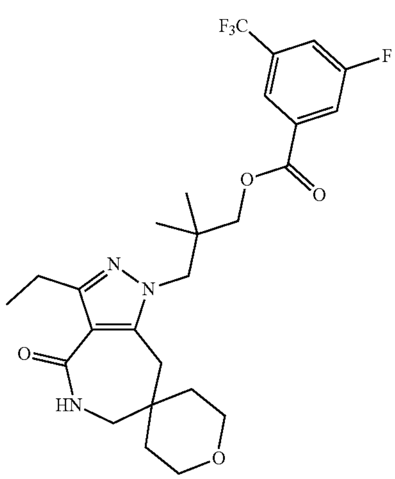 [SMILES: CCc1nn(CC(C)(C)COC(=O)c2cc(F)cc(C(F)(F)F)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-fluoro-5-(trifluoromethyl)benzoate | 2.47 | *** |

TABLE 9-continued

| Ex. | Cmpd | Structure | IUPAC Name | HPLC Rt (min) | PDE4 IC$_{50}$ range |
|---|---|---|---|---|---|
| 311 | 426 | 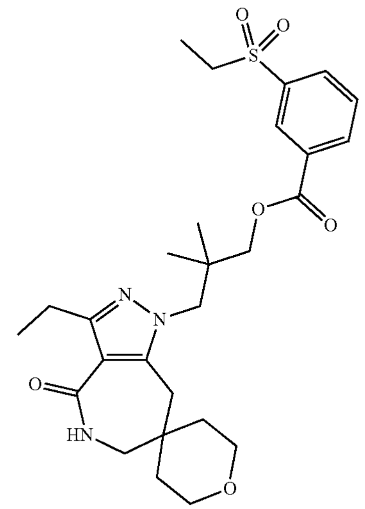 [SMILES: CCc1nn(CC(C)(C)COC(=O)c2cccc(S(=O)(=O)CC)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-ethylsulfonylbenzoate | 2.14 | *** |
| 312 | 427 | 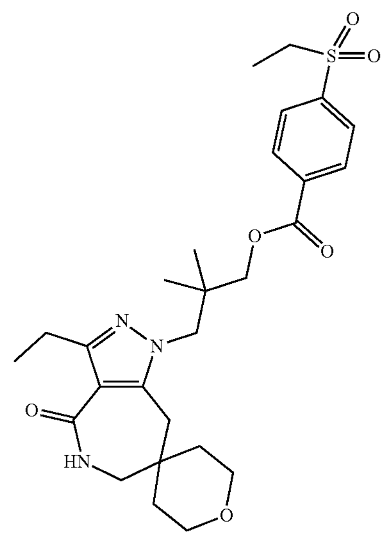 [SMILES: CCc1nn(CC(C)(C)COC(=O)c2ccc(S(=O)(=O)CC)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-ethylsulfonylbenzoate | 2.15 | *** |
| 313 | 428 | 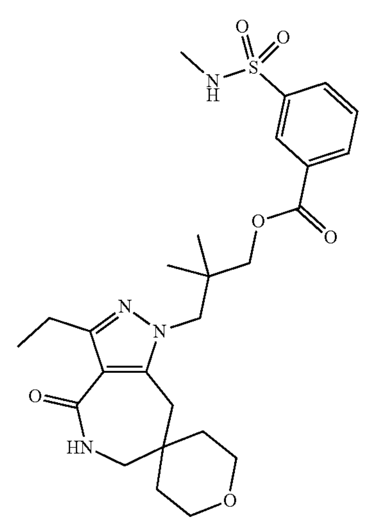 [SMILES: CCc1nn(CC(C)(C)COC(=O)c2cccc(S(=O)(=O)NC)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(methylsulfamoyl)benzoate | 2.09 | *** |

TABLE 9-continued

| Ex. | Cmpd | Structure | IUPAC Name | HPLC Rt (min) | PDE4 IC$_{50}$ range |
|---|---|---|---|---|---|
| 314 | 429 | 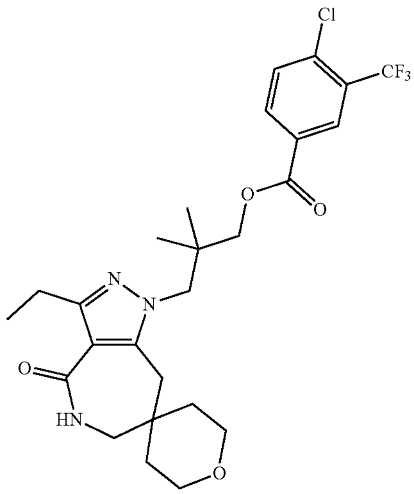 [SMILES: CCc1nn(CC(C)(C)COC(=O)c2ccc(Cl)c(C(F)(F)F)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-chloro-3-(trifluoromethyl)benzoate | 2.54 | *** |
| 315 | 430 | 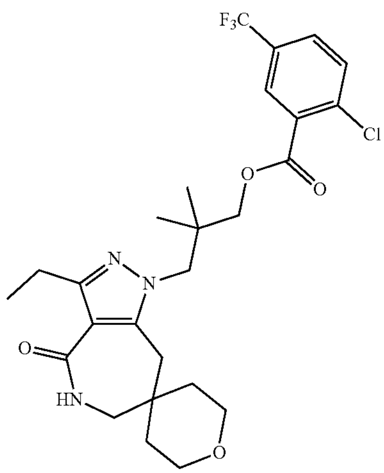 [SMILES: CCc1nn(CC(C)(C)COC(=O)c2cc(C(F)(F)F)ccc2Cl)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-5-(trifluoromethyl)benzoate | 2.48 | *** |
| 316 | 431 | 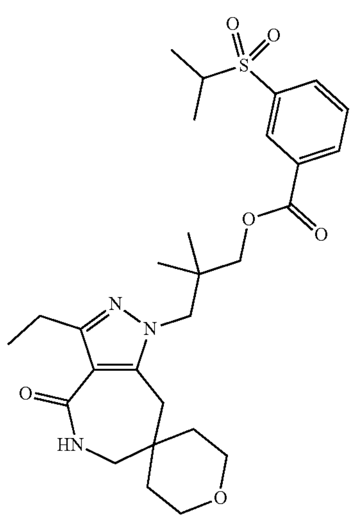 [SMILES: CCc1nn(CC(C)(C)COC(=O)c2cccc(S(=O)(=O)C(C)C)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-isopropylsulfonylbenzoate | 2.20 | *** |

TABLE 9-continued

| Ex. | Cmpd | Structure | IUPAC Name | HPLC Rt (min) | PDE4 IC$_{50}$ range |
|---|---|---|---|---|---|
| 317 | 432 | 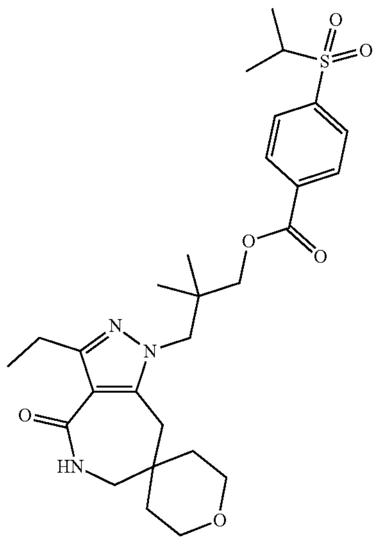 [SMILES: CCc1nn(CC(C)(C)COC(=O)c2ccc(S(=O)(=O)C(C)C)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-isopropylsulfonylbenzoate | 2.21 | *** |
| 318 | 433 | 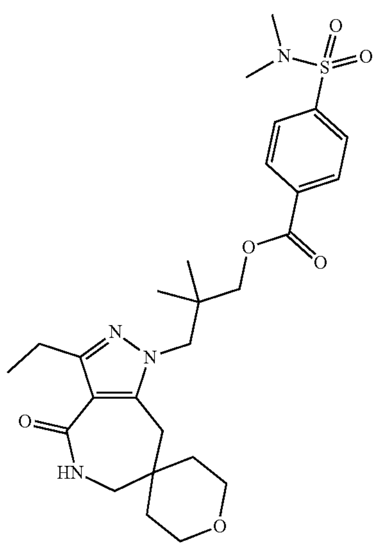 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(dimethylsulfamoyl)benzoate | 2.21 | *** |

TABLE 9-continued

| Ex. | Cmpd | Structure | IUPAC Name | HPLC Rt (min) | PDE4 IC$_{50}$ range |
|---|---|---|---|---|---|
| 319 | 434 | 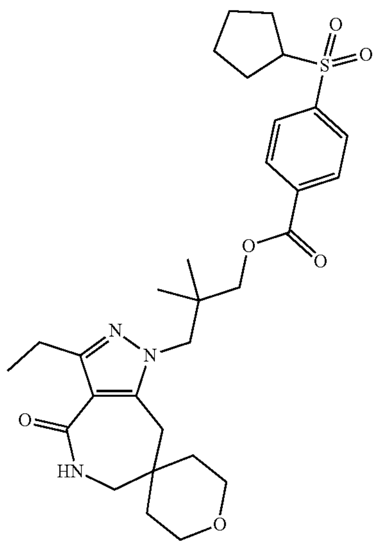 [SMILES: CCc1nn(CC(C)(C)COC(=O)c2ccc(S(=O)(=O)C3CCCC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyclopentylsulfonylbenzoate | 2.31 | *** |
| 320 | 435 | 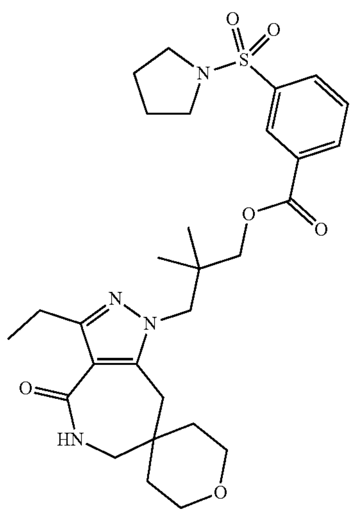 [SMILES: CCc1nn(CC(C)(C)COC(=O)c2cccc(S(=O)(=O)N3CCCC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-pyrrolidin-1-ylsulfonylbenzoate | 2.27 | *** |
| 321 | 436 | 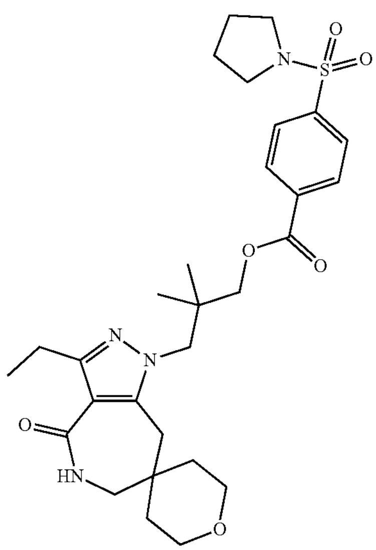 [SMILES: CCc1nn(CC(C)(C)COC(=O)c2ccc(S(=O)(=O)N3CCCC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-pyrrolidin-1-ylsulfonylbenzoate | 2.29 | *** |

TABLE 9-continued
| Ex. | Cmpd | Structure | IUPAC Name | HPLC Rt (min) | PDE4 IC$_{50}$ range |
|---|---|---|---|---|---|
| 322 | 437 | 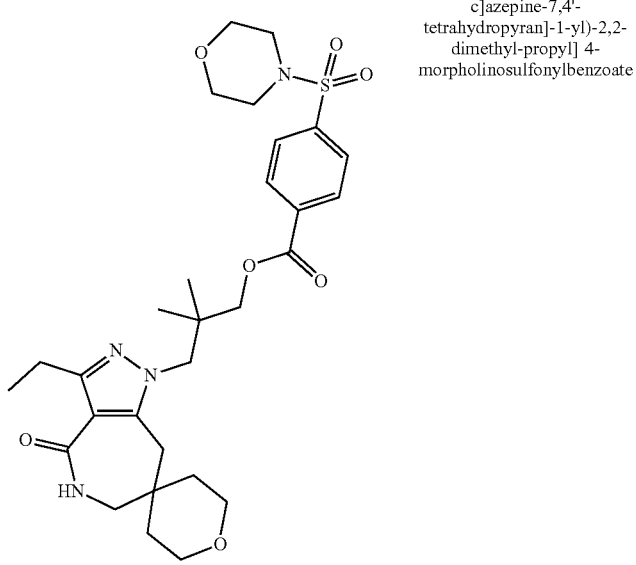 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-morpholinosulfonylbenzoate | 2.21 | *** |
| 323 | 438 | 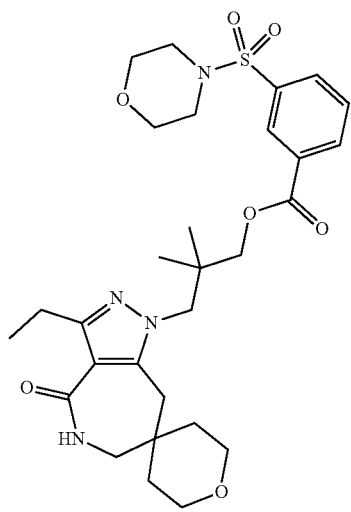 [SMILES: CCc1nn(CC(C)(C)COC(=O)c2cccc(S(=O)(=O)N3CCOCC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-morpholinosulfonylbenzoate | 2.19 | *** |

TABLE 9-continued

| Ex. | Cmpd | Structure | IUPAC Name | HPLC Rt (min) | PDE4 IC$_{50}$ range |
|---|---|---|---|---|---|
| 324 | 439 | 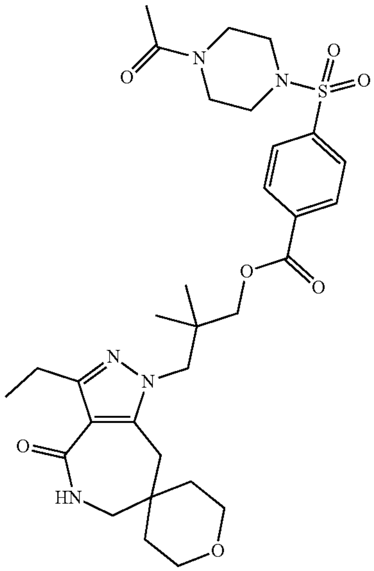 [SMILES: CCc1nn(CC(C)(C)COC(=O)c2ccc(S(=O)(=O)N3CCN(C(C)=O)CC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-acetylpiperazin-1-yl)sulfonylbenzoate | 2.10 | *** |
| 325 | 440 | 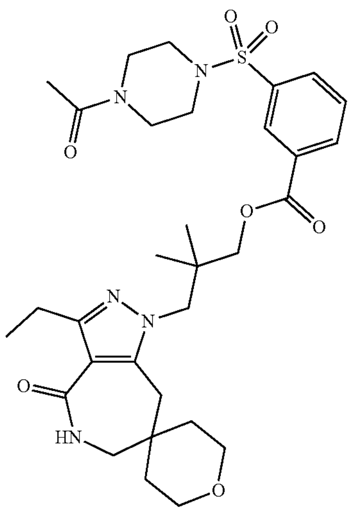 [SMILES: CCc1nn(CC(C)(C)COC(=O)c2cccc(S(=O)(=O)N3CCN(C(C)=O)CC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-acetylpiperazin-1-yl)sulfonylbenzoate | 2.08 | *** |

Example 326 (Compound 441)

[3-(3-Ethyl-4-oxo-spiro[6,8-dihydro-5H-pyrazolo[4,3-c]azepine-7,4'-tetrahydro-pyran]-1-yl)-2,2-dimethyl-propyl] 4-[benzyl(methyl)sulfamoyl]benzoate

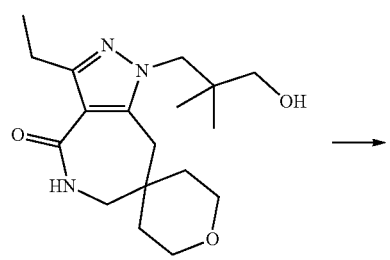

-continued

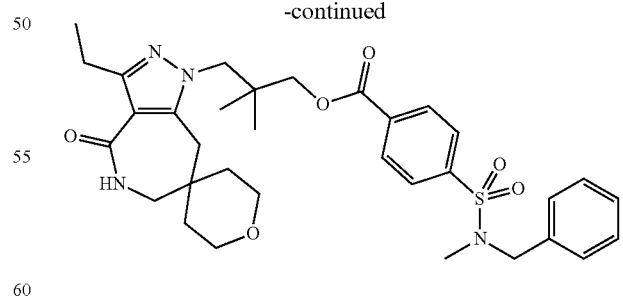

To a mixture of 3-ethyl-1-(3-hydroxy-2,2-dimethyl-propyl)spiro[6,8-dihydro-5H-pyrazolo[4,3-c]azepine-7,4'-tetrahydropyran]-4-one (8.9 mmol, 3 g), 4-[benzyl-(methyl)sulfamoyl]benzoic acid (3.2 g, 10.7 mmol) and DMAP (110 mg, 0.9 mmol) in MeCN (70 mL) was added EDAC (10.7 mmol, 2.1 g) at rt. The mixture was stirred at rt for 18 hours. The mixture gradually became a solution. After 18 h, the product was precipitated and filtered off, giving 3.6 g of product as a white solid. The mother liquor was concentrated in vacuo. The residue was purified by chromatography (ethyl acetate/MeOH 20:1, $R_f$=0.21), giving 1.3 g of product as a white foam.

$^1$H NMR (DMSO-d6) δ: 8.21-8.15 (m, 2H), 8.01-7.96 (m, 2H), 7.46 (t, J=5.8 Hz, 1H), 7.41-7.36 (m, 2H), 7.35-7.28 (m, 3H), 4.17 (d, J=5.3 Hz, 4H), 4.02 (s, 2H), 3.58 (dt, J=11.8, 4.9 Hz, 2H), 3.52-3.45 (m, 2H), 2.97 (d, J=5.8 Hz, 2H), 2.75 (s, 2H), 2.68 (q, J=7.5 Hz, 2H), 2.57 (s, 3H), 1.44-1.32 (m, 4H), 1.13-1.02 (m, 9H).

Example 327 (Compound 442)

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-(methylsulfamoyl)benzoate

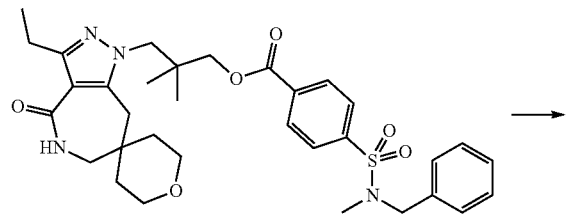

A mixture of [3-(3-ethyl-4-oxo-spiro[6,8-dihydro-5H-pyrazolo[4,3-c]azepine-7,4'-tetrahydropyran]-1-yl)-2,2-dimethyl-propyl] 4-[benzyl(methyl)sulfamoyl]benzoate (2.4 g) in methanesulfonic acid (15 mL) was heated at 80° C. for 3 hours. The reaction was cooled to rt and diluted with DCM (50 mL). A solution of NaHCO$_3$ (25 g) in water (250 mL) was cooled to approximately 5° C. To this solution was dropwise added the reaction solution. After phase separation, the aqueous phase was extracted twice with DCM. The combined organic phases were dried over Na$_2$SO$_4$ and concentrated in vacuo. The residue was purified by chromatography (ethyl acetate/MeOH), giving the product as a foam. Crystallized of the foam from n-butyl acetate (15 mL), gave the title compound as colorless crystals.

$^1$H NMR (DMSO-d6) δ: 8.21-8.13 (m, 2H), 7.95-7.87 (m, 2H), 7.67 (s, 1H), 7.40 (t, J=5.6 Hz, 1H), 4.15 (s, 2H), 4.01 (s, 2H), 3.66-3.42 (m, 4H), 2.97 (d, J=5.7 Hz, 2H), 2.74 (s, 2H), 2.70 (q, J=7.7 Hz, 2H), 2.44 (s, 3H), 1.38 (t, J=5.4 Hz, 4H), 1.11-1.01 (m, 9H).

HPLC-Retention time (XE Metode 7 CM): 2.11 minutes.

Detected "M+1"-mass: 533.23.

Preparation 33 (Compound 443)

4-[3-(3-Ethyl-4-oxo-spiro[6,8-dihydro-5H-pyrazolo[4,3-c]azepine-7,4'-tetrahydro-pyran]-1-yl)-2,2-dimethyl-propoxy]carbonylbenzoic Acid

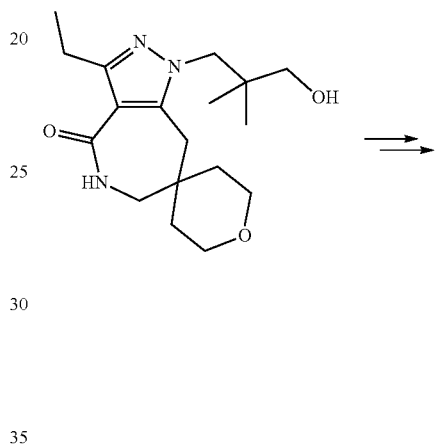

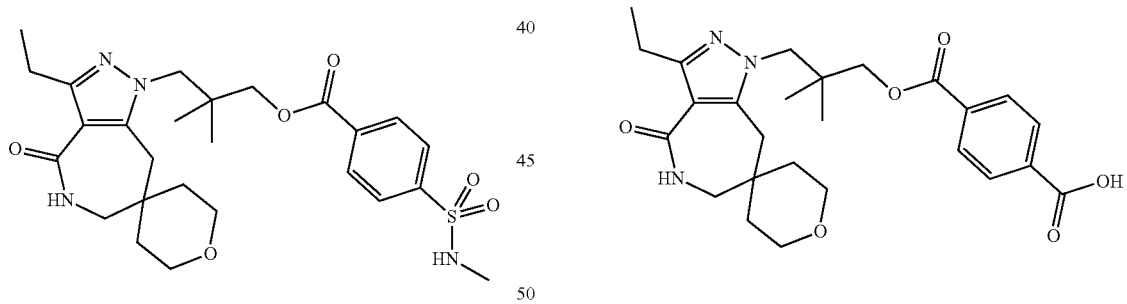

4-[3-(3-Ethyl-4-oxo-spiro[6,8-dihydro-5H-pyrazolo[4,3-c]azepine-7,4'-tetrahydro-pyran]-1-yl)-2,2-dimethyl-propoxy]carbonylbenzoic acid was prepared in a manner similar to that of 4-[(2R)-3-(3-ethyl-4-oxo-spiro[6,8-dihydro-5H-pyrazolo[4,3-c]azepine-7,4'-tetrahydropyran]-1-yl)-2-methyl-propoxy]carbonylbenzoic acid described in Preparation 22 & 23 using 3-ethyl-1-(3-hydroxy-2,2-dimethyl-propyl)spiro[6,8-dihydro-5H-pyrazolo[4,3-c]azepine-7,4'-tetrahydropyran]-4-one instead of 3-ethyl-1-[(2R)-3-hydroxy-2-methyl-propyl]spiro[6,8-dihydro-5H-pyrazolo[4,3-c]azepine-7,4'-tetrahydropyran]-4-one as starting material.

The Examples 328-338 in Table 10 were prepared by reacting Compound 443 as described in General Procedure 3 with the appropriate amine:

TABLE 10

| Ex. | Cmpd | Structure | IUPAC Name | HPLC Rt (min) | PDE4 IC$_{50}$ range |
|---|---|---|---|---|---|
| 328 | 444 | 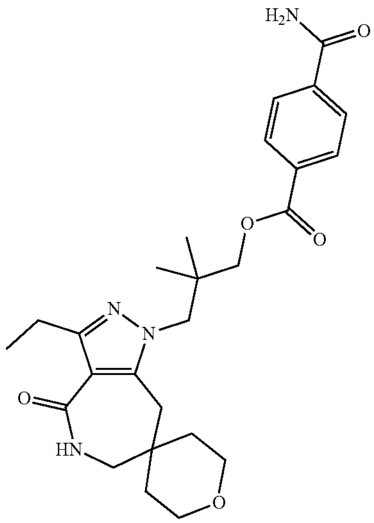 [SMILES: CCc1nn(CC(C)(C)COC(=O)c2ccc(C(N)=O)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-carbamoylbenzoate | 1.94 | *** |
| 329 | 445 | 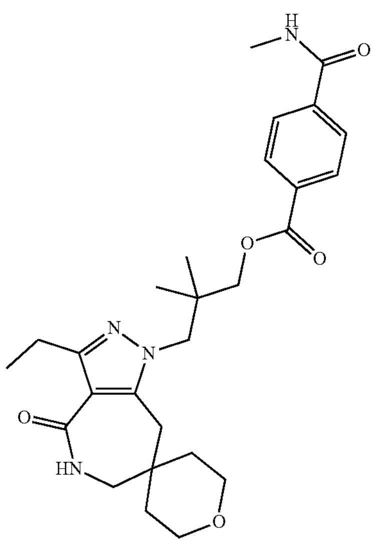 [SMILES: CCc1nn(CC(C)(C)COC(=O)c2ccc(C(=O)NC)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(methylcarbamoyl)benzoate | 1.99 | *** |
| 330 | 446 | 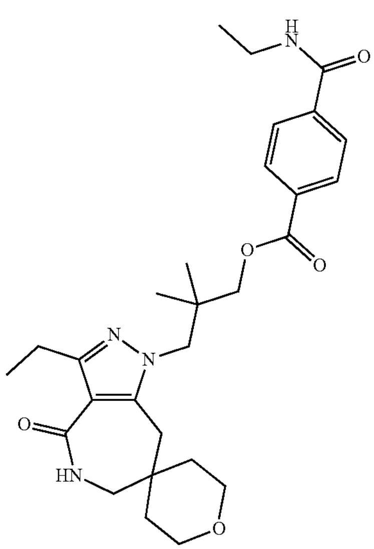 [SMILES: CCNC(=O)c1ccc(C(=O)OCC(C)(C)Cn2nc(CC)c3c2CC2(CCOCC2)CNC3=O)cc1] | [3-(3-ethyl-4-oxo-Spiro[6,8-dihydro-5H-pyrazolo[4,3-c]azepine-7,4'-tetrahydropyran]-1-yl)-2,2-dimethyl-propyl] 4-(ethylcarbamoyl)benzoate | 2.06 | *** |

TABLE 10-continued
| Ex. | Cmpd | Structure | IUPAC Name | HPLC Rt (min) | PDE4 IC$_{50}$ range |
|---|---|---|---|---|---|
| 331 | 447 | 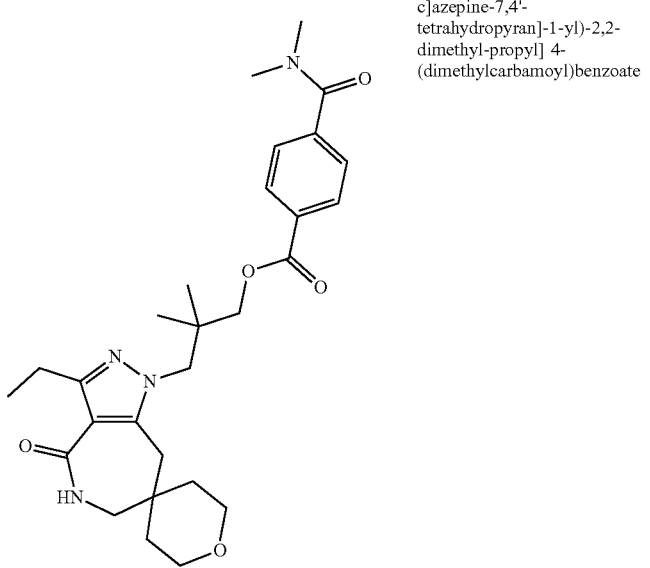 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(dimethylcarbamoyl)benzoate | 2.02 | *** |
| 332 | 448 | 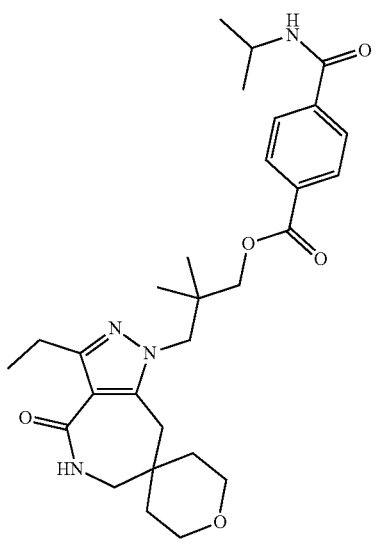 [SMILES: CCc1nn(CC(C)(C)COC(=O)c2ccc(C(=O)NC(C)C)cc2)c2c1C(=O)NCC1(CCOCC1)C2] | [3-(3-ethyl-4-oxo-spiro[6,8-dihydro-5H-pyrazolo[4,3-c]azepme-7,4'-tetrahydropyran]-1-yl)-2,2-dimethyl-propyl] 4-(isopropylcarbamoyl)benzoate | 2.13 | *** |

| Ex. | Cmpd | Structure | IUPAC Name | HPLC Rt (min) | PDE4 IC$_{50}$ range |
|---|---|---|---|---|---|
| 333 | 449 | 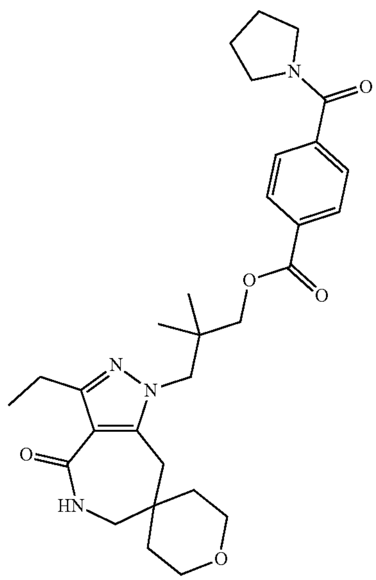 [SMILES: CCc1nn(CC(C)(C)COC(=O)c2ccc(C(=O)N3CCCC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(pyrrolidine-1-carbonyl)benzoate | 2.10 | *** |
| 334 | 450 | 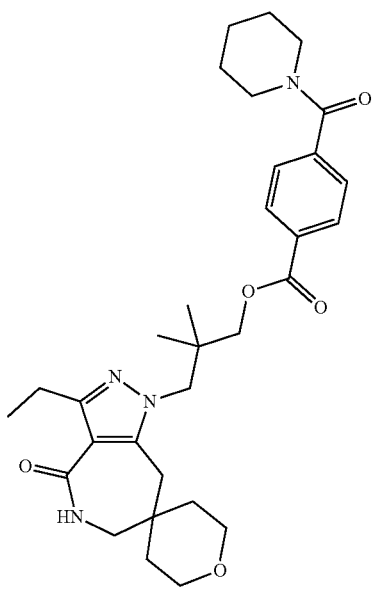 [SMILES: CCc1nn(CC(C)(C)COC(=O)c2ccc(C(=O)N3CCCCC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2 dimethyl-propyl] 4-(piperidine-1-carbonyl)benzoate | 2.21 | *** |

TABLE 10-continued

| Ex. | Cmpd | Structure | IUPAC Name | HPLC Rt (min) | PDE4 IC$_{50}$ range |
|---|---|---|---|---|---|
| 335 | 451 | 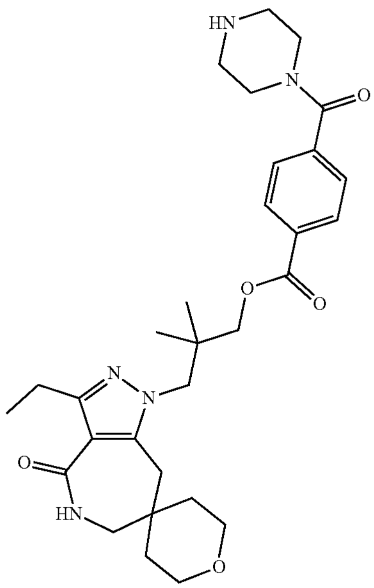 [SMILES: CCc1nn(CC(C)(C)COC(=O)c2ccc(C(=O)N3CCOCC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(piperazine-1-carbonyl)benzoate | 1.79 | *** |
| 336 | 452 | 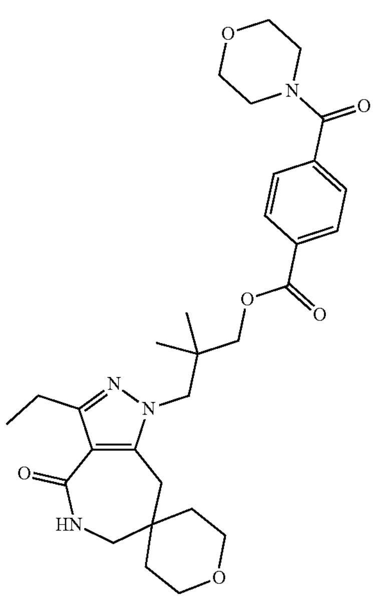 | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(morpholine-4-carbonyl)benzoate | 2.02 | *** |

TABLE 10-continued

| Ex. | Cmpd | Structure | IUPAC Name | HPLC Rt (min) | PDE4 IC$_{50}$ range |
|---|---|---|---|---|---|
| 337 | 453 | 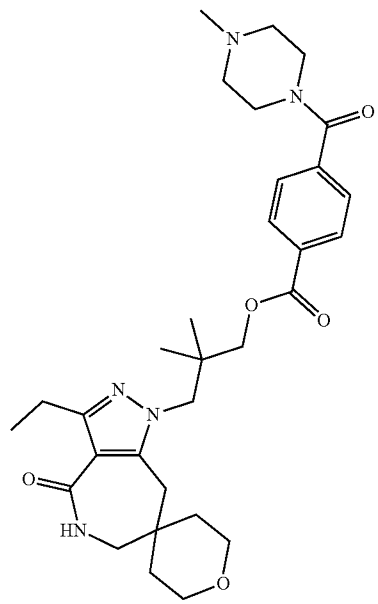 [SMILES: CCc1nn(CC(C)(C)COC(=O)c2ccc(C(=O)N3CCN(C)CC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-methylpiperazine-1-carbonyl)benzoate | 1.79 | *** |
| 338 | 454 | 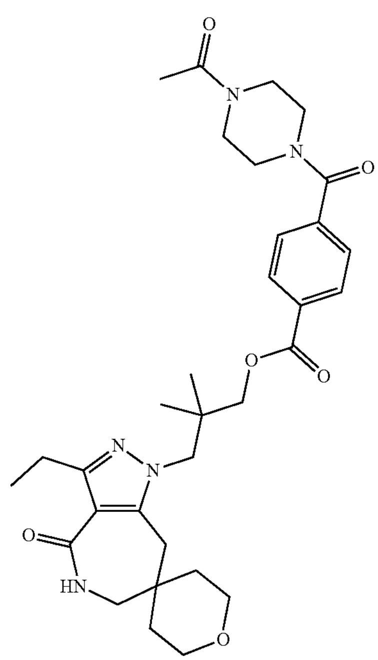 [SMILES: CCc1nn(CC(C)(C)COC(=O)c2ccc(C(=O)N3CCN(C(C)=O)CC3)cc2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-acetylpiperazine-1-carbonyl)benzoate | 1.94 | *** |

Preparation 34 (Compound 455)

3-[3-(3-Ethyl-4-oxo-spiro[6,8-dihydro-5H-pyrazolo[4,3-c]azepine-7,4'-tetrahydro-pyran]-1-yl)-2,2-dimethyl-propoxy]carbonylbenzoic Acid

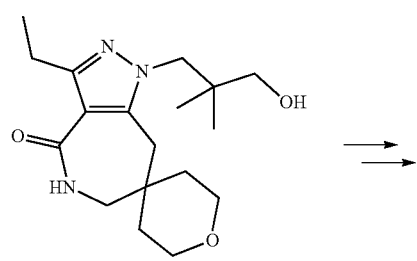

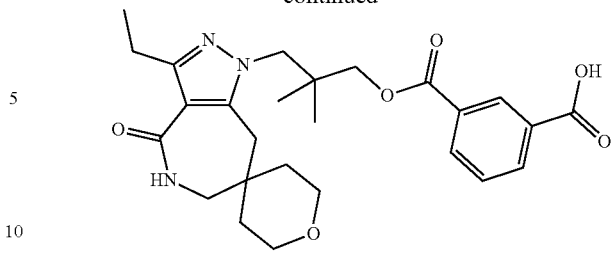

3-[3-(3-Ethyl-4-oxo-spiro[6,8-dihydro-5H-pyrazolo[4,3-c]azepine-7,4'-tetrahydro-pyran]-1-yl)-2,2-dimethyl-propoxy]carbonylbenzoic acid was prepared in a manner similar to that of 3-[(2R)-3-(3-ethyl-4-oxo-spiro[6,8-dihydro-5H-pyrazolo[4,3-c]azepine-7,4'-tetrahydropyran]-1-yl)-2-methyl-propoxy]-carbonylbenzoic acid described in Preparation 24 & 25 using 3-ethyl-1-(3-hydroxy-2,2-dimethyl-propyl)spiro[6,8-dihydro-5H-pyrazolo[4,3-c]azepine-7,4'-tetrahydro-pyran]-4-one instead of 3-ethyl-1-[(2R)-3-hydroxy-2-methyl-propyl]spiro[6,8-dihydro-5H-pyrazolo[4,3-c]azepine-7,4'-tetrahydropyran]-4-one as starting material.

The Examples 339-349 in Table 11 were prepared by reacting Compound 455 as described in General Procedure 3 with the appropriate amine:

TABLE 11

| Ex. | Cmpd | Structure | IUPAC Name | HPLC Rt (min) | PDE4 IC$_{50}$ range |
|---|---|---|---|---|---|
| 339 | 456 | 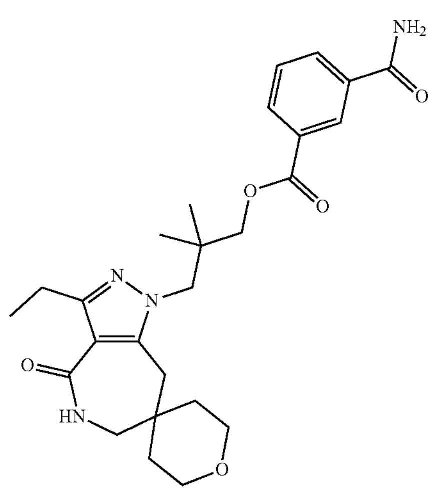 [SMILES: CCc1nn(CC(C)(C)COC(=O)c2cccc(C(N)=O)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-carbamoylbenzoate | 1.94 | |

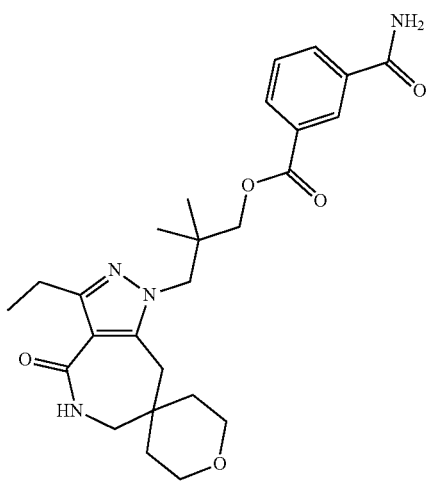

TABLE 11-continued

| Ex. | Cmpd | Structure | IUPAC Name | HPLC Rt (min) | PDE4 IC$_{50}$ range |
|---|---|---|---|---|---|
| 340 | 457 | 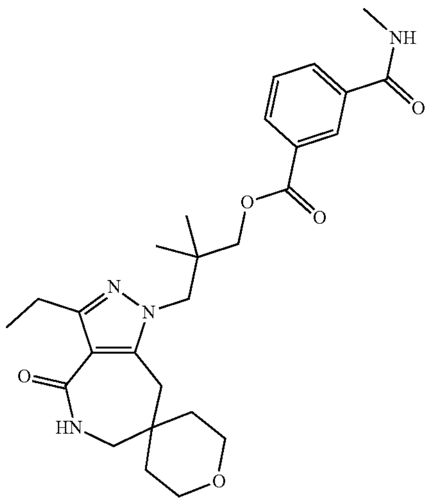 [SMILES: CCc1nn(CC(C)(C)COC(=O)c2cccc(C(=O)NC)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(methylcarbamoyl)-benzoate | 1.98 | *** |
| 341 | 458 | 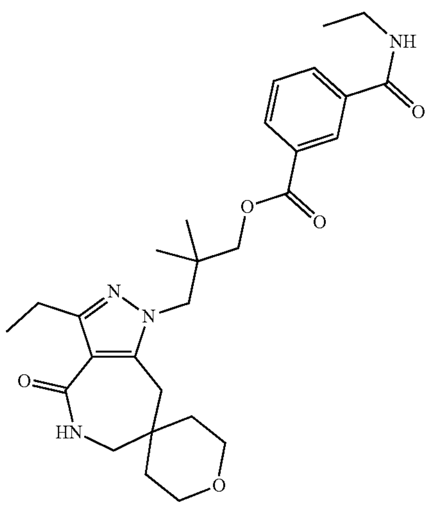 [SMILES: CCNC(=O)c1cccc(C(=O)OCC(C)(C)Cn2nc(CC)c3c2CC2(CCOCC2)CNC3=O)c1] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(ethylcarbamoyl)-benzoate | 2.05 | *** |
| 342 | 459 | 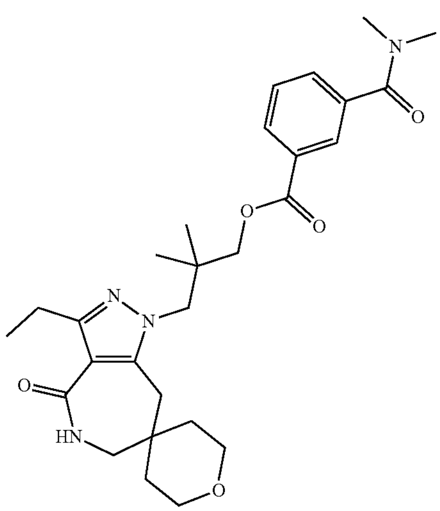 [SMILES: CCc1nn(CC(C)(C)COC(=O)c2cccc(C(=O)N(C)C)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(dimethylcarbamoyl)-benzoate | 2.02 | *** |

| Ex. | Cmpd | Structure | IUPAC Name | HPLC Rt (min) | PDE4 IC$_{50}$ range |
|---|---|---|---|---|---|
| 343 | 460 | 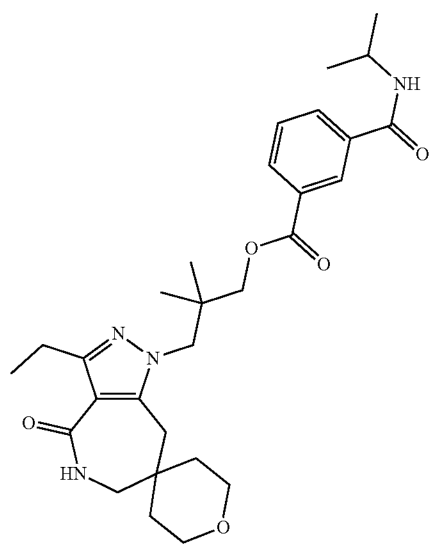 [SMILES: CCc1nn(CC(C)(C)COC(=O)c2cccc(C(=O)NC(C)C)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(isopropylcarbamoyl)-benzoate | 2.13 | *** |
| 344 | 461 | 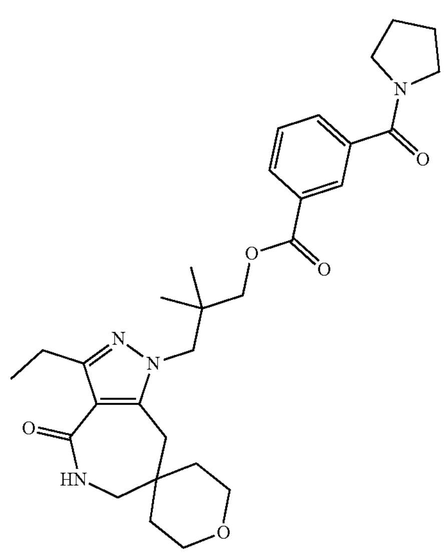 [SMILES: CCc1nn(CC(C)(C)COC(=O)c2cccc(C(=O)N3CCCC3)c2)c2c1C(=O)NCC1(CCOCC1)C2] | [3-(3-ethyl-4-oxo-Spiro[6,8-dihydro-5H-pyrazolo[4,3-c]azepine-7,4'-tetrahydropyran]-1-yl)-2,2-dimethyl-propyl] 3-(pyrrolidine-1-carbonyl)benzoate | 2.10 | *** |

TABLE 11-continued

| Ex. | Cmpd | Structure | IUPAC Name | HPLC Rt (min) | PDE4 IC$_{50}$ range |
|---|---|---|---|---|---|
| 345 | 462 | 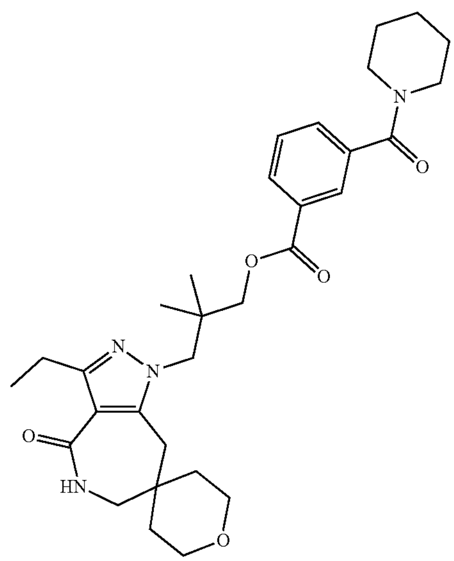 [SMILES: CCc1nn(CC(C)(C)COC(=O)c2cccc(C(=O)N3CCCCC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(piperidine-1-carbonyl)benzoate | 2.20 | *** |
| 346 | 463 | 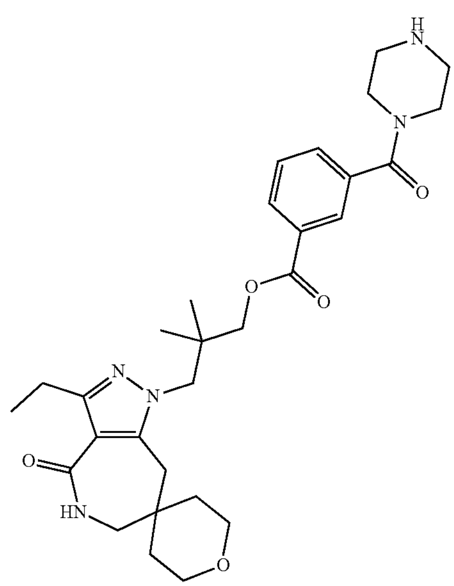 [SMILES: CCc1nn(CC(C)(C)COC(=O)c2cccc(C(=O)N3CCNCC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(piperazine-1-carbonyl)benzoate | 1.78 | *** |

TABLE 11-continued
| Ex. | Cmpd | Structure | IUPAC Name | HPLC Rt (min) | PDE4 IC$_{50}$ range |
|---|---|---|---|---|---|
| 347 | 464 | 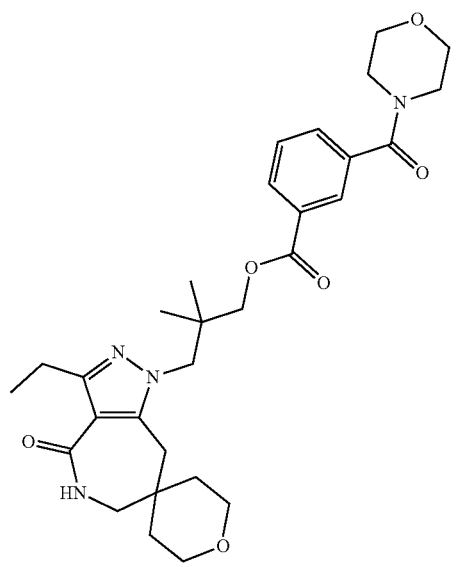 [SMILES: CCc1nn(CC(C)(C)COC(=O)c2cccc(C(=O)N3CCOCC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(morpholine-4-carbonyl)benzoate | 2.01 | *** |
| 348 | 465 | 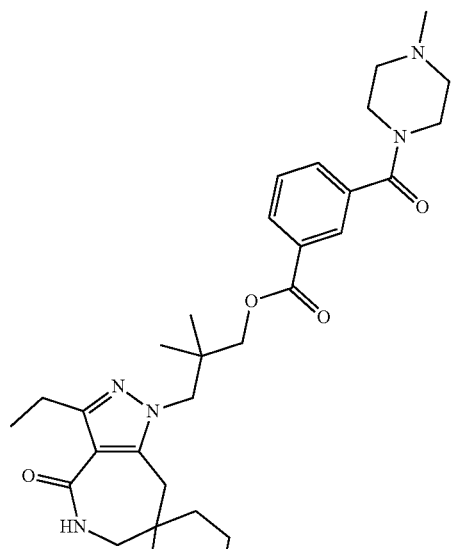 | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-methylpiperazine-1-carbonyl)benzoate | 1.79 | *** |

TABLE 11-continued

| Ex. | Cmpd | Structure | IUPAC Name | HPLC Rt (min) | PDE4 IC$_{50}$ range |
|---|---|---|---|---|---|
| 349 | 466 | 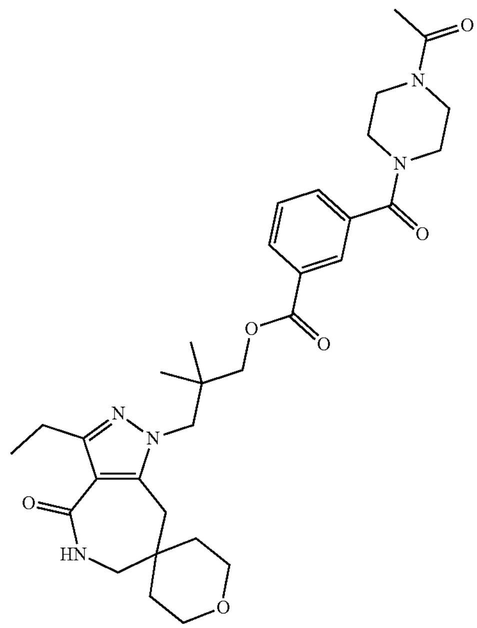 [SMILES: CCc1nn(CC(C)(C)COC(=O)c2cccc(C(=O)N3CCN(C(C)=O)CC3)c2)c2c1C(=O)NCC1(CCOCC1)C2] | [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-acetylpiperazine-1-carbonyl)benzoate | 1.93 | *** |

Preparation 35 (Compound 467)

[1-[[Tert-butyl(diphenyl)silyl]oxymethyl]cyclopropyl]methanol

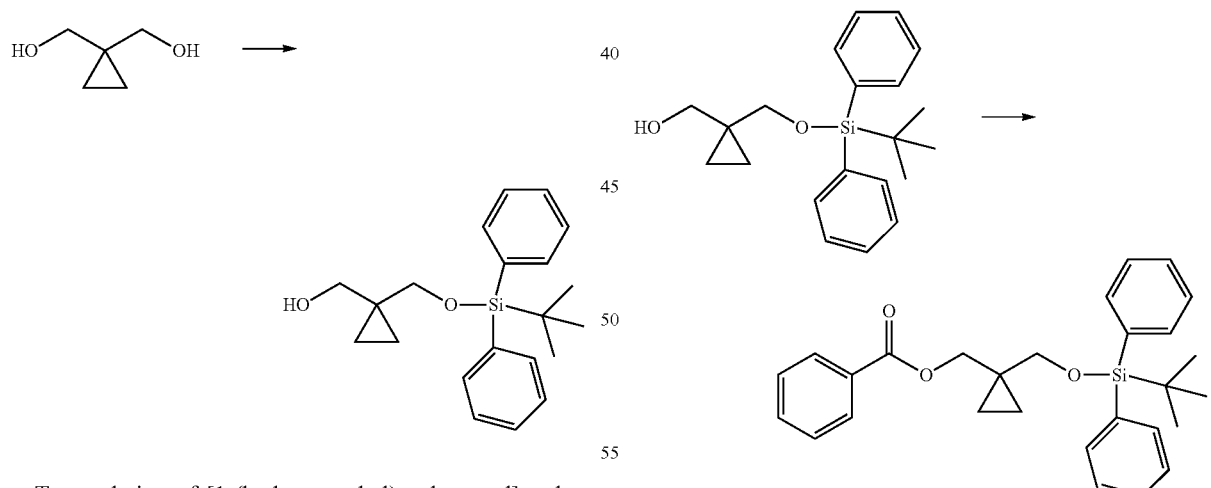

Preparation 36 (Compound 468)

[1-[[Tert-butyl(diphenyl)silyl]oxymethyl]cyclopropyl]methyl Benzoate

To a solution of [1-(hydroxymethyl)cyclopropyl]methanol (5.4 g, 52.94 mmol) and diisopropylethylamine (5.3 g, 105.96 mmol) in DCM (53 mL) was tert-butylchloro-diphenylsilane (4.3 g, 15.88 mmol) added dropwise. The mixture was stirred at 26° C. for 16 hours. On completion, the reaction mixture was concentrated under reduced pressure and the residue was diluted with water (150 mL) and extracted twice with ethyl acetate (2×100 mL). The combined organic layers were washed with brine (100 mL), dried over anhydrous Na$_2$SO$_4$ and concentrated under reduced pressure to afford the title compound as yellow oil.

Benzoyl chloride (4.5 mL, 38.8 mmol) was slowly added at 0° C. to a solution of [1-[[tert-butyl(diphenyl)silyl]oxymethyl]cyclopropyl]methanol (1.1 g, 32.3 mmol) and pyridine (4.0 mL, 48.5 mmol) in DCM (150 mL). The mixture was stirred at 26° C. for 16 hours. On completion, the reaction mixture was diluted with water (200 mL) and extracted twice with EtOAc (2×100 mL). The combined organic layers were washed with brine (100 mL), dried over Na$_2$SO$_4$, concentrated and the residue was purified by silica gel (100-200 mesh) column chromatography (5% EtOAc in Pet ether as eluent) to afford the title compound as gummy liquid.

$^1$H NMR (400 MHz, CDCl$_3$): δ 8.02-7.96 (m, 2H), 7.65 (dd, J=1.5, 7.9 Hz, 4H), 7.60-7.50 (m, 1H), 7.46-7.28 (m, 8H), 4.35 (s, 2H), 3.66 (s, 2H), 1.05 (s, 9H), 0.62-0.57 (m, 2H), 0.56-0.50 (m, 2H).

Preparation 37 (Compound 469)

[1-(Hydroxymethyl)cyclopropyl]methyl Benzoate

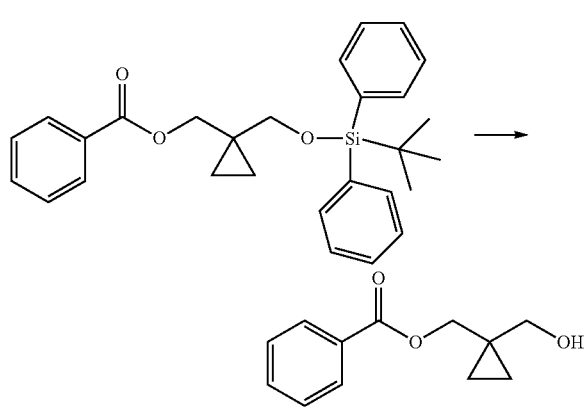

TBAF (12.9 g, 49.5 mmol) was added slowly at 0° C. to a solution of [1-[[tert-butyl-(diphenyl)silyl]oxymethyl]cyclopropyl]methyl benzoate (11 g, 24.7 mmol) in THF (250 mL). The reaction mixture was stirred at 26° C. for 16 hours. On completion the reaction was quenched with water (150 mL) and the mixture was extracted twice with EtOAc (2×100 mL). The combined organic layers were washed with brine (100 mL), dried over Na$_2$SO$_4$, and concentrated under vacuum to afford the crude title compound as gummy liquid.

Preparation 38 (Compound 470)

(1-Formylcyclopropyl)methyl Benzoate

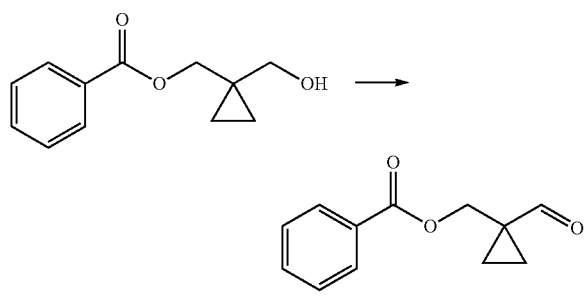

PCC (14.6 g, 67.9 mmol) was added at 0° C. to a solution of [1-(hydroxymethyl)-cyclopropyl]methyl benzoate (7 g, 24.7 mmol) in DCM (500 mL). The mixture was stirred at 26° C. for 2 hours. On completion the reaction mixture was filtered through celite. The filtrate was dried over Na$_2$SO$_4$, concentrated and the resulting residue was purified by silica gel column chromatography (15% EtOAc in Pet ether as eluent) to afford the title compound as gummy liquid.

$^1$H NMR (300 MHz, CDCl$_3$): δ 9.06 (d, J=1.8 Hz, 1H), 8.02 (br d, J=7.3 Hz, 2H), 7.61-7.50 (m, 1H), 7.48-7.37 (m, 2H), 4.57 (d, J=1.5 Hz, 2H), 1.41-1.31 (m, 2H), 1.30-1.24 (m, 2H).

Preparation 39 (Compound 471)

[1-[(2-Tert-butoxycarbonylhydrazino)methyl]cyclopropyl]methyl Benzoate

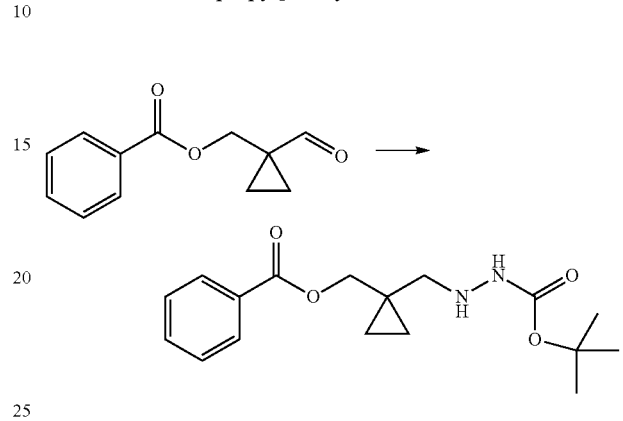

Boc-NH—NH$_2$ (5.6 g, 86.8 mmol) was added at 0° C. to a solution of (1-formyl-cyclopropyl)methyl benzoate (5 g, 24.5 mmol) in MeOH (150 mL). The mixture was stirred at 26° C. for 30 minutes. NaBH$_3$CN (3.2 g, 36.7 mmol) and AcOH (1 mL) were added to the reaction mixture at 0° C. which was then stirred for another 16 hours at 26° C. On completion, the reaction was treated with aq. NaHCO$_3$ solution, and then extracted twice with EtOAc (2×100 mL). The combined organic layers were washed with brine (100 mL), dried over Na$_2$SO$_4$, concentrated and the residue was purified by silica gel (100-200 mesh) column chromatography (10% EtOAc in Pet ether as eluent) to afford the title compound as gummy liquid.

$^1$H NMR (400 MHz, CDCl$_3$): δ 8.13-7.99 (m, 2H), 7.59-7.53 (m, 1H), 7.48-7.41 (m, 2H), 6.06 (br s, 1H), 4.29 (s, 2H), 4.05 (br s, 1H), 2.91 (s, 2H), 1.45 (s, 9H), 0.66-0.61 (m, 2H), 0.61-0.55 (m, 2H).

Preparation 40 (Compound 472)

[1-(Hydrazinomethyl)cyclopropyl]methyl Benzoate Hydrochloride

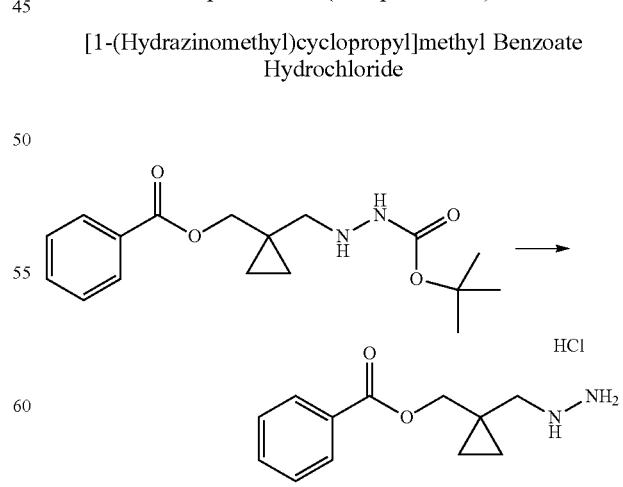

Dioxane.HCl (50 mL) was added to a solution of [1-[(2-tert-butoxycarbonylhydrazino)-methyl]cyclopropyl]methyl benzoate (2 g, 6.2 mmol) in DCM (10 mL) and the mixture

Preparation 41 (Compound 473)

[1-[(3-Ethyl-4-oxo-spiro[5,7-dihydroindazole-6,4'-tetrahydropyran]-1-yl)methyl]-cyclopropyl]methyl Benzoate

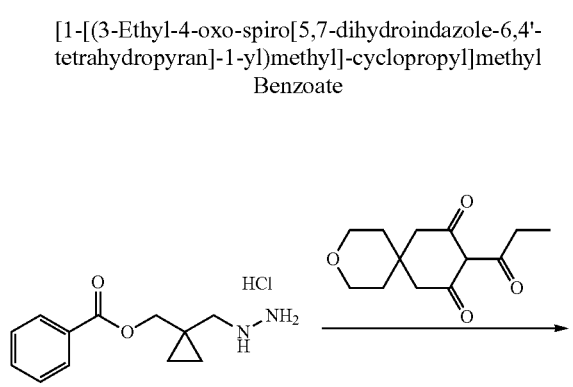

[1-(Hydrazinomethyl)cyclopropyl]methyl benzoate hydrochloride (1.3 g, 5.0 mmol) were added to a solution of 9-propanoyl-3-oxaspiro[5.5]undecane-8,10-dione (1 g, 4.2 mmol) and TEA (1.27 g, 12.6 mmol) in EtOH (150 mL). The mixture was stirred at 85° C. for 3 h. On completion, excess solvent was evaporated under vacuum and the residue was diluted with water and extracted twice with EtOAc (2×50 mL). The combined organic layer were washed with brine (50 mL), dried over $Na_2SO_4$, concentrated and the residue was purified by silica gel (100-200 mesh) column chromatography (60% EtOAc in Pet ether as eluent) to afford the title compound as brown gummy liquid.

$^1$H NMR (400 MHz, $CDCl_3$): δ 8.06-7.93 (m, 2H), 7.65-7.54 (m, 1H), 7.51-7.38 (m, 2H), 4.13 (d, J=11.7 Hz, 4H), 3.68-3.54 (m, 4H), 2.83 (q, J=7.7 Hz, 2H), 2.71 (s, 2H), 2.41 (s, 2H), 1.59-1.54 (m, 2H), 1.50-1.40 (m, 2H), 1.30-1.19 (m, 3H), 0.89-0.82 (m, 2H), 0.81-0.76 (m, 2H).

Example 350 (Compound 474)

[1-[(3-Ethyl-4-oxo-spiro[6,8-dihydro-5H-pyrazolo[4,3-c]azepine-7,4'-tetrahydro-pyran]-1-yl)methyl]cyclopropyl]methyl benzoate

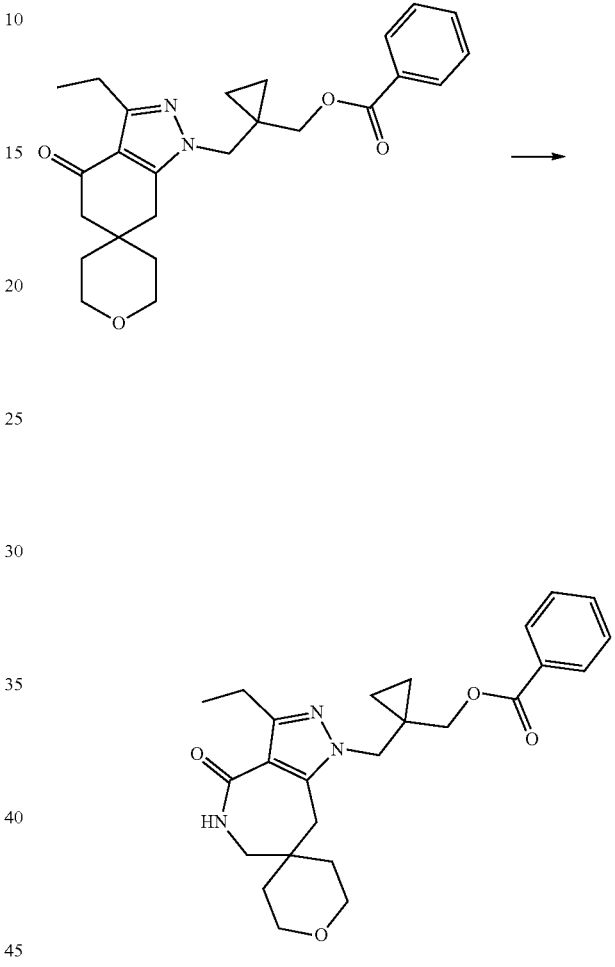

$NaN_3$ (0.383 g, 5.9 mmol) was added at 0° C. to a solution of [1-[(3-ethyl-4-oxo-spiro[5,7-dihydroindazole-6,4'-tetrahydropyran]-1-yl)methyl]cyclopropyl]methyl benzoate (1.0 g, 1.18 mmol) in $MeSO_3H$ (2.27 g, 5.9 mmol). The mixture was stirred at 26° C. for 16 hours. On completion, the reaction was treated with aq. $NaHCO_3$ solution at 0° C., and then extracted twice with EtOAc (2×50 mL). The combined organic layers were washed with brine (50 mL), dried over $Na_2SO_4$, concentrated and the residue was purified by silica gel (100-200 mesh) column chromatography (2% MeOH in DCM as eluent) to afford the title compound as colorless solid.

$^1$H NMR (300 MHz, DMSO-$d_6$): δ 8.00-7.82 (m, 2H), 7.69-7.61 (m, 1H), 7.56-7.45 (m, 2H), 7.37 (br t, J=5.7 Hz, 1H), 4.11 (d, J=9.9 Hz, 4H), 3.58-3.38 (m, 4H), 2.96 (br d, J=5.5 Hz, 2H), 2.80-2.64 (m, 4H), 1.39-1.22 (m, 4H), 1.07 (t, J=7.5 Hz, 3H), 0.80-0.73 (m, 2H), 0.73-0.66 (m, 2H).

HPLC-Retention time (XE Metode 7 CM): 2.14 minutes.

Detected "M+1"-mass: 438.23.

Preparation 42 (Compound 475)

3-Ethyl-1-[[1-(hydroxymethyl)cyclopropyl]methyl]spiro[6,8-dihydro-5H-pyrazolo[4,3-c]azepine-7,4'-tetrahydropyran]-4-one

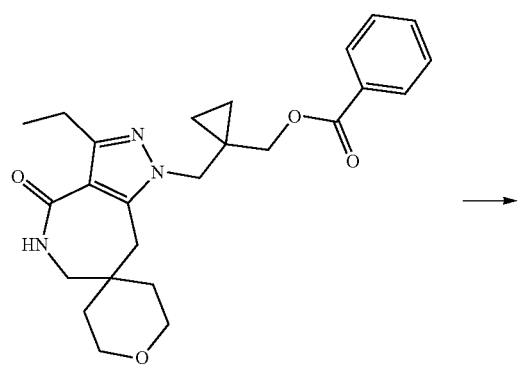

→

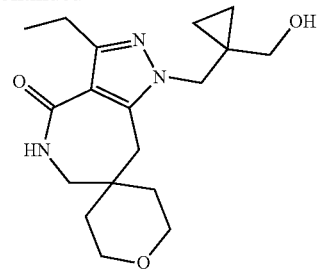

K$_2$CO$_3$ (0.235 g, 1.71 mmol) was added at 0° C. to a solution of [1-[(3-ethyl-4-oxo-spiro[6,8-dihydro-5H-pyrazolo[4,3-c]azepine-7,4'-tetrahydropyran]-1-yl)methyl]-cyclopropyl]methyl benzoate (0.25 g, 0.57 mmol) in MeOH (5 mL). The mixture was stirred at 26° C. for 1 hour. On completion, excess solvent was evaporated under vacuum and the residue was diluted with water and extracted twice with EtOAc (2×100 mL). The combined organic layers were washed with brine (25 mL), dried over Na$_2$SO$_4$, concentrated and the residue was purified by Neutral Alumina column chromatography (5% MeOH in DCM as eluent) to afford the title compound as colorless solid.

$^1$H NMR (300 MHz, DMSO-d$_6$): δ 7.40 (br t, J=5.7 Hz, 1H), 4.73 (br s, 1H), 3.99 (s, 2H), 3.74-3.45 (m, 4H), 3.14 (s, 2H), 3.01 (br d, J=5.8 Hz, 2H), 2.84 (s, 2H), 2.72 (q, J=7.3 Hz, 2H), 1.44 (br t, J=5.3 Hz, 4H), 1.10 (t, J=7.5 Hz, 3H), 0.55-0.46 (m, 2H), 0.45-0.37 (m, 2H).

HPLC-Retention time (XE Metode 7 CM): 1.70 minutes. Detected "M+1"-mass: 334.21.

The following Examples 351-355 in Table 12 were prepared by reacting Compound 475 as described in General Procedure 2 with the appropriate acid:

TABLE 12

| Ex. | Cmpd | Structure | IUPAC Name | HPLC Rt (min) | PDE4 IC$_{50}$ range |
|---|---|---|---|---|---|
| 351 | 476 | 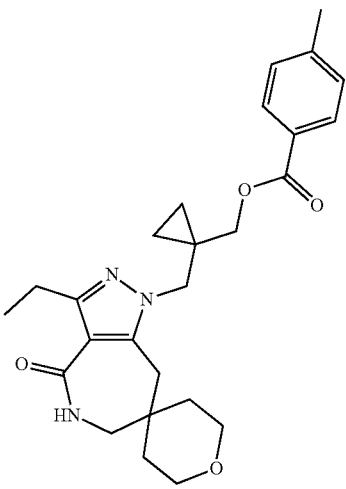 [SMILES: CCc1nn(CC2(COC(=O)c3ccc(C)cc3)CC2)c2c1C(=O)NCC1(CCOCC1)C2] | [1-[(3-ethyl-4-oxo-spiro[6,8-dihydro-5H-pyrazolo[4,3-c]azepine-7,4'-tetrahydropyran]-1-yl)methyl]cyclopropyl]methyl 4-methylbenzoate | 2.22 | *** |

TABLE 12-continued

| Ex. | Cmpd | Structure | IUPAC Name | HPLC Rt (min) | PDE4 IC$_{50}$ range |
|---|---|---|---|---|---|
| 352 | 477 | 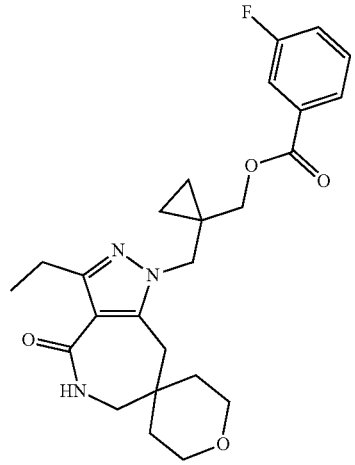 [SMILES: CCc1nn(CC2(COC(=O)c3cccc(F)c3)CC2)c2c1C(=O)NCC1(CCOCC1)C2] | [1-[(3-ethyl-4-oxo-spiro[6,8-dihydro-5H-pyrazolo[4,3-c]azepine-7,4'-tetrahydropyran]-1-yl)methyl]cyclopropyl]methyl 3-fluorobenzoate | 2.18 | *** |
| 353 | 478 | 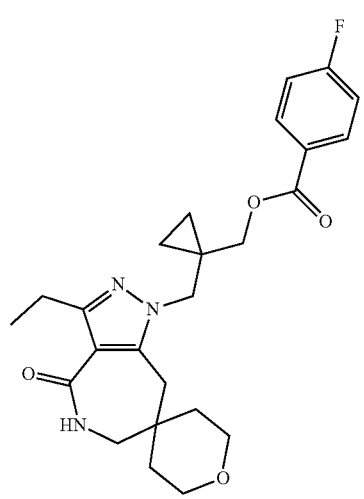 [SMILES: CCc1nn(CC2(COC(=O)c3ccc(F)cc3)CC2)c2c1C(=O)NCC1(CCOCC1)C2] | [1-[(3-ethyl-4-oxo-spiro[6,8-dihydro-5H-pyrazolo[4,3-c]azepine-7,4'-tetrahydropyran]-1-yl)methyl]cyclopropyl]methyl fluorobenzoate | 2.17 | *** |
| 354 | 479 | 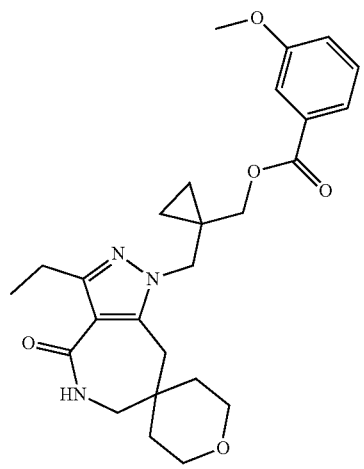 [SMILES: CCc1nn(CC2(COC(=O)c3cccc(OC)c3)CC2)c2c1C(=O)NCC1(CCOCC1)C2] | [1-[(3-ethyl-4-oxo-spiro[6,8-dihydro-5H-pyrazolo[4,3-c]azepine-7,4'-tetrahydropyran]-1-yl)methyl]cyclopropyl]methyl 3-methoxybenzoate | 2.17 | *** |

TABLE 12-continued

| Ex. | Cmpd | Structure | IUPAC Name | HPLC Rt (min) | PDE4 IC$_{50}$ range |
|---|---|---|---|---|---|
| 355 | 480 | 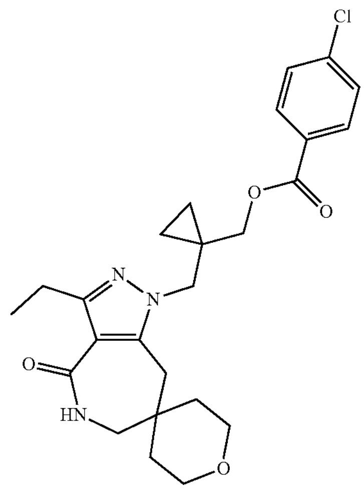 [SMILES: CCc1nn(CC2(COC(=O)c3ccc(Cl)cc3)CC2)c2c1C(=O)NCC1(CCOCC1)C2] | [1-[(3-ethyl-4-oxo-spiro[6,8 dihydro-5H-pyrazolo[4,3-c]azepine-7,4'-letrahydropyran]-1-yl)methyl]cyclopropyl]methyl 4-chlorobenzoate | 2.28 | *** |

Preparation 43 (Compound 481)

[3-(Bromomethyl)oxetan-3-yl]methanol

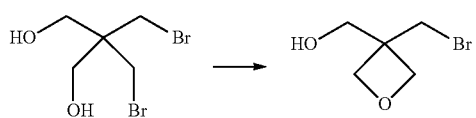 [SMILES: OCC(CO)(CBr)CBr ; OCC1(CBr)COC1]

KOH (1.07 g, 19.08 mmol) was added slowly to a solution of 2,2-bis(bromomethyl)-propane-1,3-diol (5 g, 19.08 mmol) in MeOH (50 mL). The mixture was stirred at 60° C. for 16 hours. On completion, excess solvent was evaporated under vacuum and the residue was diluted with water (100 mL) and extracted twice with diethyl ether (2×100 mL). The combined organic layers were washed with brine (100 mL), dried over Na$_2$SO$_4$, concentrated and the residue was purified by silica gel (100-200 mesh) column chromatography (50% EtOAc in Pet ether as eluent) to afford the title compound as pale yellow liquid.

$^1$H NMR (300 MHz, DMSO-d$_6$): δ 5.07 (t, J=5.5 Hz, 1H), 4.37-4.20 (m, 4H), 3.83 (s, 2H), 3.66 (d, J=5.5 Hz, 2H).

Preparation 44 (Compound 482)

3-Ethylspiro[5,7-dihydro-1H-indazole-6,4'-tetrahydropyran]-4-one

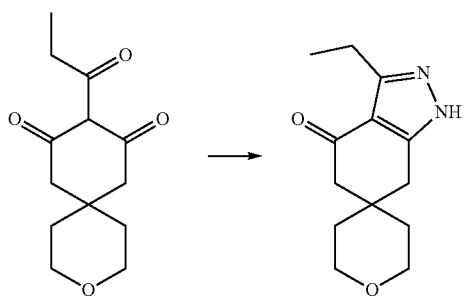 [SMILES: CCC(=O)C1C(=O)CC2(CCOCC2)CC1=O ; CCc1n[nH]c2c1C(=O)CC1(CCOCC1)C2]

NH$_2$NH$_2$.H$_2$O (0.47 g, 9.45 mmol) was added to a solution of 9-propanoyl-3-oxaspiro-[5.5]undecane-8,10-dione (1.5 g, 6.3 mmol) and Et$_3$N (1.6 mL, 12.6 mmol) in EtOH (30 mL). The mixture was stirred at 80° C. for 2 hours. On completion, excess solvent was evaporated under vacuum and the residue was diluted with water and extracted twice with EtOAc (2×50 mL). The combined organic layers were washed with brine (50 mL), dried over Na$_2$SO$_4$, concentrated and the residue was purified by silica gel (100-200 mesh) column chromatography (2% MeOH in DCM as eluent) to afford the title compound as yellow solid.

¹H NMR (400 MHz, CDCl₃): δ 3.71 (t, J=5.4 Hz, 4H), 3.04-2.91 (m, 2H), 2.86 (s, 2H), 2.53 (s, 2H), 1.68-1.53 (m, 4H), 1.33-1.21 (m, 4H).

Preparation 45 (Compound 483)

3-Ethylspiro[1,5,6,8-tetrahydropyrazolo[4,3-c]azepine-7,4'-tetrahydropyran]-4-one NaN₃ (0.305 g, 4.7 mmol) were added at 26° C. to a solution of 3-ethylspiro[5,7-dihydro-1H-indazole-6,4'-tetrahydropyran]-4-one (1 g, 4.27 mmol) in CHCl₃ (15 mL) and H₂SO₄ (3 mL). The mixture was stirred for 16 hours. On completion, excess solvent was evaporated under vacuum and the residue was treated with aq. Na₂CO₃ solution, extracted twice with EtOAc (2×50 mL). The combined organic layers were washed with brine (50 mL), dried over Na₂SO₄, concentrated and the residue was purified by silica gel (100-200 mesh) column chromatography (3% MeOH in DCM as eluent) to afford the title compound as gummy liquid.

¹H NMR (300 MHz, DMSO-d₆): δ 12.69-12.39 (m, 1H), 12.26-12.00 (m, 1H), 9.06 (br s, 1H), 7.39 (br s, 1H), 3.66-3.50 (m, 4H), 3.06-2.84 (m, 1H), 2.83-2.54 (m, 3H), 2.36 (br s, 1H), 2.14 (br s, 1H), 1.53-1.37 (m, 4H), 1.18-1.04 (m, 2H).

Preparation 46 (Compound 484)

3-Ethyl-[[3-(hydroxymethyl)oxetan-3-yl]methyl]spiro[6,8-dihydro-5H-pyrazolo[4,3-c]azepine-7,4'-tetrahydropyran]-4-one

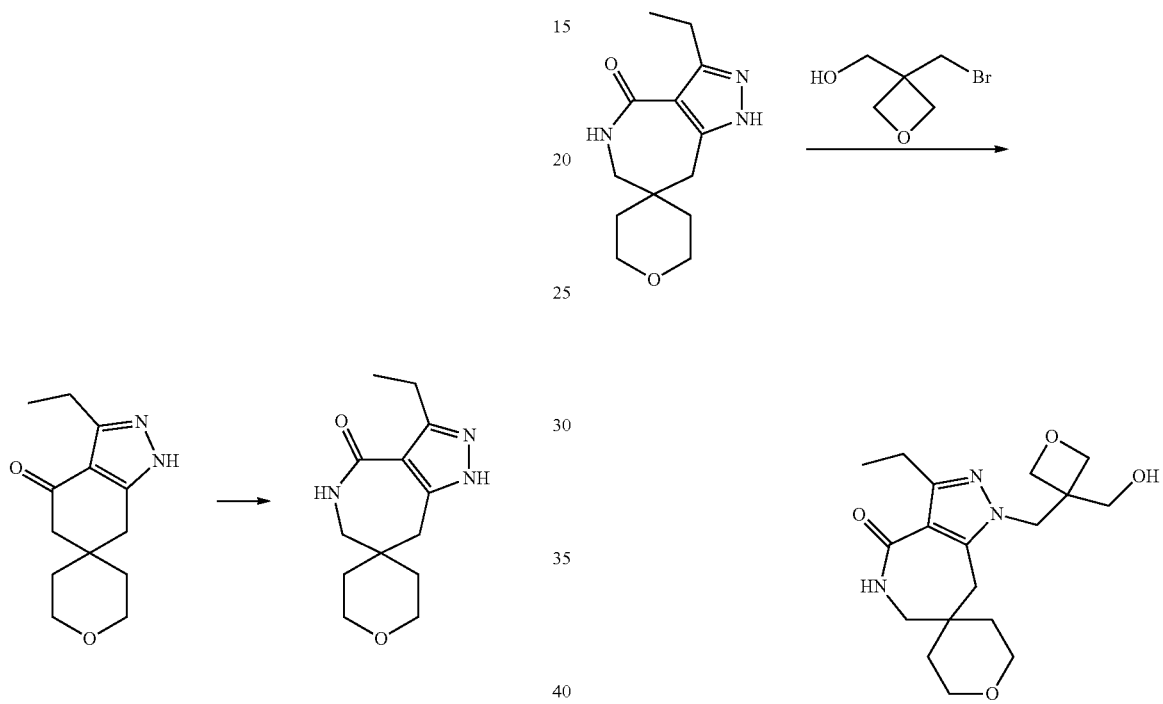

[3-(Bromomethyl)oxetan-3-yl]methanol (0.39 g, 2.2 mmol) and Cs₂CO₃ (1.3 g, 4.01 mmol) were added to a solution of 3-ethylspiro[1,5,6,8-tetrahydropyrazolo[4,3-c]azepine-7,4'-tetrahydropyran]-4-one (0.5 g, 2.008 mmol) in MeCN (10 mL). The mixture was stirred at 80° C. for 16 hours. On completion, excess solvent was evaporated under vacuum and the residue was dissolved in DCM and filtered through celite. The filtrate was concentrated and the residue was purified by prep HPLC (separations of isomers), to afford the title compound as colorless solid.

¹H NMR (300 MHz, DMSO-d₆): δ 7.43 (br t, J=5.6 Hz, 1H), 5.06 (br s, 1H), 4.55 (d, J=6.2 Hz, 2H), 4.27 (d, J=6.2 Hz, 2H), 4.21 (s, 2H), 3.68-3.49 (m, 4H), 3.42 (br s, 2H), 3.01 (br d, J=5.4 Hz, 2H), 2.81-2.66 (m, 4H), 1.42 (br t, J=5.2 Hz, 4H), 1.09 (t, J=7.4 Hz, 3H).

HPLC-Retention time (XE Metode 7 CM): 1.62 minutes.

Detected "M+1"-mass: 350.20.

The following Examples 356-361 in Table 13 were prepared by reacting Compound 484 as described in General Procedure 2 with the appropriate acid:

TABLE 13

| Ex. | Cmpd | Structure | IUPAC Name | HPLC Rt (min) | PDE4 IC$_{50}$ range |
|---|---|---|---|---|---|
| 356 | 485 | 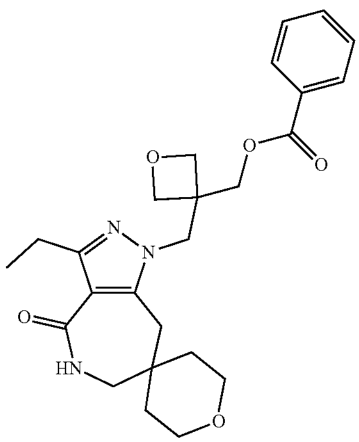 [SMILES: CCc1nn(CC2(COC(=O)c3ccccc3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl benzoate | 2.02 | *** |
| 357 | 486 | 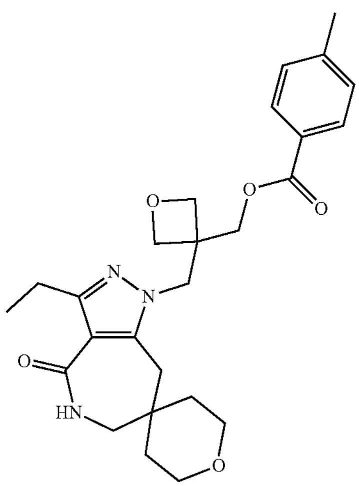 [SMILES: CCc1nn(CC2(COC(=O)c3ccc(C)cc3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-methylbenzoate | 2.10 | *** |
| 358 | 487 | 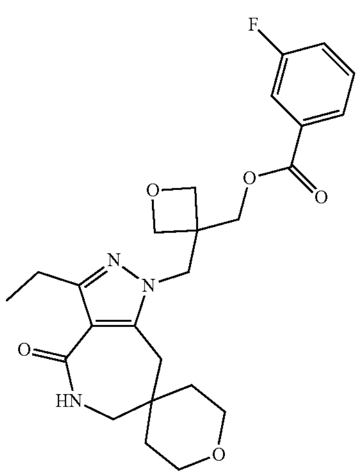 [SMILES: CCc1nn(CC2(COC(=O)c3cccc(F)c3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl 3-fluorobenzoate | 2.06 | *** |

TABLE 13-continued

| Ex. | Cmpd | Structure | IUPAC Name | HPLC Rt (min) | PDE4 IC$_{50}$ range |
|---|---|---|---|---|---|
| 359 | 488 | 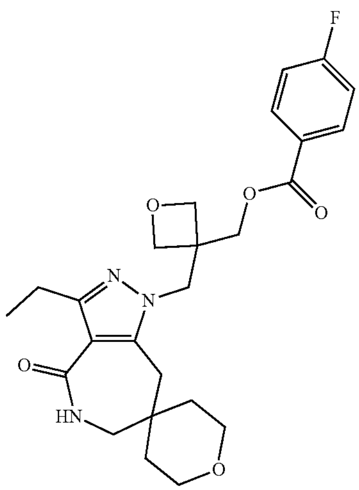 [SMILES: CCc1nn(CC2(COC(=O)c3ccc(F)cc3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-fluorobenzoate | 2.06 | *** |
| 360 | 489 | 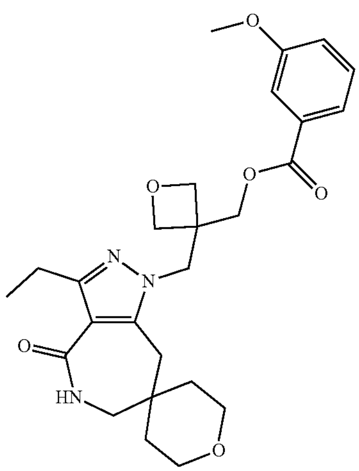 [SMILES: CCc1nn(CC2(COC(=O)c3cccc(OC)c3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl 3-methoxybenzoate | 2.05 | *** |
| 361 | 490 | 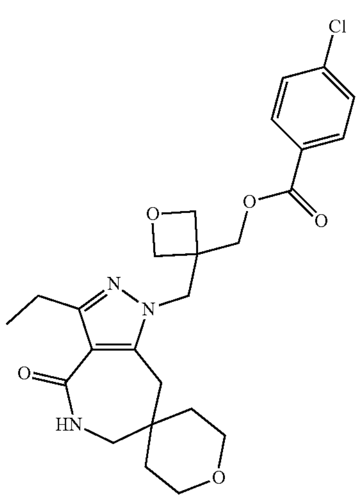 [SMILES: CCc1nn(CC2(COC(=O)c3ccc(Cl)cc3)COC2)c2c1C(=O)NCC1(CCOCC1)C2] | [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-chlorobenzoate | 2.15 | *** |

Preparation 47 (Compound 491)

(R/S)-Ethyl 3-(3-ethyl-4-oxo-spiro[5,7-dihydroindazole-6,4'-tetrahydropyran]-1-yl)butanoate

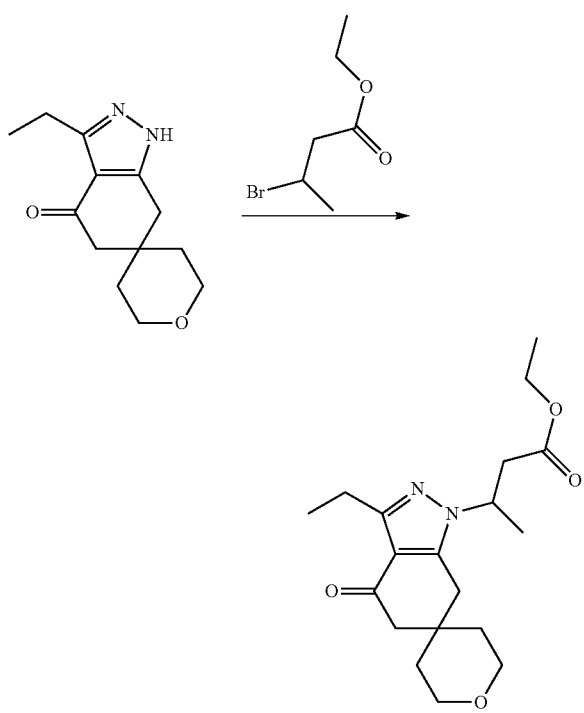

A mixture of 3-ethylspiro[5,7-dihydro-1H-indazole-6,4'-tetrahydropyran]-4-one (220 mg, 0.94 mmol), (R/S)-ethyl 3-bromobutanoate (220 mg, 1.12 mmol), $Cs_2CO_3$ (612 mg, 1.87 mmol) in DMF (2 mL) was stirred at rt for 2 hours. The mixture was diluted with water (10 mL) and EtOAc (10 mL). After phase separation, the aqueous phase was extracted twice with EtOAc (2×10 mL). The combined organic phases were dried over $MgSO_4$, filtered, and concentrated in vacuo. The residue was purified by prep acidic LCMS to afford the title compound. $^1$H NMR (300 MHz, $CDCl_3$) δ 4.76-4.61 (m, 1H), 4.12-3.97 (m, 2H), 3.82-3.64 (m, 4H), 3.17 (dd, J=16.8, 9.5 Hz, 1H), 3.03 (d, J=16.3 Hz, 1H), 2.86 (d, J=7.5 Hz, 1H), 2.81 (d, J=7.5 Hz, 1H), 2.75-2.71 (m, 1H), 2.70-2.65 (m, 1H), 2.50 (s, 2H), 1.70-1.56 (m, 4H), 1.50 (d, J=6.8 Hz, 3H), 1.25-1.13 (m, 6H).

Preparation 48 (Compound 492)

Ethyl 3-(3-ethyl-4-oxo-spiro[6,8-dihydro-5H-pyrazolo[4,3-c]azepine-7,4'-tetrahydro-pyran]-1-yl)butanoate

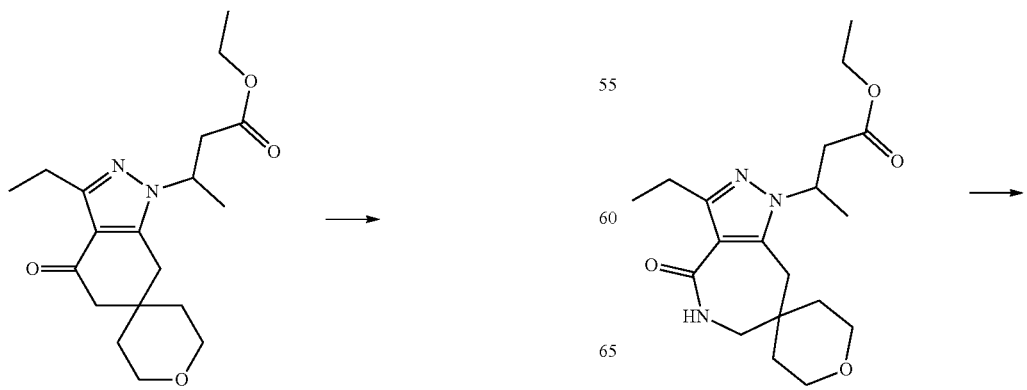

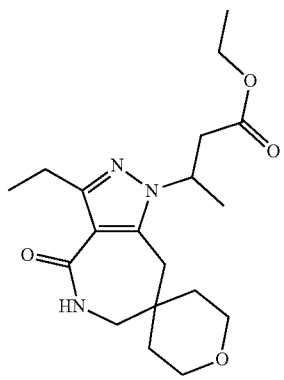

To a mixture of ethyl 3-(3-ethyl-4-oxo-spiro[5,7-dihydroindazole-6,4'-tetrahydro-pyran]-1-yl)butanoate (135 mg, 0.39 mmol) and sodium azide (76 mg, 1.16 mmol) in chloroform (2 mL) was added methanesulfonic acid (0.50 mL, 7.7 mmol) at rt. The mixture was stirred at rt for 1 h. Additional sodium azide (76 mg, 1.16 mmol) and methanesulfonic acid (0.50 mL, 7.7 mmol) was added. The mixture was stirred at rt for another hour and quenched by slow addition of the reaction mixture to saturated, aqueous $NaHCO_3$ (25 mL). The crude was extracted three times with DCM (3×15 mL). The combined organic phases were dried over $MgSO_4$, filtered and concentrated in vacuo. Column chromatography (DCM to DCM:MeOH:AcOH 100:10:1 as eluent) afforded the title compound.

$^1$H NMR (300 MHz, DMSO-d6) δ 7.40 (t, J=5.8 Hz, 1H), 4.77-4.61 (m, 1H), 3.96 (q, J=7.1 Hz, 2H), 3.73-3.49 (m, 4H), 3.06-2.93 (m, 3H), 2.87-2.65 (m, 5H), 1.46 (t, J=5.6 Hz, 4H), 1.36-1.30 (m, 3H), 1.13-1.01 (m, 6H).

Preparation 49 (Compound 493)

(R/S)-3-Ethyl-1-(3-hydroxy-1-methyl-propyl)spiro[6,8-dihydro-5H-pyrazolo[4,3-c]azepine-7,4'-tetrahydropyran]-4-one -continued

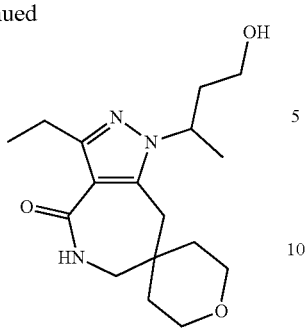

To a solution of ethyl 3-(3-ethyl-4-oxo-spiro[6,8-dihydro-5H-pyrazolo[4,3-c]azepine-7,4'-tetrahydropyran]-1-yl)butanoate (50 mg, 0.14 mmol) in EtOH (dry) (1.5 mL) under argon was added sodium borohydride (104.1 mg, 2.8 mmol) at rt. The obtained mixture was stirred at this temperature for 2 hours. The mixture was diluted with water (2 mL) and extracted three times with DCM (3×5 mL). The combined organic phases were dried over MgSO$_4$, filtered and concentrated in vacuo, giving the crude title compound.

$^1$H NMR (300 MHz, DMSO-d6) δ 7.36 (t, J=5.7 Hz, 1H), 4.44 (dt, J=9.0, 6.3 Hz, 1H), 3.75-3.47 (m, 4H), 3.40-3.30 (m, 2H), 3.11-2.91 (m, 3H), 2.93-2.62 (m, 4H), 1.97 (ddt, J=13.9, 9.7, 5.1 Hz, 1H), 1.79 (ddt, J=13.7, 8.3, 5.6 Hz, 1H), 1.44 (t, J=4.6 Hz, 411), 1.34 (d, J=6.6 Hz, 3H), 1.10 (t, J=7.5 Hz, 3H).

HPLC-Retention time (XE Metode 7 CM): 1.65 minutes.
Detected "M+1"-mass: 322.21.

Example 362 in Table 14 was prepared by reacting Compound 493 as described in General Procedure 1 with benzoic acid:

TABLE 14

| Ex. | Cmpd | Structure | IUPAC Name | HPLC Rt (min) | PDE4 IC$_{50}$ range |
|---|---|---|---|---|---|
| 362 | 494 | 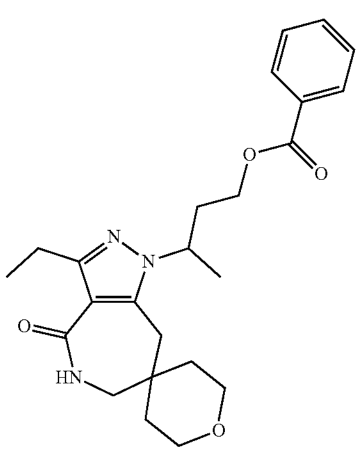 [SMILES: CCc1nn(C(C)CCOC(=O)c2ccccc2)c2c1C(=O)NCC1(CCOCC1)C2] | 3-(3-ethyl-4-oxo-spiro[6,8-dihydro-5H-pyrazolo[4,3-c]azepine-7,4'-tetrahydropyran]-1-yl)butyl benzoate | 2.12 | *** |

Preparation 50 (Compound 495)

4-Hydrazinobutan-1-ol

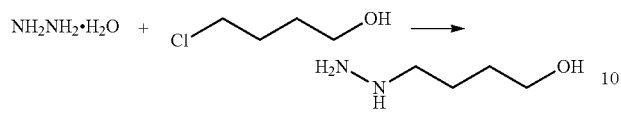

To hydrazine monohydrate (20 mL) was added 4-chlorobutanol (10.8 g, 99.5 mmol) at 0° C. The solution was stirred at rt for 2 days. To the solution was added NaOH (4 g, 99.5 mmol). The mixture was stirred for 1 hour and concentrated in vacuo. The residue was taken up in isopropanol (50 mL). The precipitate was filtered off over celite. The filtrate was concentrated in vacuo, giving an oil, which was used without further purification.

Preparation 51 (Compound 496)

3-Ethyl-1-(4-hydroxybutyl)spiro[5,7-dihydroindazole-6,4'-tetrahydropyran]-4-one

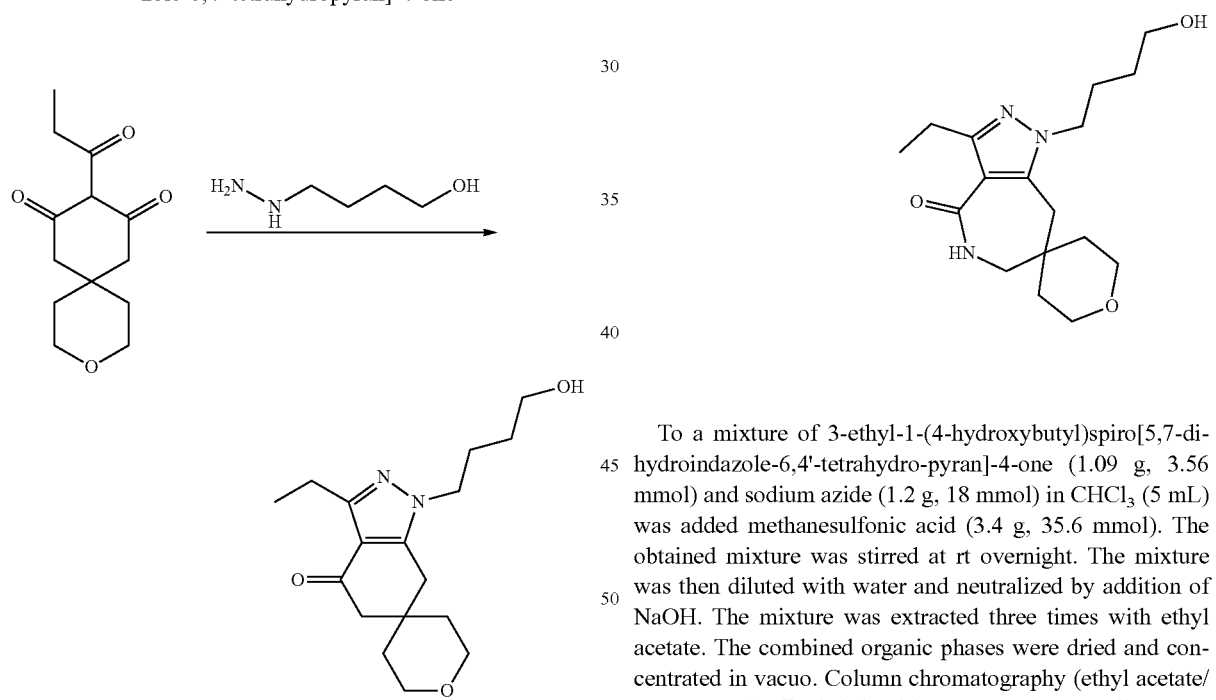

A reaction solution of 9-propanoyl-3-oxaspiro[5.5]undecane-8,10-dione (1.2 g, 5.0 mmol), 4-hydrazinobutan-1-ol (0.8 g, 8 mmol) and triethylamine (2 mL) in EtOH (20 mL) was heated to 100° C. for 1 hour. The solution was concentrated in vacuo. Column chromatography (ethyl acetate/MeOH 9:1, $R_f$=0.2), gave the title compound as an orange oil.

$^1$H NMR (300 MHz, CDCl$_3$) δ 4.07 (t, J=7.0 Hz, 2H), 3.78-3.59 (m, 6H), 2.85 (q, J=7.5 Hz, 2H), 2.75 (s, 2H), 2.52 (s, 2H), 2.01-1.86 (m, 2H), 1.75-1.45 (m, 7H), 1.24 (t, J=7.5 Hz, 3H).

Preparation 52 (Compound 497)

3-Ethyl-1-(4-hydroxybutyl)spiro[6,8-dihydro-5H-pyrazolo[4,3-c]azepine-7,4'-tetrahydropyran]-4-one

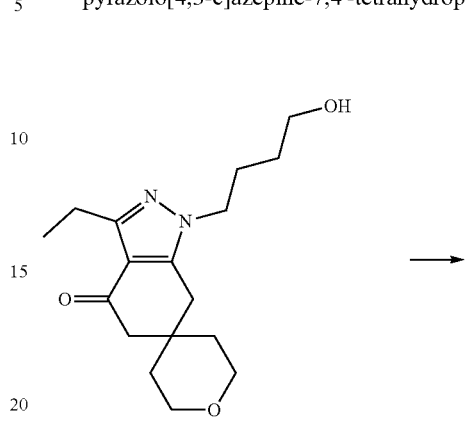

To a mixture of 3-ethyl-1-(4-hydroxybutyl)spiro[5,7-dihydroindazole-6,4'-tetrahydro-pyran]-4-one (1.09 g, 3.56 mmol) and sodium azide (1.2 g, 18 mmol) in CHCl$_3$ (5 mL) was added methanesulfonic acid (3.4 g, 35.6 mmol). The obtained mixture was stirred at rt overnight. The mixture was then diluted with water and neutralized by addition of NaOH. The mixture was extracted three times with ethyl acetate. The combined organic phases were dried and concentrated in vacuo. Column chromatography (ethyl acetate/MeOH 10:1) afforded the title compound as an oil.

$^1$H NMR (DMSO-d6) δ: 7.39 (t, J=5.7 Hz, 1H), 4.43 (t, J=5.1 Hz, 1H), 3.96 (t, J=7.3 Hz, 2H), 3.69-3.60 (m, 2H), 3.60-3.49 (m, 2H), 3.43-3.36 (m, 2H), 3.01 (d, J=5.7 Hz, 2H), 2.77-2.67 (m, 4H), 1.80-1.66 (m, 2H), 1.51-1.35 (m, 6H), 1.10 (t, J=7.5 Hz, 3H).

HPLC-Retention time (XE Metode 7 CM): 1.63 minutes. Detected "M+1"-mass: 322.21.

The following Examples 363-378 in Table 15 were prepared by reacting Compound 497 as described in General Procedure 2 with the appropriate acid:

TABLE 15

| Ex. | Cmpd | Structure | IUPAC Name | HPLC Rt (min) | PDE4 IC$_{50}$ range |
|---|---|---|---|---|---|
| 363 | 498 | 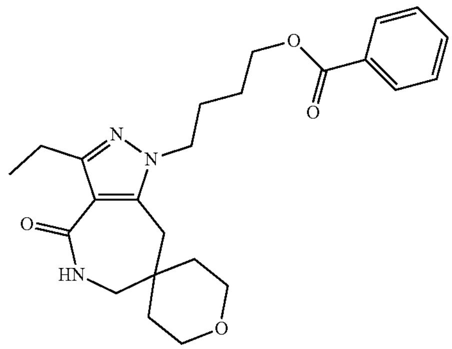 [SMILES: CCc1nn(CCCCOC(=O)c2ccccc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl benzoate | 2.12 | *** |
| 364 | 499 | 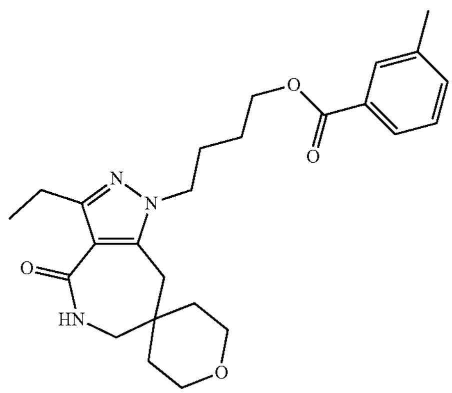 [SMILES: CCc1nn(CCCCOC(=O)c2cccc(C)c2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 3-methylbenzoate | 2.22 | *** |
| 365 | 500 | 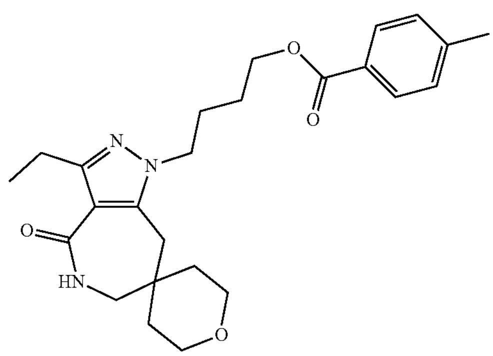 [SMILES: CCc1nn(CCCCOC(=O)c2ccc(C)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-methylbenzoate | 2.21 | *** |
| 366 | 501 | 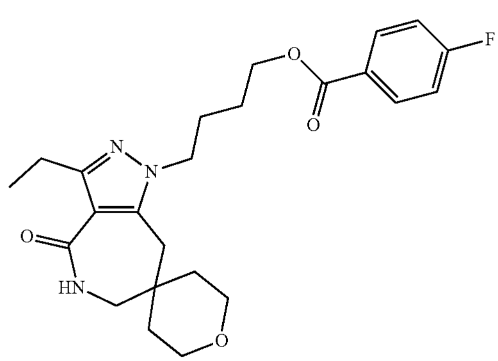 [SMILES: CCc1nn(CCCCOC(=O)c2ccc(F)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-fluorobenzoate | 2.15 | *** |

TABLE 15-continued

| Ex. | Cmpd | Structure | IUPAC Name | HPLC Rt (min) | PDE4 IC$_{50}$ range |
|---|---|---|---|---|---|
| 367 | 502 | 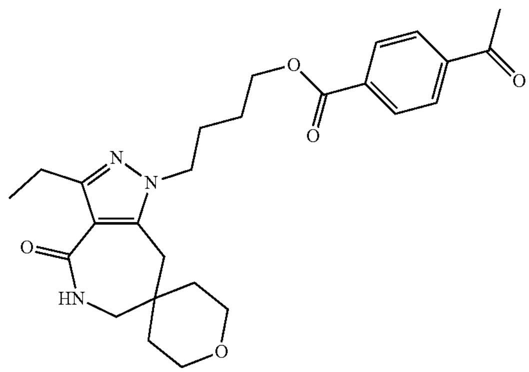 [SMILES: CCc1nn(CCCCOC(=O)c2ccc(C(C)=O)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 3-acetylbenzoate | 2.06 | *** |
| 368 | 503 | 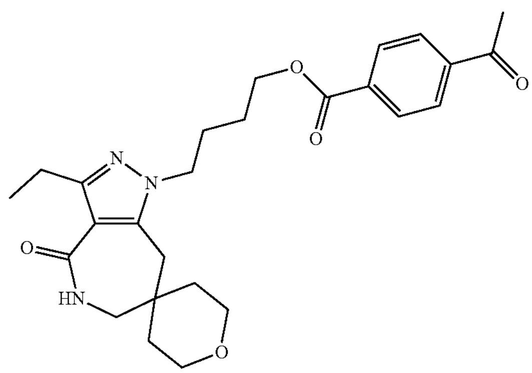 [SMILES: CCc1nn(CCCCOC(=O)c2ccc(C(C)=O)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-acetylbenzoate | 2.07 | ** |
| 369 | 504 | 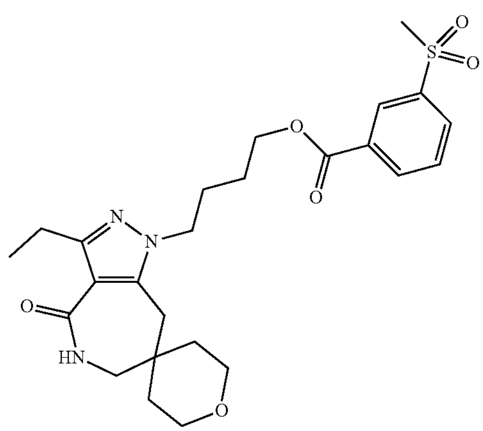 [SMILES: CCc1nn(CCCCOC(=O)c2cccc(S(C)(=O)=O)c2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 3-methylsulfonylbenzoate | 1.97 | ** |
| 370 | 505 | 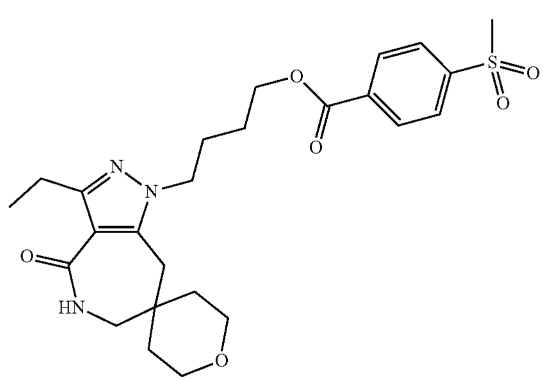 [SMILES: CCc1nn(CCCCOC(=O)c2ccc(S(C)(=O)=O)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-methylsulfonylbenzoate | 1.97 | ** |

TABLE 15-continued

| Ex. | Cmpd | Structure | IUPAC Name | HPLC Rt (min) | PDE4 IC$_{50}$ range |
|---|---|---|---|---|---|
| 371 | 506 | 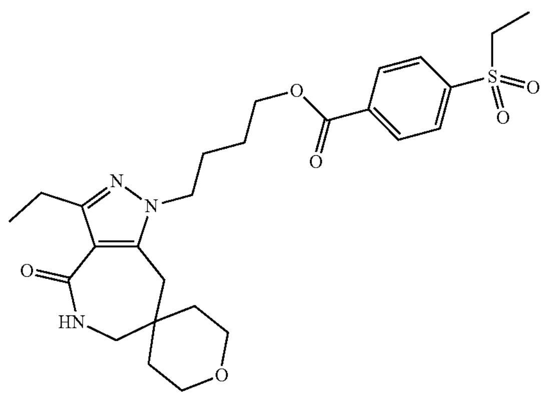 [SMILES: CCc1nn(CCCCOC(=O)c2ccc(S(=O)(=O)CC)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-ethylsulfonylbenzoate | 2.03 | ** |
| 372 | 507 | 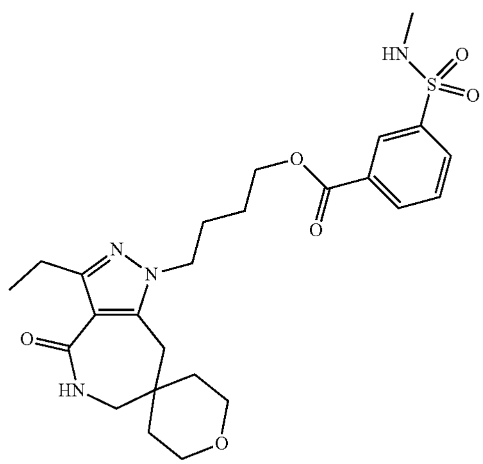 [SMILES: CCc1nn(CCCCOC(=O)c2cccc(S(=O)(=O)NC)c2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 3-(methylsulfamoyl)benzoate | 1.99 | *** |
| 373 | 508 | 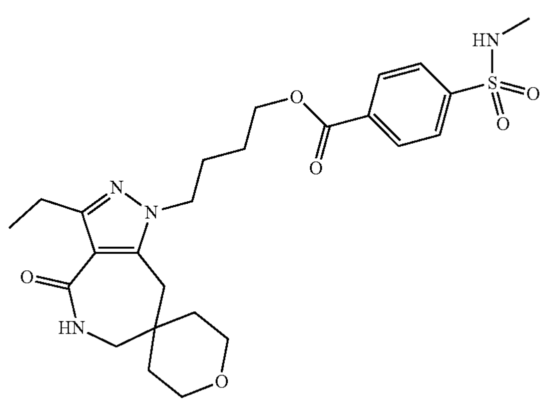 [SMILES: CCc1nn(CCCCOC(=O)c2ccc(S(=O)(=O)NC)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-(methylsulfamoyl)benzoate | 2.00 | ** |

TABLE 15-continued

| Ex. | Cmpd | Structure | IUPAC Name | HPLC Rt (min) | PDE4 IC$_{50}$ range |
|---|---|---|---|---|---|
| 374 | 509 | 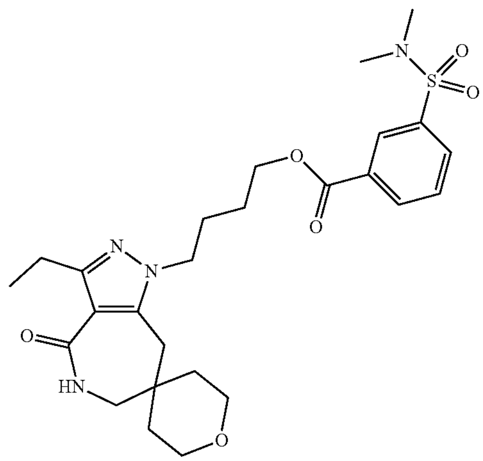 [SMILES: CCc1nn(CCCCOC(=O)c2cccc(S(=O)(=O)N(C)C)c2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-(dimethylsulfamoyl)benzoate | 2.09 | ** |
| 375 | 510 | 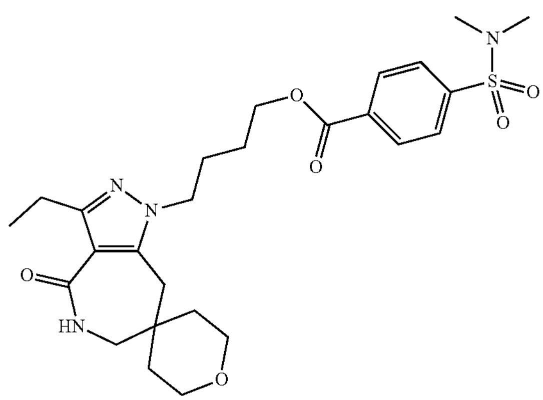 [SMILES: CCc1nn(CCCCOC(=O)c2ccc(S(=O)(=O)N(C)C)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-(dimethylsulfamoyl)benzoate | 2.10 | ** |
| 376 | 511 | 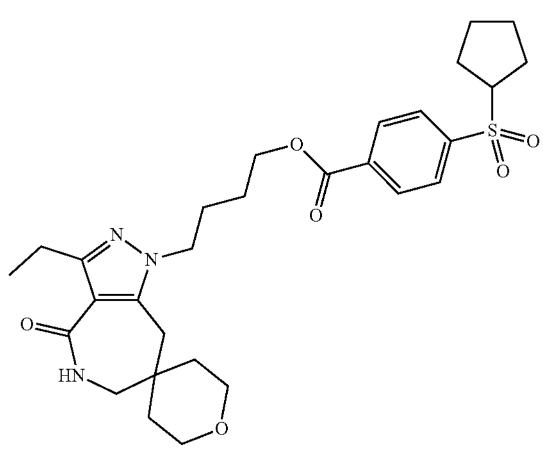 [SMILES: CCc1nn(CCCCOC(=O)c2ccc(S(=O)(=O)C3CCCC3)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-cyclopentylsulfonylbenzoate | 2.19 | ** |

TABLE 15-continued

| Ex. | Cmpd | Structure | IUPAC Name | HPLC Rt (min) | PDE4 IC$_{50}$ range |
|---|---|---|---|---|---|
| 377 | 512 | 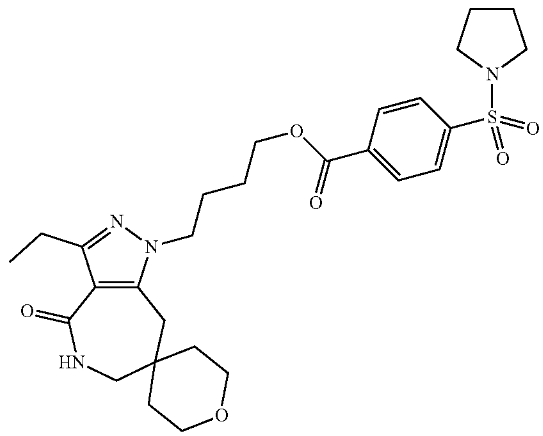 [SMILES: CCc1nn(CCCCOC(=O)c2ccc(S(=O)(=O)N3CCCC3)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-pyrrolidin-1-ylsulfonylbenzoate | 2.17 | ** |
| 378 | 513 | 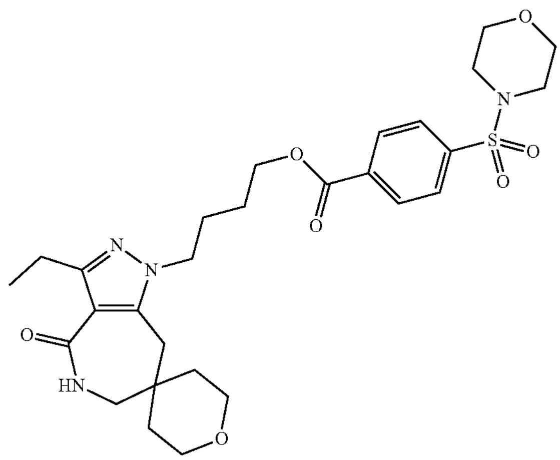 [SMILES: CCc1nn(CCCCOC(=O)c2ccc(S(=O)(=O)N3CCOCC3)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-morpholinosulfonylbenzoate | 2.09 | ** |

Preparation 53 (Compound 514)

4-[4-(3-Ethyl-4-oxo-spiro[6,8-dihydro-5H-pyrazolo[4,3-c]azepine-7,4'-tetrahydro-pyran]-1-yl)butoxy-carbonyl]benzoic Acid

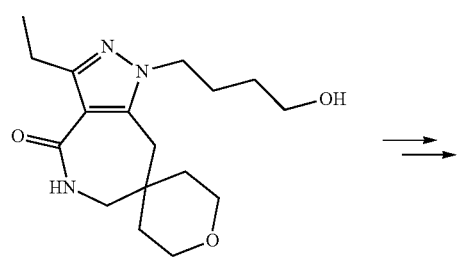

→

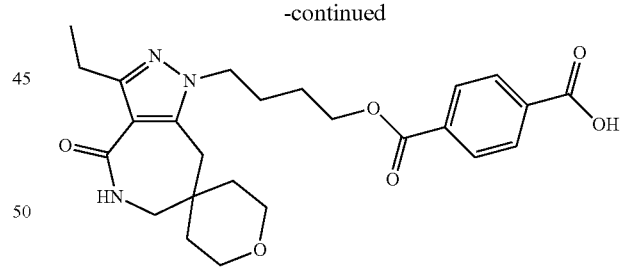

4-[4-(3-Ethyl-4-oxo-spiro[6,8-dihydro-5H-pyrazolo[4,3-c]azepine-7,4'-tetrahydro-pyran]-1-yl)butoxycarbonyl]benzoic acid was prepared in a manner similar to that of 4-[(2R)-3-(3-ethyl-4-oxo-spiro[6,8-dihydro-5H-pyrazolo[4,3-c]azepine-7,4'-tetrahydropyran]-1-yl)-2-methyl-propoxy]carbonylbenzoic acid described in Preparation 22 & 23 using 3-ethyl-1-(4-hydroxybutyl)spiro[6,8-dihydro-5H-pyrazolo[4,3-c]azepine-7,4'-tetrahydropyran]-4-one instead of 3-ethyl-1-[(2R)-3-hydroxy-2-methyl-propyl]-spiro[6,8-dihydro-5H-pyrazolo[4,3-c]azepine-7,4'-tetrahydropyran]-4-one as starting material.

$^1$H NMR (DMSO-d6) δ: 8.05 (s, 4H), 7.40 (t, J=5.8 Hz, 1H), 4.32 (t, J=6.3 Hz, 2H), 4.05 (t, J=7.2 Hz, 2H), 3.65-3.58 (m, 2H), 3.54-3.47 (m, 2H), 3.00 (d, J=5.7 Hz, 2H), 2.75 (s,

2H), 2.72 (q, J=7.5 Hz, 2H), 1.91-1.82 (m, 2H), 1.79-1.70 (m, 2H), 1.47-1.35 (m, 4H), 1.10 (t, J=7.5 Hz, 3H).

HPLC-Retention time (XE Metode 7 CM): 1.94 minutes.
Detected "M+1"-mass: 470.23.

The Examples 379-381 in Table 16 were prepared by reacting Compound 514 as described in General Procedure 3 with the appropriate amine:

TABLE 16

| Ex. | Cmpd | Structure | IUPAC Name | HPLC Rt (min) | PDE4 IC$_{50}$ range |
|---|---|---|---|---|---|
| 379 | 515 | 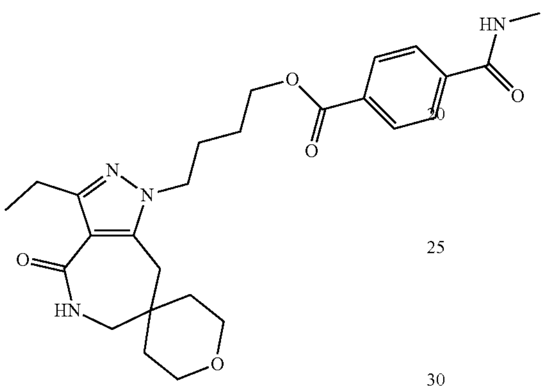 | 4-(3-ethyl-4-oxo-spiro[6,8-dihydro-5H-pyrazolo[4,3-c]azepine-7,4'-tetrahydropyran]-1-yl)butyl 4-(methylcarbamoyl)benzoate | 1.88 | ** |
| 380 | 516 | 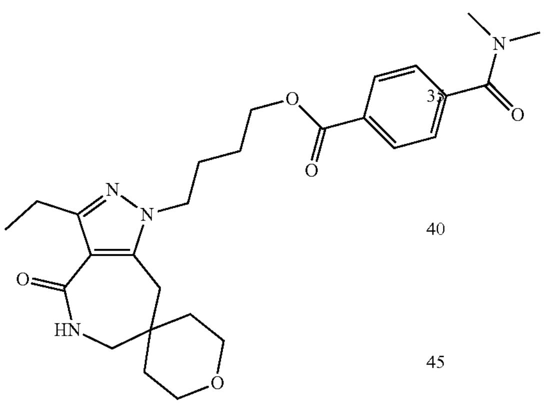 [SMILES: CCc1nn(CCCCOC(=O)c2ccc(C(=O)N(C)C)cc2)c2c1C(=O)NCC1(CCOCC1)C2] | 4-(3-ethyl-4-oxo-spiro[6,8-dihydro-5H-pyrazolo[4,3-c]azepine-7,4'-tetrahydropyran]-1-yl)butyl 4-(dimethylcarbamoyl)benzoate | 1.92 | ** |
| 381 | 517 | 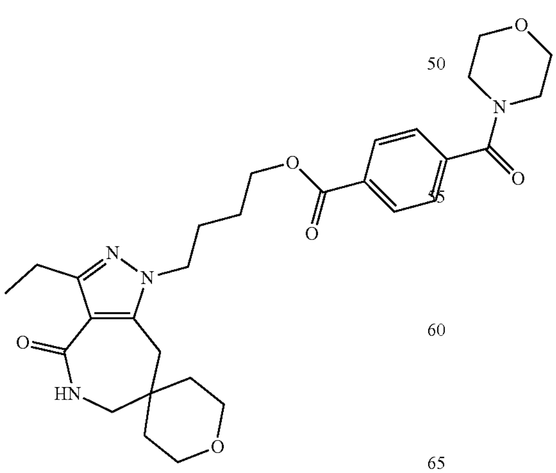 | 4-(3-ethyl-4-oxo-spiro[6,8-dihydro-5H-pyrazolo[4,3-c]azepine-7,4'-tetrahydropyran]-1-yl)butyl 4-(morpholine-4-carbonyl)benzoate | 1.92 | ** |

Preparation 54 (Compound 518)

Ethyl 2-(3-ethyl-4-oxo-spiro[5,7-dihydroindazole-6,4'-tetrahydropyran]-1-yl)acetate

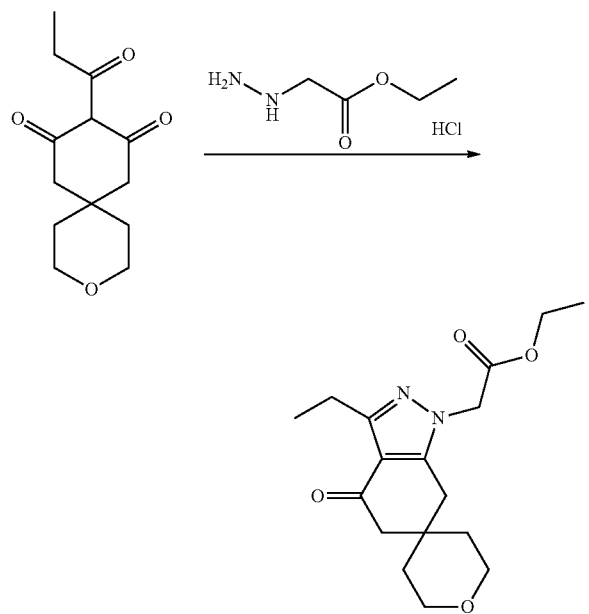

A mixture of 9-propanoyl-3-oxaspiro[5.5]undecane-8,10-dione (218 mg, 0.91 mmol), triethylamine (0.255 mL, 1.83 mmol) and ethyl 2-hydrazinoacetate hydrochloride (141 mg, 0.91 mmol) was stirred at 80° C. for 1 hour. The reaction mixture was concentrated in vacuo. Column chromatography (heptane:EtOAc (3:1)→heptane:EtOAc (1:2) as eluent) afforded the title compound as pale yellow oil.

$^1$H NMR (300 MHz, Chloroform-d) δ 4.81 (s, 2H), 4.25 (q, J=7.1 Hz, 2H), 3.79-3.59 (m, 4H), 2.86 (q, J=7.5 Hz, 2H), 2.73 (s, 2H), 2.53 (s, 2H), 1.72-1.52 (m, 4H), 1.38-1.16 (m, 6H).

Preparation 55 (Compound 519)

Ethyl 2-(3-ethyl-4-oxo-spiro[6,8-dihydro-5H-pyrazolo[4,3-c]azepine-7,4'-tetrahydro-pyran]-1-yl)acetate

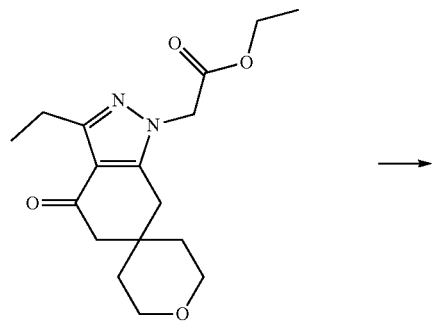

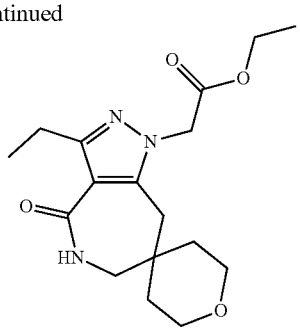

Methanesulfonic acid (1 mL) was added to a mixture of ethyl 2-(3-ethyl-4-oxo-[5,7-dihydroindazole-6,4'-tetrahydropyran]-1-yl)acetate (1.4 g, 4.37 mmol) and sodium azide (0.85 g, 13.1 mmol) in dry chloroform. The mixture was stirred at rt for 15 minutes before additional methane sulfonic acid (2 mL) was added. The mixture was stirred at rt for another 15 minutes before additional methane sulfonic acid (2 mL) was added. The mixture was stirred at rt for 45 minutes. Finally, additional sodium azide (852 mg, 13.1 mmol) and methanesulfonic acid (2 mL) was added. The mixture was stirred at rt for 1 hour. Reaction was quenched with saturated, aqueous NaHCO$_3$ (120 mL) and extracted three times with DCM (3×50 mL). The combined organic phases were concentrated in vacuo. Column chromatography (20-100% EtOAc in heptane as eluent) gave the title compound.

$^1$H NMR (300 MHz, CDCl$_3$) δ 5.74 (t, J=5.8 Hz, 1H), 4.81 (s, 2H), 4.24 (q, J=7.1 Hz, 2H), 3.79-3.60 (m, 4H), 3.21 (d, J=5.8 Hz, 2H), 2.91 (q, J=7.5 Hz, 2H), 2.69 (s, 2H), 1.68-1.54 (m, 4H), 1.33-1.21 (m, 6H).

Preparation 56 (Compound 520)

3-Ethyl-1-(2-hydroxyethyl)spiro[6,8-dihydro-5H-pyrazolo[4,3-c]azepine-7,4'-tetrahydropyran]-4-one

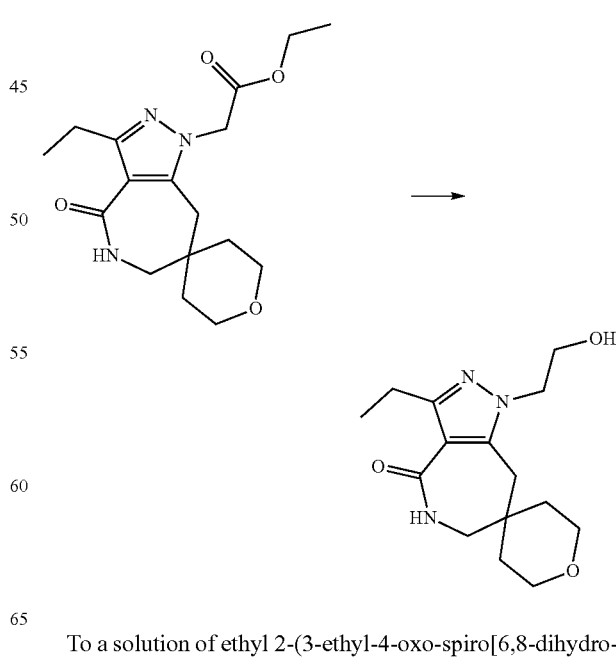

To a solution of ethyl 2-(3-ethyl-4-oxo-spiro[6,8-dihydro-5H-pyrazolo[4,3-c]azepine-7,4'-tetrahydropyran]-1-yl)acetate (546 mg, 1.63 mmol) in THF:H$_2$O (2:1, 12 mL) was added lithium borohydride (185 mg, 4.88 mmol). The mixture was stirred at rt for 1 hour. Saturated, aqueous NH$_4$Cl (10 mL) was added. The obtained mixture was stirred at rt for 5 minutes and extracted 10 times with DCM (10×20 mL) (Note that the product was very soluble in water). The combined organic phases were dried over MgSO$_4$ and filtered. Evaporation to dryness afforded the title compound.

$^1$H NMR (300 MHz, DMSO-d6) δ 7.37 (t, J=5.7 Hz, 1H), 4.01 (t, J=5.6 Hz, 2H), 3.75-3.46 (m, 6H), 3.00 (d, J=5.7 Hz, 2H), 2.82 (s, 2H), 2.73 (q, J=7.5 Hz, 2H), 1.56-1.32 (m, 4H), 1.12 (t, J=7.5 Hz, 3H).

HPLC-Retention time (XE Metode 7 CM): 1.57 minutes. Detected "M+1"-mass: 294.18.

Example 382 in Table 17 was prepared by reacting Compound 520 as described in General Procedure 1 with benzoic acid:

TABLE 17

| Ex. | Cmpd | Structure | IUPAC Name | HPLC Rt (min) | PDE4 IC$_{50}$ range |
|---|---|---|---|---|---|
| 382 | 521 | 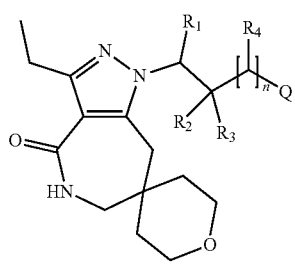 | 2-(3-ethyl-4-oxo-spiro[6,8-dihydro-5H-pyrazolo[4,3-c]azepme-7,4'-tetrahydropyran]-1-yl)ethyl berzoate | 1.99 | *** |

Clauses

In view of the description the present inventors have in particular provided:

Clause 1. A compound of general formula (I)

(I)

wherein

R$_1$ and R$_4$ are independently selected from the group consisting of hydrogen and (C$_1$-C$_4$)alkyl;

R$_2$ and R$_3$ are independently selected from the group consisting of hydrogen and (C$_1$-C$_4$)alkyl; or or R$_2$ and R$_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of —O—C(O)—R$_5$;

R$_5$ is selected from the group consisting of (C$_1$-C$_6$)alkyl, (C$_3$-C$_6$)cycloalkyl, halo(C$_1$-C$_6$)alkyl, (C$_1$-C$_6$)alkoxy, (C$_1$-C$_6$)alkoxy(C$_1$-C$_6$)alkyl, aryl; wherein said aryl is optionally substituted with one or more substituents independently selected from R$_6$, or wherein said aryl is optionally benzodioxole; and wherein said (C$_1$-C$_6$)alkyl, (C$_3$-C$_6$)cycloalkyl are optionally substituted with one or more substituents independently selected from R$_7$ R$_6$ consists of halogen, cyano, hydroxyl, (C$_1$-C$_4$)alkyl, halo(C$_1$-C$_4$)alkyl, (C$_1$-C$_4$)alkyloxy, —S(O)$_2$R$_x$, —S(O)$_2$NR$_a$R$_b$, —C(O)R$_x$, C(O)NR$_a$R$_b$ and —OR$_x$;

R$_7$ consists of halogen, hydroxyl, cyano, (C$_1$-C$_4$)alkoxy, —C(O)NR$_a$R$_b$, —C(O)OR$_a$, —S(O)$_2$R$_x$, —S(O)$_2$NR$_a$R$_b$, —OR$_x$, and —SR$_x$;

R$_x$ consists of (C$_1$-C$_6$)alkyl (C$_3$-C$_6$)cycloalkyl;

R$_a$ and R$_b$ are independently selected from the group consisting of hydrogen, (C$_1$-C$_4$)alkyl, phenyl-(C$_1$-C$_4$)alkyl, or R$_a$ and R$_b$ together with the nitrogen to which they are attached form a 4-6 membered heterocycloalkyl, wherein said heterocycloalkyl is optionally substituted with one or more (C$_1$-C$_4$)alkyl, —C(O)R$_x$; or pharmaceutically acceptable salts, hydrates or solvates thereof.

Clause 2. A compound according to clause 1 wherein

R$_1$ and R$_4$ are independently selected from the group consisting of hydrogen and (C$_1$-C$_4$)alkyl;

R$_2$ and R$_3$ are independently selected from the group consisting of hydrogen and (C$_1$-C$_4$)alkyl; or R$_2$ and R$_3$ together with the carbon atom to which they are attached form a cyclopropyl or oxetanyl ring;

n=0, 1 or 2;

Q is selected from the group consisting of —O—C(O)—R$_5$;

R$_5$ is selected from the group consisting of (C$_1$-C$_6$)alkyl, (C$_3$-C$_6$)cycloalkyl, halo(C$_1$-C$_6$)alkyl, (C$_1$-C$_6$)alkoxy, (C$_1$-C$_6$)alkoxy(C$_1$-C$_6$)alkyl, phenyl, benzodioxole; wherein said phenyl is optionally substituted with one or more substituents independently selected from Re; and wherein said (C$_1$-C$_6$)alkyl, (C$_3$-C$_6$)cycloalkyl are optionally substituted with one or more substituents independently selected from R$_7$;

R$_6$ consists of halogen, cyano, hydroxyl, (C$_1$-C$_4$)alkyl, halo(C$_1$-C$_4$)alkyl, (C$_1$-C$_4$)alkyloxy, —S(O)$_2$R$_x$, —S(O)$_2$NR$_a$R$_b$, —C(O)R$_x$, —C(O)NR$_a$R$_b$ and —OR$_x$;

$R_7$ consists of halogen, hydroxyl, cyano, $(C_1-C_4)$alkoxy, —C(O)$NR_aR_b$, —C(O)$OR_a$, —S(O)$_2R_x$, —S(O)$_2NR_aR_b$, —$OR_x$, and —$SR_x$;

$R_x$ consists of $(C_1-C_6)$alkyl and $(C_3-C_6)$cycloalkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl, —C(O)$R_x$; or a pharmaceutically acceptable salt, hydrate or solvate thereof.

Clause 3. A compound according to clause 1 of general formula (I)

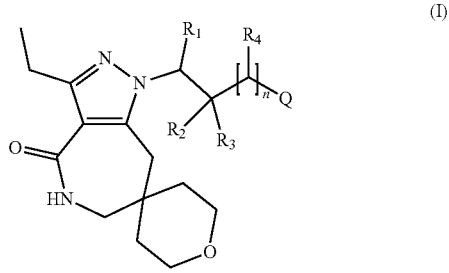

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or or $R_2$ and $R_3$ together with the carbon atom to which they are attached form a cyclopropyl, cyclobutyl, cyclopentyl, oxetanyl, tetrahydrofuranyl, or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$;

$R_6$ consists of halogen, cyano, hydroxyl, $(C_1-C_4)$alkyl, halo$(C_1-C_4)$alkyl, $(C_1-C_4)$alkyloxy, —S(O)$_2R_x$, —S(O)$_2NR_aR_b$ and —$OR_x$;

$R_x$ is $(C_1-C_6)$alkyl;

$R_a$ and $R_b$ are independently selected from the group consisting of hydrogen, $(C_1-C_4)$alkyl, phenyl-$(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl; or a pharmaceutically acceptable salt, hydrate or solvate thereof.

Clause 4. A compound according to any one of the preceding clauses wherein $R_1$ and $R_4$ are both hydrogen.

Clause 5. A compound according to any one of the preceding clauses wherein one of $R_2$ and $R_3$ is hydrogen and the other one of $R_2$ and $R_3$ is $(C_1-C_4)$alkyl.

Clause 6. A compound according to any one of the clauses 1-4 wherein $R_2$ and $R_3$ are both hydrogen.

Clause 7. A compound according to any one of the clauses 1-4 wherein $R_2$ and $R_3$ are both $(C_1-C_4)$alkyl.

Clause 8. A compound according to clause 7 wherein $R_2$ and $R_3$ are both methyl.

Clause 9. A compound according to any one of the clauses 1-4 wherein $R_2$ and $R_3$ together with the carbon atom to which they are attached form a cyclopropyl or oxetanyl ring.

Clause 10. A compound according to any one of the preceding clauses wherein n is 1.

Clause 11. A Compound according to any one of the clauses 1-9 wherein n is 2.

Clause 12. A Compound according to any one of the clauses 1-9 wherein n is 0.

Clause 13. A compound according to any one of the preceding clauses wherein $R_5$ is $(C_1-C_6)$alkyl.

Clause 14. A compound according to any one of the clauses 1-12 wherein $R_5$ is $(C_3-C_6)$cycloalkyl.

Clause 15. A compound according to clause 14 wherein $R_5$ is cyclopentyl.

Clause 16. A compound according to any one of the clauses 1-12 wherein $R_5$ is aryl, optionally substituted with one or more substituents independently selected from $R_6$.

Clause 17. A compound according to clause 16 wherein $R_5$ is phenyl, optionally substituted with one or more substituents independently selected from $R_6$.

Clause 18. A compound according to clause 17 wherein $R_5$ is phenyl, substituted with one substituent selected from $R_6$.

Clause 19. A compound according to clause 17 wherein $R_5$ is phenyl, substituted with two substituents independently selected from $R_6$.

Clause 20. A compound according to clause 17 wherein $R_5$ is phenyl.

Clause 21. A compound according to any one of the preceding clauses wherein $R_6$ consists of halogen, cyano, hydroxyl, $(C_1-C_4)$alkyl, halo$(C_1-C_4)$alkyl and $(C_1-C_4)$alkyloxy.

Clause 22. A compound according to clause 21 wherein $R_6$ is $(C_1-C_4)$alkyl.

Clause 23. A compound according to clause 22 wherein $R_6$ is methyl.

Clause 24. A compound according to clause 22 wherein $R_6$ is ethyl.

Clause 25. A compound according to clause 21 wherein $R_6$ is halogen.

Clause 26. A compound according to clause 21 wherein $R_6$ is hydroxyl.

Clause 27. A compound according to clause 21 wherein $R_6$ is trifluoromethyl.

Clause 28. A compound according to clause 21 wherein $R_6$ is difluoromethyl.

Clause 29. A compound according to any one of the clauses 1-20, wherein $R_6$ is —S(O)$_2R_x$.

Clause 30. A compound according to any one of the clauses 1-20, wherein $R_6$ is —C(O)$R_x$.

Clause 31. A compound according to any one of the clauses 1-20, wherein $R_6$ is —C(O)$NR_aR_b$.

Clause 32. A compound according to any one of the clauses 1-20, wherein $R_6$ is —S(O)$_2NR_aR_b$.

Clause 33. A Compound according to any one of the preceding clauses wherein $R_7$ consists of halogen, hydroxyl, cyano, $(C_1-C_4)$aloxy, —C(O)$NR_aR_b$, —C(O)$OR_a$, —S(O)$_2R_x$, —$OR_x$, and —$SR_x$.

Clause 34. A Compound according to clause 33 wherein $R_7$ consists of halogen, hydroxyl, $(C_1-C_4)$aloxy, —S(O)$_2R_x$, —$OR_x$, and —$SR_x$.

Clause 35. A compound according to any one of the preceding clauses, wherein $R_x$ is $(C_1-C_4)$alkyl.

Clause 36. A compound according to any one of the clauses 1-34, wherein $R_x$ is $(C_3-C_6)$cycloalkyl.

Clause 37. A compound according to any one of the preceding clauses, wherein $R_a$ and $R_b$ are independently selected from the group consisting of hydrogen and $(C_1-C_4)$alkyl.

Clause 38. A compound according to clause 37, wherein $R_a$ and $R_b$ are both $(C_1-C_4)$alkyl.

Clause 39. A compound according to clause 38, wherein $R_a$ and $R_b$ are both methyl.

Clause 40. A compound according to any one of the clauses 1-3, wherein $R_1$ and $R_4$ are both hydrogen, one of $R_2$ and $R_3$ is hydrogen and the other one of $R_2$ and $R_3$ is $(C_1-C_4)$alkyl, n is 1, $R_5$ is phenyl, $R_6$ is —S(O)$_2R_x$ or —S(O)$_2$NR$_a$R$_b$, $R_x$ is $(C_1-C_4)$alkyl and $R_a$ and $R_b$ are independently selected from the group consisting of hydrogen and $(C_1-C_4)$alkyl.

Clause 41. A compound according to any one of the clauses 1-3 wherein all of $R_1$, $R_2$, $R_3$, $R_4$ are hydrogen, n is 1, $R_5$ is phenyl, and $R_6$ is $(C_1-C_4)$alkyl.

Clause 42. A compound according to clause 1 or 2 wherein all of $R_1$, $R_2$, $R_3$, $R_4$ are hydrogen, n is 1, $R_5$ is selected from the group consisting of $(C_1-C_6)$alkyl, $(C_3-C_6)$cycloalkyl, $(C_1-C_5)$alkoxy, and aryl; wherein said aryl is optionally substituted with one or more substituents independently selected from halogen, cyano, hydroxyl, $(C_1-C_4)$alkyl, halo$(C_1-C_4)$alkyl, $(C_1-C_4)$alkyloxy, —S(O)$_2R_x$, —S(O)$_2$NR$_a$R$_b$, —C(O)R$_x$, C(O)NR$_a$R$_b$, or wherein said aryl is optionally benzodioxole; and wherein said $(C_1-C_6)$alkyl, $(C_3-C_6)$cycloalkyl are optionally substituted with one or more substituents independently selected from halogen, hydroxyl, cyano, $(C_1-C_4)$alkoxy, —C(O)NR$_a$R$_b$, —C(O)OR$_a$, —S(O)$_2R_x$, —S(O)$_2$NR$_a$R$_b$, —OR$_x$, —SR$_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$.

Clause 43. A compound according to clause 42 wherein all of $R_1$, $R_2$, $R_3$, $R_4$ are hydrogen, n is 1, $R_5$ is phenyl which is optionally substituted with one or more substituents independently selected from halogen, cyano, $(C_1-C_4)$alkyl, halo$(C_1-C_4)$alkyl, and $(C_1-C_4)$alkyloxy.

Clause 44. A compound according to clause 42 wherein all of $R_1$, $R_2$, $R_3$, $R_4$ are hydrogen, n is 1, $R_5$ is phenyl which is optionally substituted with one or more substituents independently selected from the group consisting of —S(O)$_2R_x$, —S(O)$_2$NR$_a$R$_b$, —C(O)R$_x$, C(O)NR$_a$R$_b$; $R_x$ consists of $(C_1-C_4)$alkyl and $(C_3-C_6)$cycloalkyl; $R_a$ and $R_b$ are independently selected from the group consisting of hydrogen and $(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$.

Clause 45. A compound according to clause 1 or 2 wherein all of $R_1$, $R_2$, $R_3$, $R_4$ are hydrogen, n is 1, $R_5$ is phenyl substituted with C(O)NR$_a$R$_b$, wherein $R_a$ and $R_b$ are independently selected from the group consisting of hydrogen and $(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$; and $R_x$ is $(C_1-C_4)$alkyl.

Clause 46. A compound according to clause 1 or 2 wherein $R_1$ and $R_4$ are both hydrogen, one of $R_2$ and $R_3$ is hydrogen and the other one of $R_2$ and $R_3$ is $(C_1-C_4)$alkyl, n is 1, $R_5$ is selected from the group consisting of $(C_1-C_6)$alkyl, $(C_3-C_6)$cycloalkyl and aryl; wherein said aryl is optionally substituted with one or more substituents independently selected from halogen, cyano, $(C_1-C_4)$alkyl, halo $(C_1-C_4)$alkyl, $(C_1-C_4)$-alkyloxy, —S(O)$_2R_x$, —S(O)$_2$NR$_a$R$_b$ and —C(O)R$_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$.

Clause 47. A compound according to clause 46 wherein $R_1$ and $R_4$ are both hydrogen, one of $R_2$ and $R_3$ is hydrogen and the other one of $R_2$ and $R_3$ is $(C_1-C_4)$alkyl, n is 1, $R_5$ is phenyl which is optionally substituted with one or more substituents independently selected from halogen, cyano, $(C_1-C_4)$alkyl, halo$(C_1-C_4)$alkyl, $(C_1-C_4)$alkyloxy, —S(O)$_2R_x$, —S(O)$_2$NR$_a$R$_b$, and —C(O)R$_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$-alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$.

Clause 48. A compound according to clause 1 or 2 wherein $R_1$ and $R_4$ are both hydrogen, one of $R_2$ and $R_3$ is hydrogen and the other one of $R_2$ and $R_3$ is $(C_1-C_4)$alkyl, n is 1, $R_5$ is phenyl substituted with C(O)NR$_a$R$_b$, wherein $R_a$ and $R_b$ are independently selected from the group consisting of hydrogen and $(C_1-C_4)$alkyl, or $R_a$ and $R_b$ together with the nitrogen to which they are attached form a 4-6 membered heterocycloalkyl, wherein said heterocycloalkyl is optionally substituted with one or more $(C_1-C_4)$alkyl or —C(O)R$_x$; and $R_x$ is $(C_1-C_4)$alkyl.

Clause 49. A compound according to clause 1 or 2 wherein $R_1$ and $R_4$ are both hydrogen, one of $R_2$ and $R_3$ is hydrogen and the other one of $R_2$ and $R_3$ is $(C_1-C_4)$alkyl, n is 1, $R_5$ is phenyl optionally substituted with halogen, $(C_1-C_4)$alkyl and $(C_1-C_4)$-alkyloxy.

Clause 50. A compound according to clause 1 or 2 wherein $R_1$ and $R_4$ are both hydrogen, $R_2$ and $R_3$ are both $(C_1-C_4)$alkyl, n is 1, $R_5$ is selected from the group consisting of $(C_1-C_6)$alkyl, $(C_3-C_6)$cycloalkyl and aryl; all of which are optionally substituted with one or more substituents independently selected from halogen, cyano, $(C_1-C_4)$alkyl, halo $(C_1-C_4)$alkyl, $(C_1-C_4)$alkyloxy, —S(O)$_2R_x$, —S(O)$_2$NR$_a$R$_b$, —C(O)R$_x$, C(O)NR$_a$R$_b$ and —OR$_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$alkyl, or $R_a$ and $R_b$ together with the nitrogen to which they are attached form a 4-6 membered heterocycloalkyl, wherein said heterocycloalkyl is optionally substituted with one or more of —C(O)R$_x$.

Clause 51. A compound according to clause 50 wherein $R_1$ and $R_4$ are both hydrogen, $R_2$ and $R_3$ are both $(C_1-C_4)$alkyl, n is 1, $R_5$ is phenyl which is optionally substituted with one or more substituents independently selected from halogen, cyano, $(C_1-C_4)$alkyl, halo$(C_1-C_4)$alkyl, $(C_1-C_4)$alkyloxy, —S(O)$_2R_x$, —S(O)$_2$NR$_a$R$_b$, —C(O)R$_x$, C(O)NR$_a$R$_b$ and —OR$_x$; $R_x$ consists of $(C_1-C_4)$alkyl and $(C_3-C_6)$cycloalkyl; $R_a$ and $R_b$ are independently selected from the group consisting of hydrogen, $(C_1-C_4)$alkyl, or $R_a$ and $R_b$ together with the nitrogen to which they are attached form a 4-6 membered heterocycloalkyl, wherein said heterocycloalkyl is optionally substituted with one or more of —C(O)R$_x$.

Clause 52. A compound according to clause 1 or 2 wherein $R_1$ and $R_4$ are both hydrogen, $R_2$ and $R_3$ are both $(C_1-C_4)$alkyl, n is 1, $R_5$ is phenyl substituted with C(O)NR$_a$R$_b$, wherein R$_a$ and R$_b$ are independently selected from the group consisting of hydrogen and $(C_1-C_4)$alkyl, or R$_a$ and R$_b$ together with the nitrogen to which they are attached form a 4-6 membered heterocycloalkyl, wherein said heterocycloalkyl is optionally substituted with one or more $(C_1-C_4)$alkyl or —C(O)R$_x$; and R$_x$ is $(C_1-C_4)$alkyl.

Clause 53. A compound according to clause 1 or 2 wherein $R_1$ and $R_4$ are both hydrogen, $R_2$ and $R_3$ together with the carbon atom to which they are attached form a cyclopropyl ring, n is 1, $R_5$ is phenyl substituted with one or more substituents independently selected from halogen, $(C_1-C_4)$alkyl, and $(C_1-C_4)$alkyloxy.

Clause 54. A compound according to clause 1 or 2 wherein $R_1$ and $R_4$ are both hydrogen, $R_2$ and $R_3$ together with the carbon atom to which they are attached form a oxetanyl ring, n is 1, $R_5$ is phenyl substituted with one or more substituents independently selected from halogen, $(C_1-C_4)$alkyl, and $(C_1-C_4)$alkyloxy.

Clause 55. A compound according to clause 1 or 2 wherein $R_1$ is $(C_1-C_4)$alkyl, all of $R_2$, $R_3$, $R_4$ are hydrogen, n is 1, $R_5$ is phenyl optionally substituted with one or more substituents independently selected from halogen, $(C_1-C_4)$alkyl, and $(C_1-C_4)$alkyloxy.

Clause 56. A compound according to clause 1 or 2 wherein all of $R_1$, $R_2$, $R_3$, $R_4$ are hydrogen, n is 2, $R_5$ is $R_5$ is phenyl which is optionally substituted with one or more substituents independently selected from halogen, $(C_1-C_4)$alkyl, —S(O)$_2$R$_x$, —S(O)$_2$NR$_a$R$_b$, and —C(O)R$_x$; R$_x$ consists of $(C_1-C_4)$alkyl and $(C_3-C_6)$cycloalkyl; R$_a$ and R$_b$ are independently selected from the group consisting of hydrogen, $(C_1-C_4)$alkyl, or R$_a$ and R$_b$ together with the nitrogen to which they are attached form a 4-6 membered heterocycloalkyl.

Clause 57. A compound according to clause 1 or 2 wherein all of $R_1$, $R_2$, $R_3$, $R_4$ are hydrogen, n is 2, $R_5$ is phenyl substituted with C(O)NR$_a$R$_b$, wherein R$_a$ and R$_b$ are independently selected from the group consisting of hydrogen and $(C_1-C_4)$alkyl, or R$_a$ and R$_b$ together with the nitrogen to which they are attached form a 4-6 membered heterocycloalkyl.

Clause 58. A compound according to clause 1 or 2 wherein all of $R_1$, $R_2$, $R_3$ are hydrogen, n is 0, $R_5$ is phenyl which is optionally substituted with one or more substituents independently selected from halogen, $(C_1-C_4)$alkyl, and $(C_1-C_4)$alkyloxy.

Clause 59. A compound according to any one of the clauses 1 to 58 selected from the group consisting of
3-(3-Ethyl-4-oxo-spiro[6,8-dihydro-5H-pyrazolo[4,3-c]azepine-7,4'-tetrahydropyran]-1-yl)propyl 4-methylbenzoate (compound 101);
3-(3-Ethyl-4-oxo-spiro[6,8-dihydro-5H-pyrazolo[4,3-c]azepine-7,4'-tetrahydropyran]-1-yl)propyl 4-ethylbenzoate (compound 102);
[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(methylsulfamoyl)benzoate (compound 103);
[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(dimethylsulfamoyl)benzoate (compound 104);
[(2R)-3-(3-ethyl-4-oxo-spiro[6,8-dihydro-5H-pyrazolo[4,3-c]azepine-7,4'-tetrahydro-pyran]-1-yl)-2-methyl-propyl] 4-methylsulfonylbenzoate (compound 105); or
pharmaceutically acceptable salts, hydrates or solvates thereof.

Clause 60. A compound which is
3-(3-Ethyl-4-oxo-spiro[6,8-dihydro-5H-pyrazolo[4,3-c]azepine-7,4'-tetrahydropyran]-1-yl)propyl 4-methylbenzoate (compound 101); or
a pharmaceutically acceptable salt, hydrate or solvate thereof.

Clause 61. A compound which is
3-(3-Ethyl-4-oxo-spiro[6,8-dihydro-5H-pyrazolo[4,3-c]azepine-7,4'-tetrahydropyran]-1-yl)propyl 4-ethylbenzoate (compound 102); or
a pharmaceutically acceptable salt, hydrate or solvate thereof.

Clause 62. A compound which is
[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(methylsulfamoyl)benzoate (compound 103); or
a pharmaceutically acceptable salt, hydrate or solvate thereof.

Clause 63. A compound which is
[(2R)-3-(3-Ethyl-4-oxo-spiro[6,8-dihydro-5H-pyrazolo[4,3-c]azepine-7,4'-tetrahydro-pyran]-1-yl)-2-methyl-propyl] 4-(dimethylsulfamoyl)benzoate (compound 104); or
a pharmaceutically acceptable salt, hydrate or solvate thereof.

Clause 64. A compound which is
[(2R)-3-(3-ethyl-4-oxo-spiro[6,8-dihydro-5H-pyrazolo[4,3-c]azepine-7,4'-tetrahydro-pyran]-1-yl)-2-methyl-propyl] 4-methylsulfonylbenzoate (compound 105); or
a pharmaceutically acceptable salt, hydrate or solvate thereof.

Clause 65. A compound according to any one of the clauses 1 to 58 selected from the group consisting of:
3-(3-ethyl-4-oxo-spiro[6,8-dihydro-5H-pyrazolo[4,3-c]azepine-7,4'-tetrahydropyran]-1-yl)propyl acetate
3-(3-ethyl-4-oxo-spiro[6,8-dihydro-5H-pyrazolo[4,3-c]azepine-7,4'-tetrahydropyran]-1-yl)propyl 2-methylpropanoate
3-(3-ethyl-4-oxo-spiro[6,8-dihydro-5H-pyrazolo[4,3-c]azepine-7,4'-tetrahydropyran]-1-yl)propyl 3-methoxypropanoate
3-(3-ethyl-4-oxo-spiro[6,8-dihydro-5H-pyrazolo[4,3-c]azepine-7,4'-tetrahydropyran]-1-yl)propyl cyclopentanecarboxylate
3-(3-ethyl-4-oxo-spiro[6,8-dihydro-5H-pyrazolo[4,3-c]azepine-7,4'-tetrahydropyran]-1-yl)propyl 3-hydroxycyclobutanecarboxylate
3-(3-ethyl-4-oxo-spiro[6,8-dihydro-5H-pyrazolo[4,3-c]azepine-7,4'-tetrahydropyran]-1-yl)propyl 2-ethylbutanoate
3-(3-ethyl-4-oxo-spiro[6,8-dihydro-5H-pyrazolo[4,3-c]azepine-7,4'-tetrahydropyran]-1-yl)propyl 2-isopropoxyacetate 3-(3-ethyl-4-oxo-spiro[6,8-dihydro-5H-pyrazolo[4,3-c]azepine-7,4'-tetrahydropyran]-1-yl)propyl 3-methylsulfanylpropanoate;
3-(3-ethyl-4-oxo-spiro[6,8-dihydro-5H-pyrazolo[4,3-c]azepine-7,4'-tetrahydropyran]-1-yl) propyl 3,3-difluorocyclobutanecarboxylate
3-(3-ethyl-4-oxo-spiro[6,8-dihydro-5H-pyrazolo[4,3-c]azepine-7,4'-tetrahydropyran]-1-yl)propyl 3-methylbenzoate
3-(3-ethyl-4-oxo-spiro[6,8-dihydro-5H-pyrazolo[4,3-c]azepine-7,4'-tetrahydropyran]-1-yl)propyl 2-methylbenzoate
3-(3-ethyl-4-oxo-spiro[6,8-dihydro-5H-pyrazolo[4,3-c]azepine-7,4'-tetrahydropyran]-1-yl)propyl 2-hydroxybenzoate 3-(3-ethyl-4-oxo-spiro[6,8-dihydro-5H-pyrazolo[4,3-c]azepine-7,4'-tetrahydropyran]-1-yl)propyl 3-fluorobenzoate 3-(3-ethyl-4-oxo-spiro[6,8-dihydro-5H-pyrazolo[4,3-c]azepine-7,4'-tetrahydropyran]-1-yl)propyl 2-fluorobenzoate 3-(3-ethyl-4-oxo-spiro[6,8-dihydro-5H-pyrazolo[4,3-c]azepine-7,4'-tetrahydropyran]-1-yl)propyl 4-fluorobenzoate 3-(3-ethyl-4-oxo-spiro[6,8-dihydro-5H-pyrazolo[4,3-c]azepine-7,4'-tetrahydropyran]-1-yl)propyl cis-4-hydroxycyclohexanecarboxylate 3-(3-ethyl-4-oxo-spiro[6,8-dihydro-5H-pyrazolo[4,3-c]azepine-7,4'-tetrahydropyran]-1-yl) propyl trans-4-hydroxycyclohexanecarboxylate 3-(3-ethyl-4-oxo-spiro[6,8-dihydro-5H-pyrazolo[4,3-c]azepine-7,4'-tetrahydropyran]-1-yl)propyl 3-cyanobenzoate 3-(3-ethyl-4-oxo: spiro[6,8-dihydro-5H-pyrazolo[4,3-c]azepine-7,4'-tetrahydropyran]-1-yl)propyl 4-cyanobenzoate 3-(3-ethyl-4-oxo-spiro[6,8-dihydro-5H-pyrazolo[4,3-c]azepine-7,4'-tetrahydropyran]-1-yl)propyl 2-cyanobenzoate 3-(3-ethyl-4-oxo-spiro[6,8-dihydro-5H-pyrazolo[4,3-c]azepine-7,4'-tetrahydropyran]-1-yl)propyl 3,4-dimethylbenzoate 3-(3-ethyl-4-oxo-spiro[6,8-dihydro-5H-pyrazolo[4,3-c]azepine-7,4'-tetrahydropyran]-1-yl)propyl 2,4-dimethylbenzoate 3-(3-ethyl-4-oxo-spiro[6,8-dihydro-5H-pyrazolo[4,3-c]azepine-7,4'-tetrahydropyran]-1-yl)propyl 4-methoxybenzoate 3-(3-ethyl-4-oxo-spiro[6,8-dihydro-5H-pyrazolo[4,3-c]azepine-7,4'-tetrahydropyran]-1-yl)propyl 3-methoxybenzoate 3-(3-ethyl-4-oxo-spiro[6,8-dihydro-5H-pyrazolo[4,3-c]azepine-7,4'-tetrahydropyran]-1-yl)propyl 2-methoxybenzoate 3-(3-ethyl-4-oxo-spiro[6,8-dihydro-5H-pyrazolo[4,3-c]azepine-7,4'-tetrahydropyran]-1-yl)propyl 3-methylsulfonylpropanoate 3-(3-ethyl-4-oxo-spiro[6,8-dihydro-5H-pyrazolo[4,3-c]azepine-7,4'-tetrahydropyran]-1-yl)propyl 3-fluoro-4-methyl-benzoate 3-(3-ethyl-4-oxo-spiro[6,8-dihydro-5H-pyrazolo[4,3-c]azepine-7,4'-tetrahydropyran]-1-yl)propyl 2-fluoro-4-methyl-benzoate 3-(3-ethyl-4-oxo-spiro[6,8-dihydro-5H-pyrazolo[4,3-c]azepine-7,4'-tetrahydropyran]-1-yl)propyl 5-fluoro-2-methyl-benzoate 3-(3-ethyl-4-oxo-spiro[6,8-dihydro-5H-pyrazolo[4,3-c]azepine-7,4'-tetrahydropyran]-1-yl)propyl 4-fluoro-3-methyl-benzoate 3-(3-ethyl-4-oxo-spiro[6,8-dihydro-5H-pyrazolo[4,3-c]azepine-7,4'-tetrahydropyran]-1-yl)propyl 3-fluoro-2-methyl-benzoate 3-(3-ethyl-4-oxo-spiro[6,8-dihydro-5H-pyrazolo[4,3-c]azepine-7,4'-tetrahydropyran]-1-yl) propyl 2-fluoro-5-methyl-benzoate 3-(3-ethyl-4-oxo-spiro[6,8-dihydro-5H-pyrazolo[4,3-c]azepine-7,4'-tetrahydropyran]-1-yl)propyl 4-fluoro-2-methyl-benzoate 3-(3-ethyl-4-oxo-spiro[6,8-dihydro-5H-pyrazolo[4,3-c]azepine-7,4'-tetrahydropyran]-1-yl)propyl 2-fluoro-6-methyl-benzoate 3-(3-ethyl-4-oxo-spiro[6,8-dihydro-5H-pyrazolo[4,3-c]azepine-7,4'-tetrahydropyran]-1-yl)propyl 2-chlorobenzoate 3-(3-ethyl-4-oxo-spiro[6,8-dihydro-5H-pyrazolo[4,3-c]azepine-7,4'-tetrahydropyran]-1-yl)propyl 3-chlorobenzoate 3-(3-ethyl-4-oxo-spiro[6,8-dihydro-5H-pyrazolo[4,3-c]azepine-7,4'-tetrahydropyran]-1-yl)propyl 4-chlorobenzoate 3-(3-ethyl-4-oxo-spiro[6,8-dihydro-5H-pyrazolo[4,3-c]azepine-7,4'-tetrahydropyran]-1-yl)propyl 3,5-difluorobenzoate 3-(3-ethyl-4-oxo-spiro[6,8-dihydro-5H-pyrazolo[4,3-c]azepine-7,4'-tetrahydropyran]-1-yl)propyl 3,4-difluorobenzoate 3-(3-ethyl-4-oxo-spiro[6,8-dihydro-5H-pyrazolo[4,3-c]azepine-7,4'-tetrahydropyran]-1-yl)propyl 2,3-difluorobenzoate 3-(3-ethyl-4-oxo-spiro[6,8-dihydro-5H-pyrazolo[4,3-c]azepine-7,4'-tetrahydropyran]-1-yl)propyl 2,6-difluorobenzoate 3-(3-ethyl-4-oxo-spiro[6,8-dihydro-5H-pyrazolo[4,3-c]azepine-7,4'-tetrahydropyran]-1-yl)propyl 2,5-difluorobenzoate 3-(3-ethyl-4-oxo-spiro[6,8-dihydro-5H-pyrazolo[4,3-c]azepine-7,4'-tetrahydropyran]-1-yl) propyl 4-methoxycyclohexanecarboxylate 3-(3-ethyl-4-oxo-spiro[6,8-dihydro-5H-pyrazolo[4,3-c]azepine-7,4'-tetrahydropyran]-1-yl)propyl 4,4-difluorocyclohexanecarboxylate 3-(3-ethyl-4-oxo-spiro[6,8-dihydro-5H-pyrazolo[4,3-c]azepine-7,4'-tetrahydropyran]-1-yl)propyl 4-acetylbenzoate 3-(3-ethyl-4-oxo-spiro[6,8-dihydro-5H-pyrazolo[4,3-c]azepine-7,4'-tetrahydropyran]-1-yl)propyl 3-acetylbenzoate 3-(3-ethyl-4-oxo-spiro[6,8-dihydro-5H-pyrazolo[4,3-c]azepine-7,4'-tetrahydropyran]-1-yl)propyl 4-cyano-3-fluoro-benzoate 3-(3-ethyl-4-oxo-spiro[6,8-dihydro-5H-pyrazolo[4,3-c]azepine-7,4'-tetrahydropyran]-1-yl)propyl 3-cyano-5-fluoro-benzoate 3-(3-ethyl-4-oxo-spiro[6,8-dihydro-5H-pyrazolo[4,3-c]azepine-7,4'-tetrahydropyran]-1-yl)propyl 4-cyano-2-fluoro-benzoate 3-(3-ethyl-4-oxo-spiro[6,8-dihydro-5H-pyrazolo[4,3-c]azepine-7,4'-tetrahydropyran]-1-yl)propyl 3-cyano-4-fluoro-benzoate 3-(3-ethyl-4-oxo-spiro[6,8-dihydro-5H-pyrazolo[4,3-c]azepine-7,4'-tetrahydropyran]-1-yl)propyl 5-cyano-2-fluoro-benzoate 3-(3-ethyl-4-oxo-spiro[6,8-dihydro-5H-pyrazolo[4,3-c]azepine-7,4'-tetrahydropyran]-1-yl)propyl 1,3-benzodioxole-5-carboxylate 3-(3-ethyl-4-oxo-spiro[6,8-dihydro-5H-pyrazolo[4,3-c]azepine-7,4'-tetrahydropyran]-1-yl)propyl 4-methoxy-3-methyl-benzoate 3-(3-ethyl-4-oxo-spiro[6,8-dihydro-5H-pyrazolo[4,3-c]azepine-7,4'-tetrahydropyran]-1-yl)propyl 3-methoxy-4-methyl-benzoate 3-(3-ethyl-4-oxo-spiro[6,8-dihydro-5H-pyrazolo[4,3-c]azepine-7,4'-tetrahydropyran]-1-yl)propyl 2-methoxy-4-methyl-benzoate 3-(3-ethyl-4-oxo-spiro[6,8-dihydro-5H-pyrazolo[4,3-c]azepine-7,4'-tetrahydropyran]-1-yl)propyl 3-ethoxybenzoate 3-(3-ethyl-4-oxo-spiro[6,8-dihydro-5H-pyrazolo[4,3-c]azepine-7,4'-tetrahydropyran]-1-yl)propyl 3-fluoro-4-methoxy-benzoate 3-(3-ethyl-4-oxo-spiro[6,8-dihydro-5H-pyrazolo[4,3-c]azepine-7,4'-tetrahydropyran]-1-yl)propyl 3-fluoro-5-methoxy-benzoate 3-(3-ethyl-4-oxo-spiro[6,8-dihydro-5H-pyrazolo[4,3-c]azepine-7,4'-tetrahydropyran]-1-yl)propyl 2-fluoro-4-methoxy-benzoate 3-(3-ethyl-4-oxo-spiro[6,8-dihydro-5H-pyrazolo[4,3-c]azepine-7,4'-tetrahydropyran]-1-yl)propyl 4-fluoro-3-methoxy-benzoate 3-(3-ethyl-4-oxo-spiro[6,8-dihydro-5H-pyrazolo[4,3-c]azepine-7,4'-tetrahydropyran]-1-yl)propyl 2-fluoro-3-methoxy-benzoate 3-(3-ethyl-4-oxo-spiro[6,8-dihydro-5H-pyrazolo[4,3-c]azepine-7,4'-tetrahydropyran]-1-yl)propyl 2-fluoro-5-methoxy-benzoate 3-(3-ethyl-4-oxo-spiro[6,8-dihydro-5H-pyrazolo[4,3-c]azepine-7,4'-tetrahydropyran]-1-yl)propyl 5-fluoro-2-methoxy-benzoate 3-(3-ethyl-4-oxo-spiro[6,8-dihydro-5H-pyrazolo[4,3-c]azepine-7,4'-tetrahydropyran]-1-yl)propyl 2-fluoro-6-methoxy-benzoate 3-(3-ethyl-4-oxo-spiro[6,8-dihydro-5H-pyrazolo[4,3-c]azepine-7,4'-tetrahydropyran]-1-yl)propyl 3-fluoro-2-methoxy-benzoate 3-(3-ethyl-4-oxo-spiro[6,8-dihydro-5H-pyrazolo[4,3-c]azepine-7,4'-tetrahydropyran]-1-yl)propyl 4-fluoro-2-methoxy-benzoate 3-(3-ethyl-4-oxo-spiro[6,8-dihydro-5H-pyrazolo[4,3-c]azepine-7,4'-tetrahydropyran]-1-yl)propyl 3-chloro-4-methyl-benzoate 3-(3-ethyl-4-oxo-spiro[6,8-dihydro-5H-pyrazolo[4,3-c]azepine-7,4'-tetrahydropyran]-1-yl)propyl 2-chloro-4-methyl-benzoate 3-(3-ethyl-4-oxo-spiro[6,8-dihydro-5H-pyrazolo[4,3-c]azepine-7,4'-tetrahydropyran]-1-yl)propyl 3-chloro-2-methyl-benzoate 3-(3-ethyl-4-oxo-spiro[6,8-dihydro-5H-pyrazolo[4,3-c]azepine-7,4'-tetrahydropyran]-1-yl)propyl 5-chloro-2-methyl-benzoate 3-(3-ethyl-4-oxo-spiro[6,8-dihydro-5H-pyrazolo[4,3-c]azepine-7,4'-tetrahydropyran]-1-yl)propyl 4-(difluoromethyl)benzoate 3-(3-ethyl-4-oxo-spiro[6,8-dihydro-5H-pyrazolo[4,3-c]azepine-7,4'-tetrahydropyran]-1-yl)propyl 2-chloro-4-fluoro-benzoate 3-(3-ethyl-4-oxo-spiro[6,8-dihydro-5H-pyrazolo[4,3-c]azepine-7,4'-tetrahydropyran]-1-yl)propyl 3-chloro-2-fluoro-benzoate 3-(3-ethyl-4-oxo-spiro[6,8-dihydro-5H-pyrazolo[4,3-c]azepine-7,4'-tetrahydropyran]-1-yl)propyl 3-chloro-5-fluoro-benzoate 3-(3-ethyl-4-oxo-spiro[6,8-dihydro-5H-pyrazolo[4,3-c]azepine-7,4'-tetrahydropyran]-1-yl)propyl 2-chloro-6-fluoro-benzoate 3-(3-ethyl-4-oxo-spiro[6,8-dihydro-5H-pyrazolo[4,3-c]azepine-7,4'-tetrahydropyran]-1-yl)propyl 4-chloro-3-fluoro-benzoate 3-(3-ethyl-4-oxo-spiro[6,8-dihydro-5H-pyrazolo[4,3-c]azepine-7,4'-tetrahydropyran]-1-yl)propyl 2-chloro-5-fluoro-benzoate 3-(3-ethyl-4-oxo-spiro[6,8-dihydro-5H-pyrazolo[4,3-c]azepine-7,4'-tetrahydropyran]-1-yl)propyl 5-chloro-2-fluoro-benzoate 3-(3-ethyl-4-oxo-spiro[6,8-dihydro-5H-pyrazolo[4,3-c]azepine-7,4'-tetrahydropyran]-1-yl)propyl 3-chloro-4-fluoro-benzoate 3-(3-ethyl-4-oxo-spiro[6,8-dihydro-5H-pyrazolo[4,3-c]azepine-7,4'-tetrahydropyran]-1-yl)propyl 4-chloro-2-fluoro-benzoate 3-(3-ethyl-4-oxo-spiro[6,8-dihydro-5H-pyrazolo[4,3-c]azepine-7,4'-tetrahydropyran]-1-yl)propyl 3-chloro-4-methoxy-benzoate 3-(3-ethyl-4-oxo-spiro[6,8-dihydro-5H-pyrazolo[4,3-c]azepine-7,4'-tetrahydropyran]-1-yl)propyl 4-chloro-3-methoxy-benzoate 3-(3-ethyl-4-oxo-spiro[6,8-dihydro-5H-pyrazolo[4,3-c]azepine-7,4'-tetrahydropyran]-1-yl)propyl 3-chloro-5-methoxy-benzoate 3-(3-ethyl-4-oxo-spiro[6,8-dihydro-5H-pyrazolo[4,3-c]azepine-7,4'-tetrahydropyran]-1-yl)propyl 2-chloro-4-methoxy-benzoate 3-(3-ethyl-4-oxo-spiro[6,8-dihydro-5H-pyrazolo[4,3-c]azepine-7,4'-tetrahydropyran]-1-yl)propyl 2-chloro-5-methoxy-benzoate 3-(3-ethyl-4-oxo-spiro[6,8-dihydro-5H-pyrazolo[4,3-c]azepine-7,4'-tetrahydropyran]-1-yl)propyl 2-chloro-3-methoxy-benzoate 3-(3-ethyl-4-oxo-spiro[6,8-dihydro-5H-pyrazolo[4,3-c]azepine-7,4'-tetrahydropyran]-1-yl)propyl 4-chloro-2-methoxy-benzoate 3-(3-ethyl-4-oxo-spiro[6,8-dihydro-5H-pyrazolo[4,3-c]azepine-7,4'-tetrahydropyran]-1-yl)propyl 5-chloro-2-methoxy-benzoate 3-(3-ethyl-4-oxo-spiro[6,8-dihydro-5H-pyrazolo[4,3-c]azepine-7,4'-tetrahydropyran]-1-yl)propyl 3-chloro-2-methoxy-benzoate 3-(3-ethyl-4-oxo-spiro[6,8-dihydro-5H-pyrazolo[4,3-c]azepine-7,4'-tetrahydropyran]-1-yl)propyl 2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-methylsulfonylbenzoate 3-(3-ethyl-4-oxo-spiro[6,8-dihydro-5H-pyrazolo[4,3-c]azepine-7,4'-tetrahydropyran]-1-yl)propyl 3-methylsulfonylbenzoate 3-(3-ethyl-4-oxo-spiro[6,8-dihydro-5H-pyrazolo[4,3-c]azepine-7,4'-tetrahydropyran]-1-yl)propyl 2-methylsulfonylbenzoate 3-(3-ethyl-4-oxo-spiro[6,8-dihydro-5H-pyrazolo[4,3-c]azepine-7,4'-tetrahydropyran]-1-yl)propyl 4-sulfamoyl-benzoate 3-(3-ethyl-4-oxo-spiro[6,8-dihydro-5H-pyrazolo[4,3-c]azepine-7,4'-tetrahydropyran]-1-yl)propyl 3-sulfamoyl-benzoate 3-(3-ethyl-4-oxo-spiro[6,8-dihydro-5H-pyrazolo[4,3-c]azepine-7,4'-tetrahydropyran]-1-yl)propyl 4-methyl-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-methyl-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-methyl-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-fluoro-2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-fluoro-6-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-fluoro-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-fluoro-2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-fluoro-4-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-fluoro-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-fluoro-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-fluoro-4-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-ethylsulfonylbenzoate 3-(3-ethyl-4-oxo-spiro[6,8-dihydro-5H-pyrazolo[4,3-c]azepine-7,4'-tetrahydropyran]-1-yl)propyl 4-ethylsulfonylbenzoate 3-(3-ethyl-4-oxo-spiro[6,8-dihydro-5H-pyrazolo[4,3-c]azepine-7,4'-tetrahydropyran]-1-yl)propyl 3-(methylsulfamoyl)benzoate 3-(3-ethyl-4-oxo-spiro[6,8-dihydro-5H-pyrazolo[4,3-c]azepine-7,4'-tetrahydropyran]-1-yl)propyl 4-(methylsulfamoyl)benzoate 3-(3-ethyl-4-oxo-spiro[6,8-dihydro-5H-pyrazolo[4,3-c]azepine-7,4'-tetrahydropyran]-1-yl)propyl 4-methoxy-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 5-methoxy-2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-methoxy-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-chloro-2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 4-chloro-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-chloro-3-(trifluoromethyl)benzoate 3-(3-ethyl-4-oxo-spiro[6,8-dihydro-5H-pyrazolo[4,3-c]azepine-7,4'-tetrahydropyran]-1-yl)propyl 5-chloro-2-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-chloro-4-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-chloro-4-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-chloro-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 2-chloro-5-(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-isopropylsulfonylbenzoate 3-(3-ethyl-4-oxo-spiro[6,8-dihydro-5H-pyrazolo[4,3-c]azepine-7,4'-tetrahydropyran]-1-yl)propyl 4-isopropylsulfonylbenzoate 3-(3-ethyl-4-oxo-spiro[6,8-dihydro-5H-pyrazolo[4,3-c]azepine-7,4'-tetrahydropyran]-1-yl)propyl 4-(dimethylsulfamoyl)benzoate 3-(3-ethyl-4-oxo-spiro[6,8-dihydro-5H-pyrazolo[4,3-c]azepine-7,4'-tetrahydropyran]-1-yl)propyl 4-cyclopentylsulfonylbenzoate 3-(3-ethyl-4-oxo-spiro[6,8-dihydro-5H-pyrazolo[4,3-c]azepine-7,4'-tetrahydropyran]-1-yl)propyl 4-pyrrolidin-1-ylsulfonylbenzoate 3-(3-ethyl-4-oxo-spiro[6,8-dihydro-5H-pyrazolo[4,3-c]azepine-7,4'-tetrahydropyran]-1-yl)propyl 3-pyrrolidin-1-ylsulfonylbenzoate 3-(3-ethyl-4-oxo-spiro[6,8-dihydro-5H-pyrazolo[4,3-c]azepine-7,4'-tetrahydropyran]-1-yl)propyl 2,4-bis(trifluoromethyl)benzoate 3-(3-ethyl-4-oxo-spiro[6,8-dihydro-5H-pyrazolo[4,3-c]azepine-7,4'-tetrahydropyran]-1-yl)propyl 3,4-bis(trifluoromethyl)benzoate 3-(3-ethyl-4-oxo-spiro[6,8-dihydro-5H-pyrazolo[4,3-c]azepine-7,4'-tetrahydropyran]-1-yl)propyl 3-morpholinosulfonylbenzoate 3-(3-ethyl-4-oxo-spiro[6,8-dihydro-5H-pyrazolo[4,3-c]azepine-7,4'-tetrahydropyran]-1-yl)propyl 4-morpholinosulfonylbenzoate 3-(3-ethyl-4-oxo-spiro[6,8-dihydro-5H-pyrazolo[4,3-c]azepine-7,4'-tetrahydropyran]-1-yl)propyl 4-(4-acetylpiperazin-1-yl)sulfonylbenzoate; or a pharmaceutically acceptable salt, hydrate or solvate thereof.

Clause 66. A compound according to any one of the clauses 1 to 58 selected from the group consisting of:

3-(3-ethyl-4-oxo-spiro[6,8-dihydro-5H-pyrazolo[4,3-c]azepine-7,4'-tetrahydropyran]-1-yl)propyl 4-carbamoylbenzoate 3-(3-ethyl-4-oxo-spiro[6,8-dihydro-5H-pyrazolo[4,3-c]azepine-7,4'-tetrahydropyran]-1-yl)propyl 4-(methylcarbamoyl)benzoate 3-(3-ethyl-4-oxo-spiro[6,8-dihydro-5H-pyrazolo[4,3-c]azepine-7,4'-tetrahydropyran]-1-yl)propyl 4-(ethylcarbamoyl)benzoate 3-(3-ethyl-4-oxo-spiro[6,8-dihydro-5H-pyrazolo[4,3-c]azepine-7,4'-tetrahydropyran]-1-yl)propyl 4-(dimethylcarbamoyl)benzoate 3-(3-ethyl-4-oxo-spiro[6,8-dihydro-5H-pyrazolo[4,3-c]azepine-7,4'-tetrahydropyran]-1-yl)propyl 4-(isopropylcarbamoyl)benzoate 3-(3-ethyl-4-oxo-spiro[6,8-dihydro-5H-pyrazolo[4,3-c]azepine-7,4'-tetrahydropyran]-1-yl)propyl 4-(pyrrolidine-1-carbonyl)benzoate 3-(3-ethyl-4-oxo-spiro[6,8-dihydro-5H-pyrazolo[4,3-c]azepine-7,4'-tetrahydropyran]-1-yl)propyl 4-(piperidine-1-carbonyl)benzoate 3-(3-ethyl-4-oxo-spiro[6,8-dihydro-5H-pyrazolo[4,3-c]azepine-7,4'-tetrahydropyran]-1-yl)propyl 4-(morpholine-4-carbonyl)benzoate 3-(3-ethyl-4-oxo-spiro[6,8-dihydro-5H-pyrazolo[4,3-c]azepine-7,4'-tetrahydropyran]-1-yl)propyl 4-(4-methylpiperazine-1-carbonyl)benzoate 3-(3-ethyl-4-oxo-spiro[6,8-dihydro-5H-pyrazolo[4,3-c]azepine-7,4'-tetrahydropyran]-1-yl)propyl 4-(4-acetylpiperazine-1-carbonyl)benzoate;

3-(3-ethyl-4-oxo-spiro[6,8-dihydro-5H-pyrazolo[4,3-c]azepine-7,4'-tetrahydropyran]-1-yl)propyl 3-carbamoylbenzoate 3-(3-ethyl-4-oxo-spiro[6,8-dihydro-5H-pyrazolo[4,3-c]azepine-7,4'-tetrahydropyran]-1-yl)propyl 3-(methylcarbamoyl)benzoate 3-(3-ethyl-4-oxo-spiro[6,8-dihydro-5H-pyrazolo[4,3-c]azepine-7,4'-tetrahydropyran]-1-yl)propyl 3-(ethylcarbamoyl)benzoate 3-(3-ethyl-4-oxo-spiro[6,8-dihydro-5H-pyrazolo[4,3-c]azepine-7,4'-tetrahydropyran]-1-yl)propyl 3-(dimethylcarbamoyl)benzoate 3-(3-ethyl-4-oxo-spiro[6,8-dihydro-5H-pyrazolo[4,3-c]azepine-7,4'-tetrahydropyran]-1-yl)propyl 3-(isopropylcarbamoyl)benzoate 3-(3-ethyl-4-oxo-spiro[6,8-dihydro-5H-pyrazolo[4,3-c]azepine-7,4'-tetrahydropyran]-1-yl)propyl 3-(pyrrolidine-1-carbonyl)benzoate 3-(3-ethyl-4-oxo-spiro[6,8-dihydro-5H-pyrazolo[4,3-c]azepine-7,4'-tetrahydropyran]-1-yl)propyl 3-(piperidine-1-carbonyl)benzoate 3-(3-ethyl-4-oxo-spiro[6,8-dihydro-5H-pyrazolo[4,3-c]azepine-7,4'-tetrahydropyran]-1-yl)propyl 3-(morpholine-4-carbonyl)benzoate 3-(3-ethyl-4-oxo-spiro[6,8-dihydro-5H-pyrazolo[4,3-c]azepine-7,4'-tetrahydropyran]-1-yl)propyl 3-(4-methylpiperazine-1-carbonyl)benzoate 3-(3-ethyl-4-oxo-spiro[6,8-dihydro-5H-pyrazolo[4,3-c]azepine-7,4'-tetrahydropyran]-1-yl)propyl 3-(4-acetylpiperazine-1-carbonyl)benzoate; or a pharmaceutically acceptable salt, hydrate or solvate thereof.

Clause 67. A compound according to any one of the clauses 1 to 58 selected from the group consisting of:

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylpropanoate

[(2R)-3-(3-ethyl-4-oxo-spiro[6,8-dihydro-5H-pyrazolo[4,3-c]azepine-7,4'-tetrahydropyran]-1-yl)-2-methyl-propyl] cyclopentanecarboxylate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-ethylbutanoate

[(2R)-3-(3-ethyl-4-oxo-spiro[6,8-dihydro-5H-pyrazolo[4,3-c]azepine-7,4'-tetrahydropyran]-1-yl)-2-methyl-propyl] benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-methylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyanobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyanobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-dimethylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2,4-dimethylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxybenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chlorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2,6-difluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2,5-difluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-difluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2,3-difluorobenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-acetylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-acetylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-5-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-cyano-2-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-4-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyano-3-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-methoxy-4-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-4-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-3-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-2-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methyl-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(difluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-6-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-fluoro-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methoxy-benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-methylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-sulfamoylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-sulfamoylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-3-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-ethylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-ethylsulfonylbenzoate

[(2R)-3-(3-ethyl=4-oxo-spiro[6,8-dihydro-5H-pyrazolo[4,3-c]azepine-7,4'-tetrahydropyran]-1-yl)-2-methyl-propyl] 3-(methylsulfamoyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-2-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 5-methoxy-2-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-4-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-(trifluoromethyl)benzoate

[(2R)-3-(3-ethyl-4-oxo-spiro[6,8-dihydro-5H-Pyrazolo[4,3-c]azepine-7,4'-tetrahydropyran]-1-yl)-2-methyl-propyl] 5-chloro-2-(trifluoromethyl)benzoate

[(2R)-3-(3-ethyl-4-oxo-spiro[6,8-dihydro-5H-Pyrazolo[4,3-c]azepine-7,4'-tetrahydropyran]-1-yl)-2-methyl-propyl] 3-chloro-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-isopropylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-isopropylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyclopentylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-pyrrolidin-1-ylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-pyrrolidin-1-ylsulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-bis(trifluoromethyl)benzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-morpholinosulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-morpholinosulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazin-1-yl)sulfonylbenzoate

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazin-1-yl)sulfonylbenzoate;

or a pharmaceutically acceptable salt, hydrate or solvate thereof.

Clause 68. A compound according to any one of the clauses 1 to 58 selected from the group consisting of:

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-carbamoylbenzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(methylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(ethylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(dimethylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(isopropylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(pyrrolidine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperidine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperazine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(morpholine-4-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-methylpiperazine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazine-1-carbonyl)benzoate; [(2R)-3-(3-ethyl-4-oxo-spiro[6,8-dihydro-5H-pyrazolo[4,3-c]azepine-7,4'-tetrahydropyran]-1-yl)-2-methyl-propyl] 3-carbamoylbenzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(methylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(ethylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(dimethylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(isopropylcarbamoyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(pyrrolidine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperidine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperazine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(morpholine-4-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-methylpiperazine-1-carbonyl)benzoate;

[(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazine-1-carbonyl)benzoate;

or a pharmaceutically acceptable salt, hydrate or solvate thereof.

Clause 69. A compound according to any one of the clauses 1 to 58 selected from the group consisting of:

[(2S)-3-(3-ethyl-4-oxo-spiro[6,8-dihydro-5H-pyrazolo[4,3-c]azepine-7,4'-tetrahydro-pyran]-1-yl)-2-methyl-propyl] benzoate;

[(2S)-3-(3-ethyl-4-oxo-spiro[6,8-dihydro-5H-pyrazolo[4,3-c]azepine-7,4'-tetrahydro-pyran]-1-yl)-2-methyl-propyl] 4-methylbenzoate;

[(2S)-3-(3-ethyl-4-oxo-spiro[6,8-dihydro-5H-pyrazolo[4,3-c]azepine-7,4'-tetrahydro-pyran]-1-yl)-2-methyl-propyl] 3-fluorobenzoate;

[(2S)-3-(3-ethyl-4-oxo-spiro[6,8-dihydro-5H-pyrazolo[4,3-c]azepine-7,4'-tetrahydro-pyran]-1-yl)-2-methyl-propyl] 4-fluorobenzoate;

[(2S)-3-(3-ethyl-4-oxo-spiro[6,8-dihydro-5H-pyrazolo[4,3-c]azepine-7,4'-tetrahydro-pyran]-1-yl)-2-methyl-propyl] 3-methoxybenzoate;

[(2S)-3-(3-ethyl-4-oxo-spiro[6,8-dihydro-5H-pyrazolo[4,3-c]azepine-7,4'-tetrahydro-pyran]-1-yl)-2-methyl-propyl] 4-chlorobenzoate; or a pharmaceutically acceptable salt, hydrate or solvate thereof.

Clause 70. A compound according to any one of the clauses 1 to 58 selected from the group consisting of:

[3-(3-ethyl-4-oxo-spiro[6,8-dihydro-5H-pyrazolo[4,3-c]azepine-7,4'-tetrahydro-pyran]-1-yl)-2,2-dimethyl-propyl] cyclopentanecarboxylate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-ethylbutanoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-methylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-fluorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-fluorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-fluorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-cyanobenzoate

[3-(3-ethyl-4-oxo-spiro[6,8-dihydro-5H-pyrazolo[4,3-c]azepine-7,4'-tetrahydropyran]-1-yl)-2,2-dimethyl-propyl] 4-cyanobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-methoxybenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-chlorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-chlorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-chlorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3,5-difluorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3,4-difluorobenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-acetylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-acetylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-cyano-3-fluoro-benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-cyano-2-fluoro-benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-ethoxybenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-chloro-6-fluoro-benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-chloro-4-fluoro-benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-(trifluoromethyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-(trifluoromethyl)benzoate

[3-(3-ethyl-4-oxo-spiro[6,8-dihydro-5H-pyrazolo[4,3-c]azepine-7,4'-tetrahydro-pyran]-1-yl)-2,2=dimethyl-propyl] 4-(trifluoromethyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-methylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-methylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-methylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-sulfamoylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-sulfamoylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-fluoro-5-(trifluoromethyl)benzoate

[3-(3-ethyl-4-on-spiro[6,8-dihydro-5H-pyrazolo[4,3-c]azepine-7,4'-tetrahydro-pyran]-1-yl)-2,2-dimethyl-propyl] 3-ethylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-ethylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-(methylsulfamoyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-chloro-3-(trifluoromethyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 2-chloro-5-(trifluoromethyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-isopropylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-isopropylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-(dimethylsulfamoyl)benzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-cyclopentylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 3-pyrrolidin-1-ylsulfonylbenzoate

[3-(3-ethyl-4-oxo-spiro[6,8-dihydro-5H-pyrazolo[4,3-c]azepine-7,4'-tetrahydro-pyran]-1-yl)-2,2-dimethyl-propyl] 4-pyrrolidin-1-ylsulfonylbenzoate

[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-morpholinosulfonylbenzoate
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-morpholinosulfonylbenzoate
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(4-acetylpiperazin-1-yl)sulfonylbenzoate
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(4-acetylpiperazin-1-yl)sulfonylbenzoate; or
a pharmaceutically acceptable salt, hydrate or solvate thereof.

Clause 71. A compound according to any one of the clauses 1 to 58 selected from the group consisting of:
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-carbamoylbenzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(methylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(ethylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(dimethylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(isopropylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(pyrrolidine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(piperidine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(piperazine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(morpholine-4-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(4-methylpiperazine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 4-(4-acetylpiperazine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-carbamoylbenzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(methylcarbamoyl)benzoate;
[3-(3-ethyl-4-oxo-spiro[6,8-dihydro-5H-pyrazolo[4,3-c]
azepine-7,4'-tetrahydropyran]-1-yl)-2,2-dimethyl-propyl] 3-(ethylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(dimethylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(isopropylcarbamoyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(pyrrolidine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(piperidine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(piperazine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(morpholine-4-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(4-methylpiperazine-1-carbonyl)benzoate;
[3-(3-ethyl-4-oxo-spiro[6,8-dihydro-5H-pyrazolo[4,3-c]
azepine-7,4'-tetrahydro-pyran]-1-yl)-2,2-dimethyl-propyl] 3-(4-acetylpiperazine-1-carbonyl)benzoate; or
a pharmaceutically acceptable salt, hydrate or solvate thereof.

Clause 72. A compound according to any one of the clauses 1 to 58 selected from the group consisting of:
[1-[(3-ethyl-4-oxo-spiro[6,8-dihydro-5H-pyrazolo[4,3-c]
azepine-7,4'-tetrahydropyran]-1-yl)methyl]cyclopropyl]
methyl 4-methylbenzoate;
[1-[(3-ethyl-4-oxo-spiro[6,8-dihydro-5H-pyrazolo[4,3-c]
azepine-7,4'-tetrahydropyran]-1-yl)methyl]cyclopropyl]
methyl 3-fluorobenzoate;
[1-[(3-ethyl-4-oxo-spiro[6,8-dihydro-5H-pyrazolo[4,3-c]
azepine-7,4'-tetrahydropyran]-1-yl)methyl]cyclopropyl]
methyl 4-fluorobenzoate;
[1-[(3-ethyl-4-oxo-spiro[6,8-dihydro-5H-pyrazolo[4,3-c]
azepine-7,4'-tetrahydropyran]-1-yl)methyl]cyclopropyl]
methyl 3-methoxybenzoate;
[1-[(3-ethyl-4-oxo-spiro[6,8-dihydro-5H-pyrazolo[4,3-c]
azepine-7,4'-tetrahydropyran]-1-yl)methyl]cyclopropyl]
methyl 4-chlorobenzoate; or
a pharmaceutically acceptable salt, hydrate or solvate thereof.

Clause 73. A compound according to any one of the clauses 1 to 58 selected from the group consisting of:
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl benzoate;
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl 4-methylbenzoate;
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl 3-fluorobenzoate;
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl 4-fluorobenzoate;
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl 3-methoxybenzoate;
[3-[(3-ethyl-4-oxo-spiro[6,8-dihydro-5H-pyrazolo[4,3-c]
azepine-7,4'-tetrahydropyran]-1-yl)methyl]oxetan-3-yl]
methyl 4-chlorobenzoate; or
a pharmaceutically acceptable salt, hydrate or solvate thereof.

Clause 74. A compound according to any one of the clauses 1 to 58 which is:
3-(3-ethyl-4-oxo-spiro[6,8-dihydro-5H-pyrazolo[4,3-c]
azepine-7,4'-tetrahydropyran]-1-yl)butyl benzoate; or
a pharmaceutically acceptable salt, hydrate or solvate thereof.

Clause 75. A compound according to any one of the clauses 1 to 58 selected from the group consisting of:
4-(3-ethyl-4-oxo-spiro[6,8-dihydro-5H-pyrazolo[4,3-c]azepine-7,4'-tetrahydropyran]-1-yl)butyl benzoate;
4-(3-ethyl-4-oxo-spiro[6,8-dihydro-5H-pyrazolo[4,3-c]azepine-7,4'-tetrahydropyran]-1-yl)butyl 3-methylbenzoate;
4-(3-ethyl-4-oxo-spiro[6,8-dihydro-5H-pyrazolo[4,3-c]azepine-7,4'-tetrahydropyran]-1-yl)butyl 4-methylbenzoate;
4-(3-ethyl-4-oxo-spiro[6,8-dihydro-5H-pyrazolo[4,3-c]azepine-7,4'-tetrahydropyran]-1-yl)butyl 4-fluorobenzoate;
4-(3-ethyl-4-oxo-spiro[6,8-dihydro-5H-pyrazolo[4,3-c]azepine-7,4'-tetrahydropyran]-1-yl)butyl 3-acetylbenzoate;
4-(3-ethyl-4-oxo-spiro[6,8-dihydro-5H-pyrazolo[4,3-c]azepine-7,4'-tetrahydropyran]-1-yl)butyl 4-acetylbenzoate;
4-(3-ethyl-4-oxo-spiro[6,8-dihydro-5H-pyrazolo[4,3-c]azepine-7,4'-tetrahydropyran]-1-yl)butyl 3-methylsulfonylbenzoate;
4-(3-ethyl-4-oxo-spiro[6,8-dihydro-5H-pyrazolo[4,3-c]azepine-7,4'-tetrahydropyran]-1-yl)butyl 4-methylsulfonylbenzoate;
4-(3-ethyl-4-oxo-spiro[6,8-dihydro-5H-pyrazolo[4,3-c]azepine-7,4'-tetrahydropyran]-1-yl)butyl 4-ethylsulfonylbenzoate;
4-(3-ethyl-4-oxo-spiro[6,8-dihydro-5H-pyrazolo[4,3-c]azepine-7,4'-tetrahydropyran]-1-yl)butyl 3-(methylsulfamoyl)benzoate;
4-(3-ethyl-4-oxo-spiro[6,8-dihydro-5H-pyrazolo[4,3-c]azepine-7,4'-tetrahydropyran]-1-yl)butyl 4-(methylsulfamoyl)benzoate;
4-(3-ethyl-4-oxo-spiro[6,8-dihydro-5H-pyrazolo[4,3-c]azepine-7,4'-tetrahydropyran]-1-yl)butyl 3-(dimethylsulfamoyl)benzoate;
4-(3-ethyl-4-oxo-spiro[6,8-dihydro-5H-pyrazolo[4,3-c]azepine-7,4'-tetrahydropyran]-1-yl)butyl 4-(dimethylsulfamoyl)benzoate;
4-(3-ethyl-4-oxo-spiro[6,8-dihydro-5H-pyrazolo[4,3-c]azepine-7,4'-tetrahydropyran]-1-yl)butyl 4-cyclopentylsulfonylbenzoate;
4-(3-ethyl-4-oxo-spiro[6,8-dihydro-5H-pyrazolo[4,3-c]azepine-7,4'-tetrahydropyran]-1-yl)butyl 4-pyrrolidin-1-ylsulfonylbenzoate;
4-(3-ethyl-4-oxo-spiro[6,8-dihydro-5H-pyrazolo[4,3-c]azepine-7,4'-tetrahydropyran]-1-yl)butyl 4-morpholinosulfonylbenzoate; or
a pharmaceutically acceptable salt, hydrate or solvate thereof.

Clause 76. A compound according to any one of the clauses 1 to 58 selected from the group consisting of:
4-(3-ethyl-4-oxo-spiro[6,8-dihydro-5H-pyrazolo[4,3-c]azepine-7,4'-tetrahydropyran]-1-yl)butyl 4-(methylcarbamoyl)benzoate;
4-(3-ethyl-4-oxo-spiro[6,8-dihydro-5H-pyrazolo[4,3-c]azepine-7,4'-tetrahydropyran]-1-yl)butyl 4-(dimethylcarbamoyl)benzoate;
4-(3-ethyl-4-oxo-spiro[6,8-dihydro-5H-pyrazolo[4,3-c]azepine-7,4'-tetrahydropyran]-1-yl)butyl 4-(morpholine-4-carbonyl)benzoate; or
a pharmaceutically acceptable salt, hydrate or solvate thereof.

Clause 77. A compound according to any one of the clauses 1 to 58 which is:
2-(3-ethyl-4-oxo-spiro[6,8-dihydro-5H-pyrazolo[4,3-c]azepine-7,4'-tetrahydropyran]-1-yl)ethyl benzoate; or
a pharmaceutically acceptable salt, hydrate or solvate thereof.

Clause 78. A pharmaceutical composition comprising a compound according to any one of the clauses 1-77 together with a pharmaceutically acceptable vehicle or excipient or pharmaceutically acceptable carrier(s).

Clause 79. The pharmaceutical composition according to clause 78 further comprising one or more other therapeutically active compound(s).

Clause 80. A use of the compound according to any one of the clauses 1-77, for the manufacture of a pharmaceutical composition.

Clause 81. The use of a compound according to clause 80 in the manufacture of a pharmaceutical composition for the treatment or amelioration of a disease, disorder or condition responsive to PDE4 inhibitory activity.

Clause 82. The use according to clause 81, wherein the disease, disorder or condition is dermal diseases or conditions.

Clause 83. The use according to clause 82, wherein the disease, disorder or condition is proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 84. The compound according to any one of the clauses 1-77, for use as a medicament.

Clause 85. The compound according to clause 84 for use in the treatment or amelioration of a disease, disorder or condition responsive to PDE4 inhibitory activity.

Clause 86. The compound according to clause 85 for use in the treatment or amelioration of dermal diseases or conditions.

Clause 87. The compound according to clause 86 for use in the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 88. A method for treatment or alleviation of a disease or a disorder or a condition responsive to PDE4 inhibitory activity, which method comprises the step of administering to a living animal body a therapeutically effective amount of a compound according to any one of the clauses 1-77.

Clause 89. A method of treating or ameliorating dermal diseases or conditions, the method comprising administering to a person suffering from at least one of said diseases an effective amount of one or more compounds according to according to any one of clauses 1-77, optionally together with a pharmaceutically acceptable carrier or one or more excipients, optionally in combination with other therapeutically active compounds.

Clause 90. The method according to clause 88, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

The invention claimed is:
1. A compound of general formula (I)

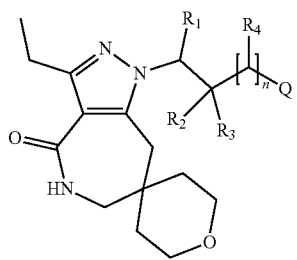

wherein
$R_1$ and $R_4$ are independently selected from the group consisting of hydrogen and $(C_1-C_4)$alkyl;
$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;
n=0, 1 or 2;
Q is selected from the group consisting of —O—C(O)—$R_5$;
$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$, or wherein said aryl is optionally benzodioxole; and wherein said $(C_1-C_6)$alkyl, $(C_3-C_6)$cycloalkyl are optionally substituted with one or more substituents independently selected from $R_7$;
$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$, —C(O)R$_x$, —C(O)NR$_a$R$_b$ and —OR$_x$;
$R_7$ consists of halogen, hydroxyl, cyano, $(C_1-C_4)$alkoxy, —C(O)NR$_a$R$_b$, —C(O)OR$_a$, —S(O)$_2$R$_x$, —S(O)$_2$NR$_a$R$_b$, —OR$_x$, and —SR$_x$;
$R_x$ consists of $(C_1-C_6)$alkyl and $(C_3-C_6)$cycloalkyl;
$R_a$ and $R_b$ are independently selected from the group consisting of hydrogen, $(C_1-C_4)$alkyl, phenyl-$(C_1-C_4)$alkyl, or
$R_a$ and $R_b$ together with the nitrogen to which they are attached form a 4-6 membered heterocycloalkyl, wherein said heterocycloalkyl is optionally substituted with one or more $(C_1-C_4)$alkyl, —C(O)R$_x$;
or a pharmaceutically acceptable salt, hydrate or solvate thereof.

2. A compound according to claim 1 wherein
$R_1$ and $R_4$ are independently selected from the group consisting of hydrogen and $(C_1-C_4)$alkyl;
$R_2$ and $R_3$ are independently selected from the group consisting of hydrogen and $(C_1-C_4)$alkyl; or $R_2$ and $R_3$ together with the carbon atom to which they are attached form a cyclopropyl or oxetanyl ring;
n=0, 1 or 2;
Q is selected from the group consisting of —O—C(O)—$R_5$;
$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, phenyl; wherein said phenyl is optionally substituted with one or more substituents independently selected from $R_6$, or wherein $R_5$ is benzodioxole; and wherein said $(C_1-C_6)$alkyl, $(C_3-C_6)$cycloalkyl are optionally substituted with one or more substituents independently selected from $R_7$;
$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$, —C(O)R$_x$, —C(O)NR$_a$R$_b$ and —OR$_x$;
$R_7$ consists of halogen, hydroxyl, cyano, $(C_1-C_4)$alkoxy, —C(O)NR$_a$R$_b$, —C(O)OR$_a$, —S(O)$_2$R$_x$, —S(O)$_2$NR$_a$R$_b$, —OR$_x$, and —SR$_x$;
$R_x$ consists of $(C_1-C_6)$alkyl and $(C_3-C_6)$cycloalkyl;
$R_a$ and $R_b$ are independently selected from the group consisting of hydrogen, $(C_1-C_4)$alkyl, phenyl-$(C_1-C_4)$alkyl, or
$R_a$ and $R_b$ together with the nitrogen to which they are attached form a 4-6 membered heterocycloalkyl, wherein said heterocycloalkyl is optionally substituted with one or more $(C_1-C_4)$alkyl, —C(O)R$_x$; or
a pharmaceutically acceptable salt, hydrate or solvate thereof.

3. A compound of general formula (I)

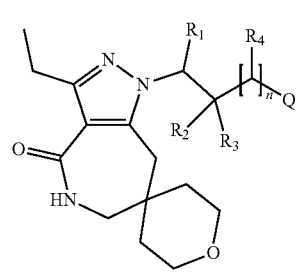

wherein
$R_1$ and $R_4$ are independently selected from the group consisting of hydrogen and $(C_1-C_4)$alkyl;
$R_2$ and $R_3$ are independently selected from the group consisting of hydrogen and $(C_1-C_4)$alkyl; or $R_2$ and $R_3$ together with the carbon atom to which they are attached form a cyclopropyl, cyclobutyl, cyclopentyl, oxetanyl, tetrahydrofuranyl, or tetrahydropyranyl ring;
n=0, 1 or 2;
Q is selected from the group consisting of —O—C(O)—$R_5$;
$R_5$ is selected from the group consisting of $(C_1-C_6)$alkyl, $(C_3-C_6)$cycloalkyl, halo$(C_1-C_6)$alkyl, $(C_1-C_6)$alkoxy, $(C_1-C_6)$alkoxy$(C_1-C_6)$alkyl, aryl; wherein said aryl is optionally substituted with one or more substituents independently selected from $R_6$;
$R_6$ consists of halogen, cyano, hydroxyl, $(C_1-C_4)$alkyl, halo$(C_1-C_4)$alkyl, $(C_1-C_4)$alkyloxy, —S(O)$_2$R$_x$, —S(O)$_2$NR$_a$R$_b$ and —OR$_x$;
$R_x$ is $(C_1-C_6)$alkyl;
$R_a$ and $R_b$ are independently selected from the group consisting of hydrogen, $(C_1-C_4)$alkyl, phenyl-$(C_1-C_4)$alkyl, or
$R_a$ and $R_b$ together with the nitrogen to which they are attached form a 4-6 membered heterocycloalkyl, wherein said heterocycloalkyl is optionally substituted with one or more $(C_1-C_4)$alkyl; or
a pharmaceutically acceptable salt, hydrate or solvate thereof.

4. A compound according to claim 1 wherein all of $R_1$, $R_2$, $R_3$, $R_4$ are hydrogen, n is 1, and $R_5$ is phenyl, optionally substituted with one or more substituents independently selected from $R_6$.

5. A compound according to claim 1 selected from the group consisting of
- 3-(3-Ethyl-4-oxo-spiro[6,8-dihydro-5H-pyrazolo[4,3-c]azepine-7,4'-tetrahydropyran]-1-yl)propyl 4-methylbenzoate (compound 101);
- 3-(3-Ethyl-4-oxo-spiro[6,8-dihydro-5H-pyrazolo[4,3-c]azepine-7,4'-tetrahydropyran]-1-yl)propyl 4-ethylbenzoate (compound 102);
- [(2R)-3-(3-Ethyl-4-oxo-spiro[6,8-dihydro-5H-pyrazolo[4,3-c]azepine-7,4'-tetrahydropyran]-1-yl)-2-methyl-propyl] 4-(methylsulfamoyl)benzoate (compound 103);
- [(2R)-3-(3-Ethyl-4-oxo-spiro[6,8-dihydro-5H-pyrazolo[4,3-c]azepine-7,4'-tetrahydropyran]-1-yl)-2-methyl-propyl] 4-(dimethylsulfamoyl)benzoate (compound 104);
- [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methylsulfonylbenzoate (compound 105);

or a pharmaceutically acceptable salt, hydrate or solvate thereof.

6. A compound according to claim 1 selected from the group consisting of:
- (i) 3-(3-ethyl-4-oxo-spiro[6,8-dihydro-5H-pyrazolo[4,3-c]azepine-7,4'-tetrahydropyran]-1-yl)propyl acetate
- (ii) 3-(3-ethyl-4-oxo-spiro[6,8-dihydro-5H-pyrazolo[4,3-c]azepine-7,4'-tetrahydropyran]-1-yl)propyl 2-methylpropanoate
- (iii) 3-(3-ethyl-4-oxo-spiro[6,8-dihydro-5H-pyrazolo[4,3-c]azepine-7,4'-tetrahydropyran]-1-yl)propyl 3-methoxypropanoate
- (iv) 3-(3-ethyl-4-oxo-spiro[6,8-dihydro-5H-pyrazolo[4,3-c]azepine-7,4'-tetrahydropyran]-1-yl)propyl cyclopentanecarboxylate
- (v) 3-(3-ethyl-4-oxo-spiro[6,8-dihydro-5H-pyrazolo[4,3-c]azepine-7,4'-tetrahydropyran]-1-yl)propyl 3-hydroxycyclobutanecarboxylate
- (vi) 3-(3-ethyl-4-oxo-spiro[6,8-dihydro-5H-pyrazolo[4,3-c]azepine-7,4'-tetrahydropyran]-1-yl)propyl 2-ethyl butanoate
- (vii) 3-(3-ethyl-4-oxo-spiro[6,8-dihydro-5H-pyrazolo[4,3-c]azepine-7,4'-tetrahydropyran]-1-yl)propyl 2-isopropoxyacetate
- (viii) 3-(3-ethyl-4-oxo-spiro[6,8-dihydro-5H-pyrazolo[4,3-c]azepine-7,4'-tetrahydropyran]-1-yl)propyl 3-methylsulfanylpropanoate
- (ix) 3-(3-ethyl-4-oxo-spiro[6,8-dihydro-5H-pyrazolo[4,3-c]azepine-7,4'-tetrahydropyran]-1-yl)propyl 3,3-difluorocyclobutanecarboxylate
- (x) 3-(3-ethyl-4-oxo-spiro[6,8-dihydro-5H-pyrazolo[4,3-c]azepine-7,4'-tetrahydropyran]-1-yl)propyl 3-methyl benzoate)
- (xi) 3-(3-ethyl-4-oxo-spiro[6,8-dihydro-5H-pyrazolo[4,3-c]azepine-7,4'-tetrahydropyran]-1-yl)propyl 2-methyl benzoate
- (xii) 3-(3-ethyl-4-oxo-spiro[6,8-dihydro-5H-pyrazolo[4,3-c]azepine-7,4'-tetrahydropyran]-1-yl)propyl 2-hydroxybenzoate
- (xiii) 3-(3-ethyl-4-oxo-spiro[6,8-dihydro-5H-pyrazolo[4,3-c]azepine-7,4'-tetrahydropyran]-1-yl)propyl 3-fluorobenzoate
- (xiv) 3-(3-ethyl-4-oxo-spiro[6,8-dihydro-5H-pyrazolo[4,3-c]azepine-7,4'-tetrahydropyran]-1-yl)propyl 2-fluorobenzoate
- (xv) 3-(3-ethyl-4-oxo-spiro[6,8-dihydro-5H-pyrazolo[4,3-c]azepine-7,4'-tetrahydropyran]-1-yl)propyl 4-fluorobenzoate
- (xvi) 3-(3-ethyl-4-oxo-spiro[6,8-dihydro-5H-pyrazolo[4,3-c]azepine-7,4'-tetrahydropyran]-1-yl)propyl cis-4-hydroxycyclohexanecarboxylate
- (xvii) 3-(3-ethyl-4-oxo-spiro[6,8-dihydro-5H-pyrazolo[4,3-c]azepine-7,4'-tetrahydropyran]-1-yl)propyl trans-4-hydroxycyclohexanecarboxylate
- (xviii) 3-(3-ethyl-4-oxo-spiro[6,8-dihydro-5H-pyrazolo[4,3-c]azepine-7,4'-tetrahydropyran]-1-yl)propyl 3-cyanobenzoate
- (xix) 3-(3-ethyl-4-oxo-spiro[6,8-dihydro-5H-pyrazolo[4,3-c]azepine-7,4'-tetrahydropyran]-1-yl)propyl 4-cyanobenzoate
- (xx) 3-(3-ethyl-4-oxo-spiro[6,8-dihydro-5H-pyrazolo[4,3-c]azepine-7,4'-tetrahydropyran]-1-yl)propyl 2-cyanobenzoate
- (xxi) 3-(3-ethyl-4-oxo-spiro[6,8-dihydro-5H-pyrazolo[4,3-c]azepine-7,4'-tetrahydropyran]-1-yl)propyl 3,4-dimethylbenzoate
- (xxii) 3-(3-ethyl-4-oxo-spiro[6,8-dihydro-5H-pyrazolo[4,3-c]azepine-7,4'-tetrahydropyran]-1-yl)propyl 2,4-dimethylbenzoate
- (xxiii) 3-(3-ethyl-4-oxo-spiro[6,8-dihydro-5H-pyrazolo[4,3-c]azepine-7,4'-tetrahydropyran]-1-yl)propyl 4-methoxybenzoate
- (xxiv) 3-(3-ethyl-4-oxo-spiro[6,8-dihydro-5H-pyrazolo[4,3-c]azepine-7,4'-tetrahydropyran]-1-yl)propyl 3-methoxybenzoate
- (xxv) 3-(3-ethyl-4-oxo-spiro[6,8-dihydro-5H-pyrazolo[4,3-c]azepine-7,4'-tetrahydropyran]-1-yl)propyl 2-methoxybenzoate
- (xxvi) 3-(3-ethyl-4-oxo-spiro[6,8-dihydro-5H-pyrazolo[4,3-c]azepine-7,4'-tetrahydropyran]-1-yl)propyl 3-methylsulfonylpropanoate
- (xxvii) 3-(3-ethyl-4-oxo-spiro[6,8-dihydro-5H-pyrazolo[4,3-c]azepine-7,4'-tetrahydropyran]-1-yl)propyl 3-fluoro-4-methyl-benzoate
- (xxviii) 3-(3-ethyl-4-oxo-spiro[6,8-dihydro-5H-pyrazolo[4,3-c]azepine-7,4'-tetrahydropyran]-1-yl)propyl 2-fluoro-4-methyl-benzoate
- (xxix) 3-(3-ethyl-4-oxo-spiro[6,8-dihydro-5H-pyrazolo[4,3-c]azepine-7,4'-tetrahydropyran]-1-yl)propyl 5-fluoro-2-methyl-benzoate
- (xxx) 3-(3-ethyl-4-oxo-spiro[6,8-dihydro-5H-pyrazolo[4,3-c]azepine-7,4'-tetrahydropyran]-1-yl)propyl 4-fluoro-3-methyl-benzoate
- (xxxi) 3-(3-ethyl-4-oxo-spiro[6,8-dihydro-5H-pyrazolo[4,3-c]azepine-7,4'-tetrahydropyran]-1-yl)propyl 3-fluoro-2-methyl-benzoate
- (xxxii) 3-(3-ethyl-4-oxo-spiro[6,8-dihydro-5H-pyrazolo[4,3-c]azepine-7,4'-tetrahydropyran]-1-yl)propyl 2-fluoro-5-methyl-benzoate
- (xxxiii) 3-(3-ethyl-4-oxo-spiro[6,8-dihydro-5H-pyrazolo[4,3-c]azepine-7,4'-tetrahydropyran]-1-yl)propyl 4-fluoro-2-methyl-benzoate
- (xxxiv) 3-(3-ethyl-4-oxo-spiro[6,8-dihydro-5H-pyrazolo[4,3-c]azepine-7,4'-tetrahydropyran]-1-yl)propyl 2-fluoro-6-methyl-benzoate
- (xxxv) 3-(3-ethyl-4-oxo-spiro[6,8-dihydro-5H-pyrazolo[4,3-c]azepine-7,4'-tetrahydropyran]-1-yl)propyl 2-chlorobenzoate
- (xxxvi) 3-(3-ethyl-4-oxo-spiro[6,8-dihydro-5H-pyrazolo[4,3-c]azepine-7,4'-tetrahydropyran]-1-yl)propyl 3-chlorobenzoate)
- (xxxvii) 3-(3-ethyl-4-oxo-spiro[6,8-dihydro-5H-pyrazolo[4,3-c]azepine-7,4'-tetrahydropyran]-1-yl)propyl 4-chlorobenzoate (xxxviii) 3-(3-ethyl-4-oxo-spiro[6,8-dihydro-5H-pyrazolo[4,3-c]azepine-7,4'-tetrahydropyran]-1-yl)propyl 3,5-difluorobenzoate
(xxxix) 3-(3-ethyl-4-oxo-spiro[6,8-dihydro-5H-pyrazolo[4,3-c]azepine-7,4'-tetrahydropyran]-1-yl)propyl 3,4-difluorobenzoate)
(xl) 3-(3-ethyl-4-oxo-spiro[6,8-dihydro-5H-pyrazolo[4,3-c]azepine-7,4'-tetrahydropyran]-1-yl)propyl 2,3-difluorobenzoate
(xli) 3-(3-ethyl-4-oxo-spiro[6,8-dihydro-5H-pyrazolo[4,3-c]azepine-7,4'-tetrahydropyran]-1-yl)propyl 2,6-difluorobenzoate
(xlii) 3-(3-ethyl-4-oxo-spiro[6,8-dihydro-5H-pyrazolo[4,3-c]azepine-7,4'-tetrahydropyran]-1-yl)propyl 2,5-difluorobenzoate
(xliii) 3-(3-ethyl-4-oxo-spiro[6,8-dihydro-5H-pyrazolo[4,3-c]azepine-7,4'-tetrahydropyran]-1-yl)propyl 4-methoxycyclohexanecarboxylate
(xliv) 3-(3-ethyl-4-oxo-spiro[6,8-dihydro-5H-pyrazolo[4,3-c]azepine-7,4'-tetrahydropyran]-1-yl)propyl 4,4-difluorocyclohexanecarboxylate
(xlv) 3-(3-ethyl-4-oxo-spiro[6,8-dihydro-5H-pyrazolo[4,3-c]azepine-7,4'-tetrahydropyran]-1-yl)propyl 4-acetylbenzoate
(xlvi) 3-(3-ethyl-4-oxo-spiro[6,8-dihydro-5H-pyrazolo[4,3-c]azepine-7,4'-tetrahydropyran]-1-yl)propyl 3-acetyl benzoate
(xlvii) 3-(3-ethyl-4-oxo-spiro[6,8-dihydro-5H-pyrazolo[4,3-c]azepine-7,4'-tetrahydropyran]-1-yl)propyl 4-cyano-3-fluoro-benzoate
(xlviii) 3-(3-ethyl-4-oxo-spiro[6,8-dihydro-5H-pyrazolo[4,3-c]azepine-7,4'-tetrahydropyran]-1-yl)propyl 3-cyano-5-fluoro-benzoate
(xlix) 3-(3-ethyl-4-oxo-spiro[6,8-dihydro-5H-pyrazolo[4,3-c]azepine-7,4'-tetrahydropyran]-1-yl)propyl 4-cyano-2-fluoro-benzoate
(l) 3-(3-ethyl-4-oxo-spiro[6,8-dihydro-5H-pyrazolo[4,3-c]azepine-7,4'-tetrahydropyran]-1-yl)propyl 3-cyano-4-fluoro-benzoate
(li) 3-(3-ethyl-4-oxo-spiro[6,8-dihydro-5H-pyrazolo[4,3-c]azepine-7,4'-tetrahydropyran]-1-yl)propyl 5-cyano-2-fluoro-benzoate
(lii) 3-(3-ethyl-4-oxo-spiro[6,8-dihydro-5H-pyrazolo[4,3-c]azepine-7,4'-tetrahydropyran]-1-yl)propyl 1,3-benzodioxole-5-carboxylate
(liii) 3-(3-ethyl-4-oxo-spiro[6,8-dihydro-5H-pyrazolo[4,3-c]azepine-7,4'-tetrahydropyran]-1-yl)propyl 4-methoxy-3-methyl-benzoate
(liv) 3-(3-ethyl-4-oxo-spiro[6,8-dihydro-5H-pyrazolo[4,3-c]azepine-7,4'-tetrahydropyran]-1-yl)propyl 3-methoxy-4-methyl-benzoate
(lv) 3-(3-ethyl-4-oxo-spiro[6,8-dihydro-5H-pyrazolo[4,3-c]azepine-7,4'-tetrahydropyran]-1-yl)propyl 2-methoxy-4-methyl-benzoate
(lvi) 3-(3-ethyl-4-oxo-spiro[6,8-dihydro-5H-pyrazolo[4,3-c]azepine-7,4'-tetrahydropyran]-1-yl)propyl 3-ethoxybenzoate
(lvii) 3-(3-ethyl-4-oxo-spiro[6,8-dihydro-5H-pyrazolo[4,3-c]azepine-7,4'-tetrahydropyran]-1-yl)propyl 3-fluoro-4-methoxy-benzoate
(lviii) 3-(3-ethyl-4-oxo-spiro[6,8-dihydro-5H-pyrazolo[4,3-c]azepine-7,4'-tetrahydropyran]-1-yl)propyl 3-fluoro-5-methoxy-benzoate
(lix) 3-(3-ethyl-4-oxo-spiro[6,8-dihydro-5H-pyrazolo[4,3-c]azepine-7,4'-tetrahydropyran]-1-yl)propyl 2-fluoro-4-methoxy-benzoate
(lx) 3-(3-ethyl-4-oxo-spiro[6,8-dihydro-5H-pyrazolo[4,3-c]azepine-7,4'-tetrahydropyran]-1-yl)propyl 4-fluoro-3-methoxy-benzoate
(lxi) 3-(3-ethyl-4-oxo-spiro[6,8-dihydro-5H-pyrazolo[4,3-c]azepine-7,4'-tetrahydropyran]-1-yl)propyl 2-fluoro-3-methoxy-benzoate
(lxii) 3-(3-ethyl-4-oxo-spiro[6,8-dihydro-5H-pyrazolo[4,3-c]azepine-7,4'-tetrahydropyran]-1-yl)propyl 2-fluoro-5-methoxy-benzoate
(lxiii) 3-(3-ethyl-4-oxo-spiro[6,8-dihydro-5H-pyrazolo[4,3-c]azepine-7,4'-tetrahydropyran]-1-yl)propyl 5-fluoro-2-methoxy-benzoate
(lxiv) 3-(3-ethyl-4-oxo-spiro[6,8-dihydro-5H-pyrazolo[4,3-c]azepine-7,4'-tetrahydropyran]-1-yl)propyl 2-fluoro-6-methoxy-benzoate
(lxv) 3-(3-ethyl-4-oxo-spiro[6,8-dihydro-5H-pyrazolo[4,3-c]azepine-7,4'-tetrahydropyran]-1-yl)propyl 3-fluoro-2-methoxy-benzoate
(lxvi) 3-(3-ethyl-4-oxo-spiro[6,8-dihydro-5H-pyrazolo[4,3-c]azepine-7,4'-tetrahydropyran]-1-yl)propyl 4-fluoro-2-methoxy-benzoate
(lxvii) 3-(3-ethyl-4-oxo-spiro[6,8-dihydro-5H-pyrazolo[4,3-c]azepine-7,4'-tetrahydropyran]-1-yl)propyl 3-chloro-4-methyl-benzoate
(lxviii) 3-(3-ethyl-4-oxo-spiro[6,8-dihydro-5H-pyrazolo[4,3-c]azepine-7,4'-tetrahydropyran]-1-yl)propyl 2-chloro-4-methyl-benzoate
(lxix) 3-(3-ethyl-4-oxo-spiro[6,8-dihydro-5H-pyrazolo[4,3-c]azepine-7,4'-tetrahydropyran]-1-yl)propyl 3-chloro-2-methyl-benzoate
(lxx) 3-(3-ethyl-4-oxo-spiro[6,8-dihydro-5H-pyrazolo[4,3-c]azepine-7,4'-tetrahydropyran]-1-yl)propyl 5-chloro-2-methyl-benzoate
(lxxi) 3-(3-ethyl-4-oxo-spiro[6,8-dihydro-5H-pyrazolo[4,3-c]azepine-7,4'-tetrahydropyran]-1-yl)propyl 4-(difluoromethyl)benzoate
(lxxii) 3-(3-ethyl-4-oxo-spiro[6,8-dihydro-5H-pyrazolo[4,3-c]azepine-7,4'-tetrahydropyran]-1-yl)propyl 2-chloro-4-fluoro-benzoate
(lxxiii) 3-(3-ethyl-4-oxo-spiro[6,8-dihydro-5H-pyrazolo[4,3-c]azepine-7,4'-tetrahydropyran]-1-yl)propyl 3-chloro-2-fluoro-benzoate
(lxxiv) 3-(3-ethyl-4-oxo-spiro[6,8-dihydro-5H-pyrazolo[4,3-c]azepine-7,4'-tetrahydropyran]-1-yl)propyl 3-chloro-5-fluoro-benzoate
(lxxv) 3-(3-ethyl-4-oxo-spiro[6,8-dihydro-5H-pyrazolo[4,3-c]azepine-7,4'-tetrahydropyran]-1-yl)propyl 2-chloro-6-fluoro-benzoate
(lxxvi) 3-(3-ethyl-4-oxo-spiro[6,8-dihydro-5H-pyrazolo[4,3-c]azepine-7,4'-tetrahydropyran]-1-yl)propyl 4-chloro-3-fluoro-benzoate
(lxxvii) 3-(3-ethyl-4-oxo-spiro[6,8-dihydro-5H-pyrazolo[4,3-c]azepine-7,4'-tetrahydropyran]-1-yl)propyl 2-chloro-5-fluoro-benzoate
(lxxviii) 3-(3-ethyl-4-oxo-spiro[6,8-dihydro-5H-pyrazolo[4,3-c]azepine-7,4'-tetrahydropyran]-1-yl)propyl 5-chloro-2-fluoro-benzoate
(lxxix) 3-(3-ethyl-4-oxo-spiro[6,8-dihydro-5H-pyrazolo[4,3-c]azepine-7,4'-tetrahydropyran]-1-yl)propyl 3-chloro-4-fluoro-benzoate
(lxxx) 3-(3-ethyl-4-oxo-spiro[6,8-dihydro-5H-pyrazolo[4,3-c]azepine-7,4'-tetrahydropyran]-1-yl)propyl 4-chloro-2-fluoro-benzoate
(lxxxi) 3-(3-ethyl-4-oxo-spiro[6,8-dihydro-5H-pyrazolo[4,3-c]azepine-7,4'-tetrahydropyran]-1-yl)propyl 3-chloro-4-methoxy-benzoate (lxxxii) 3-(3-ethyl-4-oxo-spiro[6,8-dihydro-5H-pyrazolo[4,3-c]azepine-7,4'-tetrahydropyran]-1-yl)propyl 4-chloro-3-methoxy-benzoate (lxxxiii) 3-(3-ethyl-4-oxo-spiro[6,8-dihydro-5H-pyrazolo[4,3-c]azepine-7,4'-tetrahydropyran]-1-yl)propyl 3-chloro-5-methoxy-benzoate (lxxxiv) 3-(3-ethyl-4-oxo-spiro[6,8-dihydro-5H-pyrazolo[4,3-c]azepine-7,4'-tetrahydropyran]-1-yl)propyl 2-chloro-4-methoxy-benzoate (lxxxv) 3-(3-ethyl-4-oxo-spiro[6,8-dihydro-5H-pyrazolo[4,3-c]azepine-7,4'-tetrahydropyran]-1-yl)propyl 2-chloro-5-methoxy-benzoate (lxxxvi) 3-(3-ethyl-4-oxo-spiro[6,8-dihydro-5H-pyrazolo[4,3-c]azepine-7,4'-tetrahydropyran]-1-yl)propyl 2-chloro-3-methoxy-benzoate (lxxxvii) 3-(3-ethyl-4-oxo-spiro[6,8-dihydro-5H-pyrazolo[4,3-c]azepine-7,4'-tetrahydropyran]-1-yl)propyl 4-chloro-2-methoxy-benzoate (lxxxviii) 3-(3-ethyl-4-oxo-spiro[6,8-dihydro-5H-pyrazolo[4,3-c]azepine-7,4'-tetrahydropyran]-1-yl)propyl 5-chloro-2-methoxy-benzoate (lxxxix) 3-(3-ethyl-4-oxo-spiro[6,8-dihydro-5H-pyrazolo[4,3-c]azepine-7,4'-tetrahydropyran]-1-yl)propyl 3-chloro-2-methoxy-benzoate (xc) 3-(3-ethyl-4-oxo-spiro[6,8-dihydro-5H-pyrazolo[4,3-c]azepine-7,4'-tetrahydropyran]-1-yl)propyl 2-(trifluoromethyl)benzoate (xci) 3-(3-ethyl-4-oxo-spiro[6,8-dihydro-5H-pyrazolo[4,3-c]azepine-7,4'-tetrahydropyran]-1-yl)propyl 3-(trifluoromethyl)benzoate (xcii) 3-(3-ethyl-4-oxo-spiro[6,8-dihydro-5H-pyrazolo[4,3-c]azepine-7,4'-tetrahydropyran]-1-yl)propyl 4-(trifluoromethyl)benzoate (xciii) 3-(3-ethyl-4-oxo-spiro[6,8-dihydro-5H-pyrazolo[4,3-c]azepine-7,4'-tetrahydropyran]-1-yl)propyl 4-methylsulfonylbenzoate (xciv) 3-(3-ethyl-4-oxo-spiro[6,8-dihydro-5H-pyrazolo[4,3-c]azepine-7,4'-tetrahydropyran]-1-yl)propyl 3-methylsulfonylbenzoate (xcv) 3-(3-ethyl-4-oxo-spiro[6,8-dihydro-5H-pyrazolo[4,3-c]azepine-7,4'-tetrahydropyran]-1-yl)propyl 2-methylsulfonylbenzoate (xcvi) 3-(3-ethyl-4-oxo-spiro[6,8-dihydro-5H-pyrazolo[4,3-c]azepine-7,4'-tetrahydropyran]-1-yl)propyl 4-sulfamoylbenzoate (xcvii) 3-(3-ethyl-4-oxo-spiro[6,8-dihydro-5H-pyrazolo[4,3-c]azepine-7,4'-tetrahydropyran]-1-yl)propyl 3-sulfamoylbenzoate (xcviii) 3-(3-ethyl-4-oxo-spiro[6,8-dihydro-5H-pyrazolo[4,3-c]azepine-7,4'-tetrahydropyran]-1-yl)propyl 4-methyl-3-(trifluoromethyl)benzoate (xcix) 3-(3-ethyl-4-oxo-spiro[6,8-dihydro-5H-pyrazolo[4,3-c]azepine-7,4'-tetrahydropyran]-1-yl)propyl 2-methyl-3-(trifluoromethyl)benzoate (c) 3-(3-ethyl-4-oxo-spiro[6,8-dihydro-5H-pyrazolo[4,3-c]azepine-7,4'-tetrahydropyran]-1-yl)propyl 2-methyl-5-(trifluoromethyl)benzoate (ci) 3-(3-ethyl-4-oxo-spiro[6,8-dihydro-5H-pyrazolo[4,3-c]azepine-7,4'-tetrahydropyran]-1-yl)propyl 3-fluoro-2-(trifluoromethyl)benzoate (cii) 3-(3-ethyl-4-oxo-spiro[6,8-dihydro-5H-pyrazolo[4,3-c]azepine-7,4'-tetrahydropyran]-1-yl)propyl 2-fluoro-6-(trifluoromethyl)benzoate (ciii) 3-(3-ethyl-4-oxo-spiro[6,8-dihydro-5H-pyrazolo[4,3-c]azepine-7,4'-tetrahydropyran]-1-yl)propyl 3-fluoro-5-(trifluoromethyl)benzoate (civ) 3-(3-ethyl-4-oxo-spiro[6,8-dihydro-5H-pyrazolo[4,3-c]azepine-7,4'-tetrahydropyran]-1-yl)propyl 4-fluoro-2-(trifluoromethyl)benzoate (cv) 3-(3-ethyl-4-oxo-spiro[6,8-dihydro-5H-pyrazolo[4,3-c]azepine-7,4'-tetrahydropyran]-1-yl)propyl 3-fluoro-4-(trifluoromethyl)benzoate (cvi) 3-(3-ethyl-4-oxo-spiro[6,8-dihydro-5H-pyrazolo[4,3-c]azepine-7,4'-tetrahydropyran]-1-yl)propyl 4-fluoro-3-(trifluoromethyl)benzoate (cvii) 3-(3-ethyl-4-oxo-spiro[6,8-dihydro-5H-pyrazolo[4,3-c]azepine-7,4'-tetrahydropyran]-1-yl)propyl 2-fluoro-5-(trifluoromethyl)benzoate (cviii) 3-(3-ethyl-4-oxo-spiro[6,8-dihydro-5H-pyrazolo[4,3-c]azepine-7,4'-tetrahydropyran]-1-yl)propyl 2-fluoro-4-(trifluoromethyl)benzoate (cix) 3-(3-ethyl-4-oxo-spiro[6,8-dihydro-5H-pyrazolo[4,3-c]azepine-7,4'-tetrahydropyran]-1-yl)propyl 3-ethylsulfonylbenzoate (cx) 3-(3-ethyl-4-oxo-spiro[6,8-dihydro-5H-pyrazolo[4,3-c]azepine-7,4'-tetrahydropyran]-1-yl)propyl 4-ethylsulfonylbenzoate (cxi) 3-(3-ethyl-4-oxo-spiro[6,8-dihydro-5H-pyrazolo[4,3-c]azepine-7,4'-tetrahydropyran]-1-yl)propyl 3-(methylsulfamoyl)benzoate (cxii) 3-(3-ethyl-4-oxo-spiro[6,8-dihydro-5H-pyrazolo[4,3-c]azepine-7,4'-tetrahydropyran]-1-yl)propyl 4-(methylsulfamoyl)benzoate (cxiii) 3-(3-ethyl-4-oxo-spiro[6,8-dihydro-5H-pyrazolo[4,3-c]azepine-7,4'-tetrahydropyran]-1-yl)propyl 4-methoxy-3-(trifluoromethyl)benzoate (cxiv) 3-(3-ethyl-4-oxo-spiro[6,8-dihydro-5H-pyrazolo[4,3-c]azepine-7,4'-tetrahydropyran]-1-yl)propyl 5-methoxy-2-(trifluoromethyl)benzoate (cxv) 3-(3-ethyl-4-oxo-spiro[6,8-dihydro-5H-pyrazolo[4,3-c]azepine-7,4'-tetrahydropyran]-1-yl)propyl 3-methoxy-5-(trifluoromethyl)benzoate (cxvi) 3-(3-ethyl-4-oxo-spiro[6,8-dihydro-5H-pyrazolo[4,3-c]azepine-7,4'-tetrahydropyran]-1-yl)propyl 4-chloro-2-(trifluoromethyl)benzoate (cxvii) 3-(3-ethyl-4-oxo-spiro[6,8-dihydro-5H-pyrazolo[4,3-c]azepine-7,4'-tetrahydropyran]-1-yl)propyl 4-chloro-3-(trifluoromethyl)benzoate (cxviii) 3-(3-ethyl-4-oxo-spiro[6,8-dihydro-5H-pyrazolo[4,3-c]azepine-7,4'-tetrahydropyran]-1-yl)propyl 2-chloro-3-(trifluoromethyl)benzoate (cxix) 3-(3-ethyl-4-oxo-spiro[6,8-dihydro-5H-pyrazolo[4,3-c]azepine-7,4'-tetrahydropyran]-1-yl)propyl 5-chloro-2-(trifluoromethyl)benzoate (cxx) 3-(3-ethyl-4-oxo-spiro[6,8-dihydro-5H-pyrazolo[4,3-c]azepine-7,4'-tetrahydropyran]-1-yl)propyl 3-chloro-4-(trifluoromethyl)benzoate (cxxi) 3-(3-ethyl-4-oxo-spiro[6,8-dihydro-5H-pyrazolo[4,3-c]azepine-7,4'-tetrahydropyran]-1-yl)propyl 2-chloro-4-(trifluoromethyl)benzoate (cxxii) 3-(3-ethyl-4-oxo-spiro[6,8-dihydro-5H-pyrazolo[4,3-c]azepine-7,4'-tetrahydropyran]-1-yl)propyl 3-chloro-5-(trifluoromethyl)benzoate (cxxiii) 3-(3-ethyl-4-oxo-spiro[6,8-dihydro-5H-pyrazolo[4,3-c]azepine-7,4'-tetrahydropyran]-1-yl)propyl 2-chloro-5-(trifluoromethyl)benzoate (cxxiv) 3-(3-ethyl-4-oxo-spiro[6,8-dihydro-5H-pyrazolo[4,3-c]azepine-7,4'-tetrahydropyran]-1-yl)propyl 3-isopropylsulfonylbenzoate (cxxv) 3-(3-ethyl-4-oxo-spiro[6,8-dihydro-5H-pyrazolo[4,3-c]azepine-7,4'-tetrahydropyran]-1-yl)propyl 4-isopropylsulfonylbenzoate (cxxvi) 3-(3-ethyl-4-oxo-spiro[6,8-dihydro-5H-pyrazolo[4,3-c]azepine-7,4'-tetrahydropyran]-1-yl)propyl 4-(dimethylsulfamoyl)benzoate (cxxvii) 3-(3-ethyl-4-oxo-spiro[6,8-dihydro-5H-pyrazolo[4,3-c]azepine-7,4'-tetrahydropyran]-1-yl)propyl 4-cyclopentylsulfonylbenzoate (cxxviii) 3-(3-ethyl-4-oxo-spiro[6,8-dihydro-5H-pyrazolo[4,3-c]azepine-7,4'-tetrahydropyran]-1-yl)propyl 4-pyrrolidin-1-ylsulfonylbenzoate (cxxix) 3-(3-ethyl-4-oxo-spiro[6,8-dihydro-5H-pyrazolo[4,3-c]azepine-7,4'-tetrahydropyran]-1-yl)propyl 3-pyrrolidin-1-ylsulfonylbenzoate (cxxx) 3-(3-ethyl-4-oxo-spiro[6,8-dihydro-5H-pyrazolo[4,3-c]azepine-7,4'-tetrahydropyran]-1-yl)propyl 2,4-bis(trifluoromethyl)benzoate (cxxxi) 3-(3-ethyl-4-oxo-spiro[6,8-dihydro-5H-pyrazolo[4,3-c]azepine-7,4'-tetrahydropyran]-1-yl)propyl 3,4-bis(trifluoromethyl)benzoate (cxxxii) 3-(3-ethyl-4-oxo-spiro[6,8-dihydro-5H-pyrazolo[4,3-c]azepine-7,4'-tetrahydropyran]-1-yl)propyl 3-morpholinosulfonylbenzoate (cxxxiii) 3-(3-ethyl-4-oxo-spiro[6,8-dihydro-5H-pyrazolo[4,3-c]azepine-7,4'-tetrahydropyran]-1-yl)propyl 4-morpholinosulfonylbenzoate (cxxxiv) 3-(3-ethyl-4-oxo-spiro[6,8-dihydro-5H-pyrazolo[4,3-c]azepine-7,4'-tetrahydropyran]-1-yl)propyl 4-(4-acetylpiperazin-1-yl)sulfonylbenzoate (cxxxv) 3-(3-ethyl-4-oxo-spiro[6,8-dihydro-5H-pyrazolo[4,3-c]azepine-7,4'-tetrahydropyran]-1-yl)propyl 4-carbamoyl benzoate (cxxxvi) 3-(3-ethyl-4-oxo-spiro[6,8-dihydro-5H-pyrazolo[4,3-c]azepine-7,4'-tetrahydropyran]-1-yl)propyl 4-(methylcarbamoyl)benzoate (cxxxvii) 3-(3-ethyl-4-oxo-spiro[6,8-dihydro-5H-pyrazolo[4,3-c]azepine-7,4'-tetrahydropyran]-1-yl)propyl 4-(ethylcarbamoyl)benzoate (cxxxviii) 3-(3-ethyl-4-oxo-spiro[6,8-dihydro-5H-pyrazolo[4,3-c]azepine-7,4'-tetrahydropyran]-1-yl)propyl 4-(dimethylcarbamoyl)benzoate (cxxxix) 3-(3-ethyl-4-oxo-spiro[6,8-dihydro-5H-pyrazolo[4,3-c]azepine-7,4'-tetrahydropyran]-1-yl)propyl 4-(isopropylcarbamoyl)benzoate (cxl) 3-(3-ethyl-4-oxo-spiro[6,8-dihydro-5H-pyrazolo[4,3-c]azepine-7,4'-tetrahydropyran]-1-yl)propyl 4-(pyrrolidine-1-carbonyl)benzoate (cxli) 3-(3-ethyl-4-oxo-spiro[6,8-dihydro-5H-pyrazolo[4,3-c]azepine-7,4'-tetrahydropyran]-1-yl)propyl 4-(piperidine-1-carbonyl)benzoate (cxlii) 3-(3-ethyl-4-oxo-spiro[6,8-dihydro-5H-pyrazolo[4,3-c]azepine-7,4'-tetrahydropyran]-1-yl)propyl 4-(morpholine-4-carbonyl)benzoate (cxliii) 3-(3-ethyl-4-oxo-spiro[6,8-dihydro-5H-pyrazolo[4,3-c]azepine-7,4'-tetrahydropyran]-1-yl)propyl 4-(4-methylpiperazine-1-carbonyl)benzoate (cxliv) 3-(3-ethyl-4-oxo-spiro[6,8-dihydro-5H-pyrazolo[4,3-c]azepine-7,4'-tetrahydropyran]-1-yl)propyl 4-(4-acetylpiperazine-1-carbonyl)benzoate;

(cxlv) 3-(3-ethyl-4-oxo-spiro[6,8-dihydro-5H-pyrazolo[4,3-c]azepine-7,4'-tetrahydropyran]-1-yl)propyl 3-carbamoyl benzoate (cxlvi) 3-(3-ethyl-4-oxo-spiro[6,8-dihydro-5H-pyrazolo[4,3-c]azepine-7,4'-tetrahydropyran]-1-yl)propyl 3-(methylcarbamoyl)benzoate (cxlvii) 3-(3-ethyl-4-oxo-spiro[6,8-dihydro-5H-pyrazolo[4,3-c]azepine-7,4'-tetrahydropyran]-1-yl)propyl 3-(ethylcarbamoyl)benzoate (xlviii) 3-(3-ethyl-4-oxo-spiro[6,8-dihydro-5H-pyrazolo[4,3-c]azepine-7,4'-tetrahydropyran]-1-yl)propyl 3-(dimethylcarbamoyl)benzoate (cxlix) 3-(3-ethyl-4-oxo-spiro[6,8-dihydro-5H-pyrazolo[4,3-c]azepine-7,4'-tetrahydropyran]-1-yl)propyl 3-(isopropylcarbamoyl)benzoate (cl) 3-(3-ethyl-4-oxo-spiro[6,8-dihydro-5H-pyrazolo[4,3-c]azepine-7,4'-tetrahydropyran]-1-yl)propyl 3-(pyrrolidine-1-carbonyl)benzoate (cli) 3-(3-ethyl-4-oxo-spiro[6,8-dihydro-5H-pyrazolo[4,3-c]azepine-7,4'-tetrahydropyran]-1-yl)propyl 3-(piperidine-1-carbonyl)benzoate (clii) 3-(3-ethyl-4-oxo-spiro[6,8-dihydro-5H-pyrazolo[4,3-c]azepine-7,4'-tetrahydropyran]-1-yl)propyl 3-(morpholine-4-carbonyl)benzoate (cliii) 3-(3-ethyl-4-oxo-spiro[6,8-dihydro-5H-pyrazolo[4,3-c]azepine-7,4'-tetrahydropyran]-1-yl)propyl 3-(4-methylpiperazine-1-carbonyl)benzoate (cliv) 3-(3-ethyl-4-oxo-spiro[6,8-dihydro-5H-pyrazolo[4,3-c]azepine-7,4'-tetrahydropyran]-1-yl)propyl 3-(4-acetylpiperazine-1-carbonyl)benzoate (clv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylpropanoate (clvi) [(2R)-3-(3-ethyl-4-oxo-spiro[6,8-dihydro-5H-pyrazolo[4,3-c]azepine-7,4'-tetrahydropyran]-1-yl)-2-methyl-propyl] cyclopentanecarboxylate (clvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-ethylbutanoate (clviii) [(2R)-3-(3-ethyl-4-oxo-spiro[6,8-dihydro-5H-pyrazolo[4,3-c]azepine-7,4'-tetrahydropyran]-1-yl)-2-methyl-propyl] benzoate (clix) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methylbenzoate (clx) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluorobenzoate (clxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluorobenzoate (clxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyanobenzoate (clxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyanobenzoate (clxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-dimethylbenzoate (clxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2,4-dimethylbenzoate (clxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxybenzoate (clxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methyl-benzoate (clxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-methyl-benzoate (clxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methyl-benzoate (clxx) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chlorobenzoate
(clxxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 2,6-difluorobenzoate
(clxxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2,5-difluorobenzoate
(clxxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-difluorobenzoate
(clxxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2,3-difluorobenzoate
(clxxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-acetylbenzoate
(clxxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-acetylbenzoate
(clxxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-5-fluoro-benzoate
(clxxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-cyano-2-fluoro-benzoate
(clxxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-cyano-4-fluoro-benzoate
(clxxx) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyano-3-fluoro-benzoate
(clxxxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-methyl-benzoate
(clxxxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methoxy-4-methyl-benzoate
(clxxxiii) [(2R)-3-(3-ethyl-4-oxo-spiro[6,8-dihydro-5H-pyrazolo[4,3-c]azepine-7,4'-tetrahydro-pyran]-1-yl)-2-methyl-propyl] 3-fluoro-4-methoxy-benzoate
(clxxxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-methoxy-benzoate
(clxxxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-3-methoxy-benzoate
(clxxxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-methoxy-benzoate
(clxxxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-2-methoxy-benzoate
(clxxxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-methoxy-benzoate
(clxxxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-6-methoxy-benzoate
(cxc) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-methoxy-benzoate
(cxci) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methyl-benzoate
(cxcii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(difluoromethyl)benzoate
(cxciii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-fluoro-benzoate
(cxciv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-fluoro-benzoate
(cxcv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-fluoro-benzoate
(cxcvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-fluoro-benzoate
(cxcvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-fluoro-benzoate
(cxcviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-6-fluoro-benzoate
(cxcix) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-fluoro-benzoate
(cc) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-fluoro-benzoate
(cci) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-methoxy-benzoate
(ccii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-methoxy-benzoate
(cciii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-methoxy-benzoate
(cciv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-2-methoxy-benzoate
(ccv) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-methoxy-benzoate
(ccvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-methoxy-benzoate
(ccvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(trifluoromethyl)benzoate
(ccviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methylsulfonylbenzoate
(ccix) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methylsulfonylbenzoate
(ccx) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-sulfamoylbenzoate
(ccxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-sulfamoylbenzoate
(ccxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-3-(trifluoromethyl)benzoate
(ccxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-methyl-5-(trifluoromethyl)benzoate (ccxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-4-(trifluoromethyl)benzoate
(ccxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-5-(trifluoromethyl)benzoate
(ccxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-fluoro-4-(trifluoromethyl)benzoate
(ccxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-2-(trifluoromethyl)benzoate
(ccxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-fluoro-2-(trifluoromethyl)benzoate
(ccxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-fluoro-3-(trifluoromethyl)benzoate
(ccxx) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-fluoro-5-(trifluoromethyl)benzoate
(ccxxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-ethylsulfonylbenzoate
(ccxxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-ethylsulfonylbenzoate
(ccxxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(methylsulfamoyl)benzoate
(ccxxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-2-(trifluoromethyl)benzoate
(ccxxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-methoxy-3-(trifluoromethyl)benzoate
(ccxxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-methoxy-2-(trifluoromethyl)benzoate
(ccxxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-5-(trifluoromethyl)benzoate
(ccxxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-methoxy-4-(trifluoromethyl)benzoate
(ccxxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-4-(trifluoromethyl)benzoate
(ccxxx) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-3-(trifluoromethyl)benzoate
(ccxxxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-2-(trifluoromethyl)benzoate
(ccxxxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-4-(trifluoromethyl)benzoate
(ccxxxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-chloro-3-(trifluoromethyl)benzoate
(ccxxxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 5-chloro-2-(trifluoromethyl)benzoate
(ccxxxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-chloro-5-(trifluoromethyl)benzoate
(ccxxxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 2-chloro-5-(trifluoromethyl)benzoate
(ccxxxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-isopropylsulfonylbenzoate
(ccxxxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-isopropylsulfonylbenzoate
(ccxxxix) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-cyclopentylsulfonylbenzoate
(ccxl) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-pyrrolidin-1-ylsulfonylbenzoate
(ccxli) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-pyrrolidin-1-ylsulfonylbenzoate
(ccxlii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3,4-bis(trifluoromethyl)benzoate
(ccxliii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-morpholinosulfonylbenzoate
(ccxliv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-morpholinosulfonylbenzoate
(ccxlv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazin-1-yl)sulfonylbenzoate
(ccxlvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazin-1-yl)sulfonylbenzoate
(ccxlvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-carbamoyl benzoate;
(ccxlviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(methylcarbamoyl)benzoate;
(ccxlix) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(ethylcarbamoyl)benzoate;
(ccl) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(dimethylcarbamoyl)benzoate;
(ccli) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(isopropylcarbamoyl)benzoate;
(cclii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(pyrrolidine-1-carbonyl)benzoate;
(ccliii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperidine-1-carbonyl)benzoate;
(ccliv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(piperazine-1-carbonyl)benzoate;

(cclv) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(morpholine-4-carbonyl)benzoate;

(cclvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-methylpiperazine-1-carbonyl)benzoate;

(cclvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 4-(4-acetylpiperazine-1-carbonyl)benzoate; [(2R)-3-(3-ethyl-4-oxo-spiro[6,8-dihydro-5H-pyrazolo[4,3-c]azepine-7,4'-tetrahydropyran]-1-yl)-2-methyl-propyl] 3-carbamoylbenzoate;

(cclix) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(methylcarbamoyl)benzoate;

(cclx) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(ethylcarbamoyl)benzoate;

(cclxi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(dimethylcarbamoyl)benzoate;

(cclxii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(isopropylcarbamoyl)benzoate;

(cclxiii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(pyrrolidine-1-carbonyl)benzoate;

(cclxiv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperidine-1-carbonyl)benzoate;

(cclxv) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(piperazine-1-carbonyl)benzoate;

(cclxvi) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(morpholine-4-carbonyl)benzoate;

(cclxvii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-methylpiperazine-1-carbonyl)benzoate;

(cclxviii) [(2R)-3-(3-ethyl-4-oxo-spiro[6,8-dihydro-5H-pyrazolo[4,3-c]azepine-7,4'-tetrahydropyran]-1-yl)-2-methyl-propyl] 3-(4-acetylpiperazine-1-carbonyl)benzoate (cclxix) [(2S)-3-(3-ethyl-4-oxo-spiro[6,8-dihydro-5H-pyrazolo[4,3-c]azepine-7,4'-tetrahydropyran]-1-yl)-2-methyl-propyl] benzoate;

(cclxx) [(2S)-3-(3-ethyl-4-oxo-spiro[6,8-dihydro-5H-pyrazolo[4,3-c]azepine-7,4'-tetrahydropyran]-1-yl)-2-methyl-propyl] 4-methylbenzoate;

(cclxxi) [(2S)-3-(3-ethyl-4-oxo-spiro[6,8-dihydro-5H-pyrazolo[4,3-c]azepine-7,4'-tetrahydropyran]-1-yl)-2-methyl-propyl] 3-fluorobenzoate;

(cclxxii) [(2S)-3-(3-ethyl-4-oxo-spiro[6,8-dihydro-5H-pyrazolo[4,3-c]azepine-7,4'-tetrahydropyran]-1-yl)-2-methyl-propyl] 4-fluorobenzoate;

(cclxxiii) [(2S)-3-(3-ethyl-4-oxo-spiro[6,8-dihydro-5H-pyrazolo[4,3-c]azepine-7,4'-tetrahydropyran]-1-yl)-2-methyl-propyl] 3-methoxybenzoate;

(cclxxiv) [(2S)-3-(3-ethyl-4-oxo-spiro[6,8-dihydro-5H-pyrazolo[4,3-c]azepine-7,4'-tetrahydropyran]-1-yl)-2-methyl-propyl] 4-chlorobenzoate;

(cclxxv) [3-(3-ethyl-4-oxo-spiro[6,8-dihydro-5H-pyrazolo[4,3-c]azepine-7,4'-tetrahydropyran]-1-yl)-2,2-dimethyl-propyl] cyclopentanecarboxylate (cclxxvi) [3-(3-ethyl-4-oxo-spiro[6,8-dihydro-5H-pyrazolo[4,3-c]azepine-7,4'-tetrahydropyran]-1-yl)-2,2-dimethyl-propyl] 2-ethylbutanoate (cclxxvii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-methylbenzoate (cclxxviii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-fluorobenzoate (cclxxix) [3-(3-ethyl-4-oxo-spiro[6,8-dihydro-5H-pyrazolo[4,3-c]azepine-7,4'-tetrahydropyran]-1-yl)-2,2-dimethyl-propyl] 4-fluorobenzoate (cclxxx) [3-(3-ethyl-4-oxo-spiro[6,8-dihydro-5H-pyrazolo[4,3-c]azepine-7,4'-tetrahydropyran]-1-yl)-2,2-dimethyl-propyl] 2-fluorobenzoate (cclxxxi) [3-(3-ethyl-4-oxo-spiro[6,8-dihydro-5H-pyrazolo[4,3-c]azepine-7,4'-tetrahydropyran]-1-yl)-2,2-dimethyl-propyl] 3-cyanobenzoate (cclxxxii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyanobenzoate (cclxxxiii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-methoxybenzoate (cclxxxiv) [3-(3-ethyl-4-oxo-spiro[6,8-dihydro-5H-pyrazolo[4,3-c]azepine-7,4'-tetrahydropyran]-1-yl)-2,2-dimethyl-propyl] 4-chlorobenzoate (cclxxxv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-chlorobenzoate (cclxxxvi) [3-(3-ethyl-4-oxo-spiro[6,8-dihydro-5H-pyrazolo[4,3-c]azepine-7,4'-tetrahydropyran]-1-yl)-2,2-dimethyl-propyl] 2-chlorobenzoate (cclxxxvii) [3-(3-ethyl-4-oxo-spiro[6,8-dihydro-5H-pyrazolo[4,3-c]azepine-7,4'-tetrahydropyran]-1-yl)-2,2-dimethyl-propyl] 3,5-difluorobenzoate (cclxxxviii) [3-(3-ethyl-4-oxo-spiro[6,8-dihydro-5H-pyrazolo[4,3-c]azepine-7,4'-tetrahydropyran]-1-yl)-2,2-dimethyl-propyl] 3,4-difluorobenzoate (cclxxxix) [3-(3-ethyl-4-oxo-spiro[6,8-dihydro-5H-pyrazolo[4,3-c]azepine-7,4'-tetrahydropyran]-1-yl)-2,2-dimethyl-propyl] 4-acetylbenzoate (ccxc) [3-(3-ethyl-4-oxo-spiro[6,8-dihydro-5H-pyrazolo[4,3-c]azepine-7,4'-tetrahydropyran]-1-yl)-2,2-dimethyl-propyl] 3-acetylbenzoate (ccxci) [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyano-3-fluoro-benzoate (ccxcii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyano-2-fluoro-benzoate (ccxciii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-ethoxybenzoate (ccxciv) [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-6-fluoro-benzoate (ccxcv) [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-4-fluoro-benzoate (ccxcvi) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(trifluoromethyl)benzoate (ccxcvii) [3-(3-ethyl-4-oxo-spiro[6,8-dihydro-5H-pyrazolo[4,3-c]azepine-7,4'-tetrahydropyran]-1-yl)-2,2-dimethyl-propyl] 2-(trifluoromethyl)benzoate (ccxcviii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(trifluoromethyl)benzoate
(ccxcix) [3-(3-ethyl-4-oxo-spiro[6,8-dihydro-5H-pyrazolo[4,3-c]azepine-7,4'-tetrahydropyran]-1-yl)-2,2-dimethyl-propyl] 3-methylsulfonylbenzoate
(ccc) [3-(3-ethyl-4-oxo-spiro[6,8-dihydro-5H-pyrazolo[4,3-c]azepine-7,4'-tetrahydropyran]-1-yl)-2,2-dimethyl-propyl] 4-methylsulfonylbenzoate
(ccci) [3-(3-ethyl-4-oxo-spiro[6,8-dihydro-5H-pyrazolo[4,3-c]azepine-7,4'-tetrahydropyran]-1-yl)-2,2-dimethyl-propyl] 2-methylsulfonylbenzoate
(cccii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-sulfamoylbenzoate
(ccciii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-sulfamoylbenzoate
(ccciv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-fluoro-5-(trifluoromethyl)benzoate
(cccv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-ethylsulfonylbenzoate
(cccvi) [3-(3-ethyl-4-oxo-spiro[6,8-dihydro-5H-pyrazolo[4,3-c]azepine-7,4'-tetrahydropyran]-1-yl)-2,2-dimethyl-propyl] 4-ethylsulfonylbenzoate
(cccvii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(methylsulfamoyl)benzoate
(cccviii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-chloro-3-(trifluoromethyl)benzoate
(cccix) [3-(3-ethyl-4-oxo-spiro[6,8-dihydro-5H-pyrazolo[4,3-c]azepine-7,4'-tetrahydropyran]-1-yl)-2,2-dimethyl-propyl] 2-chloro-5-(trifluoromethyl)benzoate
(cccx) [3-(3-ethyl-4-oxo-spiro[6,8-dihydro-5H-pyrazolo[4,3-c]azepine-7,4'-tetrahydropyran]-1-yl)-2,2-dimethyl-propyl] 3-isopropylsulfonylbenzoate
(cccxi) [3-(3-ethyl-4-oxo-spiro[6,8-dihydro-5H-pyrazolo[4,3-c]azepine-7,4'-tetrahydropyran]-1-yl)-2,2-dimethyl-propyl] 4-isopropylsulfonylbenzoate
(cccxii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(dimethylsulfamoyl)benzoate
(cccxiii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-cyclopentylsulfonylbenzoate
(cccxiv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-pyrrolidin-1-ylsulfonylbenzoate
(cccxv) [3-(3-ethyl-4-oxo-spiro[6,8-dihydro-5H-pyrazolo[4,3-c]azepine-7,4'-tetrahydropyran]-1-yl)-2,2-dimethyl-propyl] 4-pyrrolidin-1-ylsulfonylbenzoate
(cccxvi) [3-(3-ethyl-4-oxo-spiro[6,8-dihydro-5H-pyrazolo[4,3-c]azepine-7,4'-tetrahydropyran]-1-yl)-2,2-dimethyl-propyl] 4-morpholinosulfonylbenzoate
(cccxvii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-morpholinosulfonylbenzoate
(cccxviii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-acetylpiperazin-1-yl)sulfonylbenzoate
(cccxix) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-acetylpiperazin-1-yl)sulfonylbenzoate;
(cccxx) [3-(3-ethyl-4-oxo-spiro[6,8-dihydro-5H-pyrazolo[4,3-c]azepine-7,4'-tetrahydropyran]-1-yl)-2,2-dimethyl-propyl] 4-carbamoylbenzoate;
(cccxxi) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(methylcarbamoyl)benzoate;
(cccxxii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(ethylcarbamoyl)benzoate;
(cccxxiii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(dimethylcarbamoyl)benzoate;
(cccxxiv) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(isopropylcarbamoyl)benzoate;
(cccxxv) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(pyrrolidine-1-carbonyl)benzoate;
(cccxxvi) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(piperidine-1-carbonyl)benzoate;
(cccxxvii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(piperazine-1-carbonyl)benzoate;
(cccxxviii) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(morpholine-4-carbonyl)benzoate;
(cccxxix) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-methylpiperazine-1-carbonyl)benzoate;
(cccxxx) [3-(3-ethyl-4-oxo-spiro[6,8-dihydro-5H-pyrazolo[4,3-c]azepine-7,4'-tetrahydropyran]-1-yl)-2,2-dimethyl-propyl] 4-(4-acetylpiperazine-1-carbonyl)benzoate;
(cccxxxi) [3-(3-ethyl-4-oxo-spiro[6,8-dihydro-5H-pyrazolo[4,3-c]azepine-7,4'-tetrahydropyran]-1-yl)-2,2-dimethyl-propyl] 3-carbamoylbenzoate;
(cccxxxii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(methylcarbamoyl)benzoate;
(cccxxxiii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(ethylcarbamoyl)benzoate;
(cccxxxiv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(dimethylcarbamoyl)benzoate;
(cccxxxv) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(isopropylcarbamoyl)benzoate;
(cccxxxvi) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(pyrrolidine-1-carbonyl)benzoate;
(cccxxxvii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(piperidine-1-carbonyl)benzoate;
(cccxxxviii) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(piperazine-1-carbonyl)benzoate;
(cccxxxix) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(morpholine-4-carbonyl)benzoate;

(cccxl) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-methylpiperazine-1-carbonyl)benzoate;

(cccxli) [3-(3-ethyl-4-oxo-spiro[6,8-dihydro-5H-pyrazolo[4,3-c]azepine-7,4'-tetrahydropyran]-1-yl)-2,2-dimethyl-propyl] 3-(4-acetylpiperazine-1-carbonyl)benzoate;

(cccxlii) [1-[(3-ethyl-4-oxo-spiro[6,8-dihydro-5H-pyrazolo[4,3-c]azepine-7,4'-tetrahydropyran]-1-yl)methyl]cyclopropyl]methyl 4-methyl benzoate;

(cccxliii) [1-[(3-ethyl-4-oxo-spiro[6,8-dihydro-5H-pyrazolo[4,3-c]azepine-7,4'-tetrahydropyran]-1-yl)methyl]cyclopropyl]methyl 3-fluorobenzoate;

(cccxliv) [1-[(3-ethyl-4-oxo-spiro[6,8-dihydro-5H-pyrazolo[4,3-c]azepine-7,4'-tetrahydropyran]-1-yl)methyl]cyclopropyl]methyl 4-fluorobenzoate;

(cccxlv) [1-[(3-ethyl-4-oxo-spiro[6,8-dihydro-5H-pyrazolo[4,3-c]azepine-7,4'-tetrahydropyran]-1-yl)methyl]cyclopropyl]methyl 3-methoxybenzoate;

(cccxlvi) [1-[(3-ethyl-4-oxo-spiro[6,8-dihydro-5H-pyrazolo[4,3-c]azepine-7,4'-tetrahydropyran]-1-yl)methyl]cyclopropyl]methyl 4-chlorobenzoate;

(cccxlvii) [3-[(3-ethyl-4-oxo-spiro[6,8-dihydro-5H-pyrazolo[4,3-c]azepine-7,4'-tetrahydropyran]-1-yl)methyl]oxetan-3-yl]methyl benzoate;

(cccxlviii) [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-methyl benzoate;

(cccxlix) [3-[(3-ethyl-4-oxo-spiro[6,8-dihydro-5H-pyrazolo[4,3-c]azepine-7,4'-tetrahydropyran]-1-yl)methyl]oxetan-3-yl]methyl 3-fluorobenzoate;

(cccl) [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-fluorobenzoate;

(cccli) [3-[(3-ethyl-4-oxo-spiro[6,8-dihydro-5H-pyrazolo[4,3-c]azepine-7,4'-tetrahydropyran]-1-yl)methyl]oxetan-3-yl]methyl 3-methoxybenzoate;

(ccclii) [3-[(3-ethyl-4-oxo-spiro[6,8-dihydro-5H-pyrazolo[4,3-c]azepine-7,4'-tetrahydropyran]-1-yl)methyl]oxetan-3-yl]methyl 4-chlorobenzoate; 3-(3-ethyl-4-oxo-spiro[6,8-dihydro-5H-pyrazolo[4,3-c]azepine-7,4'-tetrahydropyran]-1-yl)butyl benzoate (cccliv) 4-(3-ethyl-4-oxo-spiro[6,8-dihydro-5H-pyrazolo[4,3-c]azepine-7,4'-tetrahydropyran]-1-yl)butyl benzoate;

(cccliv) 4-(3-ethyl-4-oxo-spiro[6,8-dihydro-5H-pyrazolo[4,3-c]azepine-7,4'-tetrahydropyran]-1-yl)butyl 3-methylbenzoate;

(ccclvi) 4-(3-ethyl-4-oxo-spiro[6,8-dihydro-5H-pyrazolo[4,3-c]azepine-7,4'-tetrahydropyran]-1-yl)butyl 4-methyl benzoate;

(ccclvii) 4-(3-ethyl-4-oxo-spiro[6,8-dihydro-5H-pyrazolo[4,3-c]azepine-7,4'-tetrahydropyran]-1-yl)butyl 4-fluorobenzoate;

(ccclviii) 4-(3-ethyl-4-oxo-spiro[6,8-dihydro-5H-pyrazolo[4,3-c]azepine-7,4'-tetrahydropyran]-1-yl)butyl 3-acetylbenzoate;

(ccclix) 4-(3-ethyl-4-oxo-spiro[6,8-dihydro-5H-pyrazolo[4,3-c]azepine-7,4'-tetrahydropyran]-1-yl)butyl 4-acetylbenzoate;

(ccclx) 4-(3-ethyl-4-oxo-spiro[6,8-dihydro-5H-pyrazolo[4,3-c]azepine-7,4'-tetrahydropyran]-1-yl)butyl 3-methylsulfonylbenzoate;

(ccclxi) 4-(3-ethyl-4-oxo-spiro[6,8-dihydro-5H-pyrazolo[4,3-c]azepine-7,4'-tetrahydropyran]-1-yl)butyl 4-methylsulfonylbenzoate;

(ccclxii) 4-(3-ethyl-4-oxo-spiro[6,8-dihydro-5H-pyrazolo[4,3-c]azepine-7,4'-tetrahydropyran]-1-yl)butyl 4-ethylsulfonylbenzoate;

(ccclxiii) 4-(3-ethyl-4-oxo-spiro[6,8-dihydro-5H-pyrazolo[4,3-c]azepine-7,4'-tetrahydropyran]-1-yl)butyl 3-(methylsulfamoyl)benzoate;

(ccclxiv) 4-(3-ethyl-4-oxo-spiro[6,8-dihydro-5H-pyrazolo[4,3-c]azepine-7,4'-tetrahydropyran]-1-yl)butyl 4-(methylsulfamoyl)benzoate;

(ccclxv) 4-(3-ethyl-4-oxo-spiro[6,8-dihydro-5H-pyrazolo[4,3-c]azepine-7,4'-tetrahydropyran]-1-yl)butyl 3-(dimethylsulfamoyl)benzoate;

(ccclxvi) 4-(3-ethyl-4-oxo-spiro[6,8-dihydro-5H-pyrazolo[4,3-c]azepine-7,4'-tetrahydropyran]-1-yl)butyl 4-(dimethylsulfamoyl)benzoate;

(ccclxvii) 4-(3-ethyl-4-oxo-spiro[6,8-dihydro-5H-pyrazolo[4,3-c]azepine-7,4'-tetrahydropyran]-1-yl)butyl 4-cyclopentylsulfonylbenzoate;

(ccclxviii) 4-(3-ethyl-4-oxo-spiro[6,8-dihydro-5H-pyrazolo[4,3-c]azepine-7,4'-tetrahydropyran]-1-yl)butyl 4-pyrrolidin-1-ylsulfonylbenzoate;

(ccclxix) 4-(3-ethyl-4-oxo-spiro[6,8-dihydro-5H-pyrazolo[4,3-c]azepine-7,4'-tetrahydropyran]-1-yl)butyl 4-morpholinosulfonylbenzoate;

(ccclxx) 4-(3-ethyl-4-oxo-spiro[6,8-dihydro-5H-pyrazolo[4,3-c]azepine-7,4'-tetrahydropyran]-1-yl)butyl 4-(methylcarbamoyl)benzoate;

(ccclxxi) 4-(3-ethyl-4-oxo-spiro[6,8-dihydro-5H-pyrazolo[4,3-c]azepine-7,4'-tetrahydropyran]-1-yl)butyl 4-(dimethylcarbamoyl)benzoate;

(ccclxxii) 4-(3-ethyl-4-oxo-spiro[6,8-dihydro-5H-pyrazolo[4,3-c]azepine-7,4'-tetrahydropyran]-1-yl)butyl 4-(morpholine-4-carbonyl)benzoate;

(ccclxxiii) 2-(3-ethyl-4-oxo-spiro[6,8-dihydro-5H-pyrazolo[4,3-c]azepine-7,4'-tetrahydropyran]-1-yl)ethyl benzoate;

or a pharmaceutically acceptable salt, hydrate or solvate thereof.

7. A pharmaceutical composition comprising a compound according to claim 1 and one or more pharmaceutically acceptable vehicles or excipients and/or one or more pharmaceutically acceptable carriers.

8. The pharmaceutical composition according to claim 7 further comprising one or more other therapeutically active compounds.

9. A method for treatment or alleviation of a disease or a disorder or a condition responsive to PDE4 inhibitory activity, comprising administering to a subject in need thereof a therapeutically effective amount of a compound according to claim 1.

10. A method of treating or ameliorating one or more dermal diseases or conditions, comprising administering to a person suffering from at least one of said diseases an effective amount of one or more compounds according to according to claim 1.

11. The method according to claim 10, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

12. A method of treating or ameliorating dermal diseases or conditions, comprising administering to a person suffering from at least one of said diseases an effective amount of the pharmaceutical composition according to claim 7.

\* \* \* \* \*